US012799500B2

(12) United States Patent
Ostertag et al.

(10) Patent No.: US 12,799,500 B2
(45) Date of Patent: Nov. 17, 2026

(54) NANOTRANSPOSON COMPOSITIONS AND METHODS OF USE

(71) Applicant: Poseida Therapeutics, Inc., San Diego, CA (US)

(72) Inventors: Eric M. Ostertag, San Diego, CA (US); Devon Shedlock, San Diego, CA (US)

(73) Assignee: Poseida Therapeutics, Inc., San Diego, CA (US)

( * ) Notice: Subject to any disclaimer, the term of this patent is extended or adjusted under 35 U.S.C. 154(b) by 1269 days.

(21) Appl. No.: 17/414,123

(22) PCT Filed: Dec. 20, 2019

(86) PCT No.: PCT/US2019/067758
§ 371 (c)(1),
(2) Date: Jun. 15, 2021

(87) PCT Pub. No.: WO2020/132396
PCT Pub. Date: Jun. 25, 2020

(65) Prior Publication Data
US 2022/0042038 A1 Feb. 10, 2022

Related U.S. Application Data

(60) Provisional application No. 62/815,845, filed on Mar. 8, 2019, provisional application No. 62/815,335, filed on Mar. 7, 2019, provisional application No. 62/783,133, filed on Dec. 20, 2018.

(51) Int. Cl.
*C12N 15/85* (2006.01)
*A61K 48/00* (2006.01)
*A61P 35/00* (2006.01)

(52) U.S. Cl.
CPC .............. *C12N 15/85* (2013.01); *A61P 35/00* (2018.01); *A61K 48/00* (2013.01); *C12N 2800/90* (2013.01)

(58) Field of Classification Search
None
See application file for complete search history.

(56) References Cited

U.S. PATENT DOCUMENTS 3,773,919 A 11/1973 Boswell et al.
4,239,754 A 12/1980 Sache et al.
4,309,989 A 1/1982 Fahim
4,544,101 A 10/1985 Hahn et al.
4,656,134 A 4/1987 Ringold
4,683,195 A 7/1987 Mullis et al.
4,683,202 A 7/1987 Mullis
4,704,692 A 11/1987 Ladner
4,766,067 A 8/1988 Biswas
4,767,402 A 8/1988 Kost et al.
4,795,699 A 1/1989 Tabor et al.
4,800,159 A 1/1989 Mullis et al.
4,889,818 A 12/1989 Gelfand et al.
4,921,794 A 5/1990 Tabor et al.
4,925,673 A 5/1990 Steiner et al.
4,939,666 A 7/1990 Hardman
4,946,778 A 8/1990 Ladner et al.
4,965,188 A 10/1990 Mullis et al.
4,994,370 A 2/1991 Silver et al.
5,066,584 A 11/1991 Gyllensten et al.
5,091,310 A 2/1992 Innis
5,122,464 A 6/1992 Wilson et al.
5,130,238 A 7/1992 Malek et al.
5,142,033 A 8/1992 Innis
5,168,062 A 12/1992 Stinski
5,223,409 A 6/1993 Ladner et al.
5,260,203 A 11/1993 Ladner et al.
5,266,491 A 11/1993 Nagata et al.
5,385,839 A 1/1995 Stinski
5,403,484 A 4/1995 Ladner et al.
5,427,908 A 6/1995 Dower et al.
5,455,030 A 10/1995 Ladner et al.
5,514,670 A 5/1996 Friedman et al.
5,518,889 A 5/1996 Ladner et al.
5,534,621 A 7/1996 Ladner et al.
5,571,698 A 11/1996 Ladner et al.
5,576,195 A 11/1996 Robinson et al.
5,580,717 A 12/1996 Dower et al.
(Continued)

FOREIGN PATENT DOCUMENTS

CN 105154473 A * 12/2015 ......... A61K 39/0011
CN 107849116 A 3/2018
(Continued)

OTHER PUBLICATIONS

US 5,733,746 A, 03/1998, Treco et al. (withdrawn)
Luke J, Carnes AE, Hodgson CP, Williams JA. Improved antibiotic-free DNA vaccine vectors utilizing a novel RNA based plasmid selection system. Vaccine. Oct. 30, 2009;27(46):6454-9. doi: 10.1016/j.vaccine.2009.06.017. Epub Jun. 24, 2009. PMID: 19559109; PMCID: PMC2767433. (Year: 2009) (Year: 2009).*
(Continued)

*Primary Examiner* — Anna Skibinsky
*Assistant Examiner* — Catherine L Mccormick
(74) *Attorney, Agent, or Firm* — Leason Ellis LLP; Brian M. Gummow; Maha M. Saber

(57) ABSTRACT

Disclosed are compositions comprising a first nucleic acid sequence comprising: (a) a first inverted terminal repeat (ITR), (b) a second ITR and (c) an intra-ITR sequence, wherein the intra-ITR sequence comprises a transposon sequence, and a second nucleic acid sequence comprising an inter-ITR sequence, wherein the length of the inter-ITR sequence is between 1 and 600 nucleotides, inclusive of the endpoints. Preferably, the compositions are nanotransposons.

33 Claims, 15 Drawing Sheets

Specification includes a Sequence Listing.

(56) References Cited

U.S. PATENT DOCUMENTS

| | | | |
|---|---|---|---|
| 5,580,734 | A | 12/1996 | Treco et al. |
| 5,595,898 | A | 1/1997 | Robinson et al. |
| 5,618,920 | A | 4/1997 | Robinson et al. |
| 5,641,670 | A | 6/1997 | Treco et al. |
| 5,643,768 | A | 7/1997 | Kawasaki |
| 5,656,730 | A | 8/1997 | Lee |
| 5,658,754 | A | 8/1997 | Kawasaki |
| 5,693,493 | A | 12/1997 | Robinson et al. |
| 5,698,417 | A | 12/1997 | Robinson et al. |
| 5,698,435 | A | 12/1997 | Robinson et al. |
| 5,733,761 | A | 3/1998 | Treco et al. |
| 5,750,373 | A | 5/1998 | Garrard et al. |
| 5,763,733 | A | 6/1998 | Whitlow et al. |
| 5,767,260 | A | 6/1998 | Whitlow et al. |
| 5,770,222 | A | 6/1998 | Unger et al. |
| 5,770,359 | A | 6/1998 | Wilson et al. |
| 5,814,599 | A | 9/1998 | Mitragotri et al. |
| 5,827,739 | A | 10/1998 | Wilson et al. |
| 5,837,500 | A | 11/1998 | Ladner et al. |
| 5,839,446 | A | 11/1998 | Waner et al. |
| 5,849,695 | A | 12/1998 | Cohen et al. |
| 5,851,198 | A | 12/1998 | Castellano et al. |
| 5,856,456 | A | 1/1999 | Whitlow et al. |
| 5,871,753 | A | 2/1999 | Crabtree et al. |
| 5,879,681 | A | 3/1999 | Leone-Bay et al. |
| 5,885,793 | A | 3/1999 | Griffiths et al. |
| 6,218,185 | B1 | 4/2001 | Shirk et al. |
| 6,309,663 | B1 | 10/2001 | Patel et al. |
| 6,835,394 | B1 | 12/2004 | Discher et al. |
| 6,962,810 | B2 | 11/2005 | Fraser et al. |
| 7,217,427 | B2 | 5/2007 | Discher et al. |
| 7,867,512 | B2 | 1/2011 | Discher et al. |
| 8,399,643 | B2 | 3/2013 | Ostertag et al. |
| 8,808,748 | B2 | 8/2014 | Ghoroghchian et al. |
| 9,393,292 | B2 | 7/2016 | Brenner |
| 9,913,882 | B2 | 3/2018 | Slawin et al. |
| 10,041,077 | B2 | 8/2018 | Minshull et al. |
| 10,329,543 | B2 | 6/2019 | Ostertag et al. |
| 10,415,024 | B2 | 9/2019 | Ostertag et al. |
| 10,456,452 | B2 | 10/2019 | Ghoroghchian et al. |
| 2014/0363496 | A1 | 12/2014 | Ghoroghchian |
| 2017/0000743 | A1 | 1/2017 | Ghoroghchian et al. |
| 2017/0107541 | A1 | 4/2017 | Ostertag et al. |
| 2017/0114149 | A1 | 4/2017 | Ostertag et al. |
| 2018/0187185 | A1 | 7/2018 | Ostertag et al. |
| 2018/0195086 | A1* | 7/2018 | Solodushko ......... C12N 9/1241 |
| 2019/0225667 | A1 | 7/2019 | Ostertag et al. |
| 2019/0255191 | A1 | 8/2019 | Ghoroghchian et al. |

FOREIGN PATENT DOCUMENTS

| | | | |
|---|---|---|---|
| CN | 108138187 | A | 6/2018 |
| CN | 108601951 | A | 9/2018 |
| JP | 2017513470 | A | 6/2017 |
| WO | WO 1991/17271 | A1 | 11/1991 |
| WO | WO 1991/18980 | A1 | 12/1991 |
| WO | WO 1991/19818 | A1 | 12/1991 |
| WO | WO 1992/05258 | A1 | 4/1992 |
| WO | WO 1992/14843 | A1 | 9/1992 |
| WO | WO 1992/16221 | A1 | 10/1992 |
| WO | WO 1993/08278 | A1 | 4/1993 |
| WO | WO 1996/19256 | A1 | 6/1996 |
| WO | WO 1998/53847 | A1 | 12/1998 |
| WO | WO 2006/133398 | A2 | 12/2006 |
| WO | WO 2010/099296 | A1 | 9/2010 |
| WO | WO-2015157432 | A1 | 10/2015 |
| WO | WO-2017101749 | A1 | 6/2017 |
| WO | WO 2018/014122 | A1 | 1/2018 |
| WO | WO-2018014038 | A1 | 1/2018 |
| WO | WO 2018/068022 | A1 | 4/2018 |
| WO | WO-2018119215 | A1 | 6/2018 |
| WO | WO 2019/126589 | A1 | 6/2019 |
| WO | WO 2019/173636 | A1 | 9/2019 |
| WO | WO-2019183248 | A1 * | 9/2019 ............ C12N 15/70 |
| WO | WO 2020/051374 | A1 | 3/2020 |
| WO | WO-2020132396 | A1 | 6/2020 |

OTHER PUBLICATIONS

Bire S, Ley D, Casteret S, Mermod N, Bigot Y, Rouleux-Bonnin F. Optimization of the piggyBac transposon using mRNA and insulators: toward a more reliable gene delivery system. PLoS One. Dec. 3, 2013;8(12):e82559. doi: 10.1371/journal.pone.0082559. PMID: 24312663; PMCID: PMC3849487. (Year: 2013).*

System Biosciences, PiggyBac Transposon System Instant, reversible and inducible transgenesis, Piggybac Transposon System ++, System Biosciences, Website: https://www.systembio.com/wp/wp-content/uploads/2020/10/PiggyBac_prodsheet_2014-1-1.pdf (Year: 2014).*

Tipanee, J., VandenDriessche, T., & Chuah, M. K. (2017). Transposons: Moving forward from preclinical studies to clinical trials. Human Gene Therapy, 28(11), 1087-1104. https://doi.org/10.1089/hum.2017.128 (Year: 2017).*

Gattinoni, L., Klebanoff, C. & Restifo, N. Paths to stemness: building the ultimate antitumour T cell. Nat Rev Cancer 12, 671-684 (2012). https://doi.org/10.1038/nrc3322 (Year: 2012).*

Zhao et al., "Transgenic technology and application of silkworm" Shanghai Science and Technology Press, (2017) p. 85-89, with English translation, 13 pages.

Capellas, M. et al. (1997) "Enzymatic Condensation of Cholecystokinin CCK-8 (4-6) and CCK-8 (7-8) Peptide Fragments in Organic Media" Biotechnol Bioeng, 56(4):456-463.

CAS Registry No. 195514-63-7, "2-Piperidinecarboxylic acid, 1-[(2S)-1-oxo-2-(3,4,5-trimethoxyphenyl)butyl]-, 2,2'-[1,2-ethanediylbis[imino(2-oxo-2,1-ethanediyl)oxy-3,1-phenylene[(1R)-3-(3,4-dimethoxyphenyl)propylidene]]]ester, (2S,2'S)-" (CA Index Name). STN International, entered Oct. 17, 1997; 3 printed pages.

CAS Registry No. 195514-80-8, "2-Piperidinecarboxylic acid, 1-[(2S)-1-oxo-2-(3,4,5-trimethoxyphenyl)butyl]-, 2,2'-[[2-(dimethylamino)methyl]-1,3-propanediyl]bis[imino(2-oxo-2,1-ethanediyl)oxy-3,1-phenylene[(1R)-3-(3,4-dimethoxyphenyl)propylidene]]] ester, (2S,2'S)-" (CA Index Name). STN International, entered Oct. 17, 1997; 3 printed pages.

Cunningham, B.C. and J.A. Wells (Jun. 2, 1989) "High-Resolution Epitope Mapping of hGH-Receptor Interactions by Alanine-Scanning Mutagenesis" Science, 244:1081-1085.

De Vos, A.M. et al. (1992) "Human Growth Hormone and Extracellular Domain of Its Receptor: Crystal Structure of the Complex" Science, 255:306-312.

Fisch, I. et al. (1992) "Site-Specific Modification of a Fragment of a Chimeric Monoclonal Antibody Using Reverse Proteolysis" Bioconjugate Chem, 3:147-153.

GenPept Accession No. AAA87375.2 (Oct. 15, 2002) "unknown protein [Trichoplusia ni]" U.S. National Library of Medicine, National Center for Biotechnology Information [online]. Retrieved from: https://www.ncbi.nlm.nih.gov/protein/AAA87375, 2 printed pages.

GenPept Accession No. BAD11135.1 (Sep. 15, 2007) "putative transposase yabusame-1 [Bombyx mori]" U.S. National Library of Medicine, National Center for Biotechnology Information [online]. Retrieved from: https://www.ncbi.nlm.nih.gov/protein/BAD11135.1, 1 page.

Gregory, T.K. et al. (Apr. 2018) "Clinical trial of P-BCMA-101 T stem cell memory (Tscm) CAR-T cells in relapsed/refractory multiple myeloma" American Association of Cancer Research Annual Meeting 2018 Poster Presentation, Chicago, IL. Retrieved from the Internet: https://poseida.com/wp-content/uploads/2020/03/P-BCMA-101-001-AACR18-poster_WEB.pdf; 1 page.

Hermanson, D. et al. (Apr. 2017) "Abstract 3759: PiggyBac-manufactured anti-BCMA Centyrin-based CAR-therapeutic exhibits improved potency and durability" Proceedings: AACR Annual Meeting 2017; Apr. 1-5, 2017; Washington, DC. Cancer Research, 77(13 Supplement) [online]. Retrieved from the Internet: https://

(56) References Cited

OTHER PUBLICATIONS cancerres.aacrjournals.org/content/77/13_Supplement/3759. abstract; 4 pages.

Itoh, K. et al. (1996) "Application of Inverse Substrates to Trypsin-Catalyzed Peptide Synthesis" Bioorg Chem, 24(1):59-68.

Junginger, H.E. et al. (1994) "Visualization of Drug Transport Across Human Skin and the Influence of Penetration Enhancers" in Drug Permeation Enhancement. Hsieh, D.S. (Ed.); New York: Marcel Dekker, Inc., pp. 59-89.

Kumaran, S. et al. (1997) "Conformationally driven protease-catalyzed splicing of peptide segments: V8 protease-mediated synthesis of fragments derived from thermolysin and ribonuclease A" Protein Sci, 6(10):2233-2241.

Kyte, J. and R.F. Doolittle. (1982) "A Simple Method for Displaying the Hydropathic Character of a Protein" J Mol Biol, 157:105-132.

Lehninger, A.L. (1975) Biochemistry: The Molecular Basis of Cell Structure and Function, Second Edition. New York, NY: Worth Publishers, Inc.; pp. 71-77.

Philip, B. et al. (Aug. 21, 2014) "A highly compact epitope-based marker/suicide gene for easier and safer T-cell therapy" Blood, 124(8):1277-1287.

Quintarelli, C. et al. (Oct. 15, 2007) "Co-expression of cytokine and suicide genes to enhance the activity and safety of tumor-specific cytotoxic T lymphocytes" Blood, 110(8):2793-2802 [online]. Retrieved from the Internet: www.ncbi.nlm.nih.gov/pmc/articles/PMC2018664/?report=printable; retrieved on Apr. 1, 2019, 22 printed pages.

Smith, L.J. et al. (1992) "Human Interleukin 4. The Solution Structure of a Four-helix Bundle Protein" J Mol Biol, 244:899-904.

Sprague, J. et al. (Feb. 1983) "Expression of a Recombinant DNA Gene Coding for the Vesicular Stomatitis Virus Nucleocapsid Protein" J Virol, 45(2):773-781.

Straathof, K.C. et al. (2005) "An inducible caspase 9 safety switch for T-cell therapy" Blood, 105:4247-4254.

Tatusova, T.A. and T. L. Madden (1999) "Blast 2 Sequences, a new tool for comparing protein and nucleotide sequences" FEMS Microbiol Lett, 174:247-250.

Werlen, R.C. et al. (1994) "Site-Specific Conjugation of an Enzyme and an Antibody Fragment" Bioconjugate Chem., 5:411-417.

* cited by examiner

Study design

Caliper Measurements

SEQUENCE LISTING

```
<160> NUMBER OF SEQ ID NOS: 98

<210> SEQ ID NO 1
<211> LENGTH: 6198
<212> TYPE: DNA
<213> ORGANISM: Artificial Sequence
<220> FEATURE:
<223> OTHER INFORMATION: P-BCMA-101 nanotransposon expressing a BCMA
      CARTyrin

<400> SEQUENCE: 1

tgtacataga ttaaccctag aaagataatc atattgtgac gtacgttaaa gataatcatg     60

cgtaaaattg acgcatgtgt tttatcggtc tgtatatcga ggtttattta ttaatttgaa    120

tagatattaa gttttattat atttacactt acatactaat aataaattca acaaacaatt    180

tatttatgtt tatttattta ttaaaaaaaa acaaaaactc aaaatttctt ctataaagta    240

acaaaacttt tatcgaatac ctgcagcccg ggggatgcag agggacagcc cccccccaaa    300

gcccccaggg atgtaattac gtccctcccc cgctaggggg cagcagcgag ccgcccgggg    360

ctccgctccg gtccggcgct ccccccgcat ccccgagccg gcagcgtgcg gggacagccc    420

gggcacgggg aaggtggcac gggatcgctt tcctctgaac gcttctcgct gctctttgag    480

cctgcagaca cctgggggga tacggggaaa agttgactgt gcctttcgat cgaaccatgg    540

acagttagct ttgcaaagat ggataaagtt ttaaacagag aggaatcttt gcagctaatg    600

gaccttctag gtcttgaaag gagtgggaat tggctccggt gcccgtcagt gggcagagcg    660

cacatcgccc acagtccccg agaagttggg gggaggggtc ggcaattgaa ccggtgccta    720

gagaaggtgg cgcggggtaa actgggaaag tgatgtcgtg tactggctcc gcctttttcc    780
```

-continued

```
cgagggtggg ggagaaccgt atataagtgc agtagtcgcc gtgaacgttc tttttcgcaa    840
cgggtttgcc gccagaacac aggtaagtgc cgtgtgtggt tcccgcgggc ctggcctctt    900
tacgggttat ggcccttgcg tgccttgaat tacttccacc tggctgcagt acgtgattct    960
tgatcccgag cttcgggttg gaagtgggtg ggagagttcg aggccttgcg cttaaggagc   1020
cccttcgcct cgtgcttgag ttgaggcctg gcctgggcgc tggggccgcc gcgtgcgaat   1080
ctggtggcac cttcgcgcct gtctcgctgc tttcgataag tctctagcca tttaaaattt   1140
ttgatgacct gctgcgacgc tttttttctg gcaagatagt cttgtaaatg cgggccaaga   1200
tctgcacact ggtatttcgg tttttggggc cgcgggcggc gacggggccc gtgcgtccca   1260
gcgcacatgt tcggcgaggc ggggcctgcg agcgcggcca ccgagaatcg gacgggggta   1320
gtctcaagct ggccggcctg ctctggtgcc tggcctcgcg ccgccgtgta tcgccccgcc   1380
ctgggcggca aggctggccc ggtcggcacc agttgcgtga gcggaaagat ggccgcttcc   1440
cggccctgct gcagggagct caaaatggag gacgcggcgc tcgggagagc gggcgggtga   1500
gtcacccaca caaaggaaaa gggcctttcc gtcctcagcc gtcgcttcat gtgactccac   1560
ggagtaccgg gcgccgtcca ggcacctcga ttagttctcg agcttttgga gtacgtcgtc   1620
tttaggttgg ggggaggggt tttatgcgat ggagtttccc cacactgagt gggtggagac   1680
tgaagttagg ccagcttggc acttgatgta attctccttg gaatttgccc tttttgagtt   1740
tggatcttgg ttcattctca agcctcagac agtggttcaa agtttttttc ttccatttca   1800
ggtgtcgtga gaattctaat acgactcact atagggtgtg ctgtctcatc attttggcaa   1860
agattggcca ccaagcttgc caccatgggg gtccaggtcg agactatttc accaggggat   1920
gggcgaacat ttccaaaaag gggccagact tgcgtcgtgc attacaccgg gatgctggag   1980
gacgggaaga aagtggacag ctccagggat cgcaacaagc ccttcaagtt catgctggga   2040
aagcaggaag tgatccgagg atgggaggaa ggcgtggcac agatgtcagt cggccagcgg   2100
gccaaactga ccattagccc tgactacgct tatggagcaa caggccaccc agggatcatt   2160
ccccctcatg ccaccctggt cttcgatgtg gaactgctga agctggaggg aggaggagga   2220
tccggatttg gggacgtggg ggccctggag tctctgcgag gaaatgccga tctggcttac   2280
atcctgagca tggaaccctg cggccactgt ctgatcatta acaatgtgaa cttctgcaga   2340
gaaagcggac tgcgaacacg gactggctcc aatattgact gtgagaagct gcggagaagg   2400
ttctctagtc tgcactttat ggtcgaagtg aaaggggatc tgaccgccaa gaaaatggtg   2460
ctggccctgc tggagctggc tcagcaggac catggagctc tggattgctg cgtggtcgtg   2520
atcctgtccc acgggtgcca ggcttctcat ctgcagttcc ccggagcagt gtacggaaca   2580
gacggctgtc ctgtcagcgt ggagaagatc gtcaacatct tcaacggcac ttcttgccct   2640
agtctggggg gaaagccaaa actgttcttt atccaggcct gtggcgggga acagaaagat   2700
cacggcttcg aggtggccag caccagccct gaggacgaat caccagggag caaccctgaa   2760
ccagatgcaa ctccattcca ggagggactg aggacctttg accagctgga tgctatctca   2820
agcctgccca ctcctagtga cattttcgtg tcttacagta ccttcccagg ctttgtctca   2880
tggcgcgatc ccaagtcagg gagctggtac gtggagacac tggacgacat ctttgaacag   2940
tgggcccatt cagaggacct gcagagcctg ctgctgcgag tggcaaacgc tgtctctgtg   3000
aagggcatct acaaacagat gcccgggtgc ttcaattttc tgagaaagaa actgttcttt   3060
aagacttccg gatctggaga gggaagggga agcctgctga cctgtggaga cgtggaggaa   3120
aacccaggac caatggcact gccagtcacc gccctgctgc tgcctctggc tctgctgctg   3180
```

-continued

```
cacgcagcta gaccaatgct gcctgcacca aagaacctgg tggtgagccg gatcacagag   3240
gactccgcca gactgtcttg gaccgcccct gacgccgcct tcgattcctt tccaatccgg   3300
tacatcgaga cactgatctg ggcgaggcc atctggctgg acgtgcccgg ctctgagagg   3360
agctacgatc tgacaggcct gaagcctggc accgagtatg cagtggtcat cacaggagtg   3420
aagggcggca ggttcagctc ccctctggtg gcctctttta ccacaaccac aacccctgcc   3480
cccagacctc ccacacccgc ccctaccatc gcgagtcagc ccctgagtct gagacctgag   3540
gcctgcaggc cagctgcagg aggagctgtg cacaccaggg gcctggactt cgcctgcgac   3600
atctacattt gggcaccact ggccgggacc tgtggagtgc tgctgctgag cctggtcatc   3660
acactgtact gcaagagagg caggaagaaa ctgctgtata ttttcaaaca gcccttcatg   3720
cgccccgtgc agactaccca ggaggaagac gggtgctcct gtcgattccc tgaggaagag   3780
gaaggcgggt gtgagctgcg cgtgaagttt agtcgatcag cagatgcccc agcttacaaa   3840
cagggacaga accagctgta taacgagctg aatctgggcc gccgagagga atatgacgtg   3900
ctggataagc ggagaggacg cgaccccgaa atgggaggca agcccaggcg caaaaaccct   3960
caggaaggcc tgtataacga gctgcagaag gacaaaatgg cagaagccta ttctgagatc   4020
ggcatgaagg gggagcgacg gagaggcaaa gggcacgatg ggctgtacca gggactgagc   4080
accgccacaa aggacaccta tgatgctctg catatgcagg cactgcctcc aaggggaagt   4140
ggagaaggac gaggatcact gctgacatgc ggcgacgtgg aggaaaaccc tggcccaatg   4200
gtcgggtctc tgaattgtat cgtcgccgtg agtcagaaca tgggcattgg gaagaatggc   4260
gatttcccat ggccacctct gcgcaacgag tcccgatact ttcagcggat gacaactacc   4320
tcctctgtgg aagggaaaca gaatctggtc atcatgggaa agaaaacttg gttcagcatt   4380
ccagagaaga accggcccct gaaaggcaga atcaatctgg tgctgtcccg agaactgaag   4440
gagccaccac agggagctca ctttctgagc cggtccctgg acgatgcact gaagctgaca   4500
gaacagcctg agctggccaa caaagtcgat atggtgtgga tcgtcggggg aagttcagtg   4560
tataaggagg ccatgaatca ccccggccat ctgaaactgt tcgtcacacg gatcatgcag   4620
gactttgaga gcgatacttt ctttcctgaa attgacctgg agaagtacaa actgctgccc   4680
gaatatcctg gcgtgctgtc cgatgtccag gaagagaaag gcatcaaata caagttcgag   4740
gtctatgaga agaatgacta ataaggtacc gatcacatat gcctttaatt aaacactagt   4800
tctatagtgt cacctaaatt ccctttagtg agggttaatg gccgtaggcc gccagaattg   4860
ggtccagaca tgataagata cattgatgag tttggacaaa ccacaactag aatgcagtga   4920
aaaaaatgct ttatttgtga aatttgtgat gctattgctt tatttgtaac cattataagc   4980
tgcaataaac aagttaacaa caacaattgc attcatttta tgtttcaggt tcaggggggag   5040
gtgtgggagg tttttcgga ctctaggacc tgcgcatgcg cttggcgtaa tcatggtcat   5100
agctgtttcc tgttttcccc gtatcccccc aggtgtctgc aggctcaaag agcagcgaga   5160
agcgttcaga ggaaagcgat cccgtgccac cttccccgtg cccgggctgt ccccgcacgc   5220
tgccggctcg gggatgcggg gggagcgccg gaccggagcg gagccccggg cggctcgctg   5280
ctgcccccta gcgggggagg gacgtaatta catccctggg ggctttgggg gggggctgtc   5340
cctctcaccg cggtggagct ccagcttttg ttcgaattgg ggcccccccct cgagggtatc   5400
gatgatatct ataacaagaa aatatatata taataagtta tcacgtaagt agaacatgaa   5460
ataacaatat aattatcgta tgagttaaat cttaaaagtc acgtaaaaga taatcatgcg   5520
```

```
tcattttgac tcacgcggtc gttatagttc aaaatcagtg acacttaccg cattgacaag   5580

cacgcctcac gggagctcca agcggcgact gagatgtcct aaatgcacag cgacggattc   5640

gcgctattta gaaagagaga gcaatatttc aagaatgcat gcgtcaattt tacgcagact   5700

atctttctag ggttaatcta gctagcctta agggcgcagc ccgcctaatg agcgggcttt   5760

tttttggctt gttgtccaca accgttaaac cttaaaagct ttaaaagcct tatatattct   5820

ttttttttctt ataaaactta aaaccttaga ggctatttaa gttgctgatt tatattaatt   5880

ttattgttca aacatgagag cttagtacgt gaaacatgag agcttagtac gttagccatg   5940

agagcttagt acgttagcca tgagggttta gttcgttaaa catgagagct tagtacgtta   6000

aacatgagag cttagtacgt actatcaaca ggttgaactg ctgatccacg ttgtggtaga   6060

attggtaaag agagtcgtgt aaaatatcga gttcgcacat cttgttgtct gattattgat   6120

ttttggcgaa accatttgat catatgacaa gatgtgtatc taccttaact taatgatttt   6180

gataaaaatc attaggta                                                 6198
```

<210> SEQ ID NO 2
<211> LENGTH: 238
<212> TYPE: DNA
<213> ORGANISM: Artificial Sequence
<220> FEATURE:
<223> OTHER INFORMATION: ITR

<400> SEQUENCE: 2

```
ccctagaaag ataatcatat tgtgacgtac gttaaagata atcatgcgta aaattgacgc     60

atgtgtttta tcggtctgta tatcgaggtt tatttattaa tttgaataga tattaagttt    120

tattatattt acacttacat actaataata aattcaacaa acaatttatt tatgtttatt    180

tatttattaa aaaaaaacaa aaactcaaaa tttcttctat aaagtaacaa aactttta      238
```

<210> SEQ ID NO 3
<211> LENGTH: 232
<212> TYPE: DNA
<213> ORGANISM: Artificial Sequence
<220> FEATURE:
<223> OTHER INFORMATION: Insulator

<400> SEQUENCE: 3

```
gagggacagc cccccccaa agcccccagg gatgtaatta cgtccctccc ccgctagggg     60

gcagcagcga gccgcccggg gctccgctcc ggtccggcgc tccccccgca tccccgagcc    120

ggcagcgtgc ggggacagcc cgggcacggg gaaggtggca cgggatcgct ttcctctgaa    180

cgcttctcgc tgctctttga gcctgcagac acctgggggg atacggggaa aa            232
```

<210> SEQ ID NO 4
<211> LENGTH: 1264
<212> TYPE: DNA
<213> ORGANISM: Artificial Sequence
<220> FEATURE:
<223> OTHER INFORMATION: EF1alpha promoter

<400> SEQUENCE: 4

```
agctttgcaa agatggataa agttttaaac agagaggaat ctttgcagct aatggacctt     60

ctaggtcttg aaaggagtgg gaattggctc cggtgcccgt cagtgggcag agcgcacatc    120

gcccacagtc cccgagaagt tggggggagg ggtcggcaat tgaaccggtg cctagagaag    180

gtggcgcggg gtaaactggg aaagtgatgt cgtgtactgg ctccgccttt ttcccgaggg    240

tgggggagaa ccgtatataa gtgcagtagt cgccgtgaac gttctttttc gcaacgggtt    300
```

```
tgccgccaga acacaggtaa gtgccgtgtg tggttcccgc gggcctggcc tctttacggg    360

ttatggccct tgcgtgcctt gaattacttc cacctggctg cagtacgtga ttcttgatcc    420

cgagcttcgg gttggaagtg ggtgggagag ttcgaggcct tgcgcttaag gagccccttc    480

gcctcgtgct tgagttgagg cctggcctgg gcgctggggc cgccgcgtgc gaatctggtg    540

gcaccttcgc gcctgtctcg ctgctttcga taagtctcta gccatttaaa atttttgatg    600

acctgctgcg acgctttttt tctggcaaga tagtcttgta aatgcgggcc aagatctgca    660

cactggtatt tcggtttttg gggccgcggg cggcgacggg gcccgtgcgt cccagcgcac    720

atgttcggcg aggcggggcc tgcgagcgcg gccaccgaga atcggacggg ggtagtctca    780

agctggccgg cctgctctgg tgcctggcct cgcgccgccg tgtatcgccc cgccctgggc    840

ggcaaggctg gcccggtcgg caccagttgc gtgagcggaa agatggccgc ttcccggccc    900

tgctgcaggg agctcaaaat ggaggacgcg gcgctcggga gagcgggcgg gtgagtcacc    960

cacacaaagg aaaagggcct ttccgtcctc agccgtcgct tcatgtgact ccacggagta   1020

ccgggcgccg tccaggcacc tcgattagtt ctcgagcttt tggagtacgt cgtctttagg   1080

ttgggggggag gggttttatg cgatggagtt tccccacact gagtgggtgg agactgaagt   1140

taggccagct tggcacttga tgtaattctc cttggaattt gcccttttttg agtttggatc   1200

ttggttcatt ctcaagcctc agacagtggt tcaaagtttt tttcttccat ttcaggtgtc   1260

gtga                                                                1264
```

```
<210> SEQ ID NO 5
<211> LENGTH: 1185
<212> TYPE: DNA
<213> ORGANISM: Artificial Sequence
<220> FEATURE:
<223> OTHER INFORMATION: Inducible proapoptotic polypeptides

<400> SEQUENCE: 5

atgggggtcc aggtcgagac tatttcacca ggggatgggc gaacatttcc aaaaaggggc     60

cagacttgcg tcgtgcatta caccgggatg ctggaggacg ggaagaaagt ggacagctcc    120

agggatcgca acaagccctt caagttcatg ctgggaaagc aggaagtgat ccgaggatgg    180

gaggaaggcg tggcacagat gtcagtcggc cagcgggcca aactgaccat tagccctgac    240

tacgcttatg gagcaacagg ccacccaggg atcattcccc ctcatgccac cctggtcttc    300

gatgtggaac tgctgaagct ggagggagga ggaggatccg gatttgggga cgtgggggcc    360

ctggagtctc tgcgaggaaa tgccgatctg gcttacatcc tgagcatgga accctgcggc    420

cactgtctga tcattaacaa tgtgaacttc tgcagagaaa gcggactgcg aacacggact    480

ggctccaata ttgactgtga gaagctgcgg agaaggttct ctagtctgca ctttatggtc    540

gaagtgaaag gggatctgac cgccaagaaa atggtgctgg ccctgctgga gctggctcag    600

caggaccatg gagctctgga ttgctgcgtg gtcgtgatcc tgtcccacgg gtgccaggct    660

tctcatctgc agttccccgg agcagtgtac ggaacagacg gctgtcctgt cagcgtggag    720

aagatcgtca acatcttcaa cggcacttct tgccctagtc tgggggggaaa gccaaaactg    780

ttctttatcc aggcctgtgg cggggaacag aaagatcacg gcttcgaggt ggccagcacc    840

agccctgagg acgaatcacc agggagcaac cctgaaccag atgcaactcc attccaggag    900

ggactgagga cctttgacca gctggatgct atctcaagcc tgcccactcc tagtgacatt    960

ttcgtgtctt acagtacctt cccaggcttt gtctcatggc gcgatcccaa gtcagggagc   1020
```

tggtacgtgg agacactgga cgacatcttt gaacagtggg cccattcaga ggacctgcag 1080
agcctgctgc tgcgagtggc aaacgctgtc tctgtgaagg gcatctacaa acagatgccc 1140
gggtgcttca attttctgag aaagaaactg ttctttaaga cttcc 1185

<210> SEQ ID NO 6
<211> LENGTH: 1185
<212> TYPE: DNA
<213> ORGANISM: Artificial Sequence
<220> FEATURE:
<223> OTHER INFORMATION: Inducible proapoptotic polypeptides

<400> SEQUENCE: 6
atgggggtcc aggtcgagac tatttcacca ggggatgggc gaacatttcc aaaaaggggc 60
cagacttgcg tcgtgcatta caccgggatg ctggaggacg ggaagaaagt ggacagctcc 120
agggatcgca acaagccctt caagttcatg ctgggaaagc aggaagtgat ccgaggatgg 180
gaggaaggcg tggcacagat gtcagtcggc cagcgggcca aactgaccat tagccctgac 240
tacgcttatg gagcaacagg ccacccaggg atcattcccc ctcatgccac cctggtcttc 300
gatgtggaac tgctgaagct ggagggagga ggaggatccg gatttgggga cgtgggggcc 360
ctggagtctc tgcgaggaaa tgccgatctg gcttacatcc tgagcatgga accctgcggc 420
cactgtctga tcattaacaa tgtgaacttc tgcagagaaa gcggactgcg aacacggact 480
ggctccaata ttgactgtga gaagctgcgg agaaggttct ctagtctgca ctttatggtc 540
gaagtgaaag ggatctgac cgccaagaaa atggtgctgg ccctgctgga gctggctcag 600
caggaccatg gagctctgga ttgctgcgtg gtcgtgatcc tgtcccacgg gtgccaggct 660
tctcatctgc agttccccgg agcagtgtac ggaacagacg gctgtcctgt cagcgtggag 720
aagatcgtca acatcttcaa cggcacttct tgccctagtc tgggggggaaa gccaaaactg 780 ttctttatcc aggcctgtgg cggggaacag aaagatcacg gcttcgaggt ggccagcacc 840
agccctgagg acgaatcacc agggagcaac cctgaaccag atgcaactcc attccaggag 900
ggactgagga cctttgacca gctggatgct atctcaagcc tgcccactcc tagtgacatt 960
ttcgtgtctt acagtacctt cccaggcttt gtctcatggc gcgatcccaa gtcagggagc 1020
tggtacgtgg agacactgga cgacatcttt gaacagtggg cccattcaga ggacctgcag 1080
agcctgctgc tgcgagtggc aaacgctgtc tctgtgaagg gcatctacaa acagatgccc 1140
gggtgcttca attttctgag aaagaaactg ttctttaaga cttcc 1185

<210> SEQ ID NO 7
<211> LENGTH: 63
<212> TYPE: DNA
<213> ORGANISM: Artificial Sequence
<220> FEATURE:
<223> OTHER INFORMATION: T2A Sequence

<400> SEQUENCE: 7
ggatctggag agggaagggg aagcctgctg acctgtggag acgtggagga aaacccagga 60
cca 63

<210> SEQ ID NO 8
<211> LENGTH: 63
<212> TYPE: DNA
<213> ORGANISM: Artificial Sequence
<220> FEATURE:
<223> OTHER INFORMATION: T2A Sequence

<400> SEQUENCE: 8
ggatctggag agggaagggg aagcctgctg acctgtggag acgtggagga aaacccagga 60
cca 63

<210> SEQ ID NO 9
<211> LENGTH: 1002
<212> TYPE: DNA
<213> ORGANISM: Artificial Sequence
<220> FEATURE:
<223> OTHER INFORMATION: BCMA CARTyrin

<400> SEQUENCE: 9
atggcactgc cagtcaccgc cctgctgctg cctctggctc tgctgctgca cgcagctaga 60
ccaatgctgc ctgcaccaaa gaacctggtg gtgagccgga tcacagagga ctccgccaga 120
ctgtcttgga ccgcccctga cgccgccttc gattcctttc caatccggta catcgagaca 180
ctgatctggg gcgaggccat ctggctggac gtgcccggct ctgagaggag ctacgatctg 240
acaggcctga agcctggcac cgagtatgca gtggtcatca caggagtgaa gggcggcagg 300
ttcagctccc ctctggtggc ctcttttacc acaaccacaa cccctgcccc cagacctccc 360
acacccgccc ctaccatcgc gagtcagccc ctgagtctga gacctgaggc ctgcaggcca 420
gctgcaggag gagctgtgca caccaggggc ctggacttcg cctgcgacat ctacatttgg 480
gcaccactgg ccgggacctg tggagtgctg ctgctgagcc tggtcatcac actgtactgc 540
aagagaggca ggaagaaact gctgtatatt ttcaaacagc ccttcatgcg ccccgtgcag 600
actacccagg aggaagacgg gtgctcctgt cgattccctg aggaagagga aggcgggtgt 660
gagctgcgcg tgaagtttag tcgatcagca gatgccccag cttacaaaca gggacagaac 720
cagctgtata acgagctgaa tctgggccgc cgagaggaat atgacgtgct ggataagcgg 780
agaggacgcg accccgaaat gggaggcaag cccaggcgca aaaaccctca ggaaggcctg 840
tataacgagc tgcagaagga caaaatggca gaagcctatt ctgagatcgg catgaagggg 900
gagcgacgga gaggcaaagg gcacgatggg ctgtaccagg gactgagcac cgccacaaag 960
gacacctatg atgctctgca tatgcaggca ctgcctccaa gg 1002

<210> SEQ ID NO 10
<211> LENGTH: 63
<212> TYPE: DNA
<213> ORGANISM: Artificial Sequence
<220> FEATURE:
<223> OTHER INFORMATION: T2A Sequence

<400> SEQUENCE: 10
ggaagtggag aaggacgagg atcactgctg acatgcggcg acgtggagga aaaccctggc 60
cca 63

<210> SEQ ID NO 11
<211> LENGTH: 561
<212> TYPE: DNA
<213> ORGANISM: Artificial Sequence
<220> FEATURE:
<223> OTHER INFORMATION: DHFR selection

<400> SEQUENCE: 11
atggtcgggt ctctgaattg tatcgtcgcc gtgagtcaga acatgggcat tgggaagaat 60
ggcgatttcc catggccacc tctgcgcaac gagtcccgat actttcagcg gatgacaact 120
acctcctctg tggaagggaa acagaatctg gtcatcatgg gaaagaaaac ttggttcagc 180
attccagaga agaaccggcc cctgaaaggc agaatcaatc tggtgctgtc ccgagaactg 240
aaggagccac cacagggagc tcactttctg agccggtccc tggacgatgc actgaagctg 300
acagaacagc ctgagctggc caacaaagtc gatatggtgt ggatcgtcgg gggaagttca 360
gtgtataagg aggccatgaa tcaccccggc catctgaaac tgttcgtcac acggatcatg 420
caggactttg agagcgatac tttctttcct gaaattgacc tggagaagta caaactgctg 480
cccgaatatc ctggcgtgct gtccgatgtc caggaagaga aaggcatcaa atacaagttc 540
gaggtctatg agaagaatga c 561

<210> SEQ ID NO 12
<211> LENGTH: 127
<212> TYPE: DNA
<213> ORGANISM: Artificial Sequence
<220> FEATURE:
<223> OTHER INFORMATION: PolyA sv40

<400> SEQUENCE: 12
cagacatgat aagatacatt gatgagtttg gacaaaccac aactagaatg cagtgaaaaa 60
aatgctttat ttgtgaaatt tgtgatgcta ttgctttatt tgtaaccatt ataagctgca 120
ataaaca 127

<210> SEQ ID NO 13
<211> LENGTH: 231
<212> TYPE: DNA
<213> ORGANISM: Artificial Sequence
<220> FEATURE:
<223> OTHER INFORMATION: Insulator

<400> SEQUENCE: 13
ttttccccgt atccccccag gtgtctgcag gctcaaagag cagcgagaag cgttcagagg 60
aaagcgatcc cgtgccacct tccccgtgcc cgggctgtcc ccgcacgctg ccggctcggg 120
gatgcggggg gagcgccgga ccggagcgga gccccgggcg gctcgctgct gccccctagc 180
gggggaggga cgtaattaca tccctggggg ctttgggggg gggctgtccc t 231

<210> SEQ ID NO 14
<211> LENGTH: 309
<212> TYPE: DNA
<213> ORGANISM: Artificial Sequence
<220> FEATURE:
<223> OTHER INFORMATION: ITR

<400> SEQUENCE: 14
gatatctata acaagaaaat atatatataa taagttatca cgtaagtaga acatgaaata 60
acaatataat tatcgtatga gttaaatctt aaaagtcacg taaaagataa tcatgcgtca 120
ttttgactca cgcggtcgtt atagttcaaa atcagtgaca cttaccgcat tgacaagcac 180
gcctcacggg agctccaagc ggcgactgag atgtcctaaa tgcacagcga cggattcgcg 240
ctatttagaa agagagagca atatttcaag aatgcatgcg tcaattttac gcagactatc 300
tttctaggg 309

<210> SEQ ID NO 15
<211> LENGTH: 281
<212> TYPE: DNA
<213> ORGANISM: Artificial Sequence
<220> FEATURE:
<223> OTHER INFORMATION: R6K Origin of Replication

<400> SEQUENCE: 15

```
ggcttgttgt ccacaaccgt taaaccttaa aagctttaaa agccttatat attctttttt     60

ttcttataaa acttaaaacc ttagaggcta tttaagttgc tgatttatat taattttatt    120

gttcaaacat gagagcttag tacgtgaaac atgagagctt agtacgttag ccatgagagc    180

ttagtacgtt agccatgagg gtttagttcg ttaaacatga gagcttagta cgttaaacat    240

gagagcttag tacgtactat caacaggttg aactgctgat c                        281


<210> SEQ ID NO 16
<211> LENGTH: 139
<212> TYPE: DNA
<213> ORGANISM: Artificial Sequence
<220> FEATURE:
<223> OTHER INFORMATION: RNA-OUT

<400> SEQUENCE: 16

gtagaattgg taaagagagt cgtgtaaaat atcgagttcg cacatcttgt tgtctgatta     60

ttgatttttg gcgaaaccat ttgatcatat gacaagatgt gtatctacct taacttaatg    120

attttgataa aaatcatta                                                 139


<210> SEQ ID NO 17
<211> LENGTH: 958
<212> TYPE: PRT
<213> ORGANISM: Artificial Sequence
<220> FEATURE:
<223> OTHER INFORMATION: P-BCMA-101 amino acid sequence

<400> SEQUENCE: 17

Met Gly Val Gln Val Glu Thr Ile Ser Pro Gly Asp Gly Arg Thr Phe
1               5                   10                  15

Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu Gly Gly Gly Gly
            100                 105                 110

Ser Gly Phe Gly Asp Val Gly Ala Leu Glu Ser Leu Arg Gly Asn Ala
        115                 120                 125

Asp Leu Ala Tyr Ile Leu Ser Met Glu Pro Cys Gly His Cys Leu Ile
    130                 135                 140

Ile Asn Asn Val Asn Phe Cys Arg Glu Ser Gly Leu Arg Thr Arg Thr
145                 150                 155                 160

Gly Ser Asn Ile Asp Cys Glu Lys Leu Arg Arg Arg Phe Ser Ser Leu
                165                 170                 175

His Phe Met Val Glu Val Lys Gly Asp Leu Thr Ala Lys Lys Met Val
            180                 185                 190

Leu Ala Leu Leu Glu Leu Ala Gln Gln Asp His Gly Ala Leu Asp Cys
        195                 200                 205

Cys Val Val Val Ile Leu Ser His Gly Cys Gln Ala Ser His Leu Gln
    210                 215                 220
```

```
Phe Pro Gly Ala Val Tyr Gly Thr Asp Gly Cys Pro Val Ser Val Glu
225                 230                 235                 240

Lys Ile Val Asn Ile Phe Asn Gly Thr Ser Cys Pro Ser Leu Gly Gly
                245                 250                 255

Lys Pro Lys Leu Phe Phe Ile Gln Ala Cys Gly Gly Glu Gln Lys Asp
            260                 265                 270

His Gly Phe Glu Val Ala Ser Thr Ser Pro Glu Asp Glu Ser Pro Gly
        275                 280                 285

Ser Asn Pro Glu Pro Asp Ala Thr Pro Phe Gln Glu Gly Leu Arg Thr
    290                 295                 300

Phe Asp Gln Leu Asp Ala Ile Ser Ser Leu Pro Thr Pro Ser Asp Ile
305                 310                 315                 320

Phe Val Ser Tyr Ser Thr Phe Pro Gly Phe Val Ser Trp Arg Asp Pro
                325                 330                 335

Lys Ser Gly Ser Trp Tyr Val Glu Thr Leu Asp Asp Ile Phe Glu Gln
            340                 345                 350

Trp Ala His Ser Glu Asp Leu Gln Ser Leu Leu Leu Arg Val Ala Asn
        355                 360                 365

Ala Val Ser Val Lys Gly Ile Tyr Lys Gln Met Pro Gly Cys Phe Asn
    370                 375                 380

Phe Leu Arg Lys Lys Leu Phe Phe Lys Thr Ser Gly Ser Gly Glu Gly
385                 390                 395                 400

Arg Gly Ser Leu Leu Thr Cys Gly Asp Val Glu Glu Asn Pro Gly Pro
                405                 410                 415

Met Ala Leu Pro Val Thr Ala Leu Leu Leu Pro Leu Ala Leu Leu Leu
            420                 425                 430

His Ala Ala Arg Pro Met Leu Pro Ala Pro Lys Asn Leu Val Val Ser
        435                 440                 445

Arg Ile Thr Glu Asp Ser Ala Arg Leu Ser Trp Thr Ala Pro Asp Ala
    450                 455                 460

Ala Phe Asp Ser Phe Pro Ile Arg Tyr Ile Glu Thr Leu Ile Trp Gly
465                 470                 475                 480

Glu Ala Ile Trp Leu Asp Val Pro Gly Ser Glu Arg Ser Tyr Asp Leu
                485                 490                 495

Thr Gly Leu Lys Pro Gly Thr Glu Tyr Ala Val Val Ile Thr Gly Val
            500                 505                 510

Lys Gly Gly Arg Phe Ser Ser Pro Leu Val Ala Ser Phe Thr Thr Thr
        515                 520                 525

Thr Thr Pro Ala Pro Arg Pro Pro Thr Pro Ala Pro Thr Ile Ala Ser
    530                 535                 540

Gln Pro Leu Ser Leu Arg Pro Glu Ala Cys Arg Pro Ala Ala Gly Gly
545                 550                 555                 560

Ala Val His Thr Arg Gly Leu Asp Phe Ala Cys Asp Ile Tyr Ile Trp
                565                 570                 575

Ala Pro Leu Ala Gly Thr Cys Gly Val Leu Leu Leu Ser Leu Val Ile
            580                 585                 590

Thr Leu Tyr Cys Lys Arg Gly Arg Lys Lys Leu Leu Tyr Ile Phe Lys
        595                 600                 605

Gln Pro Phe Met Arg Pro Val Gln Thr Thr Gln Glu Glu Asp Gly Cys
    610                 615                 620

Ser Cys Arg Phe Pro Glu Glu Glu Glu Gly Gly Cys Glu Leu Arg Val
625                 630                 635                 640

Lys Phe Ser Arg Ser Ala Asp Ala Pro Ala Tyr Lys Gln Gly Gln Asn
```

```
                645                 650                 655

Gln Leu Tyr Asn Glu Leu Asn Leu Gly Arg Arg Glu Glu Tyr Asp Val
            660                 665                 670

Leu Asp Lys Arg Arg Gly Arg Asp Pro Glu Met Gly Gly Lys Pro Arg
        675                 680                 685

Arg Lys Asn Pro Gln Glu Gly Leu Tyr Asn Glu Leu Gln Lys Asp Lys
    690                 695                 700

Met Ala Glu Ala Tyr Ser Glu Ile Gly Met Lys Gly Glu Arg Arg Arg
705                 710                 715                 720

Gly Lys Gly His Asp Gly Leu Tyr Gln Gly Leu Ser Thr Ala Thr Lys
                725                 730                 735

Asp Thr Tyr Asp Ala Leu His Met Gln Ala Leu Pro Pro Arg Gly Ser
            740                 745                 750

Gly Glu Gly Arg Gly Ser Leu Leu Thr Cys Gly Asp Val Glu Glu Asn
        755                 760                 765

Pro Gly Pro Met Val Gly Ser Leu Asn Cys Ile Val Ala Val Ser Gln
    770                 775                 780

Asn Met Gly Ile Gly Lys Asn Gly Asp Phe Pro Trp Pro Pro Leu Arg
785                 790                 795                 800

Asn Glu Ser Arg Tyr Phe Gln Arg Met Thr Thr Thr Ser Ser Val Glu
                805                 810                 815

Gly Lys Gln Asn Leu Val Ile Met Gly Lys Lys Thr Trp Phe Ser Ile
            820                 825                 830

Pro Glu Lys Asn Arg Pro Leu Lys Gly Arg Ile Asn Leu Val Leu Ser
        835                 840                 845

Arg Glu Leu Lys Glu Pro Pro Gln Gly Ala His Phe Leu Ser Arg Ser
    850                 855                 860

Leu Asp Asp Ala Leu Lys Leu Thr Glu Gln Pro Glu Leu Ala Asn Lys
865                 870                 875                 880

Val Asp Met Val Trp Ile Val Gly Gly Ser Ser Val Tyr Lys Glu Ala
                885                 890                 895

Met Asn His Pro Gly His Leu Lys Leu Phe Val Thr Arg Ile Met Gln
            900                 905                 910

Asp Phe Glu Ser Asp Thr Phe Phe Pro Glu Ile Asp Leu Glu Lys Tyr
        915                 920                 925

Lys Leu Leu Pro Glu Tyr Pro Gly Val Leu Ser Asp Val Gln Glu Glu
    930                 935                 940

Lys Gly Ile Lys Tyr Lys Phe Glu Val Tyr Glu Lys Asn Asp
945                 950                 955
```

<210> SEQ ID NO 18
<211> LENGTH: 6204
<212> TYPE: DNA
<213> ORGANISM: Artificial Sequence
<220> FEATURE:
<223> OTHER INFORMATION: P-PSMA-101 nanotransposon expressing a PSMA CARTyrin

<400> SEQUENCE: 18

```
tgtacataga ttaaccctag aaagataatc atattgtgac gtacgttaaa gataatcatg      60

cgtaaaattg acgcatgtgt tttatcggtc tgtatatcga ggtttattta ttaatttgaa     120

tagatattaa gttttattat atttacactt acatactaat aataaattca acaaacaatt     180

tatttatgtt tatttattta ttaaaaaaaa acaaaaactc aaaatttctt ctataaagta     240

acaaaacttt tatcgaatac ctgcagcccg ggggatgcag agggacagcc cccccccaaa     300
```

```
gcccccaggg atgtaattac gtccctcccc cgctaggggg cagcagcgag ccgcccgggg    360
ctccgctccg gtccggcgct ccccccgcat ccccgagccg gcagcgtgcg gggacagccc    420
gggcacgggg aaggtggcac gggatcgctt tcctctgaac gcttctcgct gctctttgag    480
cctgcagaca cctgggggga tacggggaaa agttgactgt gcctttcgat cgaaccatgg    540
acagttagct ttgcaaagat ggataaagtt ttaaacagag aggaatcttt gcagctaatg    600
gaccttctag gtcttgaaag gagtgggaat tggctccggt gcccgtcagt gggcagagcg    660
cacatcgccc acagtccccg agaagttggg gggaggggtc ggcaattgaa ccggtgccta    720
gagaaggtgg cgcggggtaa actgggaaag tgatgtcgtg tactggctcc gcctttttcc    780
cgagggtggg ggagaaccgt atataagtgc agtagtcgcc gtgaacgttc tttttcgcaa    840
cgggtttgcc gccagaacac aggtaagtgc cgtgtgtggt tcccgcgggc ctggcctctt    900
tacgggttat ggcccttgcg tgccttgaat tacttccacc tggctgcagt acgtgattct    960
tgatcccgag cttcgggttg gaagtgggtg ggagagttcg aggccttgcg cttaaggagc   1020
cccttcgcct cgtgcttgag ttgaggcctg gcctgggcgc tggggccgcc gcgtgcgaat   1080
ctggtggcac cttcgcgcct gtctcgctgc tttcgataag tctctagcca tttaaaattt   1140
ttgatgacct gctgcgacgc tttttttctg gcaagatagt cttgtaaatg cgggccaaga   1200
tctgcacact ggtatttcgg tttttggggc cgcgggcggc gacggggccc gtgcgtccca   1260
gcgcacatgt tcggcgaggc ggggcctgcg agcgcggcca ccgagaatcg gacgggggta   1320
gtctcaagct ggccggcctg ctctggtgcc tggcctcgcg ccgccgtgta tcgccccgcc   1380
ctgggcggca aggctggccc ggtcggcacc agttgcgtga gcggaaagat ggccgcttcc   1440
cggccctgct gcagggagct caaaatggag gacgcggcgc tcgggagagc gggcgggtga   1500
gtcacccaca caaaggaaaa gggcctttcc gtcctcagcc gtcgcttcat gtgactccac   1560
ggagtaccgg gcgccgtcca ggcacctcga ttagttctcg agcttttgga gtacgtcgtc   1620
tttaggttgg ggggaggggt tttatgcgat ggagtttccc cacactgagt gggtggagac   1680
tgaagttagg ccagcttggc acttgatgta attctccttg gaatttgccc tttttgagtt   1740
tggatcttgg ttcattctca agcctcagac agtggttcaa agtttttttc ttccatttca   1800
ggtgtcgtga gaattctaat acgactcact atagggtgtg ctgtctcatc attttggcaa   1860
agattggcca ccaagcttgc caccatgggg gtccaggtcg agactatttc accaggggat   1920
gggcgaacat ttccaaaaag ggccagact tgcgtcgtgc attacaccgg gatgctggag   1980
gacgggaaga aagtggacag ctccagggat cgcaacaagc ccttcaagtt catgctggga   2040
aagcaggaag tgatccgagg atgggaggaa ggcgtggcac agatgtcagt cggccagcgg   2100
gccaaactga ccattagccc tgactacgct tatggagcaa caggccaccc agggatcatt   2160
ccccctcatg ccaccctggt cttcgatgtg gaactgctga agctggaggg aggaggagga   2220
tccggatttg gggacgtggg ggccctggag tctctgcgag gaaatgccga tctggcttac   2280
atcctgagca tggaaccctg cggccactgt ctgatcatta acaatgtgaa cttctgcaga   2340
gaaagcggac tgcgaacacg gactggctcc aatattgact gtgagaagct gcggagaagg   2400
ttctctagtc tgcactttat ggtcgaagtg aaaggggatc tgaccgccaa gaaaatggtg   2460
ctggccctgc tggagctggc tcagcaggac catggagctc tggattgctg cgtggtcgtg   2520
atcctgtccc acgggtgcca ggcttctcat ctgcagttcc ccggagcagt gtacggaaca   2580
gacggctgtc ctgtcagcgt ggagaagatc gtcaacatct tcaacggcac ttcttgccct   2640
```

agtctggggg gaaagccaaa actgttcttt atccaggcct gtggcgggga acagaaagat 2700
cacggcttcg aggtggccag caccagccct gaggacgaat caccagggag caaccctgaa 2760
ccagatgcaa ctccattcca ggagggactg aggacctttg accagctgga tgctatctca 2820
agcctgccca ctcctagtga cattttcgtg tcttacagta ccttcccagg ctttgtctca 2880
tggcgcgatc ccaagtcagg gagctggtac gtggagacac tggacgacat ctttgaacag 2940
tgggcccatt cagaggacct gcagagcctg ctgctgcgag tggcaaacgc tgtctctgtg 3000
aagggcatct acaaacagat gcccgggtgc ttcaattttc tgagaaagaa actgttcttt 3060
aagacttccg gatctggaga gggaagggga agcctgctga cctgtggaga cgtggaggaa 3120
aacccaggac caatggcact gccagtcacc gccctgctgc tgcctctggc tctgctgctg 3180
cacgcagcta gaccaatgct gcctgcacca aagaacctgg tggtgtctcg ggtgaccgag 3240
gactctgcca gactgagctg ggccatcgac gagcagaggg attggttcga gagctttctg 3300
atccagtatc aggagtccga gaaagtgggc gaggccatcg tgctgacagt gcctggcagc 3360
gagcggtcct atgatctgac cggcctgaag ccaggcacag agtacaccgt gtccatctac 3420
ggcgtgtatc acgtgtacag gtccaatcct ctgtctgcca tcttcaccac aaccacaacc 3480
cctgccccca gacctcccac acccgcccct accatcgcga gtcagcccct gagtctgaga 3540
cctgaggcct gcaggccagc tgcaggagga gctgtgcaca ccaggggcct ggacttcgcc 3600
tgcgacatct acatttgggc accactggcc gggacctgtg gagtgctgct gctgagcctg 3660
gtcatcacac tgtactgcaa gagaggcagg aagaaactgc tgtatatttt caaacagccc 3720
ttcatgcgcc ccgtgcagac tacccaggag gaagacgggt gctcctgtcg attccctgag 3780
gaagaggaag gcgggtgtga gctgcgcgtg aagtttagtc gatcagcaga tgccccagct 3840
tacaaacagg gacagaacca gctgtataac gagctgaatc tgggccgccg agaggaatat 3900
gacgtgctgg ataagcggag aggacgcgac cccgaaatgg gaggcaagcc caggcgcaaa 3960
aaccctcagg aaggcctgta taacgagctg cagaaggaca aaatggcaga agcctattct 4020
gagatcggca tgaaggggga gcgacggaga ggcaaagggc acgatgggct gtaccaggga 4080
ctgagcaccg ccacaaagga cacctatgat gctctgcata tgcaggcact gcctccaagg 4140
ggaagtggag aaggacgagg atcactgctg acatgcggcg acgtggagga aaaccctggc 4200
ccaatggtcg ggtctctgaa ttgtatcgtc gccgtgagtc agaacatggg cattgggaag 4260
aatggcgatt tcccatggcc acctctgcgc aacgagtccc gatactttca gcggatgaca 4320
actacctcct ctgtggaagg gaaacagaat ctggtcatca tgggaaagaa aacttggttc 4380
agcattccag agaagaaccg gcccctgaaa ggcagaatca atctggtgct gtcccgagaa 4440
ctgaaggagc caccacaggg agctcacttt ctgagccggt ccctggacga tgcactgaag 4500
ctgacagaac agcctgagct ggccaacaaa gtcgatatgg tgtggatcgt cgggggaagt 4560
tcagtgtata aggaggccat gaatcacccc ggccatctga aactgttcgt cacacggatc 4620
atgcaggact ttgagagcga tactttcttt cctgaaattg acctggagaa gtacaaactg 4680
ctgcccgaat atcctggcgt gctgtccgat gtccaggaag agaaaggcat caaatacaag 4740
ttcgaggtct atgagaagaa tgactaataa ggtaccgatc acatatgcct ttaattaaac 4800
actagttcta tagtgtcacc taaattccct ttagtgaggg ttaatggccg taggccgcca 4860
gaattgggtc cagacatgat aagatacatt gatgagtttg gacaaaccac aactagaatg 4920
cagtgaaaaa aatgctttat ttgtgaaatt tgtgatgcta ttgctttatt tgtaaccatt 4980
ataagctgca ataaacaagt taacaacaac aattgcattc attttatgtt tcaggttcag 5040

```
ggggaggtgt gggaggtttt ttcggactct aggacctgcg catgcgcttg gcgtaatcat   5100

ggtcatagct gtttcctgtt ttccccgtat ccccccaggt gtctgcaggc tcaaagagca   5160

gcgagaagcg ttcagaggaa agcgatcccg tgccaccttc cccgtgcccg ggctgtcccc   5220

gcacgctgcc ggctcgggga tgcgggggga gcgccggacc ggagcggagc cccgggcggc   5280

tcgctgctgc cccctagcgg gggagggacg taattacatc cctgggggct ttgggggggg   5340

gctgtccctc tcaccgcggt ggagctccag cttttgttcg aattggggcc ccccctcgag   5400

ggtatcgatg atatctataa caagaaaata tatatataat aagttatcac gtaagtagaa   5460

catgaaataa caatataatt atcgtatgag ttaaatctta aaagtcacgt aaaagataat   5520

catgcgtcat tttgactcac gcggtcgtta tagttcaaaa tcagtgacac ttaccgcatt   5580

gacaagcacg cctcacggga gctccaagcg gcgactgaga tgtcctaaat gcacagcgac   5640

ggattcgcgc tatttagaaa gagagagcaa tatttcaaga atgcatgcgt caattttacg   5700

cagactatct ttctagggtt aatctagcta gccttaaggg cgcagcccgc ctaatgagcg   5760

ggcttttttt tggcttgttg tccacaaccg ttaaacctta aaagctttaa aagccttata   5820

tattcttttt tttcttataa aacttaaaac cttagaggct atttaagttg ctgatttata   5880

ttaattttat tgttcaaaca tgagagctta gtacgtgaaa catgagagct tagtacgtta   5940

gccatgagag cttagtacgt tagccatgag ggtttagttc gttaaacatg agagcttagt   6000

acgttaaaca tgagagctta gtacgtacta tcaacaggtt gaactgctga tccacgttgt   6060

ggtagaattg gtaaagagag tcgtgtaaaa tatcgagttc gcacatcttg ttgtctgatt   6120

attgattttt ggcgaaacca tttgatcata tgacaagatg tgtatctacc ttaacttaat   6180

gattttgata aaaatcatta ggta                                          6204
```

```
<210> SEQ ID NO 19
<211> LENGTH: 1008
<212> TYPE: DNA
<213> ORGANISM: Artificial Sequence
<220> FEATURE:
<223> OTHER INFORMATION: PSMA CARTyrin

<400> SEQUENCE: 19
```

```
atggcactgc cagtcaccgc cctgctgctg cctctggctc tgctgctgca cgcagctaga     60

ccaatgctgc ctgcaccaaa gaacctggtg gtgtctcggg tgaccgagga ctctgccaga    120

ctgagctggg ccatcgacga gcagagggat tggttcgaga gctttctgat ccagtatcag    180

gagtccgaga aagtgggcga ggccatcgtg ctgacagtgc ctggcagcga gcggtcctat    240

gatctgaccg gcctgaagcc aggcacagag tacaccgtgt ccatctacgg cgtgtatcac    300

gtgtacaggt ccaatcctct gtctgccatc ttcaccacaa ccacaacccc tgcccccaga    360

cctcccacac ccgcccctac catcgcgagt cagcccctga gtctgagacc tgaggcctgc    420

aggccagctg caggaggagc tgtgcacacc aggggcctgg acttcgcctg cgacatctac    480

atttgggcac cactggccgg gacctgtgga gtgctgctgc tgagcctggt catcacactg    540

tactgcaaga gaggcaggaa gaaactgctg tatattttca aacagccctt catgcgcccc    600

gtgcagacta cccaggagga agacgggtgc tcctgtcgat tccctgagga agaggaaggc    660

gggtgtgagc tgcgcgtgaa gtttagtcga tcagcagatg ccccagctta caaacaggga    720

cagaaccagc tgtataacga gctgaatctg ggccgccgag aggaatatga cgtgctggat    780

aagcggagag gacgcgaccc cgaaatggga ggcaagccca ggcgcaaaaa ccctcaggaa    840
```

ggcctgtata acgagctgca gaaggacaaa atggcagaag cctattctga gatcggcatg 900
aagggggagc gacggagagg caaagggcac gatgggctgt accagggact gagcaccgcc 960
acaaaggaca cctatgatgc tctgcatatg caggcactgc ctccaagg 1008

<210> SEQ ID NO 20
<211> LENGTH: 960
<212> TYPE: PRT
<213> ORGANISM: Artificial Sequence
<220> FEATURE:
<223> OTHER INFORMATION: P-PSMA-101 amino acid sequence

<400> SEQUENCE: 20

Met Gly Val Gln Val Glu Thr Ile Ser Pro Gly Asp Gly Arg Thr Phe
1 5 10 15

Pro Lys Arg Gly Gln Thr Cys Val Val His Tyr Thr Gly Met Leu Glu
20 25 30

Asp Gly Lys Lys Val Asp Ser Ser Arg Asp Arg Asn Lys Pro Phe Lys
35 40 45

Phe Met Leu Gly Lys Gln Glu Val Ile Arg Gly Trp Glu Glu Gly Val
50 55 60

Ala Gln Met Ser Val Gly Gln Arg Ala Lys Leu Thr Ile Ser Pro Asp
65 70 75 80

Tyr Ala Tyr Gly Ala Thr Gly His Pro Gly Ile Ile Pro Pro His Ala
85 90 95

Thr Leu Val Phe Asp Val Glu Leu Leu Lys Leu Glu Gly Gly Gly Gly
100 105 110

Ser Gly Phe Gly Asp Val Gly Ala Leu Glu Ser Leu Arg Gly Asn Ala
115 120 125

Asp Leu Ala Tyr Ile Leu Ser Met Glu Pro Cys Gly His Cys Leu Ile
130 135 140

Ile Asn Asn Val Asn Phe Cys Arg Glu Ser Gly Leu Arg Thr Arg Thr
145 150 155 160

Gly Ser Asn Ile Asp Cys Glu Lys Leu Arg Arg Arg Phe Ser Ser Leu
165 170 175

His Phe Met Val Glu Val Lys Gly Asp Leu Thr Ala Lys Lys Met Val
180 185 190

Leu Ala Leu Leu Glu Leu Ala Gln Gln Asp His Gly Ala Leu Asp Cys
195 200 205

Cys Val Val Val Ile Leu Ser His Gly Cys Gln Ala Ser His Leu Gln
210 215 220

Phe Pro Gly Ala Val Tyr Gly Thr Asp Gly Cys Pro Val Ser Val Glu
225 230 235 240

Lys Ile Val Asn Ile Phe Asn Gly Thr Ser Cys Pro Ser Leu Gly Gly
245 250 255

Lys Pro Lys Leu Phe Phe Ile Gln Ala Cys Gly Gly Glu Gln Lys Asp
260 265 270

His Gly Phe Glu Val Ala Ser Thr Ser Pro Glu Asp Glu Ser Pro Gly
275 280 285

Ser Asn Pro Glu Pro Asp Ala Thr Pro Phe Gln Glu Gly Leu Arg Thr
290 295 300

Phe Asp Gln Leu Asp Ala Ile Ser Ser Leu Pro Thr Pro Ser Asp Ile
305 310 315 320

Phe Val Ser Tyr Ser Thr Phe Pro Gly Phe Val Ser Trp Arg Asp Pro
325 330 335

-continued

```
Lys Ser Gly Ser Trp Tyr Val Glu Thr Leu Asp Asp Ile Phe Glu Gln
            340                 345                 350

Trp Ala His Ser Glu Asp Leu Gln Ser Leu Leu Leu Arg Val Ala Asn
        355                 360                 365

Ala Val Ser Val Lys Gly Ile Tyr Lys Gln Met Pro Gly Cys Phe Asn
    370                 375                 380

Phe Leu Arg Lys Lys Leu Phe Phe Lys Thr Ser Gly Ser Gly Glu Gly
385                 390                 395                 400

Arg Gly Ser Leu Leu Thr Cys Gly Asp Val Glu Glu Asn Pro Gly Pro
                405                 410                 415

Met Ala Leu Pro Val Thr Ala Leu Leu Leu Pro Leu Ala Leu Leu Leu
            420                 425                 430

His Ala Ala Arg Pro Met Leu Pro Ala Pro Lys Asn Leu Val Val Ser
        435                 440                 445

Arg Val Thr Glu Asp Ser Ala Arg Leu Ser Trp Ala Ile Asp Glu Gln
    450                 455                 460

Arg Asp Trp Phe Glu Ser Phe Leu Ile Gln Tyr Gln Glu Ser Glu Lys
465                 470                 475                 480

Val Gly Glu Ala Ile Val Leu Thr Val Pro Gly Ser Glu Arg Ser Tyr
                485                 490                 495

Asp Leu Thr Gly Leu Lys Pro Gly Thr Glu Tyr Thr Val Ser Ile Tyr
            500                 505                 510

Gly Val Tyr His Val Tyr Arg Ser Asn Pro Leu Ser Ala Ile Phe Thr
        515                 520                 525

Thr Thr Thr Thr Pro Ala Pro Arg Pro Pro Thr Pro Ala Pro Thr Ile
    530                 535                 540

Ala Ser Gln Pro Leu Ser Leu Arg Pro Glu Ala Cys Arg Pro Ala Ala
545                 550                 555                 560

Gly Gly Ala Val His Thr Arg Gly Leu Asp Phe Ala Cys Asp Ile Tyr
                565                 570                 575

Ile Trp Ala Pro Leu Ala Gly Thr Cys Gly Val Leu Leu Leu Ser Leu
            580                 585                 590

Val Ile Thr Leu Tyr Cys Lys Arg Gly Arg Lys Lys Leu Leu Tyr Ile
        595                 600                 605

Phe Lys Gln Pro Phe Met Arg Pro Val Gln Thr Thr Gln Glu Glu Asp
    610                 615                 620

Gly Cys Ser Cys Arg Phe Pro Glu Glu Glu Glu Gly Gly Cys Glu Leu
625                 630                 635                 640

Arg Val Lys Phe Ser Arg Ser Ala Asp Ala Pro Ala Tyr Lys Gln Gly
                645                 650                 655

Gln Asn Gln Leu Tyr Asn Glu Leu Asn Leu Gly Arg Arg Glu Glu Tyr
            660                 665                 670

Asp Val Leu Asp Lys Arg Arg Gly Arg Asp Pro Glu Met Gly Gly Lys
        675                 680                 685

Pro Arg Arg Lys Asn Pro Gln Glu Gly Leu Tyr Asn Glu Leu Gln Lys
    690                 695                 700

Asp Lys Met Ala Glu Ala Tyr Ser Glu Ile Gly Met Lys Gly Glu Arg
705                 710                 715                 720

Arg Arg Gly Lys Gly His Asp Gly Leu Tyr Gln Gly Leu Ser Thr Ala
                725                 730                 735

Thr Lys Asp Thr Tyr Asp Ala Leu His Met Gln Ala Leu Pro Pro Arg
            740                 745                 750

Gly Ser Gly Glu Gly Arg Gly Ser Leu Leu Thr Cys Gly Asp Val Glu
```

```
        755                 760                 765

Glu Asn Pro Gly Pro Met Val Gly Ser Leu Asn Cys Ile Val Ala Val
    770                 775                 780

Ser Gln Asn Met Gly Ile Gly Lys Asn Gly Asp Phe Pro Trp Pro Pro
785                 790                 795                 800

Leu Arg Asn Glu Ser Arg Tyr Phe Gln Arg Met Thr Thr Thr Ser Ser
                805                 810                 815

Val Glu Gly Lys Gln Asn Leu Val Ile Met Gly Lys Lys Thr Trp Phe
            820                 825                 830

Ser Ile Pro Glu Lys Asn Arg Pro Leu Lys Gly Arg Ile Asn Leu Val
        835                 840                 845

Leu Ser Arg Glu Leu Lys Glu Pro Pro Gln Gly Ala His Phe Leu Ser
    850                 855                 860

Arg Ser Leu Asp Asp Ala Leu Lys Leu Thr Glu Gln Pro Glu Leu Ala
865                 870                 875                 880

Asn Lys Val Asp Met Val Trp Ile Val Gly Gly Ser Ser Val Tyr Lys
                885                 890                 895

Glu Ala Met Asn His Pro Gly His Leu Lys Leu Phe Val Thr Arg Ile
            900                 905                 910

Met Gln Asp Phe Glu Ser Asp Thr Phe Phe Pro Glu Ile Asp Leu Glu
        915                 920                 925

Lys Tyr Lys Leu Leu Pro Glu Tyr Pro Gly Val Leu Ser Asp Val Gln
    930                 935                 940

Glu Glu Lys Gly Ile Lys Tyr Lys Phe Glu Val Tyr Glu Lys Asn Asp
945                 950                 955                 960


<210> SEQ ID NO 21
<211> LENGTH: 6248
<212> TYPE: DNA
<213> ORGANISM: Artificial Sequence
<220> FEATURE:
<223> OTHER INFORMATION: P-BCMA-ALLO1 nanotransposon expressing a BCMA
      VCAR

<400> SEQUENCE: 21

tgtacataga ttaaccctag aaagataatc atattgtgac gtacgttaaa gataatcatg     60

cgtaaaattg acgcatgtgt tttatcggtc tgtatatcga ggtttattta ttaatttgaa    120

tagatattaa gttttattat atttacactt acatactaat aataaattca acaaacaatt    180

tatttatgtt tatttattta ttaaaaaaaa acaaaaactc aaaatttctt ctataaagta    240

acaaaacttt tatcgaatac ctgcagcccg ggggatgcag agggacagcc cccccccaaa    300

gcccccaggg atgtaattac gtccctcccc cgctaggggg cagcagcgag ccgcccgggg    360

ctccgctccg gtccggcgct ccccccgcat ccccgagccg gcagcgtgcg gggacagccc    420

gggcacgggg aaggtggcac gggatcgctt tcctctgaac gcttctcgct gctctttgag    480

cctgcagaca cctgggggga tacggggaaa agttgactgt gcctttcgat cgaaccatgg    540

acagttagct ttgcaaagat ggataaagtt ttaaacagag aggaatcttt gcagctaatg    600

gaccttctag gtcttgaaag gagtgggaat tggctccggt gcccgtcagt gggcagagcg    660

cacatcgccc acagtccccg agaagttggg gggaggggtc ggcaattgaa ccggtgccta    720

gagaaggtgg cgcggggtaa actgggaaag tgatgtcgtg tactggctcc gcctttttcc    780

cgagggtggg ggagaaccgt atataagtgc agtagtcgcc gtgaacgttc tttttcgcaa    840

cgggtttgcc gccagaacac aggtaagtgc cgtgtgtggt tcccgcgggc ctggcctctt    900
```

```
tacgggttat ggcccttgcg tgccttgaat tacttccacc tggctgcagt acgtgattct    960
tgatcccgag cttcgggttg gaagtgggtg ggagagttcg aggccttgcg cttaaggagc   1020
cccttcgcct cgtgcttgag ttgaggcctg gcctgggcgc tggggccgcc gcgtgcgaat   1080
ctggtggcac cttcgcgcct gtctcgctgc tttcgataag tctctagcca tttaaaattt   1140
ttgatgacct gctgcgacgc tttttttctg gcaagatagt cttgtaaatg cgggccaaga   1200
tctgcacact ggtatttcgg tttttggggc cgcgggcggc gacggggccc gtgcgtccca   1260
gcgcacatgt tcggcgaggc ggggcctgcg agcgcggcca ccgagaatcg gacgggggta   1320
gtctcaagct ggccggcctg ctctggtgcc tggcctcgcg ccgccgtgta tcgccccgcc   1380
ctgggcggca aggctggccc ggtcggcacc agttgcgtga gcggaaagat ggccgcttcc   1440
cggccctgct gcagggagct caaaatggag gacgcggcgc tcgggagagc gggcgggtga   1500
gtcacccaca caaaggaaaa gggcctttcc gtcctcagcc gtcgcttcat gtgactccac   1560
ggagtaccgg gcgccgtcca ggcacctcga ttagttctcg agcttttgga gtacgtcgtc   1620
tttaggttgg ggggaggggt tttatgcgat ggagtttccc cacactgagt gggtggagac   1680
tgaagttagg ccagcttggc acttgatgta attctccttg gaatttgccc tttttgagtt   1740
tggatcttgg ttcattctca agcctcagac agtggttcaa agtttttttc ttccatttca   1800
ggtgtcgtga gaattctaat acgactcact atagggtgaa gcttgccacc atgggggtcc   1860
aggtggaaac aatctctccg gggatgggc ggacattccc taaaaggggc cagacctgcg   1920
tggtgcatta caccggcatg ctggaagatg gcaagaaggt ggacagcagc cgggacagaa   1980
acaagccctt caagttcatg ctgggcaagc aagaagtgat cagaggctgg gaagagggcg   2040
tcgcccagat gtctgttgga cagagagcca agctgacaat cagccccgat tacgcctatg   2100
gcgccacagg acaccctggc atcattcctc cacatgccac actggtgttc gacgtggaac   2160
tgctgaagct ggaaggcggc ggaggatctg gctttggaga tgtgggagcc ctggaaagcc   2220
tgagaggcaa tgccgatctg gcctacatcc tgagcatgga accttgcggc cactgcctga   2280
ttatcaacaa cgtgaacttc tgtagagaga gcggcctgcg gaccagaacc ggcagcaata   2340
tcgattgcga gaagctgcgg cggagattca gcagcctgca cttcatggtg gaagtgaagg   2400
gcgacctgac cgccaagaaa atggtgctgg ctctgctgga actggcccag caagatcatg   2460
gcgccctgga ttgctgtgtg gtcgtgatcc tgtctcacgg ctgtcaggcc agccaccttc   2520
aattccctgg cgccgtgtat ggcacagatg gctgtcctgt gtccgtggaa aagatcgtga   2580
acatcttcaa cggcaccagc tgtcctagcc tcggcggaaa gcccaagctg ttcttcatcc   2640
aagcctgtgg cggcgagcag aaggatcacg gatttgaggt ggccagcaca agccccgagg   2700
atgagtctcc tggaagcaac cctgagcctg acgccacacc tttccaagag ggcctgagaa   2760
ccttcgacca gctggacgct atcagctccc tgcctacacc tagcgacatc ttcgtgtcct   2820
acagcacatt ccccggcttt gtgtcttggc gggaccctaa gtctggctct tggtacgtgg   2880
aaaccctgga cgacatcttt gagcagtggg ctcacagcga ggacctccag tctctgctgc   2940
tgagagtggc caatgccgtg tccgtgaagg gcatctacaa gcagatgcct ggctgcttca   3000
acttcctgcg gaagaagctg tttttcaaga ccagcggcag cggcgaaggc agaggatccc   3060
ttttgacatg cggcgatgtg gaagagaacc ccggacctat ggctctgcct gtgacagctc   3120
tgcttctgcc tctggcactg cttcttcatg cggcgcgccc tgaagttcag ctgcttgaat   3180
ctggcggagg cctggttcaa cctggcggat ctctgagact gagctgtgcc gccagcggct   3240
tcaccttcag caattacgcc atgacctgga tcagacaggc ccctggcaaa ggcctggaat   3300
```

gggtgtccgg aattacaggc gacggcggca gcacctttta cgccgattct gtgaagggca 3360
gattcaccat cagccgggac aacagcaaga acaccctgta cctgcagatg aacagcctga 3420
gagccgagga caccgccgtg tactactgcg tgaaggactg gaacaccacc atgatcaccg 3480
agagaggcca gggcacactg gtcaccgtgt cctctacaac aacaccggcg cctagacctc 3540
caacaccagc tcctacaatc gcgagtcagc ccctgtctct cagacccgaa gcctgcaggc 3600
cagctgcagg aggagctgtg cacaccaggg gcctggactt cgcctgcgac atctacattt 3660
gggcaccact ggccgggacc tgtggagtgc tgctgctgag cctggtcatc acactgtact 3720
gcaagagagg caggaagaaa ctgctgtata ttttcaaaca gcccttcatg cgccccgtgc 3780
agactaccca ggaggaagac gggtgctcct gtcgattccc tgaggaagag gaaggcgggt 3840
gtgagctgcg cgtgaagttt agtcgatcag cagatgcccc agcttacaaa cagggacaga 3900
accagctgta taacgagctg aatctgggcc gccgagagga atatgacgtg ctggataagc 3960
ggagaggacg cgaccccgaa atgggaggca agcccaggcg caaaaaccct caggaaggcc 4020
tgtataacga gctgcagaag gacaaaatgg cagaagccta ttctgagatc ggcatgaagg 4080
gggagcgacg gagaggcaaa gggcacgatg ggctgtacca gggactgagc accgccacaa 4140
aggacaccta tgatgctctg catatgcagg cactgcctcc aaggggaagt ggagaaggac 4200
gaggatcact gctgacatgc ggcgacgtgg aggaaaaccc tggcccaatg gtcgggtctc 4260
tgaattgtat cgtcgccgtg agtcagaaca tgggcattgg gaagaatggc gatttcccat 4320
ggccacctct gcgcaacgag tcccgatact ttcagcggat gacaactacc tcctctgtgg 4380
aagggaaaca gaatctggtc atcatgggaa agaaaacttg gttcagcatt ccagagaaga 4440
accggcccct gaaaggcaga atcaatctgg tgctgtcccg agaactgaag gagccaccac 4500
agggagctca ctttctgagc cggtccctgg acgatgcact gaagctgaca gaacagcctg 4560
agctggccaa caaagtcgat atggtgtgga tcgtcggggg aagttcagtg tataaggagg 4620
ccatgaatca ccccggccat ctgaaactgt tcgtcacacg gatcatgcag gactttgaga 4680
gcgatacttt ctttcctgaa attgacctgg agaagtacaa actgctgccc gaatatcctg 4740
gcgtgctgtc cgatgtccag gaagagaaag gcatcaaata caagttcgag gtctatgaga 4800
agaatgacta ataaggtacc gatcacatat gcctttaatt aaacactagt tctatagtgt 4860
cacctaaatt ccctttagtg agggttaatg gccgtaggcc gccagaattg ggtccagaca 4920
tgataagata cattgatgag tttggacaaa ccacaactag aatgcagtga aaaaaatgct 4980
ttatttgtga aatttgtgat gctattgctt tatttgtaac cattataagc tgcaataaac 5040
aagttaacaa caacaattgc attcatttta tgtttcaggt tcagggggag gtgtgggagg 5100
tttttcgga ctctaggacc tgcgcatgcg cttggcgtaa tcatggtcat agctgtttcc 5160
tgttttcccc gtatcccccc aggtgtctgc aggctcaaag agcagcgaga agcgttcaga 5220
ggaaagcgat cccgtgccac cttccccgtg cccgggctgt ccccgcacgc tgccggctcg 5280
gggatgcggg gggagcgccg gaccggagcg gagccccggg cggctcgctg ctgcccccta 5340
gcgggggagg gacgtaatta catccctggg ggctttgggg gggggctgtc cctctcaccg 5400
cggtggagct ccagcttttg ttcgaattgg ggcccccccct cgagggtatc gatgatatct 5460
ataacaagaa aatatatata taataagtta tcacgtaagt agaacatgaa ataacaatat 5520
aattatcgta tgagttaaat cttaaaagtc acgtaaaaga taatcatgcg tcattttgac 5580
tcacgcggtc gttatagttc aaaatcagtg acacttaccg cattgacaag cacgcctcac 5640

```
gggagctcca agcggcgact gagatgtcct aaatgcacag cgacggattc gcgctattta   5700

gaaagagaga gcaatatttc aagaatgcat gcgtcaattt tacgcagact atctttctag   5760

ggttaatcta gctagcctta agggcgcagc ccgcctaatg agcgggcttt tttttggctt   5820

gttgtccaca accgttaaac cttaaaagct ttaaaagcct tatatattct ttttttttctt   5880

ataaaactta aaaccttaga ggctatttaa gttgctgatt tatattaatt ttattgttca   5940

aacatgagag cttagtacgt gaaacatgag agcttagtac gttagccatg agagcttagt   6000

acgttagcca tgagggttta gttcgttaaa catgagagct tagtacgtta aacatgagag   6060

cttagtacgt actatcaaca ggttgaactg ctgatccacg ttgtggtaga attggtaaag   6120

agagtcgtgt aaaatatcga gttcgcacat cttgttgtct gattattgat ttttggcgaa   6180

accatttgat catatgacaa gatgtgtatc taccttaact taatgatttt gataaaaatc   6240

attaggta                                                            6248
```

<210> SEQ ID NO 22
<211> LENGTH: 1086
<212> TYPE: DNA
<213> ORGANISM: Artificial Sequence
<220> FEATURE:
<223> OTHER INFORMATION: BCMA VCAR

<400> SEQUENCE: 22

```
atggctctgc ctgtgacagc tctgcttctg cctctggcac tgcttcttca tgcggcgcgc     60

cctgaagttc agctgcttga atctggcgga ggcctggttc aacctggcgg atctctgaga    120

ctgagctgtg ccgccagcgg cttcaccttc agcaattacg ccatgacctg gatcagacag    180

gcccctggca aaggcctgga atgggtgtcc ggaattacag gcgacggcgg cagcaccttt    240

tacgccgatt ctgtgaaggg cagattcacc atcagccggg acaacagcaa gaacaccctg    300

tacctgcaga tgaacagcct gagagccgag gacaccgccg tgtactactg cgtgaaggac    360

tggaacacca ccatgatcac cgagagaggc cagggcacac tggtcaccgt gtcctctaca    420

acaacaccgg cgcctagacc tccaacacca gctcctacaa tcgcgagtca gcccctgtct    480

ctcagacccg aagcctgcag gccagctgca ggaggagctg tgcacaccag gggcctggac    540

ttcgcctgcg acatctacat ttgggcacca ctggccggga cctgtggagt gctgctgctg    600

agcctggtca tcacactgta ctgcaagaga ggcaggaaga aactgctgta tattttcaaa    660

cagcccttca tgcgccccgt gcagactacc caggaggaag acgggtgctc ctgtcgattc    720

cctgaggaag aggaaggcgg gtgtgagctg cgcgtgaagt ttagtcgatc agcagatgcc    780

ccagcttaca aacagggaca gaaccagctg tataacgagc tgaatctggg ccgccgagag    840

gaatatgacg tgctggataa gcggagagga cgcgaccccg aaatgggagg caagcccagg    900

cgcaaaaacc ctcaggaagg cctgtataac gagctgcaga aggacaaaat ggcagaagcc    960

tattctgaga tcggcatgaa gggggagcga cggagaggca aagggcacga tgggctgtac   1020

cagggactga gcaccgccac aaaggacacc tatgatgctc tgcatatgca ggcactgcct   1080

ccaagg                                                              1086
```

<210> SEQ ID NO 23
<211> LENGTH: 570
<212> TYPE: PRT
<213> ORGANISM: Artificial Sequence
<220> FEATURE:
<223> OTHER INFORMATION: P-BCMA-ALLO1 amino acid sequence

<400> SEQUENCE: 23

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Asn Tyr Ala Met Thr Trp Ile Arg Gln Ala Pro Gly Lys
    50                  55                  60

Gly Leu Glu Trp Val Ser Gly Ile Thr Gly Asp Gly Gly Ser Thr Phe
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Asp Trp Asn Thr Thr Met Ile Thr Glu
        115                 120                 125

Arg Gly Gln Gly Thr Leu Val Thr Val Ser Ser Thr Thr Thr Pro Ala
    130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
                165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
        195                 200                 205

Lys Arg Gly Arg Lys Lys Leu Leu Tyr Ile Phe Lys Gln Pro Phe Met
    210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Lys Gln Gly Gln Asn Gln Leu Tyr Asn
            260                 265                 270

Glu Leu Asn Leu Gly Arg Arg Glu Glu Tyr Asp Val Leu Asp Lys Arg
        275                 280                 285

Arg Gly Arg Asp Pro Glu Met Gly Gly Lys Pro Arg Arg Lys Asn Pro
    290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg Gly Ser Gly Glu Gly Arg
        355                 360                 365

Gly Ser Leu Leu Thr Cys Gly Asp Val Glu Glu Asn Pro Gly Pro Met
    370                 375                 380

Val Gly Ser Leu Asn Cys Ile Val Ala Val Ser Gln Asn Met Gly Ile
385                 390                 395                 400

Gly Lys Asn Gly Asp Phe Pro Trp Pro Pro Leu Arg Asn Glu Ser Arg
                405                 410                 415
```

```
Tyr Phe Gln Arg Met Thr Thr Thr Ser Ser Val Glu Gly Lys Gln Asn
            420                 425                 430

Leu Val Ile Met Gly Lys Lys Thr Trp Phe Ser Ile Pro Glu Lys Asn
        435                 440                 445

Arg Pro Leu Lys Gly Arg Ile Asn Leu Val Leu Ser Arg Glu Leu Lys
    450                 455                 460

Glu Pro Pro Gln Gly Ala His Phe Leu Ser Arg Ser Leu Asp Asp Ala
465                 470                 475                 480

Leu Lys Leu Thr Glu Gln Pro Glu Leu Ala Asn Lys Val Asp Met Val
                485                 490                 495

Trp Ile Val Gly Gly Ser Ser Val Tyr Lys Glu Ala Met Asn His Pro
            500                 505                 510

Gly His Leu Lys Leu Phe Val Thr Arg Ile Met Gln Asp Phe Glu Ser
        515                 520                 525

Asp Thr Phe Phe Pro Glu Ile Asp Leu Glu Lys Tyr Lys Leu Leu Pro
    530                 535                 540

Glu Tyr Pro Gly Val Leu Ser Asp Val Gln Glu Glu Lys Gly Ile Lys
545                 550                 555                 560

Tyr Lys Phe Glu Val Tyr Glu Lys Asn Asp
                565                 570
```

<210> SEQ ID NO 24
<211> LENGTH: 35
<212> TYPE: DNA
<213> ORGANISM: Artificial Sequence
<220> FEATURE:
<223> OTHER INFORMATION: ITR

<400> SEQUENCE: 24
ccctagaaag atagtctgcg taaaattgac gcatg 35

<210> SEQ ID NO 25
<211> LENGTH: 63
<212> TYPE: DNA
<213> ORGANISM: Artificial Sequence
<220> FEATURE:
<223> OTHER INFORMATION: ITR

<400> SEQUENCE: 25
ccctagaaag ataatcatat tgtgacgtac gttaaagata atcatgcgta aaattgacgc 60
atg 63

<210> SEQ ID NO 26
<211> LENGTH: 63
<212> TYPE: DNA
<213> ORGANISM: Artificial Sequence
<220> FEATURE:
<223> OTHER INFORMATION: ITR

<400> SEQUENCE: 26
ccctagaaag ataatcatat tgtgacgtac gttaaagata atcatgcgta aaattgacgc 60
atg 63

<210> SEQ ID NO 27
<211> LENGTH: 241
<212> TYPE: DNA
<213> ORGANISM: Artificial Sequence
<220> FEATURE:
<223> OTHER INFORMATION: ITR

<400> SEQUENCE: 27

```
ttaaccctag aaagataatc atattgtgac gtacgttaaa gataatcatg tgtaaaattg      60

acgcatgtgt tttatcggtc tgtatatcga ggtttattta ttaatttgaa tagatattaa     120

gttttattat atttacactt acatactaat aataaattca acaaacaatt tatttatgtt     180

tatttattta ttaaaaaaaa caaaaactca aaatttcttc tataaagtaa caaaactttt     240

a                                                                     241


<210> SEQ ID NO 28
<211> LENGTH: 270
<212> TYPE: PRT
<213> ORGANISM: Artificial Sequence
<220> FEATURE:
<223> OTHER INFORMATION: BCMA centyrin

<400> SEQUENCE: 28

Ala Thr Gly Cys Thr Gly Cys Cys Thr Gly Cys Ala Cys Cys Ala Ala
1               5                   10                  15

Ala Gly Ala Ala Cys Cys Thr Gly Gly Thr Gly Gly Thr Gly Ala Gly
            20                  25                  30

Cys Cys Gly Gly Ala Thr Cys Ala Cys Ala Gly Ala Gly Gly Ala Cys
        35                  40                  45

Thr Cys Cys Gly Cys Cys Ala Gly Ala Cys Thr Gly Thr Cys Thr Thr
    50                  55                  60

Gly Gly Ala Cys Cys Gly Cys Cys Cys Cys Thr Gly Ala Cys Gly Cys
65                  70                  75                  80

Cys Gly Cys Cys Thr Thr Cys Gly Ala Thr Thr Cys Cys Thr Thr Thr
                85                  90                  95

Cys Cys Ala Ala Thr Cys Cys Gly Gly Thr Ala Cys Ala Thr Cys Gly
            100                 105                 110

Ala Gly Ala Cys Ala Cys Thr Gly Ala Thr Cys Thr Gly Gly Gly Gly
        115                 120                 125

Cys Gly Ala Gly Gly Cys Cys Ala Thr Cys Thr Gly Gly Cys Thr Gly
    130                 135                 140

Gly Ala Cys Gly Thr Gly Cys Cys Cys Gly Gly Cys Thr Cys Thr Gly
145                 150                 155                 160

Ala Gly Ala Gly Gly Ala Gly Cys Thr Ala Cys Gly Ala Thr Cys Thr
                165                 170                 175

Gly Ala Cys Ala Gly Gly Cys Cys Thr Gly Ala Ala Gly Cys Cys Thr
            180                 185                 190

Gly Gly Cys Ala Cys Cys Gly Ala Gly Thr Ala Thr Gly Cys Ala Gly
        195                 200                 205

Thr Gly Gly Thr Cys Ala Thr Cys Ala Cys Ala Gly Gly Ala Gly Thr
    210                 215                 220

Gly Ala Ala Gly Gly Gly Cys Gly Gly Cys Ala Gly Gly Thr Thr Cys
225                 230                 235                 240

Ala Gly Cys Thr Cys Cys Cys Cys Thr Cys Thr Gly Gly Thr Gly Gly
                245                 250                 255

Cys Cys Thr Cys Thr Thr Thr Thr Ala Cys Cys Ala Cys Ala
            260                 265                 270


<210> SEQ ID NO 29
<211> LENGTH: 90
<212> TYPE: PRT
<213> ORGANISM: Artificial Sequence
<220> FEATURE:
<223> OTHER INFORMATION: BCMA centyrin
```

<400> SEQUENCE: 29

```
Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Pro Ile Arg Tyr Ile Glu Thr Leu Ile Trp Gly Glu Ala Ile Trp Leu
        35                  40                  45

Asp Val Pro Gly Ser Glu Arg Ser Tyr Asp Leu Thr Gly Leu Lys Pro
    50                  55                  60

Gly Thr Glu Tyr Ala Val Val Ile Thr Gly Val Lys Gly Gly Arg Phe
65                  70                  75                  80

Ser Ser Pro Leu Val Ala Ser Phe Thr Thr
                85                  90
```

<210> SEQ ID NO 30
<211> LENGTH: 334
<212> TYPE: PRT
<213> ORGANISM: Artificial Sequence
<220> FEATURE:
<223> OTHER INFORMATION: BCMA CARTyrin

<400> SEQUENCE: 30

```
Met Ala Leu Pro Val Thr Ala Leu Leu Leu Pro Leu Ala Leu Leu Leu
1               5                   10                  15

His Ala Ala Arg Pro Met Leu Pro Ala Pro Lys Asn Leu Val Val Ser
            20                  25                  30

Arg Ile Thr Glu Asp Ser Ala Arg Leu Ser Trp Thr Ala Pro Asp Ala
        35                  40                  45

Ala Phe Asp Ser Phe Pro Ile Arg Tyr Ile Glu Thr Leu Ile Trp Gly
    50                  55                  60

Glu Ala Ile Trp Leu Asp Val Pro Gly Ser Glu Arg Ser Tyr Asp Leu
65                  70                  75                  80

Thr Gly Leu Lys Pro Gly Thr Glu Tyr Ala Val Val Ile Thr Gly Val
                85                  90                  95

Lys Gly Gly Arg Phe Ser Ser Pro Leu Val Ala Ser Phe Thr Thr Thr
            100                 105                 110

Thr Thr Pro Ala Pro Arg Pro Pro Thr Pro Ala Pro Thr Ile Ala Ser
        115                 120                 125

Gln Pro Leu Ser Leu Arg Pro Glu Ala Cys Arg Pro Ala Ala Gly Gly
    130                 135                 140

Ala Val His Thr Arg Gly Leu Asp Phe Ala Cys Asp Ile Tyr Ile Trp
145                 150                 155                 160

Ala Pro Leu Ala Gly Thr Cys Gly Val Leu Leu Leu Ser Leu Val Ile
                165                 170                 175

Thr Leu Tyr Cys Lys Arg Gly Arg Lys Lys Leu Leu Tyr Ile Phe Lys
            180                 185                 190

Gln Pro Phe Met Arg Pro Val Gln Thr Thr Gln Glu Glu Asp Gly Cys
        195                 200                 205

Ser Cys Arg Phe Pro Glu Glu Glu Glu Gly Gly Cys Glu Leu Arg Val
    210                 215                 220

Lys Phe Ser Arg Ser Ala Asp Ala Pro Ala Tyr Lys Gln Gly Gln Asn
225                 230                 235                 240

Gln Leu Tyr Asn Glu Leu Asn Leu Gly Arg Arg Glu Glu Tyr Asp Val
                245                 250                 255
```

```
Leu Asp Lys Arg Arg Gly Arg Asp Pro Glu Met Gly Gly Lys Pro Arg
            260                 265                 270

Arg Lys Asn Pro Gln Glu Gly Leu Tyr Asn Glu Leu Gln Lys Asp Lys
        275                 280                 285

Met Ala Glu Ala Tyr Ser Glu Ile Gly Met Lys Gly Glu Arg Arg Arg
    290                 295                 300

Gly Lys Gly His Asp Gly Leu Tyr Gln Gly Leu Ser Thr Ala Thr Lys
305                 310                 315                 320

Asp Thr Tyr Asp Ala Leu His Met Gln Ala Leu Pro Pro Arg
                325                 330


<210> SEQ ID NO 31
<211> LENGTH: 21
<212> TYPE: PRT
<213> ORGANISM: Artificial Sequence
<220> FEATURE:
<223> OTHER INFORMATION: CD8 signal peptide

<400> SEQUENCE: 31

Met Ala Leu Pro Val Thr Ala Leu Leu Leu Pro Leu Ala Leu Leu Leu
1               5                   10                  15

His Ala Ala Arg Pro
            20


<210> SEQ ID NO 32
<211> LENGTH: 63
<212> TYPE: DNA
<213> ORGANISM: Artificial Sequence
<220> FEATURE:
<223> OTHER INFORMATION: CD8 Signal Peptide

<400> SEQUENCE: 32

atggctctgc ctgtgacagc tctgcttctg cctctggcac tgcttcttca tgcggcgcgc     60

cct                                                                   63


<210> SEQ ID NO 33
<211> LENGTH: 15
<212> TYPE: PRT
<213> ORGANISM: Artificial Sequence
<220> FEATURE:
<223> OTHER INFORMATION: linker

<400> SEQUENCE: 33

Gly Gly Gly Gly Ser Gly Gly Gly Gly Ser Gly Gly Gly Gly Ser
1               5                   10                  15


<210> SEQ ID NO 34
<211> LENGTH: 45
<212> TYPE: DNA
<213> ORGANISM: Artificial Sequence
<220> FEATURE:
<223> OTHER INFORMATION: linker

<400> SEQUENCE: 34

ggcggaggcg gtagcggtgg cggaggtagc ggaggtggtg gatct                     45


<210> SEQ ID NO 35
<211> LENGTH: 45
<212> TYPE: PRT
<213> ORGANISM: Artificial Sequence
<220> FEATURE:
<223> OTHER INFORMATION: CD8a Hinge

<400> SEQUENCE: 35
```

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 36
<211> LENGTH: 135
<212> TYPE: DNA
<213> ORGANISM: Artificial Sequence
<220> FEATURE:
<223> OTHER INFORMATION: CD8a Hinge

<400> SEQUENCE: 36
accacaacac cggcgcctag acctccaaca ccagctccta caatcgcgag tcagcccctg 60
tctctcagac ccgaagcctg caggccagct gcaggaggag ctgtgcacac caggggcctg 120
gacttcgcct gcgac 135

<210> SEQ ID NO 37
<211> LENGTH: 24
<212> TYPE: PRT
<213> ORGANISM: Artificial Sequence
<220> FEATURE:
<223> OTHER INFORMATION: CD8a TM

<400> SEQUENCE: 37

Ile Tyr Ile Trp Ala Pro Leu Ala Gly Thr Cys Gly Val Leu Leu Leu
1 5 10 15

Ser Leu Val Ile Thr Leu Tyr Cys
20

<210> SEQ ID NO 38
<211> LENGTH: 72
<212> TYPE: DNA
<213> ORGANISM: Artificial Sequence
<220> FEATURE:
<223> OTHER INFORMATION: CD8a TM

<400> SEQUENCE: 38
atctacattt gggcaccact ggccgggacc tgtggagtgc tgctgctgag cctggtcatc 60
acactgtact gc 72

<210> SEQ ID NO 39
<211> LENGTH: 42
<212> TYPE: PRT
<213> ORGANISM: Artificial Sequence
<220> FEATURE:
<223> OTHER INFORMATION: 41BB ICS

<400> SEQUENCE: 39

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 40
<211> LENGTH: 126
<212> TYPE: DNA

<213> ORGANISM: Artificial Sequence
<220> FEATURE:
<223> OTHER INFORMATION: 41BB ICS

<400> SEQUENCE: 40
aagagaggca ggaagaaact gctgtatatt ttcaaacagc ccttcatgcg ccccgtgcag 60
actacccagg aggaagacgg gtgctcctgt cgattccctg aggaagagga aggcgggtgt 120
gagctg 126

<210> SEQ ID NO 41
<211> LENGTH: 112
<212> TYPE: PRT
<213> ORGANISM: Artificial Sequence
<220> FEATURE:
<223> OTHER INFORMATION: CD3z ICS

<400> SEQUENCE: 41

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 42
<211> LENGTH: 336
<212> TYPE: DNA
<213> ORGANISM: Artificial Sequence
<220> FEATURE:
<223> OTHER INFORMATION: 41BB ICS

<400> SEQUENCE: 42
cgcgtgaagt ttagtcgatc agcagatgcc ccagcttaca aacagggaca gaaccagctg 60
tataacgagc tgaatctggg ccgccgagag gaatatgacg tgctggataa gcggagagga 120
cgcgaccccg aaatgggagg caagcccagg cgcaaaaacc ctcaggaagg cctgtataac 180
gagctgcaga aggacaaaat ggcagaagcc tattctgaga tcggcatgaa gggggagcga 240
cggagaggca aagggcacga tggcctgtac cagggactga gcaccgccac aaaggacacc 300
tatgatgctc tgcatatgca ggcactgcct ccaagg 336

<210> SEQ ID NO 43
<211> LENGTH: 1053
<212> TYPE: PRT
<213> ORGANISM: Artificial Sequence
<220> FEATURE:
<223> OTHER INFORMATION: SCas9 - 40-18163

<400> SEQUENCE: 43

Met Lys Arg Asn Tyr Ile Leu Gly Leu Asp Ile Gly Ile Thr Ser Val
1 5 10 15

Gly Tyr Gly Ile Ile Asp Tyr Glu Thr Arg Asp Val Ile Asp Ala Gly

```
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
    50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
    130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445
```

```
Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
            485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Asn Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860
```

Leu Thr Lys Tyr Ser Lys Lys Asp Asn Gly Pro Val Ile Lys Lys Ile
865 870 875 880

Lys Tyr Tyr Gly Asn Lys Leu Asn Ala His Leu Asp Ile Thr Asp Asp
885 890 895

Tyr Pro Asn Ser Arg Asn Lys Val Val Lys Leu Ser Leu Lys Pro Tyr
900 905 910

Arg Phe Asp Val Tyr Leu Asp Asn Gly Val Tyr Lys Phe Val Thr Val
915 920 925

Lys Asn Leu Asp Val Ile Lys Lys Glu Asn Tyr Tyr Glu Val Asn Ser
930 935 940

Lys Cys Tyr Glu Glu Ala Lys Lys Leu Lys Lys Ile Ser Asn Gln Ala
945 950 955 960

Glu Phe Ile Ala Ser Phe Tyr Asn Asn Asp Leu Ile Lys Ile Asn Gly
965 970 975

Glu Leu Tyr Arg Val Ile Gly Val Asn Asn Asp Leu Leu Asn Arg Ile
980 985 990

Glu Val Asn Met Ile Asp Ile Thr Tyr Arg Glu Tyr Leu Glu Asn Met
995 1000 1005

Asn Asp Lys Arg Pro Pro Arg Ile Ile Lys Thr Ile Ala Ser Lys
1010 1015 1020

Thr Gln Ser Ile Lys Lys Tyr Ser Thr Asp Ile Leu Gly Asn Leu
1025 1030 1035

Tyr Glu Val Lys Ser Lys Lys His Pro Gln Ile Ile Lys Lys Gly
1040 1045 1050

<210> SEQ ID NO 44
<211> LENGTH: 1053
<212> TYPE: PRT
<213> ORGANISM: Artificial Sequence
<220> FEATURE:
<223> OTHER INFORMATION: dSaCas9 - 40-18164

<400> SEQUENCE: 44

Met Lys Arg Asn Tyr Ile Leu Gly Leu Ala Ile Gly Ile Thr Ser Val
1 5 10 15

Gly Tyr Gly Ile Ile Asp Tyr Glu Thr Arg Asp Val Ile Asp Ala Gly
20 25 30

Val Arg Leu Phe Lys Glu Ala Asn Val Glu Asn Asn Glu Gly Arg Arg
35 40 45

Ser Lys Arg Gly Ala Arg Arg Leu Lys Arg Arg Arg Arg His Arg Ile
50 55 60

Gln Arg Val Lys Lys Leu Leu Phe Asp Tyr Asn Leu Leu Thr Asp His
65 70 75 80

Ser Glu Leu Ser Gly Ile Asn Pro Tyr Glu Ala Arg Val Lys Gly Leu
85 90 95

Ser Gln Lys Leu Ser Glu Glu Glu Phe Ser Ala Ala Leu Leu His Leu
100 105 110

Ala Lys Arg Arg Gly Val His Asn Val Asn Glu Val Glu Glu Asp Thr
115 120 125

Gly Asn Glu Leu Ser Thr Lys Glu Gln Ile Ser Arg Asn Ser Lys Ala
130 135 140

Leu Glu Glu Lys Tyr Val Ala Glu Leu Gln Leu Glu Arg Leu Lys Lys
145 150 155 160

Asp Gly Glu Val Arg Gly Ser Ile Asn Arg Phe Lys Thr Ser Asp Tyr
165 170 175

```
Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
    210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
    290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335

Ala Arg Lys Glu Ile Ile Glu Asn Ala Glu Leu Leu Asp Gln Ile Ala
            340                 345                 350

Lys Ile Leu Thr Ile Tyr Gln Ser Ser Glu Asp Ile Gln Glu Glu Leu
        355                 360                 365

Thr Asn Leu Asn Ser Glu Leu Thr Gln Glu Glu Ile Glu Gln Ile Ser
    370                 375                 380

Asn Leu Lys Gly Tyr Thr Gly Thr His Asn Leu Ser Leu Lys Ala Ile
385                 390                 395                 400

Asn Leu Ile Leu Asp Glu Leu Trp His Thr Asn Asp Asn Gln Ile Ala
                405                 410                 415

Ile Phe Asn Arg Leu Lys Leu Val Pro Lys Lys Val Asp Leu Ser Gln
            420                 425                 430

Gln Lys Glu Ile Pro Thr Thr Leu Val Asp Asp Phe Ile Leu Ser Pro
        435                 440                 445

Val Val Lys Arg Ser Phe Ile Gln Ser Ile Lys Val Ile Asn Ala Ile
    450                 455                 460

Ile Lys Lys Tyr Gly Leu Pro Asn Asp Ile Ile Ile Glu Leu Ala Arg
465                 470                 475                 480

Glu Lys Asn Ser Lys Asp Ala Gln Lys Met Ile Asn Glu Met Gln Lys
                485                 490                 495

Arg Asn Arg Gln Thr Asn Glu Arg Ile Glu Glu Ile Ile Arg Thr Thr
            500                 505                 510

Gly Lys Glu Asn Ala Lys Tyr Leu Ile Glu Lys Ile Lys Leu His Asp
        515                 520                 525

Met Gln Glu Gly Lys Cys Leu Tyr Ser Leu Glu Ala Ile Pro Leu Glu
    530                 535                 540

Asp Leu Leu Asn Asn Pro Phe Asn Tyr Glu Val Asp His Ile Ile Pro
545                 550                 555                 560

Arg Ser Val Ser Phe Asp Asn Ser Phe Asn Asn Lys Val Leu Val Lys
                565                 570                 575

Gln Glu Glu Ala Ser Lys Lys Gly Asn Arg Thr Pro Phe Gln Tyr Leu
            580                 585                 590

Ser Ser Ser Asp Ser Lys Ile Ser Tyr Glu Thr Phe Lys Lys His Ile
```

```
        595                 600                 605

Leu Asn Leu Ala Lys Gly Lys Gly Arg Ile Ser Lys Thr Lys Lys Glu
    610                 615                 620

Tyr Leu Leu Glu Glu Arg Asp Ile Asn Arg Phe Ser Val Gln Lys Asp
625                 630                 635                 640

Phe Ile Asn Arg Asn Leu Val Asp Thr Arg Tyr Ala Thr Arg Gly Leu
                645                 650                 655

Met Asn Leu Leu Arg Ser Tyr Phe Arg Val Asn Asn Leu Asp Val Lys
            660                 665                 670

Val Lys Ser Ile Asn Gly Gly Phe Thr Ser Phe Leu Arg Arg Lys Trp
        675                 680                 685

Lys Phe Lys Lys Glu Arg Asn Lys Gly Tyr Lys His His Ala Glu Asp
    690                 695                 700

Ala Leu Ile Ile Ala Asn Ala Asp Phe Ile Phe Lys Glu Trp Lys Lys
705                 710                 715                 720

Leu Asp Lys Ala Lys Lys Val Met Glu Asn Gln Met Phe Glu Glu Lys
                725                 730                 735

Gln Ala Glu Ser Met Pro Glu Ile Glu Thr Glu Gln Glu Tyr Lys Glu
            740                 745                 750

Ile Phe Ile Thr Pro His Gln Ile Lys His Ile Lys Asp Phe Lys Asp
        755                 760                 765

Tyr Lys Tyr Ser His Arg Val Asp Lys Lys Pro Asn Arg Glu Leu Ile
    770                 775                 780

Asn Asp Thr Leu Tyr Ser Thr Arg Lys Asp Asp Lys Gly Asn Thr Leu
785                 790                 795                 800

Ile Val Asn Asn Leu Asn Gly Leu Tyr Asp Lys Asp Asn Asp Lys Leu
                805                 810                 815

Lys Lys Leu Ile Asn Lys Ser Pro Glu Lys Leu Leu Met Tyr His His
            820                 825                 830

Asp Pro Gln Thr Tyr Gln Lys Leu Lys Leu Ile Met Glu Gln Tyr Gly
        835                 840                 845

Asp Glu Lys Asn Pro Leu Tyr Lys Tyr Tyr Glu Glu Thr Gly Asn Tyr
    850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
        915                 920                 925

Lys Asn Leu Asp Val Ile Lys Lys Glu Asn Tyr Tyr Glu Val Asn Ser
    930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asn Asp Leu Leu Asn Arg Ile
            980                 985                 990

Glu Val Asn Met Ile Asp Ile Thr  Tyr Arg Glu Tyr Leu  Glu Asn Met
        995                 1000                1005

Asn Asp  Lys Arg Pro Pro Arg  Ile Ile Lys Thr Ile  Ala Ser Lys
    1010                1015                1020
```

```
Thr Gln  Ser Ile Lys Lys Tyr  Ser Thr Asp Ile Leu  Gly Asn Leu
    1025                1030                1035

Tyr Glu  Val Lys Ser Lys Lys  His Pro Gln Ile Ile  Lys Lys Gly
    1040                1045                1050


<210> SEQ ID NO 45
<211> LENGTH: 1368
<212> TYPE: PRT
<213> ORGANISM: Artificial Sequence
<220> FEATURE:
<223> OTHER INFORMATION: dCas9 - 40-18165
<220> FEATURE:
<221> NAME/KEY: misc_feature
<222> LOCATION: (1)..(1)
<223> OTHER INFORMATION: Xaa can be any naturally occurring amino acid

<400> SEQUENCE: 45

Xaa Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
```

```
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735
```

```
Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140
```

```
Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365


<210> SEQ ID NO 46
<211> LENGTH: 1368
<212> TYPE: PRT
<213> ORGANISM: Artificial Sequence
<220> FEATURE:
<223> OTHER INFORMATION: dCas9 - 40-18166

<400> SEQUENCE: 46

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125
```

-continued

```
His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
```

```
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975
```

```
Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                 1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 47
<211> LENGTH: 199
<212> TYPE: PRT
<213> ORGANISM: Artificial Sequence
<220> FEATURE:
<223> OTHER INFORMATION: Clo051 - 40-18030

<400> SEQUENCE: 47

Glu Gly Ile Lys Ser Asn Ile Ser Leu Leu Lys Asp Glu Leu Arg Gly
1 5 10 15

Gln Ile Ser His Ile Ser His Glu Tyr Leu Ser Leu Ile Asp Leu Ala
20 25 30

Phe Asp Ser Lys Gln Asn Arg Leu Phe Glu Met Lys Val Leu Glu Leu
35 40 45

Leu Val Asn Glu Tyr Gly Phe Lys Gly Arg His Leu Gly Gly Ser Arg
50 55 60

Lys Pro Asp Gly Ile Val Tyr Ser Thr Thr Leu Glu Asp Asn Phe Gly
65 70 75 80

Ile Ile Val Asp Thr Lys Ala Tyr Ser Glu Gly Tyr Ser Leu Pro Ile
85 90 95

Ser Gln Ala Asp Glu Met Glu Arg Tyr Val Arg Glu Asn Ser Asn Arg
100 105 110

Asp Glu Glu Val Asn Pro Asn Lys Trp Trp Glu Asn Phe Ser Glu Glu
115 120 125

Val Lys Lys Tyr Tyr Phe Val Phe Ile Ser Gly Ser Phe Lys Gly Lys
130 135 140

Phe Glu Glu Gln Leu Arg Arg Leu Ser Met Thr Thr Gly Val Asn Gly
145 150 155 160

Ser Ala Val Asn Val Val Asn Leu Leu Leu Gly Ala Glu Lys Ile Arg
165 170 175

Ser Gly Glu Met Thr Ile Glu Glu Leu Glu Arg Ala Met Phe Asn Asn
180 185 190

Ser Glu Phe Ile Leu Lys Tyr
195

<210> SEQ ID NO 48
<211> LENGTH: 1591
<212> TYPE: PRT
<213> ORGANISM: Artificial Sequence
<220> FEATURE:
<223> OTHER INFORMATION: dCas9-Clo051 - 40-18168

<400> SEQUENCE: 48

Met Ala Pro Lys Lys Lys Arg Lys Val Glu Gly Ile Lys Ser Asn Ile
1 5 10 15

Ser Leu Leu Lys Asp Glu Leu Arg Gly Gln Ile Ser His Ile Ser His
20 25 30

Glu Tyr Leu Ser Leu Ile Asp Leu Ala Phe Asp Ser Lys Gln Asn Arg
35 40 45

Leu Phe Glu Met Lys Val Leu Glu Leu Leu Val Asn Glu Tyr Gly Phe
50 55 60

Lys Gly Arg His Leu Gly Gly Ser Arg Lys Pro Asp Gly Ile Val Tyr
65 70 75 80

Ser Thr Thr Leu Glu Asp Asn Phe Gly Ile Ile Val Asp Thr Lys Ala
85 90 95

Tyr Ser Glu Gly Tyr Ser Leu Pro Ile Ser Gln Ala Asp Glu Met Glu
100 105 110

```
Arg Tyr Val Arg Glu Asn Ser Asn Arg Asp Glu Glu Val Asn Pro Asn
        115                 120                 125

Lys Trp Trp Glu Asn Phe Ser Glu Glu Val Lys Lys Tyr Tyr Phe Val
    130                 135                 140

Phe Ile Ser Gly Ser Phe Lys Gly Lys Phe Glu Glu Gln Leu Arg Arg
145                 150                 155                 160

Leu Ser Met Thr Thr Gly Val Asn Gly Ser Ala Val Asn Val Val Asn
                165                 170                 175

Leu Leu Leu Gly Ala Glu Lys Ile Arg Ser Gly Glu Met Thr Ile Glu
            180                 185                 190

Glu Leu Glu Arg Ala Met Phe Asn Asn Ser Glu Phe Ile Leu Lys Tyr
        195                 200                 205

Gly Gly Gly Gly Ser Asp Lys Lys Tyr Ser Ile Gly Leu Ala Ile Gly
    210                 215                 220

Thr Asn Ser Val Gly Trp Ala Val Ile Thr Asp Glu Tyr Lys Val Pro
225                 230                 235                 240

Ser Lys Lys Phe Lys Val Leu Gly Asn Thr Asp Arg His Ser Ile Lys
                245                 250                 255

Lys Asn Leu Ile Gly Ala Leu Leu Phe Asp Ser Gly Glu Thr Ala Glu
            260                 265                 270

Ala Thr Arg Leu Lys Arg Thr Ala Arg Arg Arg Tyr Thr Arg Arg Lys
        275                 280                 285

Asn Arg Ile Cys Tyr Leu Gln Glu Ile Phe Ser Asn Glu Met Ala Lys
    290                 295                 300

Val Asp Asp Ser Phe Phe His Arg Leu Glu Glu Ser Phe Leu Val Glu
305                 310                 315                 320

Glu Asp Lys Lys His Glu Arg His Pro Ile Phe Gly Asn Ile Val Asp
                325                 330                 335

Glu Val Ala Tyr His Glu Lys Tyr Pro Thr Ile Tyr His Leu Arg Lys
            340                 345                 350

Lys Leu Val Asp Ser Thr Asp Lys Ala Asp Leu Arg Leu Ile Tyr Leu
        355                 360                 365

Ala Leu Ala His Met Ile Lys Phe Arg Gly His Phe Leu Ile Glu Gly
    370                 375                 380

Asp Leu Asn Pro Asp Asn Ser Asp Val Asp Lys Leu Phe Ile Gln Leu
385                 390                 395                 400

Val Gln Thr Tyr Asn Gln Leu Phe Glu Glu Asn Pro Ile Asn Ala Ser
                405                 410                 415

Gly Val Asp Ala Lys Ala Ile Leu Ser Ala Arg Leu Ser Lys Ser Arg
            420                 425                 430

Arg Leu Glu Asn Leu Ile Ala Gln Leu Pro Gly Glu Lys Lys Asn Gly
        435                 440                 445

Leu Phe Gly Asn Leu Ile Ala Leu Ser Leu Gly Leu Thr Pro Asn Phe
    450                 455                 460

Lys Ser Asn Phe Asp Leu Ala Glu Asp Ala Lys Leu Gln Leu Ser Lys
465                 470                 475                 480

Asp Thr Tyr Asp Asp Asp Leu Asp Asn Leu Leu Ala Gln Ile Gly Asp
                485                 490                 495

Gln Tyr Ala Asp Leu Phe Leu Ala Ala Lys Asn Leu Ser Asp Ala Ile
            500                 505                 510

Leu Leu Ser Asp Ile Leu Arg Val Asn Thr Glu Ile Thr Lys Ala Pro
        515                 520                 525
```

```
Leu Ser Ala Ser Met Ile Lys Arg Tyr Asp Glu His His Gln Asp Leu
    530                 535                 540

Thr Leu Leu Lys Ala Leu Val Arg Gln Gln Leu Pro Glu Lys Tyr Lys
545                 550                 555                 560

Glu Ile Phe Phe Asp Gln Ser Lys Asn Gly Tyr Ala Gly Tyr Ile Asp
                565                 570                 575

Gly Gly Ala Ser Gln Glu Glu Phe Tyr Lys Phe Ile Lys Pro Ile Leu
            580                 585                 590

Glu Lys Met Asp Gly Thr Glu Glu Leu Leu Val Lys Leu Asn Arg Glu
        595                 600                 605

Asp Leu Leu Arg Lys Gln Arg Thr Phe Asp Asn Gly Ser Ile Pro His
    610                 615                 620

Gln Ile His Leu Gly Glu Leu His Ala Ile Leu Arg Arg Gln Glu Asp
625                 630                 635                 640

Phe Tyr Pro Phe Leu Lys Asp Asn Arg Glu Lys Ile Glu Lys Ile Leu
                645                 650                 655

Thr Phe Arg Ile Pro Tyr Tyr Val Gly Pro Leu Ala Arg Gly Asn Ser
            660                 665                 670

Arg Phe Ala Trp Met Thr Arg Lys Ser Glu Glu Thr Ile Thr Pro Trp
        675                 680                 685

Asn Phe Glu Glu Val Val Asp Lys Gly Ala Ser Ala Gln Ser Phe Ile
    690                 695                 700

Glu Arg Met Thr Asn Phe Asp Lys Asn Leu Pro Asn Glu Lys Val Leu
705                 710                 715                 720

Pro Lys His Ser Leu Leu Tyr Glu Tyr Phe Thr Val Tyr Asn Glu Leu
                725                 730                 735

Thr Lys Val Lys Tyr Val Thr Glu Gly Met Arg Lys Pro Ala Phe Leu
            740                 745                 750

Ser Gly Glu Gln Lys Lys Ala Ile Val Asp Leu Leu Phe Lys Thr Asn
        755                 760                 765

Arg Lys Val Thr Val Lys Gln Leu Lys Glu Asp Tyr Phe Lys Lys Ile
    770                 775                 780

Glu Cys Phe Asp Ser Val Glu Ile Ser Gly Val Glu Asp Arg Phe Asn
785                 790                 795                 800

Ala Ser Leu Gly Thr Tyr His Asp Leu Leu Lys Ile Ile Lys Asp Lys
                805                 810                 815

Asp Phe Leu Asp Asn Glu Glu Asn Glu Asp Ile Leu Glu Asp Ile Val
            820                 825                 830

Leu Thr Leu Thr Leu Phe Glu Asp Arg Glu Met Ile Glu Glu Arg Leu
        835                 840                 845

Lys Thr Tyr Ala His Leu Phe Asp Asp Lys Val Met Lys Gln Leu Lys
    850                 855                 860

Arg Arg Arg Tyr Thr Gly Trp Gly Arg Leu Ser Arg Lys Leu Ile Asn
865                 870                 875                 880

Gly Ile Arg Asp Lys Gln Ser Gly Lys Thr Ile Leu Asp Phe Leu Lys
                885                 890                 895

Ser Asp Gly Phe Ala Asn Arg Asn Phe Met Gln Leu Ile His Asp Asp
            900                 905                 910

Ser Leu Thr Phe Lys Glu Asp Ile Gln Lys Ala Gln Val Ser Gly Gln
        915                 920                 925

Gly Asp Ser Leu His Glu His Ile Ala Asn Leu Ala Gly Ser Pro Ala
    930                 935                 940

Ile Lys Lys Gly Ile Leu Gln Thr Val Lys Val Val Asp Glu Leu Val
```

```
945                 950                 955                 960

Lys Val Met Gly Arg His Lys Pro Glu Asn Ile Val Ile Glu Met Ala
                965                 970                 975

Arg Glu Asn Gln Thr Thr Gln Lys Gly Gln Lys Asn Ser Arg Glu Arg
            980                 985                 990

Met Lys Arg Ile Glu Glu Gly Ile  Lys Glu Leu Gly Ser  Gln Ile Leu
        995                 1000                1005

Lys Glu  His Pro Val Glu Asn  Thr Gln Leu Gln Asn  Glu Lys Leu
    1010                1015                1020

Tyr Leu  Tyr Tyr Leu Gln Asn  Gly Arg Asp Met Tyr  Val Asp Gln
    1025                1030                1035

Glu Leu  Asp Ile Asn Arg Leu  Ser Asp Tyr Asp Val  Asp Ala Ile
    1040                1045                1050

Val Pro  Gln Ser Phe Leu Lys  Asp Asp Ser Ile Asp  Asn Lys Val
    1055                1060                1065

Leu Thr  Arg Ser Asp Lys Asn  Arg Gly Lys Ser Asp  Asn Val Pro
    1070                1075                1080

Ser Glu  Glu Val Val Lys Lys  Met Lys Asn Tyr Trp  Arg Gln Leu
    1085                1090                1095

Leu Asn  Ala Lys Leu Ile Thr  Gln Arg Lys Phe Asp  Asn Leu Thr
    1100                1105                1110

Lys Ala  Glu Arg Gly Gly Leu  Ser Glu Leu Asp Lys  Ala Gly Phe
    1115                1120                1125

Ile Lys  Arg Gln Leu Val Glu  Thr Arg Gln Ile Thr  Lys His Val
    1130                1135                1140

Ala Gln  Ile Leu Asp Ser Arg  Met Asn Thr Lys Tyr  Asp Glu Asn
    1145                1150                1155

Asp Lys  Leu Ile Arg Glu Val  Lys Val Ile Thr Leu  Lys Ser Lys
    1160                1165                1170

Leu Val  Ser Asp Phe Arg Lys  Asp Phe Gln Phe Tyr  Lys Val Arg
    1175                1180                1185

Glu Ile  Asn Asn Tyr His His  Ala His Asp Ala Tyr  Leu Asn Ala
    1190                1195                1200

Val Val  Gly Thr Ala Leu Ile  Lys Lys Tyr Pro Lys  Leu Glu Ser
    1205                1210                1215

Glu Phe  Val Tyr Gly Asp Tyr  Lys Val Tyr Asp Val  Arg Lys Met
    1220                1225                1230

Ile Ala  Lys Ser Glu Gln Glu  Ile Gly Lys Ala Thr  Ala Lys Tyr
    1235                1240                1245

Phe Phe  Tyr Ser Asn Ile Met  Asn Phe Phe Lys Thr  Glu Ile Thr
    1250                1255                1260

Leu Ala  Asn Gly Glu Ile Arg  Lys Arg Pro Leu Ile  Glu Thr Asn
    1265                1270                1275

Gly Glu  Thr Gly Glu Ile Val  Trp Asp Lys Gly Arg  Asp Phe Ala
    1280                1285                1290

Thr Val  Arg Lys Val Leu Ser  Met Pro Gln Val Asn  Ile Val Lys
    1295                1300                1305

Lys Thr  Glu Val Gln Thr Gly  Gly Phe Ser Lys Glu  Ser Ile Leu
    1310                1315                1320

Pro Lys  Arg Asn Ser Asp Lys  Leu Ile Ala Arg Lys  Lys Asp Trp
    1325                1330                1335

Asp Pro  Lys Lys Tyr Gly Gly  Phe Asp Ser Pro Thr  Val Ala Tyr
    1340                1345                1350
```

```
Ser Val  Leu Val Val Ala Lys  Val Glu Lys Gly Lys  Ser Lys Lys
    1355                 1360                 1365

Leu Lys  Ser Val Lys Glu Leu  Leu Gly Ile Thr Ile  Met Glu Arg
    1370                 1375                 1380

Ser Ser  Phe Glu Lys Asn Pro  Ile Asp Phe Leu Glu  Ala Lys Gly
    1385                 1390                 1395

Tyr Lys  Glu Val Lys Lys Asp  Leu Ile Ile Lys Leu  Pro Lys Tyr
    1400                 1405                 1410

Ser Leu  Phe Glu Leu Glu Asn  Gly Arg Lys Arg Met  Leu Ala Ser
    1415                 1420                 1425

Ala Gly  Glu Leu Gln Lys Gly  Asn Glu Leu Ala Leu  Pro Ser Lys
    1430                 1435                 1440

Tyr Val  Asn Phe Leu Tyr Leu  Ala Ser His Tyr Glu  Lys Leu Lys
    1445                 1450                 1455

Gly Ser  Pro Glu Asp Asn Glu  Gln Lys Gln Leu Phe  Val Glu Gln
    1460                 1465                 1470

His Lys  His Tyr Leu Asp Glu  Ile Ile Glu Gln Ile  Ser Glu Phe
    1475                 1480                 1485

Ser Lys  Arg Val Ile Leu Ala  Asp Ala Asn Leu Asp  Lys Val Leu
    1490                 1495                 1500

Ser Ala  Tyr Asn Lys His Arg  Asp Lys Pro Ile Arg  Glu Gln Ala
    1505                 1510                 1515

Glu Asn  Ile Ile His Leu Phe  Thr Leu Thr Asn Leu  Gly Ala Pro
    1520                 1525                 1530

Ala Ala  Phe Lys Tyr Phe Asp  Thr Thr Ile Asp Arg  Lys Arg Tyr
    1535                 1540                 1545

Thr Ser  Thr Lys Glu Val Leu  Asp Ala Thr Leu Ile  His Gln Ser
    1550                 1555                 1560

Ile Thr  Gly Leu Tyr Glu Thr  Arg Ile Asp Leu Ser  Gln Leu Gly
    1565                 1570                 1575

Gly Asp  Gly Ser Pro Lys Lys  Lys Arg Lys Val Ser  Ser
    1580                 1585                 1590
```

<210> SEQ ID NO 49
<211> LENGTH: 4776
<212> TYPE: DNA
<213> ORGANISM: Artificial Sequence
<220> FEATURE:
<223> OTHER INFORMATION: dCas9-Clo051 - 40-18169

<400> SEQUENCE: 49

```
atggcaccaa agaagaaaag aaaagtggag ggcatcaagt caaacatcag cctgctgaaa      60

gacgaactgc ggggacagat tagtcacatc agtcacgagt acctgtcact gattgatctg     120

gccttcgaca gcaagcagaa tagactgttt gagatgaaag tgctggaact gctggtcaac     180

gagtatggct tcaagggcag acatctgggc gggtctagga aacctgacgg catcgtgtac     240

agtaccacac tggaagacaa cttcggaatc attgtcgata ccaaggctta ttccgagggc     300

tactctctgc caattagtca ggcagatgag atggaaaggt acgtgcgcga aaactcaaat     360

agggacgagg aagtcaaccc caataagtgg tgggagaatt tcagcgagga agtgaagaaa     420

tactacttcg tctttatctc aggcagcttc aaagggaagt ttgaggaaca gctgcggaga     480

ctgtccatga ctaccggggt gaacggatct gctgtcaacg tggtcaatct gctgctgggc     540

gcagaaaaga tcaggtccgg ggagatgaca attgaggaac tggaacgcgc catgttcaac     600
```

```
aattctgagt ttatcctgaa gtatggaggc gggggaagcg ataagaaata ctccatcgga    660
ctggccattg gcaccaattc cgtgggctgg gctgtcatca cagacgagta caaggtgcca    720
agcaagaagt tcaaggtcct ggggaacacc gatcgccaca gtatcaagaa aaatctgatt    780
ggagccctgc tgttcgactc aggcgagact gctgaagcaa cccgactgaa gcggactgct    840
aggcgccgat atacccggag aaaaaatcgg atctgctacc tgcaggaaat tttcagcaac    900
gagatggcca aggtggacga tagtttcttt caccgcctgg aggaatcatt cctggtggag    960
gaagataaga aacacgagcg gcatcccatc tttggcaaca ttgtggacga agtcgcttat   1020
cacgagaagt accctactat ctatcatctg aggaagaaac tggtggactc caccgataag   1080
gcagacctgc gcctgatcta tctggccctg gctcacatga tcaagttccg gggggcattt   1140
ctgatcgagg gagatctgaa ccctgacaat tctgatgtgg acaagctgtt catccagctg   1200
gtccagacat acaatcagct gtttgaggaa aacccaatta atgcctcagg cgtggacgca   1260
aaggccatcc tgagcgccag actgtccaaa tctaggcgcc tggaaaacct gatcgctcag   1320
ctgccaggag agaagaaaaa cggcctgttt gggaatctga ttgcactgtc cctgggcctg   1380
acacccaact tcaagtctaa ttttgatctg gccgaggacg ctaagctgca gctgtccaaa   1440
gacacttatg acgatgacct ggataacctg ctggctcaga tcggcgatca gtacgcagac   1500
ctgttcctgg ccgctaagaa tctgagtgac gccatcctgc tgtcagatat tctgcgcgtg   1560
aacacagaga ttactaaggc ccccactgagt gcttcaatga tcaaaagata tgacgagcac   1620
catcaggatc tgaccctgct gaaggctctg gtgaggcagc agctgcccga gaaatacaag   1680
gaaatcttct ttgatcagag caagaatgga tacgccggct atattgacgg cggggcttcc   1740
caggaggagt tctacaagtt catcaagccc attctggaaa agatggacgg caccgaggaa   1800
ctgctggtga agctgaatcg ggaggacctg ctgagaaaac agaggacatt tgataacgga   1860
agcatccctc accagattca tctgggcgaa ctgcacgcca tcctgcgacg gcaggaggac   1920
ttctacccat ttctgaagga taaccgcgag aaaatcgaaa agatcctgac cttcagaatc   1980
ccctactatg tggggcctct ggcacgggga aatagtagat ttgcctggat gacaagaaag   2040
tcagaggaaa ctatcacccc ctggaacttc gaggaagtgg tcgataaagg cgctagcgca   2100
cagtccttca ttgaaaggat gacaaatttt gacaagaacc tgccaaatga gaaggtgctg   2160
cccaaacaca gcctgctgta cgaatatttc acagtgtata acgagctgac taaagtgaag   2220
tacgtcaccg aagggatgcg caagcccgca ttcctgtccg gagagcagaa gaaagccatc   2280
gtggacctgc tgtttaagac aaatcggaaa gtgactgtca aacagctgaa ggaagactat   2340
ttcaagaaaa ttgagtgttt cgattcagtg gaaatcagcg gcgtcgagga caggtttaac   2400
gcctccctgg ggacctacca cgatctgctg aagatcatca aggataagga cttcctggac   2460
aacgaggaaa atgaggacat cctggaggac attgtgctga cactgactct gtttgaggat   2520
cgcgaaatga tcgaggaacg actgaagact tatgcccatc tgttcgatga caaagtgatg   2580
aagcagctga aaagaaggcg ctacaccgga tggggacgcc tgagccgaaa actgatcaat   2640
gggattagag acaagcagag cggaaaaact atcctggact ttctgaagtc cgatggcttc   2700
gccaacagga acttcatgca gctgattcac gatgactctc tgaccttcaa ggaggacatc   2760
cagaaagcac aggtgtctgg ccaggggggac agtctgcacg agcatatcgc aaacctggcc   2820
ggcagccccg ccatcaagaa agggattctg cagaccgtga aggtggtgga cgaactggtc   2880
aaggtcatgg gacgacacaa acctgagaac atcgtgattg agatggcccg cgaaaatcag   2940
acaactcaga agggccagaa aaacagtcga gaacggatga agagaatcga ggaaggcatc   3000
```

```
aaggagctgg ggtcacagat cctgaaggag catcctgtgg aaaacactca gctgcagaat   3060
gagaaactgt atctgtacta tctgcagaat ggacgggata tgtacgtgga ccaggagctg   3120
gatattaaca gactgagtga ttatgacgtg gatgccatcg tccctcagag cttcctgaag   3180
gatgactcca ttgacaacaa ggtgctgacc aggtccgaca agaaccgcgg caaatcagat   3240
aatgtgccaa gcgaggaagt ggtcaagaaa atgaagaact actggaggca gctgctgaat   3300
gccaagctga tcacacagcg gaaatttgat aacctgacta aggcagaaag aggaggcctg   3360
tctgagctgg acaaggccgg cttcatcaag cggcagctgg tggagacaag acagatcact   3420
aagcacgtcg ctcagattct ggatagcaga atgaacacaa agtacgatga aaacgacaag   3480
ctgatcaggg aggtgaaagt cattactctg aaatccaagc tggtgtctga ctttagaaag   3540
gatttccagt tttataaagt cagggagatc aacaactacc accatgctca tgacgcatac   3600
ctgaacgcag tggtcgggac cgccctgatt aagaaatacc ccaagctgga gtccgagttc   3660
gtgtacggag actataaagt gtacgatgtc cggaagatga tcgccaaatc tgagcaggaa   3720
attggcaagg ccaccgctaa gtatttcttt tacagtaaca tcatgaattt ctttaagacc   3780
gaaatcacac tggcaaatgg ggagatcaga aaaaggcctc tgattgagac caacggggag   3840
acaggagaaa tcgtgtggga caagggaagg gattttgcta ccgtgcgcaa agtcctgtcc   3900
atgccccaag tgaatattgt caagaaaact gaagtgcaga ccgggggatt ctctaaggag   3960
agtattctgc ctaagcgaaa ctctgataaa ctgatcgccc ggaagaaaga ctgggacccc   4020
aagaagtatg gcgggttcga ctctccaaca gtggcttaca gtgtcctggt ggtcgcaaag   4080
gtggaaaagg ggaagtccaa gaaactgaag tctgtcaaag agctgctggg aatcactatt   4140
atggaacgca gctccttcga gaagaatcct atcgattttc tggaagccaa gggctataaa   4200
gaggtgaaga aagacctgat cattaagctg ccaaaatact cactgtttga gctggaaaac   4260
ggacgaaagc gaatgctggc aagcgccgga gaactgcaga agggcaatga gctggccctg   4320
ccctccaaat acgtgaactt cctgtatctg gctagccact acgagaaact gaaggggtcc   4380
cctgaggata acgaacagaa gcagctgttt gtggagcagc acaaacatta tctggacgag   4440
atcattgaac agatttcaga gttcagcaag agagtgatcc tggctgacgc aaatctggat   4500
aaagtcctga gcgcatacaa caagcaccga gacaaaccaa tccgggagca ggccgaaaat   4560
atcattcatc tgttcaccct gacaaacctg ggcgcccctg cagccttcaa gtattttgac   4620
accacaatcg atcggaagag atacacttct accaaagagg tgctggatgc taccctgatc   4680
caccagagta ttaccggcct gtatgagaca cgcatcgacc tgtcacagct gggaggcgat   4740
gggagcccca agaaaaagcg gaaggtgtct agttaa                             4776
```

```
<210> SEQ ID NO 50
<211> LENGTH: 1588
<212> TYPE: PRT
<213> ORGANISM: Artificial Sequence
<220> FEATURE:
<223> OTHER INFORMATION: dCas9-Clo051 - 40-18170

<400> SEQUENCE: 50

Met Pro Lys Lys Lys Arg Lys Val Glu Gly Ile Lys Ser Asn Ile Ser
1               5                   10                  15

Leu Leu Lys Asp Glu Leu Arg Gly Gln Ile Ser His Ile Ser His Glu
            20                  25                  30

Tyr Leu Ser Leu Ile Asp Leu Ala Phe Asp Ser Lys Gln Asn Arg Leu
        35                  40                  45
```

```
Phe Glu Met Lys Val Leu Glu Leu Leu Val Asn Glu Tyr Gly Phe Lys
    50                  55                  60

Gly Arg His Leu Gly Gly Ser Arg Lys Pro Asp Gly Ile Val Tyr Ser
65                  70                  75                  80

Thr Thr Leu Glu Asp Asn Phe Gly Ile Ile Val Asp Thr Lys Ala Tyr
                85                  90                  95

Ser Glu Gly Tyr Ser Leu Pro Ile Ser Gln Ala Asp Glu Met Glu Arg
            100                 105                 110

Tyr Val Arg Glu Asn Ser Asn Arg Asp Glu Glu Val Asn Pro Asn Lys
        115                 120                 125

Trp Trp Glu Asn Phe Ser Glu Glu Val Lys Lys Tyr Tyr Phe Val Phe
    130                 135                 140

Ile Ser Gly Ser Phe Lys Gly Lys Phe Glu Glu Gln Leu Arg Arg Leu
145                 150                 155                 160

Ser Met Thr Thr Gly Val Asn Gly Ser Ala Val Asn Val Val Asn Leu
                165                 170                 175

Leu Leu Gly Ala Glu Lys Ile Arg Ser Gly Glu Met Thr Ile Glu Glu
            180                 185                 190

Leu Glu Arg Ala Met Phe Asn Asn Ser Glu Phe Ile Leu Lys Tyr Gly
        195                 200                 205

Gly Gly Gly Ser Asp Lys Lys Tyr Ser Ile Gly Leu Ala Ile Gly Thr
    210                 215                 220

Asn Ser Val Gly Trp Ala Val Ile Thr Asp Glu Tyr Lys Val Pro Ser
225                 230                 235                 240

Lys Lys Phe Lys Val Leu Gly Asn Thr Asp Arg His Ser Ile Lys Lys
                245                 250                 255

Asn Leu Ile Gly Ala Leu Leu Phe Asp Ser Gly Glu Thr Ala Glu Ala
            260                 265                 270

Thr Arg Leu Lys Arg Thr Ala Arg Arg Arg Tyr Thr Arg Arg Lys Asn
        275                 280                 285

Arg Ile Cys Tyr Leu Gln Glu Ile Phe Ser Asn Glu Met Ala Lys Val
    290                 295                 300

Asp Asp Ser Phe Phe His Arg Leu Glu Glu Ser Phe Leu Val Glu Glu
305                 310                 315                 320

Asp Lys Lys His Glu Arg His Pro Ile Phe Gly Asn Ile Val Asp Glu
                325                 330                 335

Val Ala Tyr His Glu Lys Tyr Pro Thr Ile Tyr His Leu Arg Lys Lys
            340                 345                 350

Leu Val Asp Ser Thr Asp Lys Ala Asp Leu Arg Leu Ile Tyr Leu Ala
        355                 360                 365

Leu Ala His Met Ile Lys Phe Arg Gly His Phe Leu Ile Glu Gly Asp
    370                 375                 380

Leu Asn Pro Asp Asn Ser Asp Val Asp Lys Leu Phe Ile Gln Leu Val
385                 390                 395                 400

Gln Thr Tyr Asn Gln Leu Phe Glu Glu Asn Pro Ile Asn Ala Ser Gly
                405                 410                 415

Val Asp Ala Lys Ala Ile Leu Ser Ala Arg Leu Ser Lys Ser Arg Arg
            420                 425                 430

Leu Glu Asn Leu Ile Ala Gln Leu Pro Gly Glu Lys Lys Asn Gly Leu
        435                 440                 445

Phe Gly Asn Leu Ile Ala Leu Ser Leu Gly Leu Thr Pro Asn Phe Lys
    450                 455                 460
```

```
Ser Asn Phe Asp Leu Ala Glu Asp Ala Lys Leu Gln Leu Ser Lys Asp
465                 470                 475                 480

Thr Tyr Asp Asp Asp Leu Asp Asn Leu Leu Ala Gln Ile Gly Asp Gln
                485                 490                 495

Tyr Ala Asp Leu Phe Leu Ala Ala Lys Asn Leu Ser Asp Ala Ile Leu
            500                 505                 510

Leu Ser Asp Ile Leu Arg Val Asn Thr Glu Ile Thr Lys Ala Pro Leu
        515                 520                 525

Ser Ala Ser Met Ile Lys Arg Tyr Asp Glu His His Gln Asp Leu Thr
    530                 535                 540

Leu Leu Lys Ala Leu Val Arg Gln Gln Leu Pro Glu Lys Tyr Lys Glu
545                 550                 555                 560

Ile Phe Phe Asp Gln Ser Lys Asn Gly Tyr Ala Gly Tyr Ile Asp Gly
                565                 570                 575

Gly Ala Ser Gln Glu Glu Phe Tyr Lys Phe Ile Lys Pro Ile Leu Glu
            580                 585                 590

Lys Met Asp Gly Thr Glu Glu Leu Leu Val Lys Leu Asn Arg Glu Asp
        595                 600                 605

Leu Leu Arg Lys Gln Arg Thr Phe Asp Asn Gly Ser Ile Pro His Gln
    610                 615                 620

Ile His Leu Gly Glu Leu His Ala Ile Leu Arg Arg Gln Glu Asp Phe
625                 630                 635                 640

Tyr Pro Phe Leu Lys Asp Asn Arg Glu Lys Ile Glu Lys Ile Leu Thr
                645                 650                 655

Phe Arg Ile Pro Tyr Tyr Val Gly Pro Leu Ala Arg Gly Asn Ser Arg
            660                 665                 670

Phe Ala Trp Met Thr Arg Lys Ser Glu Glu Thr Ile Thr Pro Trp Asn
        675                 680                 685

Phe Glu Glu Val Val Asp Lys Gly Ala Ser Ala Gln Ser Phe Ile Glu
    690                 695                 700

Arg Met Thr Asn Phe Asp Lys Asn Leu Pro Asn Glu Lys Val Leu Pro
705                 710                 715                 720

Lys His Ser Leu Leu Tyr Glu Tyr Phe Thr Val Tyr Asn Glu Leu Thr
                725                 730                 735

Lys Val Lys Tyr Val Thr Glu Gly Met Arg Lys Pro Ala Phe Leu Ser
            740                 745                 750

Gly Glu Gln Lys Lys Ala Ile Val Asp Leu Leu Phe Lys Thr Asn Arg
        755                 760                 765

Lys Val Thr Val Lys Gln Leu Lys Glu Asp Tyr Phe Lys Lys Ile Glu
    770                 775                 780

Cys Phe Asp Ser Val Glu Ile Ser Gly Val Glu Asp Arg Phe Asn Ala
785                 790                 795                 800

Ser Leu Gly Thr Tyr His Asp Leu Leu Lys Ile Ile Lys Asp Lys Asp
                805                 810                 815

Phe Leu Asp Asn Glu Glu Asn Glu Asp Ile Leu Glu Asp Ile Val Leu
            820                 825                 830

Thr Leu Thr Leu Phe Glu Asp Arg Glu Met Ile Glu Glu Arg Leu Lys
        835                 840                 845

Thr Tyr Ala His Leu Phe Asp Asp Lys Val Met Lys Gln Leu Lys Arg
    850                 855                 860

Arg Arg Tyr Thr Gly Trp Gly Arg Leu Ser Arg Lys Leu Ile Asn Gly
865                 870                 875                 880

Ile Arg Asp Lys Gln Ser Gly Lys Thr Ile Leu Asp Phe Leu Lys Ser
```

```
                885                 890                 895

Asp Gly Phe Ala Asn Arg Asn Phe Met Gln Leu Ile His Asp Asp Ser
            900                 905                 910

Leu Thr Phe Lys Glu Asp Ile Gln Lys Ala Gln Val Ser Gly Gln Gly
        915                 920                 925

Asp Ser Leu His Glu His Ile Ala Asn Leu Ala Gly Ser Pro Ala Ile
    930                 935                 940

Lys Lys Gly Ile Leu Gln Thr Val Lys Val Val Asp Glu Leu Val Lys
945                 950                 955                 960

Val Met Gly Arg His Lys Pro Glu Asn Ile Val Ile Glu Met Ala Arg
                965                 970                 975

Glu Asn Gln Thr Thr Gln Lys Gly Gln Lys Asn Ser Arg Glu Arg Met
            980                 985                 990

Lys Arg Ile Glu Glu Gly Ile Lys  Glu Leu Gly Ser Gln  Ile Leu Lys
        995                 1000                1005

Glu His  Pro Val Glu Asn Thr  Gln Leu Gln Asn Glu  Lys Leu Tyr
    1010                1015                1020

Leu Tyr  Tyr Leu Gln Asn Gly  Arg Asp Met Tyr Val  Asp Gln Glu
    1025                1030                1035

Leu Asp  Ile Asn Arg Leu Ser  Asp Tyr Asp Val Asp  Ala Ile Val
    1040                1045                1050

Pro Gln  Ser Phe Leu Lys Asp  Asp Ser Ile Asp Asn  Lys Val Leu
    1055                1060                1065

Thr Arg  Ser Asp Lys Asn Arg  Gly Lys Ser Asp Asn  Val Pro Ser
    1070                1075                1080

Glu Glu  Val Val Lys Lys Met  Lys Asn Tyr Trp Arg  Gln Leu Leu
    1085                1090                1095

Asn Ala  Lys Leu Ile Thr Gln  Arg Lys Phe Asp Asn  Leu Thr Lys
    1100                1105                1110

Ala Glu  Arg Gly Gly Leu Ser  Glu Leu Asp Lys Ala  Gly Phe Ile
    1115                1120                1125

Lys Arg  Gln Leu Val Glu Thr  Arg Gln Ile Thr Lys  His Val Ala
    1130                1135                1140

Gln Ile  Leu Asp Ser Arg Met  Asn Thr Lys Tyr Asp  Glu Asn Asp
    1145                1150                1155

Lys Leu  Ile Arg Glu Val Lys  Val Ile Thr Leu Lys  Ser Lys Leu
    1160                1165                1170

Val Ser  Asp Phe Arg Lys Asp  Phe Gln Phe Tyr Lys  Val Arg Glu
    1175                1180                1185

Ile Asn  Asn Tyr His His Ala  His Asp Ala Tyr Leu  Asn Ala Val
    1190                1195                1200

Val Gly  Thr Ala Leu Ile Lys  Lys Tyr Pro Lys Leu  Glu Ser Glu
    1205                1210                1215

Phe Val  Tyr Gly Asp Tyr Lys  Val Tyr Asp Val Arg  Lys Met Ile
    1220                1225                1230

Ala Lys  Ser Glu Gln Glu Ile  Gly Lys Ala Thr Ala  Lys Tyr Phe
    1235                1240                1245

Phe Tyr  Ser Asn Ile Met Asn  Phe Phe Lys Thr Glu  Ile Thr Leu
    1250                1255                1260

Ala Asn  Gly Glu Ile Arg Lys  Arg Pro Leu Ile Glu  Thr Asn Gly
    1265                1270                1275

Glu Thr  Gly Glu Ile Val Trp  Asp Lys Gly Arg Asp  Phe Ala Thr
    1280                1285                1290
```

```
Val Arg  Lys Val Leu Ser Met  Pro Gln Val Asn Ile  Val Lys Lys
    1295                 1300                 1305

Thr Glu  Val Gln Thr Gly Gly  Phe Ser Lys Glu Ser  Ile Leu Pro
    1310                 1315                 1320

Lys Arg  Asn Ser Asp Lys Leu  Ile Ala Arg Lys Lys  Asp Trp Asp
    1325                 1330                 1335

Pro Lys  Lys Tyr Gly Gly Phe  Asp Ser Pro Thr Val  Ala Tyr Ser
    1340                 1345                 1350

Val Leu  Val Val Ala Lys Val  Glu Lys Gly Lys Ser  Lys Lys Leu
    1355                 1360                 1365

Lys Ser  Val Lys Glu Leu Leu  Gly Ile Thr Ile Met  Glu Arg Ser
    1370                 1375                 1380

Ser Phe  Glu Lys Asn Pro Ile  Asp Phe Leu Glu Ala  Lys Gly Tyr
    1385                 1390                 1395

Lys Glu  Val Lys Lys Asp Leu  Ile Ile Lys Leu Pro  Lys Tyr Ser
    1400                 1405                 1410

Leu Phe  Glu Leu Glu Asn Gly  Arg Lys Arg Met Leu  Ala Ser Ala
    1415                 1420                 1425

Gly Glu  Leu Gln Lys Gly Asn  Glu Leu Ala Leu Pro  Ser Lys Tyr
    1430                 1435                 1440

Val Asn  Phe Leu Tyr Leu Ala  Ser His Tyr Glu Lys  Leu Lys Gly
    1445                 1450                 1455

Ser Pro  Glu Asp Asn Glu Gln  Lys Gln Leu Phe Val  Glu Gln His
    1460                 1465                 1470

Lys His  Tyr Leu Asp Glu Ile  Ile Glu Gln Ile Ser  Glu Phe Ser
    1475                 1480                 1485

Lys Arg  Val Ile Leu Ala Asp  Ala Asn Leu Asp Lys  Val Leu Ser
    1490                 1495                 1500

Ala Tyr  Asn Lys His Arg Asp  Lys Pro Ile Arg Glu  Gln Ala Glu
    1505                 1510                 1515

Asn Ile  Ile His Leu Phe Thr  Leu Thr Asn Leu Gly  Ala Pro Ala
    1520                 1525                 1530

Ala Phe  Lys Tyr Phe Asp Thr  Thr Ile Asp Arg Lys  Arg Tyr Thr
    1535                 1540                 1545

Ser Thr  Lys Glu Val Leu Asp  Ala Thr Leu Ile His  Gln Ser Ile
    1550                 1555                 1560

Thr Gly  Leu Tyr Glu Thr Arg  Ile Asp Leu Ser Gln  Leu Gly Gly
    1565                 1570                 1575

Asp Gly  Ser Pro Lys Lys Lys  Arg Lys Val
    1580                 1585
```

<210> SEQ ID NO 51
<211> LENGTH: 4767
<212> TYPE: DNA
<213> ORGANISM: Artificial Sequence
<220> FEATURE:
<223> OTHER INFORMATION: dCas9-Clo051 - 40-18171

<400> SEQUENCE: 51

```
atgcctaaga agaagcggaa ggtggaaggc atcaaaagca acatctccct cctgaaagac     60

gaactccggg ggcagattag ccacattagt cacgaatacc tctccctcat cgacctggct    120

ttcgatagca agcagaacag gctctttgag atgaaagtgc tggaactgct cgtcaatgag    180

tacgggttca agggtcgaca cctcggcgga tctaggaaac cagacggcat cgtgtatagt    240
```

```
accacactgg aagacaactt tgggatcatt gtggatacca aggcatactc tgagggttat    300
agtctgccca tttcacaggc cgacgagatg gaacggtacg tgcgcgagaa ctcaaataga    360
gatgaggaag tcaaccctaa caagtggtgg gagaacttct ctgaggaagt gaagaaatac    420
tacttcgtct ttatcagcgg gtccttcaag ggtaaatttg aggaacagct caggagactg    480
agcatgacta ccggcgtgaa tggcagcgcc gtcaacgtgg tcaatctgct cctgggcgct    540
gaaaagattc ggagcggaga gatgaccatc gaagagctgg agagggcaat gtttaataat    600
agcgagttta tcctgaaata cggtggcggt ggatccgata aaaagtattc tattggttta    660
gccatcggca ctaattccgt tggatgggct gtcataaccg atgaatacaa agtaccttca    720
aagaaattta aggtgttggg gaacacagac cgtcattcga ttaaaaagaa tcttatcggt    780
gccctcctat tcgatagtgg cgaaacggca gaggcgactc gcctgaaacg aaccgctcgg    840
agaaggtata cacgtcgcaa gaaccgaata tgttacttac aagaaatttt tagcaatgag    900
atggccaaag ttgacgattc tttctttcac cgtttggaag agtccttcct tgtcgaagag    960
gacaagaaac atgaacggca ccccatcttt ggaaacatag tagatgaggt ggcatatcat   1020
gaaaagtacc caacgattta tcacctcaga aaaaagctag ttgactcaac tgataaagcg   1080
gacctgaggt taatctactt ggctcttgcc catatgataa agttccgtgg gcactttctc   1140
attgagggtg atctaaatcc ggacaactcg gatgtcgaca aactgttcat ccagttagta   1200
caaacctata atcagttgtt tgaagagaac cctataaatg caagtggcgt ggatgcgaag   1260
gctattctta gcgcccgcct ctctaaatcc cgacggctag aaaacctgat cgcacaatta   1320
cccggagaga agaaaaatgg gttgttcggt aaccttatag cgctctcact aggcctgaca   1380
ccaaatttta agtcgaactt cgacttagct gaagatgcca aattgcagct tagtaaggac   1440
acgtacgatg acgatctcga caatctactg gcacaaattg gagatcagta tgcggactta   1500
tttttggctg ccaaaaacct tagcgatgca atcctcctat ctgacatact gagagttaat   1560
actgagatta ccaaggcgcc gttatccgct tcaatgatca aaaggtacga tgaacatcac   1620
caagacttga cacttctcaa ggccctagtc cgtcagcaac tgcctgagaa atataaggaa   1680
atattctttg atcagtcgaa aaacgggtac gcaggttata ttgacggcgg agcgagtcaa   1740
gaggaattct acaagtttat caaacccata ttagagaaga tggatgggac ggaagagttg   1800
cttgtaaaac tcaatcgcga agatctactg cgaaagcagc ggactttcga caacggtagc   1860
attccacatc aaatccactt aggcgaattg catgctatac ttagaaggca ggaggatttt   1920
tatccgttcc tcaaagacaa tcgtgaaaag attgagaaaa tcctaacctt tcgcatacct   1980
tactatgtgg gacccctggc ccgagggaac tctcggttcg catggatgac aagaaagtcc   2040
gaagaaacga ttactccatg gaattttgag gaagttgtcg ataaaggtgc gtcagctcaa   2100
tcgttcatcg agaggatgac caactttgac aagaatttac cgaacgaaaa agtattgcct   2160
aagcacagtt tactttacga gtatttcaca gtgtacaatg aactcacgaa agttaagtat   2220
gtcactgagg gcatgcgtaa acccgccttt ctaagcggag aacagaagaa agcaatagta   2280
gatctgttat tcaagaccaa ccgcaaagtg acagttaagc aattgaaaga ggactacttt   2340
aagaaaattg aatgcttcga ttctgtcgag atctccgggg tagaagatcg atttaatgcg   2400
tcacttggta cgtatcatga cctcctaaag ataattaaag ataaggactt cctggataac   2460
gaagagaatg aagatatctt agaagatata gtgttgactc ttaccctctt tgaagatcgg   2520
gaaatgattg aggaaagact aaaaacatac gctcacctgt tcgacgataa ggttatgaaa   2580
cagttaaaga ggcgtcgcta tacgggctgg ggacgattgt cgcggaaact tatcaacggg   2640
```

```
ataagagaca agcaaagtgg taaaactatt ctcgattttc taaagagcga cggcttcgcc   2700
aataggaact ttatgcagct gatccatgat gactctttaa ccttcaaaga ggatatacaa   2760
aaggcacagg tttccggaca aggggactca ttgcacgaac atattgcgaa tcttgctggt   2820
tcgccagcca tcaaaaaggg catactccag acagtcaaag tagtggatga gctagttaag   2880
gtcatgggac gtcacaaacc ggaaaacatt gtaatcgaga tggcacgcga aaatcaaacg   2940
actcagaagg ggcaaaaaaa cagtcgagag cggatgaaga gaatagaaga gggtattaaa   3000
gaactgggca gccagatctt aaaggagcat cctgtggaaa atacccaatt gcagaacgag   3060
aaactttacc tctattacct acaaaatgga agggacatgt atgttgatca ggaactggac   3120
ataaaccgtt tatctgatta cgacgtcgat gccattgtac cccaatcctt tttgaaggac   3180
gattcaatcg acaataaagt gcttacacgc tcggataaga accgagggaa aagtgacaat   3240
gttccaagcg aggaagtcgt aaagaaaatg aagaactatt ggcggcagct cctaaatgcg   3300
aaactgataa cgcaaagaaa gttcgataac ttaactaaag ctgagagggg tggcttgtct   3360
gaacttgaca aggccggatt tattaaacgt cagctcgtgg aaacccgcca aatcacaaag   3420
catgttgcac agatactaga ttcccgaatg aatacgaaat acgacgagaa cgataagctg   3480
attcgggaag tcaaagtaat cactttaaag tcaaaattgg tgtcggactt cagaaaggat   3540
tttcaattct ataaagttag ggagataaat aactaccacc atgcgcacga cgcttatctt   3600
aatgccgtcg tagggaccgc actcattaag aaatacccga agctagaaag tgagtttgtg   3660
tatggtgatt acaaagttta tgacgtccgt aagatgatcg cgaaaagcga acaggagata   3720
ggcaaggcta cagccaaata cttcttttat tctaacatta tgaatttctt taagacggaa   3780
atcactctgg caaacggaga gatacgcaaa cgacctttaa ttgaaaccaa tggggagaca   3840
ggtgaaatcg tatgggataa gggccgggac ttcgcgacgg tgagaaaagt tttgtccatg   3900
ccccaagtca acatagtaaa gaaaactgag gtgcagaccg gagggttttc aaaggaatcg   3960
attcttccaa aaaggaatag tgataagctc atcgctcgta aaaaggactg ggacccgaaa   4020
aagtacggtg gcttcgatag ccctacagtt gcctattctg tcctagtagt ggcaaaagtt   4080
gagaagggaa aatccaagaa actgaagtca gtcaaagaat tattggggat aacgattatg   4140
gagcgctcgt cttttgaaaa gaaccccatc gacttccttg aggcgaaagg ttacaaggaa   4200
gtaaaaaagg atctcataat taaactacca aagtatagtc tgtttgagtt agaaaatggc   4260
cgaaaacgga tgttggctag cgccggagag cttcaaaagg ggaacgaact cgcactaccg   4320
tctaaatacg tgaatttcct gtatttagcg tcccattacg agaagttgaa aggttcacct   4380
gaagataacg aacagaagca actttttgtt gagcagcaca aacattatct cgacgaaatc   4440
atagagcaaa tttcggaatt cagtaagaga gtcatcctag ctgatgccaa tctggacaaa   4500
gtattaagcg catacaacaa gcacagggat aaacccatac gtgagcaggc ggaaaatatt   4560
atccatttgt ttactcttac caacctcggc gctccagccg cattcaagta ttttgacaca   4620
acgatagatc gcaaacgata cacttctacc aaggaggtgc tagacgcgac actgattcac   4680
caatccatca cgggattata tgaaactcgg atagatttgt cacagcttgg gggtgacgga   4740
tcccccaaga agaagaggaa agtctga                                       4767
```

```
<210> SEQ ID NO 52
<211> LENGTH: 187
<212> TYPE: PRT
<213> ORGANISM: Artificial Sequence
<220> FEATURE:
```

<223> OTHER INFORMATION: DHFR mutein - 40-17012

<400> SEQUENCE: 52

```
Met Val Gly Ser Leu Asn Cys Ile Val Ala Val Ser Gln Asn Met Gly
1               5                   10                  15

Ile Gly Lys Asn Gly Asp Phe Pro Trp Pro Pro Leu Arg Asn Glu Ser
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Glu Lys Gly Ile
                165                 170                 175

Lys Tyr Lys Phe Glu Val Tyr Glu Lys Asn Asp
            180                 185
```

<210> SEQ ID NO 53
<211> LENGTH: 561
<212> TYPE: DNA
<213> ORGANISM: Artificial Sequence
<220> FEATURE:
<223> OTHER INFORMATION: DHFR mutein - 40-17095

<400> SEQUENCE: 53

```
atggtcgggt ctctgaattg tatcgtcgcc gtgagtcaga acatgggcat tgggaagaat     60

ggcgatttcc catggccacc tctgcgcaac gagtcccgat actttcagcg gatgacaact    120

acctcctctg tggaagggaa acagaatctg gtcatcatgg gaaagaaaac ttggttcagc    180

attccagaga agaaccggcc cctgaaaggc agaatcaatc tggtgctgtc ccgagaactg    240

aaggagccac cacagggagc tcactttctg agccggtccc tggacgatgc actgaagctg    300

acagaacagc ctgagctggc caacaaagtc gatatggtgt ggatcgtcgg gggaagttca    360

gtgtataagg aggccatgaa tcaccccggc catctgaaac tgttcgtcac acggatcatg    420

caggactttg agagcgatac tttctttcct gaaattgacc tggagaagta caaactgctg    480

cccgaatatc ctggcgtgct gtccgatgtc caggaagaga aaggcatcaa atacaagttc    540

gaggtctatg agaagaatga c                                              561
```

<210> SEQ ID NO 54
<211> LENGTH: 18
<212> TYPE: PRT
<213> ORGANISM: Homo Sapiens

<400> SEQUENCE: 54

```
Glu Gly Arg Gly Ser Leu Leu Thr Cys Gly Asp Val Glu Glu Asn Pro
```

```
1               5                   10                  15

Gly Pro


<210> SEQ ID NO 55
<211> LENGTH: 21
<212> TYPE: PRT
<213> ORGANISM: Homo Sapiens

<400> SEQUENCE: 55

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 56
<211> LENGTH: 63
<212> TYPE: DNA
<213> ORGANISM: Homo Sapiens

<400> SEQUENCE: 56

ggatctggag agggaagggg aagcctgctg acctgtggag acgtggagga aaacccagga     60

cca                                                                   63


<210> SEQ ID NO 57
<211> LENGTH: 20
<212> TYPE: PRT
<213> ORGANISM: Homo Sapiens

<400> SEQUENCE: 57

Gln Cys Thr Asn Tyr Ala Leu Leu Lys Leu Ala Gly Asp Val Glu Ser
1               5                   10                  15

Asn Pro Gly Pro
            20


<210> SEQ ID NO 58
<211> LENGTH: 23
<212> TYPE: PRT
<213> ORGANISM: Homo Sapiens

<400> SEQUENCE: 58

Gly Ser Gly Gln Cys Thr Asn Tyr Ala Leu Leu Lys Leu Ala Gly Asp
1               5                   10                  15

Val Glu Ser Asn Pro Gly Pro
            20


<210> SEQ ID NO 59
<211> LENGTH: 22
<212> TYPE: PRT
<213> ORGANISM: Homo Sapiens

<400> SEQUENCE: 59

Val Lys Gln Thr Leu Asn Phe Asp Leu Leu Lys Leu Ala Gly Asp Val
1               5                   10                  15

Glu Ser Asn Pro Gly Pro
            20


<210> SEQ ID NO 60
<211> LENGTH: 25
<212> TYPE: PRT
<213> ORGANISM: Homo Sapiens

<400> SEQUENCE: 60
```

```
Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25


<210> SEQ ID NO 61
<211> LENGTH: 19
<212> TYPE: PRT
<213> ORGANISM: Homo Sapiens

<400> SEQUENCE: 61

Ala Thr Asn Phe Ser Leu Leu Lys Gln Ala Gly Asp Val Glu Glu Asn
1               5                   10                  15

Pro Gly Pro


<210> SEQ ID NO 62
<211> LENGTH: 22
<212> TYPE: PRT
<213> ORGANISM: Homo Sapiens

<400> SEQUENCE: 62

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 63
<211> LENGTH: 594
<212> TYPE: PRT
<213> ORGANISM: Artificial Sequence
<220> FEATURE:
<223> OTHER INFORMATION: T2A - 40-18099

<400> SEQUENCE: 63

Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Ile Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Gly Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190
```

```
His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
        275                 280                 285

Ser Lys Tyr Gly Ile Lys Ile Leu Met Met Cys Asp Ser Gly Tyr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
    370                 375                 380

Ser Arg Ser Arg Pro Val Gly Thr Ser Met Phe Cys Phe Asp Gly Pro
385                 390                 395                 400

Leu Thr Leu Val Ser Tyr Lys Pro Lys Pro Ala Lys Met Val Tyr Leu
                405                 410                 415

Leu Ser Ser Cys Asp Glu Asp Ala Ser Ile Asn Glu Ser Thr Gly Lys
            420                 425                 430

Pro Gln Met Val Met Tyr Tyr Asn Gln Thr Lys Gly Gly Val Asp Thr
        435                 440                 445

Leu Asp Gln Met Cys Ser Val Met Thr Cys Ser Arg Lys Thr Asn Arg
    450                 455                 460

Trp Pro Met Ala Leu Leu Tyr Gly Met Ile Asn Ile Ala Cys Ile Asn
465                 470                 475                 480

Ser Phe Ile Ile Tyr Ser His Asn Val Ser Ser Lys Gly Glu Lys Val
                485                 490                 495

Gln Ser Arg Lys Lys Phe Met Arg Asn Leu Tyr Met Ser Leu Thr Ser
            500                 505                 510

Ser Phe Met Arg Lys Arg Leu Glu Ala Pro Thr Leu Lys Arg Tyr Leu
        515                 520                 525

Arg Asp Asn Ile Ser Asn Ile Leu Pro Asn Glu Val Pro Gly Thr Ser
    530                 535                 540

Asp Asp Ser Thr Glu Glu Pro Val Met Lys Lys Arg Thr Tyr Cys Thr
545                 550                 555                 560

Tyr Cys Pro Ser Lys Ile Arg Arg Lys Ala Asn Ala Ser Cys Lys Lys
                565                 570                 575

Cys Lys Lys Val Ile Cys Arg Glu His Asn Ile Asp Met Cys Gln Ser
            580                 585                 590

Cys Phe
```

<210> SEQ ID NO 64
<211> LENGTH: 594
<212> TYPE: PRT
<213> ORGANISM: Artificial Sequence
<220> FEATURE:
<223> OTHER INFORMATION: SPB transposase -40-14484

<400> SEQUENCE: 64

```
Met Gly Ser Ser Leu Asp Asp Glu His Ile Leu Ser Ala Leu Leu Gln
1               5                   10                  15

Ser Asp Asp Glu Leu Val Gly Glu Asp Ser Asp Ser Glu Val Ser Asp
            20                  25                  30

His Val Ser Glu Asp Asp Val Gln Ser Asp Thr Glu Glu Ala Phe Ile
        35                  40                  45

Asp Glu Val His Glu Val Gln Pro Thr Ser Ser Gly Ser Glu Ile Leu
    50                  55                  60

Asp Glu Gln Asn Val Ile Glu Gln Pro Gly Ser Ser Leu Ala Ser Asn
65                  70                  75                  80

Arg Ile Leu Thr Leu Pro Gln Arg Thr Ile Arg Gly Lys Asn Lys His
                85                  90                  95

Cys Trp Ser Thr Ser Lys Ser Thr Arg Arg Ser Arg Val Ser Ala Leu
            100                 105                 110

Asn Ile Val Arg Ser Gln Arg Gly Pro Thr Arg Met Cys Arg Asn Ile
        115                 120                 125

Tyr Asp Pro Leu Leu Cys Phe Lys Leu Phe Phe Thr Asp Glu Ile Ile
    130                 135                 140

Ser Glu Ile Val Lys Trp Thr Asn Ala Glu Ile Ser Leu Lys Arg Arg
145                 150                 155                 160

Glu Ser Met Thr Ser Ala Thr Phe Arg Asp Thr Asn Glu Asp Glu Ile
                165                 170                 175

Tyr Ala Phe Phe Gly Ile Leu Val Met Thr Ala Val Arg Lys Asp Asn
            180                 185                 190

His Met Ser Thr Asp Asp Leu Phe Asp Arg Ser Leu Ser Met Val Tyr
        195                 200                 205

Val Ser Val Met Ser Arg Asp Arg Phe Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Val Tyr Ile Pro Asn Lys Pro
        275                 280                 285

Ser Lys Tyr Gly Ile Lys Ile Leu Met Met Cys Asp Ser Gly Thr Lys
    290                 295                 300

Tyr Met Ile Asn Gly Met Pro Tyr Leu Gly Arg Gly Thr Gln Thr Asn
305                 310                 315                 320

Gly Val Pro Leu Gly Glu Tyr Tyr Val Lys Glu Leu Ser Lys Pro Val
                325                 330                 335

His Gly Ser Cys Arg Asn Ile Thr Cys Asp Asn Trp Phe Thr Ser Ile
            340                 345                 350

Pro Leu Ala Lys Asn Leu Leu Gln Glu Pro Tyr Lys Leu Thr Ile Val
        355                 360                 365

Gly Thr Val Arg Ser Asn Lys Arg Glu Ile Pro Glu Val Leu Lys Asn
```

370 375 380

Ser Arg Ser Arg Pro Val Gly Thr Ser Met Phe Cys Phe Asp Gly Pro
385 390 395 400

Leu Thr Leu Val Ser Tyr Lys Pro Lys Pro Ala Lys Met Val Tyr Leu
405 410 415

Leu Ser Ser Cys Asp Glu Asp Ala Ser Ile Asn Glu Ser Thr Gly Lys
420 425 430

Pro Gln Met Val Met Tyr Tyr Asn Gln Thr Lys Gly Gly Val Asp Thr
435 440 445

Leu Asp Gln Met Cys Ser Val Met Thr Cys Ser Arg Lys Thr Asn Arg
450 455 460

Trp Pro Met Ala Leu Leu Tyr Gly Met Ile Asn Ile Ala Cys Ile Asn
465 470 475 480

Ser Phe Ile Ile Tyr Ser His Asn Val Ser Ser Lys Gly Glu Lys Val
485 490 495

Gln Ser Arg Lys Lys Phe Met Arg Asn Leu Tyr Met Ser Leu Thr Ser
500 505 510

Ser Phe Met Arg Lys Arg Leu Glu Ala Pro Thr Leu Lys Arg Tyr Leu
515 520 525

Arg Asp Asn Ile Ser Asn Ile Leu Pro Lys Glu Val Pro Gly Thr Ser
530 535 540

Asp Asp Ser Thr Glu Glu Pro Val Met Lys Lys Arg Thr Tyr Cys Thr
545 550 555 560

Tyr Cys Pro Ser Lys Ile Arg Arg Lys Ala Asn Ala Ser Cys Lys Lys
565 570 575

Cys Lys Lys Val Ile Cys Arg Glu His Asn Ile Asp Met Cys Gln Ser
580 585 590

Cys Phe

<210> SEQ ID NO 65
<211> LENGTH: 340
<212> TYPE: PRT
<213> ORGANISM: Artificial Sequence
<220> FEATURE:
<223> OTHER INFORMATION: SB100X transposase - 40-14485

<400> SEQUENCE: 65

Met Gly Lys Ser Lys Glu Ile Ser Gln Asp Leu Arg Lys Lys Ile Val
1 5 10 15

Asp Leu His Lys Ser Gly Ser Ser Leu Gly Ala Ile Ser Lys Arg Leu
20 25 30

Lys Val Pro Arg Ser Ser Val Gln Thr Ile Val Arg Lys Tyr Lys His
35 40 45

His Gly Thr Thr Gln Pro Ser Tyr Arg Ser Gly Arg Arg Arg Val Leu
50 55 60

Ser Pro Arg Asp Glu Arg Thr Leu Val Arg Lys Val Gln Ile Asn Pro
65 70 75 80

Arg Thr Thr Ala Lys Asp Leu Val Lys Met Leu Glu Glu Thr Gly Thr
85 90 95

Lys Val Ser Ile Ser Thr Val Lys Arg Val Leu Tyr Arg His Asn Leu
100 105 110

Lys Gly Arg Ser Ala Arg Lys Lys Pro Leu Leu Gln Asn Arg His Lys
115 120 125

Lys Ala Arg Leu Arg Phe Ala Thr Ala His Gly Asp Lys Asp Arg Thr
130 135 140

```
Phe Trp Arg Asn Val Leu Trp Ser Asp Glu Thr Lys Ile Glu Leu Phe
145                 150                 155                 160

Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Arg Lys Glu Asn Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln Met Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Thr Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340


<210> SEQ ID NO 66
<211> LENGTH: 340
<212> TYPE: PRT
<213> ORGANISM: Artificial Sequence
<220> FEATURE:
<223> OTHER INFORMATION: hyperSB100X transposase -40-14486

<400> SEQUENCE: 66

Met Gly Lys Ser Lys Glu Ile Ser Gln Asp Leu Arg Lys Arg Ile Val
1               5                   10                  15

Asp Leu His Lys Ser Gly Ser Ser Leu Gly Ala Ile Ser Lys Arg Leu
            20                  25                  30

Ala Val Pro Arg Ser Ser Val Gln Thr Ile Val Arg Lys Tyr Lys His
        35                  40                  45

His Gly Thr Thr Gln Pro Ser Tyr Arg Ser Gly Arg Arg Arg Val Leu
    50                  55                  60

Ser Pro Arg Asp Glu Arg Thr Leu Val Arg Lys Val Gln Ile Asn Pro
65                  70                  75                  80

Arg Thr Thr Ala Lys Asp Leu Val Lys Met Leu Glu Glu Thr Gly Thr
                85                  90                  95

Lys Val Ser Ile Ser Thr Val Lys Arg Val Leu Tyr Arg His Asn Leu
            100                 105                 110

Lys Gly His Ser Ala Arg Lys Lys Pro Leu Leu Gln Asn Arg His Lys
        115                 120                 125

Lys Ala Arg Leu Arg Phe Ala Thr Ala His Gly Asp Lys Asp Arg Thr
    130                 135                 140

Phe Trp Arg Asn Val Leu Trp Ser Asp Glu Thr Lys Ile Glu Leu Phe
145                 150                 155                 160
```

```
Gly His Asn Asp His Arg Tyr Val Trp Arg Lys Lys Gly Glu Ala Cys
                165                 170                 175

Lys Pro Lys Asn Thr Ile Pro Thr Val Lys His Gly Gly Gly Ser Ile
            180                 185                 190

Met Leu Trp Gly Cys Phe Ala Ala Gly Gly Thr Gly Ala Leu His Lys
        195                 200                 205

Ile Asp Gly Ile Met Asp Ala Val Gln Tyr Val Asp Ile Leu Lys Gln
    210                 215                 220

His Leu Lys Thr Ser Val Arg Lys Leu Lys Leu Gly Arg Lys Trp Val
225                 230                 235                 240

Phe Gln His Asp Asn Asp Pro Lys His Thr Ser Lys Val Val Ala Lys
                245                 250                 255

Trp Leu Lys Asp Asn Lys Val Lys Val Leu Glu Trp Pro Ser Gln Ser
            260                 265                 270

Pro Asp Leu Asn Pro Ile Glu Asn Leu Trp Ala Glu Leu Lys Lys Arg
        275                 280                 285

Val Arg Ala Arg Arg Pro Thr Asn Leu Thr Gln Leu His Gln Leu Cys
    290                 295                 300

Gln Glu Glu Trp Ala Lys Ile His Pro Asn Tyr Cys Gly Lys Leu Val
305                 310                 315                 320

Glu Gly Tyr Pro Lys Arg Leu Thr Gln Val Lys Gln Phe Lys Gly Asn
                325                 330                 335

Ala Thr Lys Tyr
            340
```

<210> SEQ ID NO 67
<211> LENGTH: 5296
<212> TYPE: DNA
<213> ORGANISM: Artificial Sequence
<220> FEATURE:
<223> OTHER INFORMATION: Helraiser transposon - 40-18174

<400> SEQUENCE: 67

```
tcctatataa taaaagagaa acatgcaaat tgaccatccc tccgctacgc tcaagccacg     60

cccaccagcc aatcagaagt gactatgcaa attaacccaa caaagatggc agttaaattt    120

gcatacgcag gtgtcaagcg ccccaggagg caacggcggc cgcgggctcc caggaccttc    180

gctggccccg ggaggcgagg ccggccgcgc ctagccacac ccgcgggctc ccgggacctt    240

cgccagcaga gagcagagcg ggagagcggg cggagagcgg gaggtttgga ggacttggca    300

gagcaggagg ccgctggaca tagagcagag cgagagagag ggtggcttgg agggcgtggc    360

tccctctgtc accccagctt cctcatcaca gctgtggaaa ctgacagcag ggaggaggaa    420

gtcccacccc cacagaatca gccagaatca gccgttggtc agacagctct cagcggcctg    480

acagccagga ctctcattca cctgcatctc agaccgtgac agtagagagg tgggactatg    540

tctaaagaac aactgttgat acaacgtagc tctgcagccg aaagatgccg gcgttatcga    600

cagaaaatgt ctgcagagca acgtgcgtct gatcttgaaa gaaggcggcg cctgcaacag    660

aatgtatctg aagagcagct actggaaaaa cgtcgctctg aagccgaaaa acagcggcgt    720

catcgacaga aaatgtctaa agaccaacgt gcctttgaag ttgaaagaag gcggtggcga    780

cgacagaata tgtctagaga acagtcatca acaagtacta ccaataccgg taggaactgc    840

cttctcagca aaaatggagt acatgaggat gcaattctcg aacatagttg tggtggaatg    900

actgttcgat gtgaattttg cctatcacta aatttctctg atgaaaaacc atccgatggg    960
```

-continued

```
aaatttactc gatgttgtag caaagggaaa gtctgtccaa atgatataca ttttccagat   1020
tacccggcat atttaaaaag attaatgaca aacgaagatt ctgacagtaa aaatttcatg   1080
gaaaatattc gttccataaa tagttctttt gcttttgctt ccatgggtgc aaatattgca   1140
tcgccatcag gatatgggcc atactgtttt agaatacacg gacaagttta tcaccgtact   1200
ggaactttac atccttcgga tggtgtttct cggaagtttg ctcaactcta tattttggat   1260
acagccgaag ctacaagtaa aagattagca atgccagaaa accagggctg ctcagaaaga   1320
ctcatgatca acatcaacaa cctcatgcat gaaataaatg aattaacaaa atcgtacaag   1380
atgctacatg aggtagaaaa ggaagcccaa tctgaagcag cagcaaaagg tattgctccc   1440
acagaagtaa caatggcgat taaatacgat cgtaacagtg acccaggtag atataattct   1500
ccccgtgtaa ccgaggttgc tgtcatattc agaaacgaag atggagaacc tccttttgaa   1560
agggacttgc tcattcattg taaaccagat cccaataatc caaatgccac taaaatgaaa   1620
caaatcagta tcctgtttcc tacattagat gcaatgacat atcctattct tttccacat    1680
ggtgaaaaag gctggggaac agatattgca ttaagactca gagacaacag tgtaatcgac   1740
aataatacta gacaaaatgt aaggacacga gtcacacaaa tgcagtatta tggatttcat   1800
ctctctgtgc gggacacgtt caatcctatt ttaaatgcag gaaaattaac tcaacagttt   1860
attgtggatt catattcaaa aatggaggcc aatcggataa atttcatcaa agcaaaccaa   1920
tctaagttga gagttgaaaa atatagtggt ttgatggatt atctcaaatc tagatctgaa   1980
aatgacaatg tgccgattgg taaaatgata atacttccat catcttttga gggtagtccc   2040
agaaatatgc agcagcgata tcaggatgct atggcaattg taacgaagta tggcaagccc   2100
gatttattca taaccatgac atgcaacccc aaatgggcag atattacaaa caatttacaa   2160
cgctggcaaa aagttgaaaa cagacctgac ttggtagcca gagtttttaa tattaagctg   2220
aatgctcttt taaatgatat atgtaaattc catttatttg gcaaagtaat agctaaaatt   2280
catgtcattg aatttcagaa acgcggactg cctcacgctc acatattatt gatattagat   2340
agtgagtcca aattacgttc agaagatgac attgaccgta tagttaaggc agaaattcca   2400
gatgaagacc agtgtcctcg actttttcaa attgtaaaat caaatatggt acatggacca   2460
tgtggaatac aaaatccaaa tagtccatgt atggaaaatg gaaaatgttc aaagggatat   2520
ccaaaagaat ttcaaaatgc gaccattgga aatattgatg gatatcccaa atacaaacga   2580
agatctggta gcaccatgtc tattggaaat aaagttgtcg ataacacttg gattgtccct   2640
tataacccgt atttgtgcct taaatataac tgtcatataa atgttgaagt ctgtgcatca   2700
attaaaagtg tcaaatattt atttaaatac atctataaag ggcacgattg tgcaaatatt   2760
caaatttctg aaaaaaatat tatcaatcat gacgaagtac aggacttcat tgactccagg   2820
tatgtgagcg ctcctgaggc tgtttggaga ctttttgcaa tgcgaatgca tgaccaatct   2880
catgcaatca caagattagc tattcatttg ccaaatgatc agaatttgta ttttcatacc   2940
gatgattttg ctgaagtttt agatagggct aaaaggcata actcgacttt gatggcttgg   3000
ttcttattga atagagaaga ttctgatgca cgtaattatt attattggga gattccacag   3060
cattatgtgt ttaataattc tttgtggaca aaacgccgaa agggtgggaa taaagtatta   3120
ggtagactgt tcactgtgag ctttagagaa ccagaacgat attaccttag acttttgctt   3180
ctgcatgtaa aaggtgcgat aagttttgag gatctgcgaa ctgtaggagg tgtaacttat   3240
gatacatttc atgaagctgc taaacaccga ggattattac ttgatgacac tatctggaaa   3300
gatacgattg acgatgcaat catccttaat atgcccaaac aactacggca actttttgca   3360
```

```
tatatatgtg tgtttggatg tccttctgct gcagacaaat tatgggatga gaataaatct   3420
cattttattg aagatttctg ttggaaatta caccgaagag aaggtgcctg tgtgaactgt   3480
gaaatgcatg cccttaacga aattcaggag gtattcacat tgcatggaat gaaatgttca   3540
catttcaaac ttccggacta tcctttatta atgaatgcaa atacatgtga tcaattgtac   3600
gagcaacaac aggcagaggt tttgataaat tctctgaatg atgaacagtt ggcagccttt   3660
cagactataa cttcagccat cgaagatcaa actgtacacc ccaaatgctt tttcttggat   3720
ggtccaggtg gtagtggaaa aacatatctg tataaagttt taacacatta tattagaggt   3780
cgtggtggta ctgttttacc cacagcatct acaggaattg ctgcaaattt acttcttggt   3840
ggaagaacct ttcattccca atataaatta ccaattccat taaatgaaac ttcaatttct   3900
agactcgata taaagagtga agttgctaaa accattaaaa aggcccaact tctcattatt   3960
gatgaatgca ccatggcatc cagtcatgct ataaacgcca tagatagatt actaagagaa   4020
attatgaatt tgaatgttgc atttggtggg aaagttctcc ttctcggagg ggattttcga   4080
caatgtctca gtattgtacc acatgctatg cgatcggcca tagtacaaac gagtttaaag   4140
tactgtaatg tttggggatg tttcagaaag ttgtctctta aacaaatat gagatcagag    4200
gattctgctt atagtgaatg gttagtaaaa cttggagatg gcaaacttga tagcagtttt   4260
catttaggaa tggatattat tgaaatcccc catgaaatga tttgtaacgg atctattatt   4320
gaagctacct ttggaaatag tatatctata gataatatta aaaatatatc taaacgtgca   4380
attctttgtc caaaaaatga gcatgttcaa aaattaaatg aagaaatttt ggatatactt   4440
gatggagatt ttcacacata tttgagtgat gattccattg attcaacaga tgatgctgaa   4500
aaggaaaatt ttcccatcga atttcttaat agtattactc cttcgggaat gccgtgtcat   4560
aaattaaaat tgaaagtggg tgcaatcatc atgctattga gaaatcttaa tagtaaatgg   4620
ggtctttgta atggtactag atttattatc aaaagattac gacctaacat tatcgaagct   4680
gaagtattaa caggatctgc agagggagag gttgttctga ttccaagaat tgatttgtcc   4740
ccatctgaca ctggcctccc atttaaatta attcgaagac agtttcccgt gatgccagca   4800
tttgcgatga ctattaataa atcacaagga caaactctag acagagtagg aatattccta   4860
cctgaacccg ttttcgcaca tggtcagtta tatgttgctt tctctcgagt tcgaagagca   4920
tgtgacgtta aagttaaagt tgtaaatact tcatcacaag ggaaattagt caagcactct   4980
gaaagtgttt ttactcttaa tgtggtatac agggagatat tagaataagt ttaatcactt   5040
tatcagtcat tgtttgcatc aatgttgttt ttatatcatg tttttgttgt ttttatatca   5100
tgtctttgtt gttgttatat catgttgtta ttgtttattt attaataaat ttatgtatta   5160
ttttcatata cattttactc atttcctttc atctctcaca cttctattat agagaaaggg   5220
caaatagcaa tattaaaata tttcctctaa ttaattccct ttcaatgtgc acgaatttcg   5280
tgcaccgggc cactag                                                   5296
```

<210> SEQ ID NO 68
<211> LENGTH: 1496
<212> TYPE: PRT
<213> ORGANISM: Artificial Sequence
<220> FEATURE:
<223> OTHER INFORMATION: Helitron transposase - 40-14488

<400> SEQUENCE: 68

```
Met Ser Lys Glu Gln Leu Leu Ile Gln Arg Ser Ser Ala Ala Glu Arg
1               5                   10                  15
```

```
Cys Arg Arg Tyr Arg Gln Lys Met Ser Ala Glu Gln Arg Ala Ser Asp
            20                  25                  30

Leu Glu Arg Arg Arg Arg Leu Gln Gln Asn Val Ser Glu Glu Gln Leu
        35                  40                  45

Leu Glu Lys Arg Arg Ser Glu Ala Glu Lys Gln Arg Arg His Arg Gln
    50                  55                  60

Lys Met Ser Lys Asp Gln Arg Ala Phe Glu Val Glu Arg Arg Arg Trp
65                  70                  75                  80

Arg Arg Gln Asn Met Ser Arg Glu Gln Ser Ser Thr Ser Thr Thr Asn
                85                  90                  95

Thr Gly Arg Asn Cys Leu Leu Ser Lys Asn Gly Val His Glu Asp Ala
            100                 105                 110

Ile Leu Glu His Ser Cys Gly Gly Met Thr Val Arg Cys Glu Phe Cys
        115                 120                 125

Leu Ser Leu Asn Phe Ser Asp Glu Lys Pro Ser Asp Gly Lys Phe Thr
    130                 135                 140

Arg Cys Cys Ser Lys Gly Lys Val Cys Pro Asn Asp Ile His Phe Pro
145                 150                 155                 160

Asp Tyr Pro Ala Tyr Leu Lys Arg Leu Met Thr Asn Glu Asp Ser Asp
                165                 170                 175

Ser Lys Asn Phe Met Glu Asn Ile Arg Ser Ile Asn Ser Ser Phe Ala
            180                 185                 190

Phe Ala Ser Met Gly Ala Asn Ile Ala Ser Pro Ser Gly Tyr Gly Pro
        195                 200                 205

Tyr Cys Phe Arg Ile His Gly Gln Val Tyr His Arg Thr Gly Thr Leu
    210                 215                 220

His Pro Ser Asp Gly Val Ser Arg Lys Phe Ala Gln Leu Tyr Ile Leu
225                 230                 235                 240

Asp Thr Ala Glu Ala Thr Ser Lys Arg Leu Ala Met Pro Glu Asn Gln
                245                 250                 255

Gly Cys Ser Glu Arg Leu Met Ile Asn Ile Asn Asn Leu Met His Glu
            260                 265                 270

Ile Asn Glu Leu Thr Lys Ser Tyr Lys Met Leu His Glu Val Glu Lys
        275                 280                 285

Glu Ala Gln Ser Glu Ala Ala Ala Lys Gly Ile Ala Pro Thr Glu Val
    290                 295                 300

Thr Met Ala Ile Lys Tyr Asp Arg Asn Ser Asp Pro Gly Arg Tyr Asn
305                 310                 315                 320

Ser Pro Arg Val Thr Glu Val Ala Val Ile Phe Arg Asn Glu Asp Gly
                325                 330                 335

Glu Pro Pro Phe Glu Arg Asp Leu Leu Ile His Cys Lys Pro Asp Pro
            340                 345                 350

Asn Asn Pro Asn Ala Thr Lys Met Lys Gln Ile Ser Ile Leu Phe Pro
        355                 360                 365

Thr Leu Asp Ala Met Thr Tyr Pro Ile Leu Phe Pro His Gly Glu Lys
    370                 375                 380

Gly Trp Gly Thr Asp Ile Ala Leu Arg Leu Arg Asp Asn Ser Val Ile
385                 390                 395                 400

Asp Asn Asn Thr Arg Gln Asn Val Arg Thr Arg Val Thr Gln Met Gln
                405                 410                 415

Tyr Tyr Gly Phe His Leu Ser Val Arg Asp Thr Phe Asn Pro Ile Leu
            420                 425                 430
```

-continued

```
Asn Ala Gly Lys Leu Thr Gln Gln Phe Ile Val Asp Ser Tyr Ser Lys
        435                 440                 445

Met Glu Ala Asn Arg Ile Asn Phe Ile Lys Ala Asn Gln Ser Lys Leu
    450                 455                 460

Arg Val Glu Lys Tyr Ser Gly Leu Met Asp Tyr Leu Lys Ser Arg Ser
465                 470                 475                 480

Glu Asn Asp Asn Val Pro Ile Gly Lys Met Ile Ile Leu Pro Ser Ser
                485                 490                 495

Phe Glu Gly Ser Pro Arg Asn Met Gln Gln Arg Tyr Gln Asp Ala Met
            500                 505                 510

Ala Ile Val Thr Lys Tyr Gly Lys Pro Asp Leu Phe Ile Thr Met Thr
        515                 520                 525

Cys Asn Pro Lys Trp Ala Asp Ile Thr Asn Asn Leu Gln Arg Trp Gln
    530                 535                 540

Lys Val Glu Asn Arg Pro Asp Leu Val Ala Arg Val Phe Asn Ile Lys
545                 550                 555                 560

Leu Asn Ala Leu Leu Asn Asp Ile Cys Lys Phe His Leu Phe Gly Lys
                565                 570                 575

Val Ile Ala Lys Ile His Val Ile Glu Phe Gln Lys Arg Gly Leu Pro
            580                 585                 590

His Ala His Ile Leu Leu Ile Leu Asp Ser Glu Ser Lys Leu Arg Ser
        595                 600                 605

Glu Asp Asp Ile Asp Arg Ile Val Lys Ala Glu Ile Pro Asp Glu Asp
    610                 615                 620

Gln Cys Pro Arg Leu Phe Gln Ile Val Lys Ser Asn Met Val His Gly
625                 630                 635                 640

Pro Cys Gly Ile Gln Asn Pro Asn Ser Pro Cys Met Glu Asn Gly Lys
                645                 650                 655

Cys Ser Lys Gly Tyr Pro Lys Glu Phe Gln Asn Ala Thr Ile Gly Asn
            660                 665                 670

Ile Asp Gly Tyr Pro Lys Tyr Lys Arg Arg Ser Gly Ser Thr Met Ser
        675                 680                 685

Ile Gly Asn Lys Val Val Asp Asn Thr Trp Ile Val Pro Tyr Asn Pro
    690                 695                 700

Tyr Leu Cys Leu Lys Tyr Asn Cys His Ile Asn Val Glu Val Cys Ala
705                 710                 715                 720

Ser Ile Lys Ser Val Lys Tyr Leu Phe Lys Tyr Ile Tyr Lys Gly His
                725                 730                 735

Asp Cys Ala Asn Ile Gln Ile Ser Glu Lys Asn Ile Ile Asn His Asp
            740                 745                 750

Glu Val Gln Asp Phe Ile Asp Ser Arg Tyr Val Ser Ala Pro Glu Ala
        755                 760                 765

Val Trp Arg Leu Phe Ala Met Arg Met His Asp Gln Ser His Ala Ile
    770                 775                 780

Thr Arg Leu Ala Ile His Leu Pro Asn Asp Gln Asn Leu Tyr Phe His
785                 790                 795                 800

Thr Asp Asp Phe Ala Glu Val Leu Asp Arg Ala Lys Arg His Asn Ser
                805                 810                 815

Thr Leu Met Ala Trp Phe Leu Leu Asn Arg Glu Asp Ser Asp Ala Arg
            820                 825                 830

Asn Tyr Tyr Tyr Trp Glu Ile Pro Gln His Tyr Val Phe Asn Asn Ser
        835                 840                 845

Leu Trp Thr Lys Arg Arg Lys Gly Gly Asn Lys Val Leu Gly Arg Leu
```

```
    850                 855                 860

Phe Thr Val Ser Phe Arg Glu Pro Glu Arg Tyr Tyr Leu Arg Leu Leu
865                 870                 875                 880

Leu Leu His Val Lys Gly Ala Ile Ser Phe Glu Asp Leu Arg Thr Val
                885                 890                 895

Gly Gly Val Thr Tyr Asp Thr Phe His Glu Ala Ala Lys His Arg Gly
            900                 905                 910

Leu Leu Leu Asp Asp Thr Ile Trp Lys Asp Thr Ile Asp Asp Ala Ile
        915                 920                 925

Ile Leu Asn Met Pro Lys Gln Leu Arg Gln Leu Phe Ala Tyr Ile Cys
    930                 935                 940

Val Phe Gly Cys Pro Ser Ala Ala Asp Lys Leu Trp Asp Glu Asn Lys
945                 950                 955                 960

Ser His Phe Ile Glu Asp Phe Cys Trp Lys Leu His Arg Arg Glu Gly
                965                 970                 975

Ala Cys Val Asn Cys Glu Met His Ala Leu Asn Glu Ile Gln Glu Val
            980                 985                 990

Phe Thr Leu His Gly Met Lys Cys  Ser His Phe Lys Leu  Pro Asp Tyr
        995                 1000                1005

Pro Leu  Leu Met Asn Ala Asn  Thr Cys Asp Gln Leu  Tyr Glu Gln
    1010                1015                1020

Gln Gln  Ala Glu Val Leu Ile  Asn Ser Leu Asn Asp  Glu Gln Leu
    1025                1030                1035

Ala Ala  Phe Gln Thr Ile Thr  Ser Ala Ile Glu Asp  Gln Thr Val
    1040                1045                1050

His Pro  Lys Cys Phe Phe Leu  Asp Gly Pro Gly Gly  Ser Gly Lys
    1055                1060                1065

Thr Tyr  Leu Tyr Lys Val Leu  Thr His Tyr Ile Arg  Gly Arg Gly
    1070                1075                1080

Gly Thr  Val Leu Pro Thr Ala  Ser Thr Gly Ile Ala  Ala Asn Leu
    1085                1090                1095

Leu Leu  Gly Gly Arg Thr Phe  His Ser Gln Tyr Lys  Leu Pro Ile
    1100                1105                1110

Pro Leu  Asn Glu Thr Ser Ile  Ser Arg Leu Asp Ile  Lys Ser Glu
    1115                1120                1125

Val Ala  Lys Thr Ile Lys Lys  Ala Gln Leu Leu Ile  Ile Asp Glu
    1130                1135                1140

Cys Thr  Met Ala Ser Ser His  Ala Ile Asn Ala Ile  Asp Arg Leu
    1145                1150                1155

Leu Arg  Glu Ile Met Asn Leu  Asn Val Ala Phe Gly  Gly Lys Val
    1160                1165                1170

Leu Leu  Leu Gly Gly Asp Phe  Arg Gln Cys Leu Ser  Ile Val Pro
    1175                1180                1185

His Ala  Met Arg Ser Ala Ile  Val Gln Thr Ser Leu  Lys Tyr Cys
    1190                1195                1200

Asn Val  Trp Gly Cys Phe Arg  Lys Leu Ser Leu Lys  Thr Asn Met
    1205                1210                1215

Arg Ser  Glu Asp Ser Ala Tyr  Ser Glu Trp Leu Val  Lys Leu Gly
    1220                1225                1230

Asp Gly  Lys Leu Asp Ser Ser  Phe His Leu Gly Met  Asp Ile Ile
    1235                1240                1245

Glu Ile  Pro His Glu Met Ile  Cys Asn Gly Ser Ile  Ile Glu Ala
    1250                1255                1260
```

```
Thr Phe  Gly Asn Ser Ile Ser  Ile Asp Asn Ile Lys  Asn Ile Ser
    1265                 1270                 1275

Lys Arg  Ala Ile Leu Cys Pro  Lys Asn Glu His Val  Gln Lys Leu
    1280                 1285                 1290

Asn Glu  Glu Ile Leu Asp Ile  Leu Asp Gly Asp Phe  His Thr Tyr
    1295                 1300                 1305

Leu Ser  Asp Asp Ser Ile Asp  Ser Thr Asp Asp Ala  Glu Lys Glu
    1310                 1315                 1320

Asn Phe  Pro Ile Glu Phe Leu  Asn Ser Ile Thr Pro  Ser Gly Met
    1325                 1330                 1335

Pro Cys  His Lys Leu Lys Leu  Lys Val Gly Ala Ile  Ile Met Leu
    1340                 1345                 1350

Leu Arg  Asn Leu Asn Ser Lys  Trp Gly Leu Cys Asn  Gly Thr Arg
    1355                 1360                 1365

Phe Ile  Ile Lys Arg Leu Arg  Pro Asn Ile Ile Glu  Ala Glu Val
    1370                 1375                 1380

Leu Thr  Gly Ser Ala Glu Gly  Glu Val Val Leu Ile  Pro Arg Ile
    1385                 1390                 1395

Asp Leu  Ser Pro Ser Asp Thr  Gly Leu Pro Phe Lys  Leu Ile Arg
    1400                 1405                 1410

Arg Gln  Phe Pro Val Met Pro  Ala Phe Ala Met Thr  Ile Asn Lys
    1415                 1420                 1425

Ser Gln  Gly Gln Thr Leu Asp  Arg Val Gly Ile Phe  Leu Pro Glu
    1430                 1435                 1440

Pro Val  Phe Ala His Gly Gln  Leu Tyr Val Ala Phe  Ser Arg Val
    1445                 1450                 1455

Arg Arg  Ala Cys Asp Val Lys  Val Lys Val Val Asn  Thr Ser Ser
    1460                 1465                 1470

Gln Gly  Lys Leu Val Lys His  Ser Glu Ser Val Phe  Thr Leu Asn
    1475                 1480                 1485

Val Val  Tyr Arg Glu Ile Leu  Glu
    1490                 1495


<210> SEQ ID NO 69
<211> LENGTH: 4682
<212> TYPE: PRT
<213> ORGANISM: Artificial Sequence
<220> FEATURE:
<223> OTHER INFORMATION: Tol2 transposon - 40-14491

<400> SEQUENCE: 69

Cys Ala Gly Ala Gly Gly Thr Gly Thr Ala Ala Ala Gly Thr Ala Cys
1               5                   10                  15

Thr Thr Gly Ala Gly Thr Ala Ala Thr Thr Thr Thr Ala Cys Thr Thr
            20                  25                  30

Gly Ala Thr Thr Ala Cys Thr Gly Thr Ala Cys Thr Thr Ala Ala Gly
        35                  40                  45

Thr Ala Thr Thr Ala Thr Thr Thr Thr Thr Gly Gly Gly Gly Ala Thr
    50                  55                  60

Thr Thr Thr Thr Ala Cys Thr Thr Thr Ala Cys Thr Thr Gly Ala Gly
65                  70                  75                  80

Thr Ala Cys Ala Ala Thr Thr Ala Ala Ala Ala Ala Thr Cys Ala Ala
                85                  90                  95

Thr Ala Cys Thr Thr Thr Thr Ala Cys Thr Thr Thr Thr Ala Cys Thr
            100                 105                 110
```

Thr Ala Ala Thr Thr Ala Cys Ala Thr Thr Thr Thr Thr Thr Thr Ala
115 120 125

Gly Ala Ala Ala Ala Ala Ala Ala Ala Gly Thr Ala Cys Thr Thr Thr
130 135 140

Thr Thr Ala Cys Thr Cys Cys Thr Thr Ala Cys Ala Ala Thr Thr Thr
145 150 155 160

Thr Ala Thr Thr Thr Ala Cys Ala Gly Thr Cys Ala Ala Ala Ala Ala
165 170 175

Gly Thr Ala Cys Thr Thr Ala Thr Thr Thr Thr Thr Thr Gly Gly Ala
180 185 190

Gly Ala Thr Cys Ala Cys Thr Thr Cys Ala Thr Thr Cys Thr Ala Thr
195 200 205

Thr Thr Thr Cys Cys Cys Thr Thr Gly Cys Thr Ala Thr Thr Ala Cys
210 215 220

Cys Ala Ala Ala Cys Cys Ala Ala Thr Thr Gly Ala Ala Thr Thr Gly
225 230 235 240

Cys Gly Cys Thr Gly Ala Thr Gly Cys Cys Ala Gly Thr Thr Thr
245 250 255

Ala Ala Thr Thr Thr Ala Ala Ala Thr Gly Thr Thr Ala Thr Thr Thr
260 265 270

Ala Thr Thr Cys Thr Gly Cys Cys Thr Ala Thr Gly Ala Ala Ala Ala
275 280 285

Thr Cys Gly Thr Thr Thr Thr Cys Ala Cys Ala Thr Thr Ala Thr Ala
290 295 300

Thr Gly Ala Ala Ala Thr Thr Gly Gly Thr Cys Ala Gly Ala Cys Ala
305 310 315 320

Thr Gly Thr Thr Cys Ala Thr Thr Gly Gly Thr Cys Cys Thr Thr Thr
325 330 335

Gly Gly Ala Ala Gly Thr Gly Ala Cys Gly Thr Cys Ala Thr Gly Thr
340 345 350

Cys Ala Cys Ala Thr Cys Thr Ala Thr Thr Ala Cys Cys Ala Cys Ala
355 360 365

Ala Thr Gly Cys Ala Cys Ala Gly Cys Ala Cys Cys Thr Thr Gly Ala
370 375 380

Cys Cys Thr Gly Gly Ala Ala Ala Thr Thr Ala Gly Gly Gly Ala Ala
385 390 395 400

Ala Thr Thr Ala Thr Ala Ala Cys Ala Gly Thr Cys Ala Ala Thr Cys
405 410 415

Ala Gly Thr Gly Gly Ala Ala Gly Ala Ala Ala Ala Thr Gly Gly Ala
420 425 430

Gly Gly Ala Ala Gly Thr Ala Thr Gly Thr Gly Ala Thr Thr Cys Ala
435 440 445

Thr Cys Ala Gly Cys Ala Gly Cys Thr Gly Cys Gly Ala Gly Cys Ala
450 455 460

Gly Cys Ala Cys Ala Gly Thr Cys Cys Ala Ala Ala Ala Thr Cys Ala
465 470 475 480

Gly Cys Cys Ala Cys Ala Gly Gly Ala Thr Cys Ala Ala Gly Ala Gly
485 490 495

Cys Ala Cys Cys Cys Gly Thr Gly Gly Cys Cys Gly Thr Ala Thr Cys
500 505 510

Thr Thr Cys Gly Cys Gly Ala Ala Thr Thr Cys Thr Thr Thr Thr Cys
515 520 525

```
Thr Thr Thr Ala Ala Gly Thr Gly Gly Thr Gly Thr Ala Ala Ala Thr
    530                 535                 540

Ala Ala Ala Gly Ala Thr Thr Cys Ala Thr Thr Cys Ala Ala Gly Ala
545                 550                 555                 560

Thr Gly Ala Ala Ala Thr Gly Thr Gly Thr Cys Cys Thr Cys Thr Gly
                565                 570                 575

Thr Cys Thr Cys Cys Cys Gly Cys Thr Thr Ala Ala Thr Ala Ala Ala
            580                 585                 590

Gly Ala Ala Ala Thr Ala Thr Cys Gly Gly Cys Cys Thr Thr Cys Ala
        595                 600                 605

Ala Ala Ala Gly Thr Thr Cys Gly Cys Cys Ala Thr Cys Ala Ala Ala
    610                 615                 620

Cys Cys Thr Ala Ala Gly Gly Ala Ala Gly Cys Ala Thr Ala Thr Thr
625                 630                 635                 640

Gly Ala Gly Gly Thr Ala Ala Gly Thr Ala Cys Ala Thr Thr Ala Ala
                645                 650                 655

Gly Thr Ala Thr Thr Thr Thr Gly Thr Thr Thr Thr Ala Cys Thr Gly
            660                 665                 670

Ala Thr Ala Gly Thr Thr Thr Thr Thr Thr Thr Thr Thr Thr Thr Thr
        675                 680                 685

Thr Thr Thr Thr Thr Thr Thr Thr Thr Thr Thr Thr Thr Thr Thr Thr
    690                 695                 700

Thr Gly Gly Gly Thr Gly Thr Gly Cys Ala Thr Gly Thr Thr Thr Thr
705                 710                 715                 720

Gly Ala Cys Gly Thr Thr Gly Ala Thr Gly Gly Cys Gly Cys Gly Cys
                725                 730                 735

Cys Thr Thr Thr Thr Ala Thr Ala Thr Gly Thr Gly Thr Ala Gly Thr
            740                 745                 750

Ala Gly Gly Cys Cys Thr Ala Thr Thr Thr Thr Cys Ala Cys Thr Ala
        755                 760                 765

Ala Thr Gly Cys Ala Thr Gly Cys Gly Ala Thr Thr Gly Ala Cys Ala
    770                 775                 780

Ala Thr Ala Thr Ala Ala Gly Gly Cys Thr Cys Ala Cys Gly Thr Ala
785                 790                 795                 800

Ala Thr Ala Ala Ala Ala Thr Gly Cys Thr Ala Ala Ala Ala Thr Gly
                805                 810                 815

Cys Ala Thr Thr Thr Gly Thr Ala Ala Thr Thr Gly Gly Thr Ala Ala
            820                 825                 830

Cys Gly Thr Thr Ala Gly Gly Thr Cys Cys Ala Cys Gly Gly Gly Ala
        835                 840                 845

Ala Ala Thr Thr Thr Gly Gly Cys Gly Cys Cys Thr Ala Thr Thr Gly
    850                 855                 860

Cys Ala Gly Cys Thr Thr Thr Gly Ala Ala Thr Ala Ala Thr Cys Ala
865                 870                 875                 880

Thr Thr Ala Thr Cys Ala Thr Thr Cys Cys Gly Thr Gly Cys Thr Cys
                885                 890                 895

Thr Cys Ala Thr Thr Gly Thr Gly Thr Thr Thr Gly Ala Ala Thr Thr
            900                 905                 910

Cys Ala Thr Gly Cys Ala Ala Ala Ala Cys Ala Cys Ala Ala Gly Ala
        915                 920                 925

Ala Ala Ala Cys Cys Ala Ala Gly Cys Gly Ala Gly Ala Ala Ala Thr
    930                 935                 940

Thr Thr Thr Thr Thr Thr Cys Cys Ala Ala Ala Cys Ala Thr Gly Thr
```

```
945                 950                 955                 960

Thr Gly Thr Ala Thr Thr Gly Thr Cys Ala Ala Ala Ala Cys Gly Gly
                965                 970                 975

Thr Ala Ala Cys Ala Cys Thr Thr Thr Ala Cys Ala Ala Thr Gly Ala
            980                 985                 990

Gly Gly Thr Thr Gly Ala Thr Thr  Ala Gly Thr Thr Cys  Ala Thr Gly
        995                 1000                1005

Thr Ala  Thr Thr Ala Ala Cys  Thr Ala Ala Cys Ala  Thr Thr Ala
    1010                 1015                 1020

Ala Ala  Thr Ala Ala Cys Cys  Ala Thr Gly Ala Gly  Cys Ala Ala
    1025                 1030                 1035

Thr Ala  Cys Ala Thr Thr Thr  Gly Thr Thr Ala Cys  Thr Gly Thr
    1040                 1045                 1050

Ala Thr  Cys Thr Gly Thr Thr  Ala Ala Thr Cys Thr  Thr Thr Gly
    1055                 1060                 1065

Thr Thr  Ala Ala Cys Gly Thr  Thr Ala Gly Thr Thr  Ala Ala Thr
    1070                 1075                 1080

Ala Gly  Ala Ala Ala Thr Ala  Cys Ala Gly Ala Thr  Gly Thr Thr
    1085                 1090                 1095

Cys Ala  Thr Thr Gly Thr Thr  Thr Gly Thr Thr Cys  Ala Thr Gly
    1100                 1105                 1110

Thr Thr  Ala Gly Thr Thr Cys  Ala Cys Ala Gly Thr  Gly Cys Ala
    1115                 1120                 1125

Thr Thr  Ala Ala Cys Thr Ala  Ala Thr Gly Thr Thr  Ala Ala Cys
    1130                 1135                 1140

Ala Ala  Gly Ala Thr Ala Thr  Ala Ala Ala Gly Thr  Ala Thr Thr
    1145                 1150                 1155

Ala Gly  Thr Ala Ala Ala Thr  Gly Thr Thr Gly Ala  Ala Ala Thr
    1160                 1165                 1170

Thr Ala  Ala Cys Ala Thr Gly  Thr Ala Thr Ala Cys  Gly Thr Gly
    1175                 1180                 1185

Cys Ala  Gly Thr Thr Cys Ala  Thr Thr Ala Thr Thr  Ala Gly Thr
    1190                 1195                 1200

Thr Cys  Ala Thr Gly Thr Thr  Ala Ala Cys Thr Ala  Ala Thr Gly
    1205                 1210                 1215

Thr Ala  Gly Thr Thr Ala Ala  Cys Thr Ala Ala Cys  Gly Ala Ala
    1220                 1225                 1230

Cys Cys  Thr Thr Ala Thr Thr  Gly Thr Ala Ala Ala  Ala Gly Thr
    1235                 1240                 1245

Gly Thr  Thr Ala Cys Cys Ala  Thr Cys Ala Ala Ala  Ala Cys Thr
    1250                 1255                 1260

Ala Ala  Thr Gly Thr Ala Ala  Thr Gly Ala Ala Ala  Thr Cys Ala
    1265                 1270                 1275

Ala Thr  Thr Cys Ala Cys Cys  Cys Thr Gly Thr Cys  Ala Thr Gly
    1280                 1285                 1290

Thr Cys  Ala Gly Cys Cys Thr  Thr Ala Cys Ala Gly  Thr Cys Cys
    1295                 1300                 1305

Thr Gly  Thr Gly Thr Thr Thr  Thr Thr Gly Thr Cys  Ala Ala Thr
    1310                 1315                 1320

Ala Thr  Ala Ala Thr Cys Ala  Gly Ala Ala Ala Thr  Ala Ala Ala
    1325                 1330                 1335

Ala Thr  Thr Ala Ala Thr Gly  Thr Thr Thr Gly Ala  Thr Thr Gly
    1340                 1345                 1350
```

Thr Cys Ala Cys Thr Ala Ala Ala Thr Gly Cys Thr Ala Cys Thr
1355 1360 1365

Gly Thr Ala Thr Thr Thr Cys Thr Ala Ala Ala Ala Thr Cys Ala
1370 1375 1380

Ala Cys Ala Ala Gly Thr Ala Thr Thr Thr Ala Ala Cys Ala Thr
1385 1390 1395

Thr Ala Thr Ala Ala Ala Gly Thr Gly Thr Gly Cys Ala Ala Thr
1400 1405 1410

Thr Gly Gly Cys Thr Gly Cys Ala Ala Ala Thr Gly Thr Cys Ala
1415 1420 1425

Gly Thr Thr Thr Thr Ala Thr Thr Ala Ala Ala Gly Gly Gly Thr
1430 1435 1440

Thr Ala Gly Thr Thr Cys Ala Cys Cys Cys Ala Ala Ala Ala Ala
1445 1450 1455

Thr Gly Ala Ala Ala Ala Thr Ala Ala Thr Gly Thr Cys Ala Thr
1460 1465 1470

Thr Ala Ala Thr Gly Ala Cys Thr Cys Gly Cys Cys Cys Thr Cys
1475 1480 1485

Ala Thr Gly Thr Cys Gly Thr Thr Cys Cys Ala Ala Gly Cys Cys
1490 1495 1500

Cys Gly Thr Ala Ala Gly Ala Cys Cys Thr Cys Cys Gly Thr Thr
1505 1510 1515

Cys Ala Thr Cys Thr Thr Cys Ala Gly Ala Ala Cys Ala Cys Ala
1520 1525 1530

Gly Thr Thr Thr Ala Ala Gly Ala Thr Ala Thr Thr Thr Thr Ala
1535 1540 1545

Gly Ala Thr Thr Thr Ala Gly Thr Cys Cys Gly Ala Gly Ala Gly
1550 1555 1560

Cys Thr Thr Thr Cys Thr Gly Thr Gly Cys Cys Thr Cys Cys Ala
1565 1570 1575

Thr Thr Gly Ala Gly Ala Ala Thr Gly Thr Ala Thr Gly Thr Ala
1580 1585 1590

Cys Gly Gly Thr Ala Thr Ala Cys Thr Gly Thr Cys Cys Ala Thr
1595 1600 1605

Gly Thr Cys Cys Ala Gly Ala Ala Ala Gly Gly Thr Ala Ala Thr
1610 1615 1620

Ala Ala Ala Ala Ala Cys Ala Thr Cys Ala Ala Ala Gly Thr Ala
1625 1630 1635

Gly Thr Cys Cys Ala Thr Gly Thr Gly Ala Cys Ala Thr Cys Ala
1640 1645 1650

Gly Thr Gly Gly Gly Thr Thr Ala Gly Thr Thr Ala Gly Ala Ala
1655 1660 1665

Thr Thr Thr Thr Thr Thr Gly Ala Ala Gly Cys Ala Thr Cys Gly
1670 1675 1680

Ala Ala Thr Ala Cys Ala Thr Thr Thr Thr Gly Gly Thr Cys Cys
1685 1690 1695

Ala Ala Ala Ala Ala Thr Ala Ala Cys Ala Ala Ala Ala Cys Cys
1700 1705 1710

Thr Ala Cys Gly Ala Cys Thr Thr Thr Ala Thr Thr Cys Gly Gly
1715 1720 1725

Cys Ala Thr Thr Gly Thr Ala Thr Thr Cys Thr Cys Thr Thr Cys
1730 1735 1740

Cys Gly Gly Gly Thr Cys Thr Gly Thr Thr Gly Thr Cys Ala Ala
1745 1750 1755

Thr Cys Cys Gly Cys Gly Thr Thr Cys Ala Cys Gly Ala Cys Thr
1760 1765 1770

Thr Cys Gly Cys Ala Gly Thr Gly Ala Cys Gly Cys Thr Ala Cys
1775 1780 1785

Ala Ala Thr Gly Cys Thr Gly Ala Ala Thr Ala Ala Ala Gly Thr
1790 1795 1800

Cys Gly Thr Ala Gly Gly Thr Thr Thr Thr Gly Thr Thr Ala Thr
1805 1810 1815

Thr Thr Thr Thr Gly Gly Ala Cys Cys Ala Ala Ala Ala Thr Gly
1820 1825 1830

Thr Ala Thr Thr Thr Thr Cys Gly Ala Thr Gly Cys Thr Thr Cys
1835 1840 1845

Ala Ala Ala Thr Ala Ala Thr Thr Cys Thr Ala Cys Cys Thr Ala
1850 1855 1860

Ala Cys Cys Cys Ala Cys Thr Gly Ala Thr Gly Thr Cys Ala Cys
1865 1870 1875

Ala Thr Gly Gly Ala Cys Thr Ala Cys Thr Thr Thr Gly Ala Thr
1880 1885 1890

Gly Thr Thr Thr Thr Thr Ala Thr Thr Ala Cys Cys Thr Thr Thr
1895 1900 1905

Cys Thr Gly Gly Ala Cys Ala Thr Gly Gly Ala Cys Ala Gly Thr
1910 1915 1920

Ala Thr Ala Cys Cys Gly Thr Ala Cys Ala Thr Ala Cys Ala Thr
1925 1930 1935

Thr Thr Thr Cys Ala Gly Thr Gly Gly Ala Gly Gly Gly Ala Cys
1940 1945 1950

Ala Gly Ala Ala Ala Gly Cys Thr Cys Thr Cys Gly Gly Ala Cys
1955 1960 1965

Thr Ala Ala Ala Thr Cys Thr Ala Ala Ala Ala Thr Ala Thr Cys
1970 1975 1980

Thr Thr Ala Ala Ala Cys Thr Gly Thr Gly Thr Thr Cys Cys Gly
1985 1990 1995

Ala Ala Gly Ala Thr Gly Ala Ala Cys Gly Gly Ala Gly Gly Thr
2000 2005 2010

Gly Thr Thr Ala Cys Gly Gly Gly Cys Thr Thr Gly Gly Ala Ala
2015 2020 2025

Cys Gly Ala Cys Ala Thr Gly Ala Gly Gly Gly Thr Gly Ala Gly
2030 2035 2040

Thr Cys Ala Thr Thr Ala Ala Thr Gly Ala Cys Ala Thr Cys Thr
2045 2050 2055

Thr Thr Thr Cys Ala Thr Thr Thr Thr Thr Gly Gly Gly Thr Gly
2060 2065 2070

Ala Ala Cys Thr Ala Ala Cys Cys Cys Thr Thr Thr Ala Ala Thr
2075 2080 2085

Gly Cys Thr Gly Thr Ala Ala Thr Cys Ala Gly Ala Gly Ala Gly
2090 2095 2100

Thr Gly Thr Ala Thr Gly Thr Gly Thr Ala Ala Thr Thr Gly Thr
2105 2110 2115

Thr Ala Cys Ala Thr Thr Thr Ala Thr Thr Gly Cys Ala Thr Ala
2120 2125 2130

Cys Ala Ala Thr Ala Thr Ala Ala Ala Thr Ala Thr Thr Thr Ala 2135 2140 2145

Thr Thr Thr Gly Thr Thr Gly Thr Thr Thr Thr Thr Ala Cys Ala
2150 2155 2160

Gly Ala Gly Ala Ala Thr Gly Cys Ala Cys Cys Cys Ala Ala Ala
2165 2170 2175

Thr Thr Ala Cys Cys Thr Cys Ala Ala Ala Ala Ala Cys Thr Ala
2180 2185 2190

Cys Thr Cys Thr Ala Ala Ala Thr Thr Gly Ala Cys Ala Gly Cys
2195 2200 2205

Ala Cys Ala Gly Ala Ala Gly Ala Gly Ala Ala Ala Gly Ala Thr
2210 2215 2220

Cys Gly Gly Gly Ala Cys Cys Thr Cys Cys Ala Cys Cys Cys Ala
2225 2230 2235

Thr Gly Cys Thr Thr Cys Cys Ala Gly Cys Ala Gly Thr Ala Ala
2240 2245 2250

Gly Cys Ala Ala Cys Thr Gly Ala Ala Ala Gly Thr Thr Gly Ala
2255 2260 2265

Cys Thr Cys Ala Gly Thr Thr Thr Thr Cys Cys Cys Ala Gly Thr
2270 2275 2280

Cys Ala Ala Ala Cys Ala Thr Gly Thr Gly Thr Cys Thr Cys Cys
2285 2290 2295

Ala Gly Thr Cys Ala Cys Thr Gly Thr Gly Ala Ala Cys Ala Ala
2300 2305 2310

Ala Gly Cys Thr Ala Thr Ala Thr Thr Ala Ala Gly Gly Thr Ala
2315 2320 2325

Cys Ala Thr Cys Ala Thr Thr Cys Ala Ala Gly Gly Ala Cys Thr
2330 2335 2340

Thr Cys Ala Thr Cys Cys Thr Thr Thr Cys Ala Gly Cys Ala Cys
2345 2350 2355

Thr Gly Thr Thr Gly Ala Thr Cys Thr Gly Cys Cys Ala Thr Cys
2360 2365 2370

Ala Thr Thr Thr Ala Ala Ala Gly Ala Gly Cys Thr Gly Ala Thr
2375 2380 2385

Thr Ala Gly Thr Ala Cys Ala Cys Thr Gly Cys Ala Gly Cys Cys
2390 2395 2400

Thr Gly Gly Cys Ala Thr Thr Thr Cys Thr Gly Thr Cys Ala Thr
2405 2410 2415

Thr Ala Cys Ala Ala Gly Gly Cys Cys Thr Ala Cys Thr Thr Thr
2420 2425 2430

Ala Cys Gly Cys Thr Cys Cys Ala Ala Gly Ala Thr Ala Gly Cys
2435 2440 2445

Thr Gly Ala Ala Gly Cys Thr Gly Cys Thr Cys Thr Gly Ala Thr
2450 2455 2460

Cys Ala Thr Gly Ala Ala Ala Cys Ala Gly Ala Ala Ala Gly Thr
2465 2470 2475

Gly Ala Cys Thr Gly Cys Thr Gly Cys Cys Ala Thr Gly Ala Gly
2480 2485 2490

Thr Gly Ala Ala Gly Thr Thr Gly Ala Ala Thr Gly Gly Ala Thr
2495 2500 2505

Thr Gly Cys Ala Ala Cys Cys Ala Cys Ala Ala Cys Gly Gly Ala
2510 2515 2520

Thr Thr Gly Thr Thr Gly Gly Ala Cys Thr Gly Cys Ala Cys Gly
2525 2530 2535

```
Thr Ala  Gly Ala Ala Ala Gly  Thr Cys Ala Thr Thr  Cys Ala Thr
    2540                 2545                 2550

Thr Gly  Gly Thr Gly Thr Ala  Ala Cys Thr Gly Cys  Thr Cys Ala
    2555                 2560                 2565

Cys Thr  Gly Gly Ala Thr Cys  Ala Ala Cys Cys Cys  Thr Gly Gly
    2570                 2575                 2580

Ala Ala  Gly Thr Cys Thr Thr  Gly Ala Ala Ala Gly  Ala Cys Ala
    2585                 2590                 2595

Thr Thr  Cys Cys Gly Cys Thr  Gly Cys Ala Cys Thr  Thr Gly Cys
    2600                 2605                 2610

Cys Thr  Gly Cys Ala Ala Ala  Ala Gly Ala Thr Thr  Ala Ala Thr
    2615                 2620                 2625

Gly Gly  Gly Cys Thr Cys Thr  Cys Ala Thr Ala Cys  Thr Thr Thr
    2630                 2635                 2640

Thr Gly  Ala Gly Gly Thr Ala  Cys Thr Gly Gly Cys  Cys Ala Gly
    2645                 2650                 2655

Thr Gly  Cys Cys Ala Thr Gly  Ala Ala Thr Gly Ala  Thr Ala Thr
    2660                 2665                 2670

Cys Cys  Ala Cys Thr Cys Ala  Gly Ala Gly Thr Ala  Thr Gly Ala
    2675                 2680                 2685

Ala Ala  Thr Ala Cys Gly Thr  Gly Ala Cys Ala Ala  Gly Gly Thr
    2690                 2695                 2700

Thr Gly  Thr Thr Thr Gly Cys  Ala Cys Ala Ala Cys  Cys Ala Cys
    2705                 2710                 2715

Ala Gly  Ala Cys Ala Gly Thr  Gly Gly Thr Thr Cys  Cys Ala Ala
    2720                 2725                 2730

Cys Thr  Thr Thr Ala Thr Gly  Ala Ala Gly Gly Cys  Thr Thr Thr
    2735                 2740                 2745

Cys Ala  Gly Ala Gly Thr Thr  Thr Thr Thr Gly Gly  Thr Gly Thr
    2750                 2755                 2760

Gly Gly  Ala Ala Ala Ala Cys  Ala Ala Thr Gly Ala  Thr Ala Thr
    2765                 2770                 2775

Cys Gly  Ala Gly Ala Cys Thr  Gly Ala Gly Gly Cys  Ala Ala Gly
    2780                 2785                 2790

Ala Ala  Gly Gly Thr Gly Thr  Gly Ala Ala Ala Gly  Thr Gly Ala
    2795                 2800                 2805

Thr Gly  Ala Cys Ala Cys Thr  Gly Ala Thr Thr Cys  Thr Gly Ala
    2810                 2815                 2820

Ala Gly  Gly Cys Thr Gly Thr  Gly Gly Thr Gly Ala  Gly Gly Gly
    2825                 2830                 2835

Ala Ala  Gly Thr Gly Ala Thr  Gly Gly Thr Gly Thr  Gly Gly Ala
    2840                 2845                 2850

Ala Thr  Thr Cys Cys Ala Ala  Gly Ala Thr Gly Cys  Cys Thr Cys
    2855                 2860                 2865

Ala Cys  Gly Ala Gly Thr Cys  Cys Thr Gly Gly Ala  Cys Cys Ala
    2870                 2875                 2880

Ala Gly  Ala Cys Gly Ala Thr  Gly Gly Cys Thr Thr  Cys Gly Ala
    2885                 2890                 2895

Ala Thr  Thr Cys Cys Ala Gly  Cys Thr Ala Cys Cys  Ala Ala Ala
    2900                 2905                 2910

Ala Cys  Ala Thr Cys Ala Ala  Ala Ala Gly Thr Gly  Thr Gly Cys
    2915                 2920                 2925
```

Cys Thr Gly Thr Cys Ala Cys Thr Thr Ala Cys Thr Thr Ala Ala
2930 2935 2940

Cys Cys Thr Ala Gly Thr Cys Thr Cys Ala Ala Gly Cys Gly Thr
2945 2950 2955

Thr Gly Ala Thr Gly Cys Cys Cys Ala Ala Ala Ala Ala Gly Cys
2960 2965 2970

Thr Cys Thr Cys Thr Cys Ala Ala Ala Thr Gly Ala Ala Cys Ala
2975 2980 2985

Cys Thr Ala Cys Ala Ala Gly Ala Ala Ala Cys Thr Cys Thr Ala
2990 2995 3000

Cys Ala Gly Ala Thr Cys Thr Gly Thr Cys Thr Thr Thr Gly Gly
3005 3010 3015

Cys Ala Ala Ala Thr Gly Cys Cys Ala Ala Gly Cys Thr Thr Thr
3020 3025 3030

Ala Thr Gly Gly Ala Ala Thr Ala Ala Ala Ala Gly Cys Ala Gly
3035 3040 3045

Cys Cys Gly Ala Thr Cys Gly Gly Cys Thr Cys Thr Ala Gly Cys
3050 3055 3060

Ala Gly Cys Thr Gly Ala Ala Gly Cys Thr Gly Thr Thr Gly Ala
3065 3070 3075

Ala Thr Cys Ala Gly Ala Ala Ala Gly Cys Cys Gly Gly Cys Thr
3080 3085 3090

Thr Cys Ala Gly Cys Thr Thr Thr Thr Ala Ala Gly Gly Cys Cys
3095 3100 3105

Ala Ala Ala Cys Cys Ala Ala Ala Cys Gly Cys Gly Gly Thr Gly
3110 3115 3120

Gly Ala Ala Thr Thr Cys Ala Ala Cys Thr Thr Thr Thr Ala Thr
3125 3130 3135

Gly Gly Cys Thr Gly Thr Thr Gly Ala Cys Ala Gly Ala Ala Thr
3140 3145 3150

Thr Cys Thr Thr Cys Ala Ala Ala Thr Thr Thr Gly Cys Ala Ala
3155 3160 3165

Ala Gly Ala Ala Gly Cys Ala Gly Gly Ala Gly Ala Ala Gly Gly
3170 3175 3180

Cys Gly Cys Ala Cys Thr Thr Cys Gly Gly Ala Ala Thr Ala Thr
3185 3190 3195

Ala Thr Gly Cys Ala Cys Cys Thr Cys Thr Cys Thr Thr Gly Ala
3200 3205 3210

Gly Gly Thr Thr Cys Cys Ala Ala Thr Gly Thr Ala Ala Gly Thr
3215 3220 3225

Gly Thr Thr Thr Thr Thr Cys Cys Cys Cys Thr Cys Thr Ala Thr
3230 3235 3240

Cys Gly Ala Thr Gly Thr Ala Ala Ala Cys Ala Ala Ala Thr Gly
3245 3250 3255

Thr Gly Gly Gly Thr Thr Gly Thr Thr Thr Thr Thr Gly Thr Thr
3260 3265 3270

Thr Ala Ala Thr Ala Cys Thr Cys Thr Thr Thr Gly Ala Thr Thr
3275 3280 3285

Ala Thr Gly Cys Thr Gly Ala Thr Thr Thr Cys Thr Cys Cys Thr
3290 3295 3300

Gly Thr Ala Gly Gly Thr Thr Thr Ala Ala Thr Cys Cys Ala Gly
3305 3310 3315

Cys Ala Gly Ala Ala Ala Thr Gly Cys Thr Gly Thr Thr Cys Thr

```
    3320                3325                3330

Thr Gly Ala Cys Ala Gly Ala Gly Thr Gly Gly Gly Cys Cys Ala
    3335                3340                3345

Ala Cys Ala Cys Ala Ala Thr Gly Cys Gly Thr Cys Cys Ala Gly
    3350                3355                3360

Thr Thr Gly Cys Ala Ala Ala Ala Gly Thr Ala Cys Thr Cys Gly
    3365                3370                3375

Ala Cys Ala Thr Cys Thr Thr Gly Cys Ala Ala Gly Cys Gly Gly
    3380                3385                3390

Ala Ala Ala Cys Gly Ala Ala Thr Ala Cys Ala Cys Ala Gly Cys
    3395                3400                3405

Thr Gly Gly Gly Gly Thr Gly Gly Cys Thr Gly Cys Thr Gly Cys
    3410                3415                3420

Cys Thr Ala Gly Thr Gly Thr Cys Cys Ala Thr Cys Ala Gly Thr
    3425                3430                3435

Thr Ala Ala Gly Cys Thr Thr Gly Ala Ala Ala Cys Thr Thr Cys
    3440                3445                3450

Ala Gly Cys Gly Ala Cys Thr Cys Cys Ala Cys Cys Ala Thr Thr
    3455                3460                3465

Cys Thr Cys Thr Cys Ala Gly Gly Thr Ala Cys Thr Gly Thr Gly
    3470                3475                3480

Ala Cys Cys Cys Ala Cys Thr Thr Gly Thr Gly Gly Ala Thr Gly
    3485                3490                3495

Cys Cys Cys Thr Ala Cys Ala Ala Cys Ala Ala Gly Gly Ala Ala
    3500                3505                3510

Thr Cys Cys Ala Ala Ala Cys Ala Cys Gly Ala Thr Thr Cys Ala
    3515                3520                3525

Ala Gly Cys Ala Thr Ala Thr Gly Thr Thr Thr Gly Ala Ala Gly
    3530                3535                3540

Ala Thr Cys Cys Thr Gly Ala Gly Ala Thr Cys Ala Thr Ala Gly
    3545                3550                3555

Cys Ala Gly Cys Thr Gly Cys Cys Ala Thr Cys Cys Thr Thr Cys
    3560                3565                3570

Thr Cys Cys Cys Thr Ala Ala Ala Thr Thr Thr Cys Gly Gly Ala
    3575                3580                3585

Cys Cys Thr Cys Thr Thr Gly Gly Ala Cys Ala Ala Ala Thr Gly
    3590                3595                3600

Ala Thr Gly Ala Ala Ala Cys Cys Ala Thr Cys Ala Thr Ala Ala
    3605                3610                3615

Ala Ala Cys Gly Ala Gly Gly Thr Ala Ala Ala Thr Gly Ala Ala
    3620                3625                3630

Thr Gly Cys Ala Ala Gly Cys Ala Ala Cys Ala Thr Ala Cys Ala
    3635                3640                3645

Cys Thr Thr Gly Ala Cys Gly Ala Ala Thr Thr Cys Thr Ala Ala
    3650                3655                3660

Thr Cys Thr Gly Gly Gly Cys Ala Ala Cys Cys Thr Thr Thr Gly
    3665                3670                3675

Ala Gly Cys Cys Ala Thr Ala Cys Cys Ala Ala Ala Ala Thr Thr
    3680                3685                3690

Ala Thr Thr Cys Thr Thr Thr Thr Ala Thr Thr Thr Ala Thr Thr
    3695                3700                3705

Thr Ala Thr Thr Thr Thr Thr Gly Cys Ala Cys Thr Thr Thr Thr
    3710                3715                3720
```

```
Thr Ala  Gly Gly Ala Ala Thr  Gly Thr Thr Ala Thr  Ala Thr Cys
    3725                 3730                 3735

Cys Cys  Ala Thr Cys Thr Thr  Thr Gly Gly Cys Thr  Gly Thr Gly
    3740                 3745                 3750

Ala Thr  Cys Thr Cys Ala Ala  Thr Ala Thr Gly Ala  Ala Thr Ala
    3755                 3760                 3765

Thr Thr  Gly Ala Thr Gly Thr  Ala Ala Ala Gly Thr  Ala Thr Thr
    3770                 3775                 3780

Cys Thr  Thr Gly Cys Ala Gly  Cys Ala Gly Gly Thr  Thr Gly Thr
    3785                 3790                 3795

Ala Gly  Thr Thr Ala Thr Cys  Cys Cys Thr Cys Ala  Gly Thr Gly
    3800                 3805                 3810

Thr Thr  Thr Cys Thr Thr Gly  Ala Ala Ala Cys Cys  Ala Ala Ala
    3815                 3820                 3825

Cys Thr  Cys Ala Thr Ala Thr  Gly Thr Ala Thr Cys  Ala Thr Ala
    3830                 3835                 3840

Thr Gly  Thr Gly Gly Thr Thr  Thr Gly Gly Ala Ala  Ala Thr Gly
    3845                 3850                 3855

Cys Ala  Gly Thr Thr Ala Gly  Ala Thr Thr Thr Thr  Ala Thr Gly
    3860                 3865                 3870

Cys Thr  Ala Ala Ala Ala Thr  Ala Ala Gly Gly Gly  Ala Thr Thr
    3875                 3880                 3885

Thr Gly  Cys Ala Thr Gly Ala  Thr Thr Thr Thr Ala  Gly Ala Thr
    3890                 3895                 3900

Gly Thr  Ala Gly Ala Thr Gly  Ala Cys Thr Gly Cys  Ala Cys Gly
    3905                 3910                 3915

Thr Ala  Ala Ala Thr Gly Thr  Ala Gly Thr Thr Ala  Ala Thr Gly
    3920                 3925                 3930

Ala Cys  Ala Ala Ala Ala Thr  Cys Cys Ala Thr Ala  Ala Ala Ala
    3935                 3940                 3945

Thr Thr  Thr Gly Thr Thr Cys  Cys Cys Ala Gly Thr  Cys Ala Gly
    3950                 3955                 3960

Ala Ala  Gly Cys Cys Cys Cys  Thr Cys Ala Ala Cys  Cys Ala Ala
    3965                 3970                 3975

Ala Cys  Thr Thr Thr Thr Cys  Thr Thr Thr Gly Thr  Gly Thr Cys
    3980                 3985                 3990

Thr Gly  Cys Thr Cys Ala Cys  Thr Gly Thr Gly Cys  Thr Thr Gly
    3995                 4000                 4005

Thr Ala  Gly Gly Cys Ala Thr  Gly Gly Ala Cys Thr  Ala Cys Ala
    4010                 4015                 4020

Thr Cys  Ala Gly Ala Gly Thr  Gly Cys Ala Thr Cys  Thr Gly Gly
    4025                 4030                 4035

Ala Gly  Cys Cys Thr Thr Thr  Gly Gly Ala Cys Cys  Ala Cys Ala
    4040                 4045                 4050

Ala Gly  Ala Ala Gly Gly Ala  Ala Thr Thr Gly Gly  Cys Cys Ala
    4055                 4060                 4065

Ala Cys  Ala Gly Thr Thr Cys  Ala Thr Cys Thr Gly  Ala Thr Gly
    4070                 4075                 4080

Ala Thr  Gly Ala Ala Gly Ala  Thr Thr Thr Thr Thr  Thr Cys Gly
    4085                 4090                 4095

Cys Thr  Thr Cys Thr Thr Thr  Gly Ala Ala Ala Cys  Cys Gly Ala
    4100                 4105                 4110
```

Cys Ala Ala Cys Ala Cys Ala Thr Gly Ala Ala Gly Cys Cys Ala
4115 4120 4125

Gly Cys Ala Ala Ala Gly Ala Gly Thr Thr Gly Gly Ala Thr Gly
4130 4135 4140

Gly Ala Thr Ala Thr Cys Thr Gly Gly Cys Cys Thr Gly Thr Gly
4145 4150 4155

Thr Thr Thr Cys Ala Gly Ala Cys Ala Cys Cys Ala Gly Gly Gly
4160 4165 4170

Ala Gly Thr Cys Thr Cys Thr Gly Cys Thr Cys Ala Cys Gly Thr
4175 4180 4185

Thr Thr Cys Cys Thr Gly Cys Thr Ala Thr Thr Thr Gly Cys Ala
4190 4195 4200

Gly Cys Cys Thr Cys Thr Cys Thr Ala Thr Cys Ala Ala Gly Ala
4205 4210 4215

Cys Thr Ala Ala Thr Ala Cys Ala Cys Cys Thr Cys Thr Thr Cys
4220 4225 4230

Cys Cys Gly Cys Ala Thr Cys Gly Gly Cys Thr Gly Cys Cys Thr
4235 4240 4245

Gly Thr Gly Ala Gly Ala Gly Gly Cys Thr Thr Thr Thr Cys Ala
4250 4255 4260

Gly Cys Ala Cys Thr Gly Cys Ala Gly Gly Ala Thr Thr Gly Cys
4265 4270 4275

Thr Thr Thr Thr Cys Ala Gly Cys Cys Cys Cys Ala Ala Ala Ala
4280 4285 4290

Gly Ala Gly Cys Thr Ala Gly Gly Cys Thr Thr Gly Ala Cys Ala
4295 4300 4305

Cys Thr Ala Ala Cys Ala Ala Thr Thr Thr Thr Gly Ala Gly Ala
4310 4315 4320

Ala Thr Cys Ala Gly Cys Thr Thr Cys Thr Ala Cys Thr Gly Ala
4325 4330 4335

Ala Gly Thr Thr Ala Ala Ala Thr Cys Thr Gly Ala Gly Gly Thr
4340 4345 4350

Thr Thr Thr Ala Cys Ala Ala Cys Thr Thr Thr Gly Ala Gly Thr
4355 4360 4365

Ala Gly Cys Gly Thr Gly Thr Ala Cys Thr Gly Gly Cys Ala Thr
4370 4375 4380

Thr Ala Gly Ala Thr Thr Gly Thr Cys Thr Gly Thr Cys Thr Thr
4385 4390 4395

Ala Thr Ala Gly Thr Thr Thr Gly Ala Thr Ala Ala Thr Thr Ala
4400 4405 4410

Ala Ala Thr Ala Cys Ala Ala Ala Cys Ala Gly Thr Thr Cys Thr
4415 4420 4425

Ala Ala Ala Gly Cys Ala Gly Gly Ala Thr Ala Ala Ala Ala Cys
4430 4435 4440

Cys Thr Thr Gly Thr Ala Thr Gly Cys Ala Thr Thr Thr Cys Ala
4445 4450 4455

Thr Thr Thr Ala Ala Thr Gly Thr Thr Thr Thr Thr Thr Gly Ala
4460 4465 4470

Gly Ala Thr Thr Ala Ala Ala Ala Gly Cys Thr Thr Ala Ala Ala
4475 4480 4485

Cys Ala Ala Gly Ala Ala Thr Cys Thr Cys Thr Ala Gly Thr Thr
4490 4495 4500

Thr Thr Cys Thr Thr Thr Cys Thr Thr Gly Cys Thr Thr Thr Thr

```
    4505                4510                4515

Ala Cys  Thr Thr Thr Thr Ala  Cys Thr Thr Cys Cys  Thr Thr Ala
    4520                4525                4530

Ala Thr  Ala Cys Thr Cys Ala  Ala Gly Thr Ala Cys  Ala Ala Thr
    4535                4540                4545

Thr Thr  Thr Ala Ala Thr Gly  Gly Ala Gly Thr Ala  Cys Thr Thr
    4550                4555                4560

Thr Thr  Thr Thr Ala Cys Thr  Thr Thr Thr Ala Cys  Thr Cys Ala
    4565                4570                4575

Ala Gly  Thr Ala Ala Gly Ala  Thr Thr Cys Thr Ala  Gly Cys Cys
    4580                4585                4590

Ala Gly  Ala Thr Ala Cys Thr  Thr Thr Thr Ala Cys  Thr Thr Thr
    4595                4600                4605

Thr Ala  Ala Thr Thr Gly Ala  Gly Thr Ala Ala Ala  Ala Thr Thr
    4610                4615                4620

Thr Thr  Cys Cys Cys Thr Ala  Ala Gly Thr Ala Cys  Thr Thr Gly
    4625                4630                4635

Thr Ala  Cys Thr Thr Thr Cys  Ala Cys Thr Thr Gly  Ala Gly Thr
    4640                4645                4650

Ala Ala  Ala Ala Thr Thr Thr  Thr Thr Gly Ala Gly  Thr Ala Cys
    4655                4660                4665

Thr Thr  Thr Thr Thr Ala Cys  Ala Cys Cys Thr Cys  Thr Gly
    4670                4675                4680


<210> SEQ ID NO 70
<211> LENGTH: 649
<212> TYPE: PRT
<213> ORGANISM: Artificial Sequence
<220> FEATURE:
<223> OTHER INFORMATION: Tol2 transposase - 40-14490

<400> SEQUENCE: 70

Met Glu Glu Val Cys Asp Ser Ser Ala Ala Ala Ser Ser Thr Val Gln
1               5                   10                  15

Asn Gln Pro Gln Asp Gln Glu His Pro Trp Pro Tyr Leu Arg Glu Phe
            20                  25                  30

Phe Ser Leu Ser Gly Val Asn Lys Asp Ser Phe Lys Met Lys Cys Val
        35                  40                  45

Leu Cys Leu Pro Leu Asn Lys Glu Ile Ser Ala Phe Lys Ser Ser Pro
    50                  55                  60

Ser Asn Leu Arg Lys His Ile Glu Arg Met His Pro Asn Tyr Leu Lys
65                  70                  75                  80

Asn Tyr Ser Lys Leu Thr Ala Gln Lys Arg Lys Ile Gly Thr Ser Thr
                85                  90                  95

His Ala Ser Ser Ser Lys Gln Leu Lys Val Asp Ser Val Phe Pro Val
            100                 105                 110

Lys His Val Ser Pro Val Thr Val Asn Lys Ala Ile Leu Arg Tyr Ile
        115                 120                 125

Ile Gln Gly Leu His Pro Phe Ser Thr Val Asp Leu Pro Ser Phe Lys
    130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Ala Leu Ile Met Lys Gln Lys
                165                 170                 175

Val Thr Ala Ala Met Ser Glu Val Glu Trp Ile Ala Thr Thr Thr Asp
```

-continued

```
            180                 185                 190

Cys Trp Thr Ala Arg Arg Lys Ser Phe Ile Gly Val Thr Ala His Trp
        195                 200                 205

Ile Asn Pro Gly Ser Leu Glu Arg His Ser Ala Ala Leu Ala Cys Lys
    210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
                245                 250                 255

Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285

Thr Asp Ser Glu Gly Cys Gly Glu Gly Ser Asp Gly Val Glu Phe Gln
    290                 295                 300

Asp Ala Ser Arg Val Leu Asp Gln Asp Asp Gly Phe Glu Phe Gln Leu
305                 310                 315                 320

Pro Lys His Gln Lys Cys Ala Cys His Leu Leu Asn Leu Val Ser Ser
                325                 330                 335

Val Asp Ala Gln Lys Ala Leu Ser Asn Glu His Tyr Lys Lys Leu Tyr
            340                 345                 350

Arg Ser Val Phe Gly Lys Cys Gln Ala Leu Trp Asn Lys Ser Ser Arg
        355                 360                 365

Ser Ala Leu Ala Ala Glu Ala Val Glu Ser Glu Ser Arg Leu Gln Leu
    370                 375                 380

Leu Arg Pro Asn Gln Thr Arg Trp Asn Ser Thr Phe Met Ala Val Asp
385                 390                 395                 400

Arg Ile Leu Gln Ile Cys Lys Glu Ala Gly Glu Gly Ala Leu Arg Asn
                405                 410                 415

Ile Cys Thr Ser Leu Glu Val Pro Met Phe Asn Pro Ala Glu Met Leu
            420                 425                 430

Phe Leu Thr Glu Trp Ala Asn Thr Met Arg Pro Val Ala Lys Val Leu
        435                 440                 445

Asp Ile Leu Gln Ala Glu Thr Asn Thr Gln Leu Gly Trp Leu Leu Pro
    450                 455                 460

Ser Val His Gln Leu Ser Leu Lys Leu Gln Arg Leu His His Ser Leu
465                 470                 475                 480

Arg Tyr Cys Asp Pro Leu Val Asp Ala Leu Gln Gln Gly Ile Gln Thr
                485                 490                 495

Arg Phe Lys His Met Phe Glu Asp Pro Glu Ile Ile Ala Ala Ala Ile
            500                 505                 510

Leu Leu Pro Lys Phe Arg Thr Ser Trp Thr Asn Asp Glu Thr Ile Ile
        515                 520                 525

Lys Arg Gly Met Asp Tyr Ile Arg Val His Leu Glu Pro Leu Asp His
    530                 535                 540

Lys Lys Glu Leu Ala Asn Ser Ser Ser Asp Asp Glu Asp Phe Phe Ala
545                 550                 555                 560

Ser Leu Lys Pro Thr Thr His Glu Ala Ser Lys Glu Leu Asp Gly Tyr
                565                 570                 575

Leu Ala Cys Val Ser Asp Thr Arg Glu Ser Leu Leu Thr Phe Pro Ala
            580                 585                 590

Ile Cys Ser Leu Ser Ile Lys Thr Asn Thr Pro Leu Pro Ala Ser Ala
        595                 600                 605
```

Ala Cys Glu Arg Leu Phe Ser Thr Ala Gly Leu Leu Phe Ser Pro Lys
610 615 620

Arg Ala Arg Leu Asp Thr Asn Asn Phe Glu Asn Gln Leu Leu Leu Lys
625 630 635 640

Leu Asn Leu Arg Phe Tyr Asn Phe Glu
645

<210> SEQ ID NO 71
<211> LENGTH: 636
<212> TYPE: PRT
<213> ORGANISM: Artificial Sequence
<220> FEATURE:
<223> OTHER INFORMATION: TcBuster transposase - 40-18214

<400> SEQUENCE: 71

Met Met Leu Asn Trp Leu Lys Ser Gly Lys Leu Glu Ser Gln Ser Gln
1 5 10 15

Glu Gln Ser Ser Cys Tyr Leu Glu Asn Ser Asn Cys Leu Pro Pro Thr
20 25 30

Leu Asp Ser Thr Asp Ile Ile Gly Glu Glu Asn Lys Ala Gly Thr Thr
35 40 45

Ser Arg Lys Lys Arg Lys Tyr Asp Glu Asp Tyr Leu Asn Phe Gly Phe
50 55 60

Thr Trp Thr Gly Asp Lys Asp Glu Pro Asn Gly Leu Cys Val Ile Cys
65 70 75 80

Glu Gln Val Val Asn Asn Ser Ser Leu Asn Pro Ala Lys Leu Lys Arg
85 90 95

His Leu Asp Thr Lys His Pro Thr Leu Lys Gly Lys Ser Glu Tyr Phe
100 105 110

Lys Arg Lys Cys Asn Glu Leu Asn Gln Lys Lys His Thr Phe Glu Arg
115 120 125

Tyr Val Arg Asp Asp Asn Lys Asn Leu Leu Lys Ala Ser Tyr Leu Val
130 135 140

Ser Leu Arg Ile Ala Lys Gln Gly Glu Ala Tyr Thr Ile Ala Glu Lys
145 150 155 160

Leu Ile Lys Pro Cys Thr Lys Asp Leu Thr Thr Cys Val Phe Gly Glu
165 170 175

Lys Phe Ala Ser Lys Val Asp Leu Val Pro Leu Ser Asp Thr Thr Ile
180 185 190

Ser Arg Arg Ile Glu Asp Met Ser Tyr Phe Cys Glu Ala Val Leu Val
195 200 205

Asn Arg Leu Glu Asn Ala Lys Cys Gly Phe Thr Leu Gln Met Asp Glu
210 215 220

Ser Thr Asp Val Ala Gly Leu Ala Ile Leu Leu Val Phe Val Arg Tyr
225 230 235 240

Ile His Glu Ser Ser Phe Glu Glu Asp Met Leu Phe Cys Lys Ala Leu
245 250 255

Pro Thr Gln Thr Thr Gly Glu Glu Ile Phe Asn Leu Leu Asn Ala Tyr
260 265 270

Phe Glu Lys His Ser Ile Pro Trp Asn Leu Cys Tyr His Ile Cys Thr
275 280 285

Asp Gly Ala Lys Ala Met Val Gly Val Ile Lys Gly Val Ile Ala Arg
290 295 300

Ile Lys Lys Leu Val Pro Asp Ile Lys Ala Ser His Cys Cys Leu His
305 310 315 320

```
Arg His Ala Leu Ala Val Lys Arg Ile Pro Asn Ala Leu His Glu Val
                325                 330                 335

Leu Asn Asp Ala Val Lys Met Ile Asn Phe Ile Lys Ser Arg Pro Leu
            340                 345                 350

Asn Ala Arg Val Phe Ala Leu Leu Cys Asp Asp Leu Gly Ser Leu His
        355                 360                 365

Lys Asn Leu Leu Leu His Thr Glu Val Arg Trp Leu Ser Arg Gly Lys
    370                 375                 380

Val Leu Thr Arg Phe Trp Glu Leu Arg Asp Glu Ile Arg Ile Phe Phe
385                 390                 395                 400

Asn Glu Arg Glu Phe Ala Gly Lys Leu Asn Asp Thr Ser Trp Leu Gln
                405                 410                 415

Asn Leu Ala Tyr Ile Ala Asp Ile Phe Ser Tyr Leu Asn Glu Val Asn
            420                 425                 430

Leu Ser Leu Gln Gly Pro Asn Ser Thr Ile Phe Lys Val Asn Ser Arg
        435                 440                 445

Ile Asn Ser Ile Lys Ser Lys Leu Lys Leu Trp Glu Glu Cys Ile Thr
    450                 455                 460

Lys Asn Asn Thr Glu Cys Phe Ala Asn Leu Asn Asp Phe Leu Glu Thr
465                 470                 475                 480

Ser Asn Thr Ala Leu Asp Pro Asn Leu Lys Ser Asn Ile Leu Glu His
                485                 490                 495

Leu Asn Gly Leu Lys Asn Thr Phe Leu Glu Tyr Phe Pro Pro Thr Cys
            500                 505                 510

Asn Asn Ile Ser Trp Val Glu Asn Pro Phe Asn Glu Cys Gly Asn Val
        515                 520                 525

Asp Thr Leu Pro Ile Lys Glu Arg Glu Gln Leu Ile Asp Ile Arg Thr
    530                 535                 540

Asp Thr Thr Leu Lys Ser Ser Phe Val Pro Asp Gly Ile Gly Pro Phe
545                 550                 555                 560

Trp Ile Lys Leu Met Asp Glu Phe Pro Glu Ile Ser Lys Arg Ala Val
                565                 570                 575

Lys Glu Leu Met Pro Phe Val Thr Thr Tyr Leu Cys Glu Lys Ser Phe
            580                 585                 590

Ser Val Tyr Val Ala Thr Lys Thr Lys Tyr Arg Asn Arg Leu Asp Ala
        595                 600                 605

Glu Asp Asp Met Arg Leu Gln Leu Thr Thr Ile His Pro Asp Ile Asp
    610                 615                 620

Asn Leu Cys Asn Asn Lys Gln Ala Gln Lys Ser His
625                 630                 635
```

<210> SEQ ID NO 72
<211> LENGTH: 1911
<212> TYPE: PRT
<213> ORGANISM: Artificial Sequence
<220> FEATURE:
<223> OTHER INFORMATION: TcBuster transposase - 40-18215

<400> SEQUENCE: 72

```
Ala Thr Gly Ala Thr Gly Thr Thr Gly Ala Ala Thr Thr Gly Gly Cys
1               5                   10                  15

Thr Gly Ala Ala Ala Ala Gly Thr Gly Gly Ala Ala Ala Gly Cys Thr
            20                  25                  30

Thr Gly Ala Ala Ala Gly Thr Cys Ala Ala Thr Cys Ala Cys Ala Gly
        35                  40                  45
```

```
Gly Ala Ala Cys Ala Gly Ala Gly Thr Thr Cys Cys Thr Gly Cys Thr
    50                  55                  60

Ala Cys Cys Thr Thr Gly Ala Gly Ala Ala Cys Thr Cys Thr Ala Ala
65                  70                  75                  80

Cys Thr Gly Cys Cys Thr Gly Cys Cys Ala Cys Cys Ala Ala Cys Gly
                85                  90                  95

Cys Thr Cys Gly Ala Thr Thr Cys Thr Ala Cys Ala Gly Ala Thr Ala
            100                 105                 110

Thr Thr Ala Thr Cys Gly Gly Thr Gly Ala Ala Gly Ala Gly Ala Ala
        115                 120                 125

Cys Ala Ala Ala Gly Cys Thr Gly Gly Thr Ala Cys Cys Ala Cys Cys
    130                 135                 140

Thr Cys Thr Cys Gly Cys Ala Ala Gly Ala Ala Gly Cys Gly Gly Ala
145                 150                 155                 160

Ala Ala Thr Ala Thr Gly Ala Cys Gly Ala Gly Gly Ala Cys Thr Ala
                165                 170                 175

Thr Cys Thr Gly Ala Ala Cys Thr Thr Cys Gly Gly Thr Thr Thr Thr
            180                 185                 190

Ala Cys Ala Thr Gly Gly Ala Cys Thr Gly Gly Cys Gly Ala Cys Ala
        195                 200                 205

Ala Gly Gly Ala Thr Gly Ala Gly Cys Cys Cys Ala Ala Cys Gly Gly
    210                 215                 220

Ala Cys Thr Thr Thr Gly Thr Gly Thr Gly Ala Thr Thr Thr Gly Cys
225                 230                 235                 240

Gly Ala Gly Cys Ala Gly Gly Thr Ala Gly Thr Cys Ala Ala Cys Ala
                245                 250                 255

Ala Thr Thr Cys Cys Thr Cys Ala Cys Thr Thr Ala Ala Cys Cys Cys
            260                 265                 270

Gly Gly Cys Cys Ala Ala Ala Cys Thr Gly Ala Ala Ala Cys Gly Cys
        275                 280                 285

Cys Ala Thr Thr Thr Gly Gly Ala Cys Ala Cys Ala Ala Ala Gly Cys
    290                 295                 300

Ala Thr Cys Cys Gly Ala Cys Gly Cys Thr Thr Ala Ala Ala Gly Gly
305                 310                 315                 320

Cys Ala Ala Gly Ala Gly Cys Gly Ala Ala Thr Ala Cys Thr Thr Cys
                325                 330                 335

Ala Ala Ala Ala Gly Ala Ala Ala Ala Thr Gly Thr Ala Ala Cys Gly
            340                 345                 350

Ala Gly Cys Thr Cys Ala Ala Thr Cys Ala Ala Ala Ala Gly Ala Ala
        355                 360                 365

Gly Cys Ala Thr Ala Cys Thr Thr Thr Thr Gly Ala Gly Cys Gly Ala
    370                 375                 380

Thr Ala Cys Gly Thr Ala Ala Gly Gly Gly Ala Cys Gly Ala Thr Ala
385                 390                 395                 400

Ala Cys Ala Ala Gly Ala Ala Cys Cys Thr Cys Cys Thr Gly Ala Ala
                405                 410                 415

Ala Gly Cys Thr Thr Cys Thr Thr Ala Thr Cys Thr Cys Gly Thr Cys
            420                 425                 430

Ala Gly Thr Thr Thr Gly Ala Gly Ala Ala Thr Ala Gly Cys Thr Ala
        435                 440                 445

Ala Ala Cys Ala Gly Gly Gly Cys Gly Ala Gly Gly Cys Ala Thr Ala
    450                 455                 460
```

```
Thr Ala Cys Cys Ala Thr Ala Gly Cys Gly Gly Ala Gly Ala Ala Gly
465                 470                 475                 480

Thr Thr Gly Ala Thr Cys Ala Ala Gly Cys Cys Thr Thr Gly Cys Ala
                485                 490                 495

Cys Cys Ala Ala Gly Gly Ala Thr Cys Thr Gly Ala Cys Ala Ala Cys
            500                 505                 510

Thr Thr Gly Cys Gly Thr Ala Thr Thr Thr Gly Gly Ala Gly Ala Ala
        515                 520                 525

Ala Ala Ala Thr Thr Cys Gly Cys Gly Ala Gly Cys Ala Ala Ala Gly
    530                 535                 540

Thr Thr Gly Ala Thr Cys Thr Cys Gly Thr Cys Cys Cys Cys Cys Thr
545                 550                 555                 560

Gly Thr Cys Cys Gly Ala Cys Ala Cys Gly Ala Cys Thr Ala Thr Thr
                565                 570                 575

Thr Cys Ala Ala Gly Gly Cys Gly Ala Ala Thr Cys Gly Ala Ala Gly
            580                 585                 590

Ala Cys Ala Thr Gly Ala Gly Thr Thr Ala Cys Thr Thr Cys Thr Gly
        595                 600                 605

Thr Gly Ala Ala Gly Cys Cys Gly Thr Gly Cys Thr Gly Gly Thr Gly
    610                 615                 620

Ala Ala Cys Ala Gly Gly Thr Thr Gly Ala Ala Ala Ala Ala Thr Gly
625                 630                 635                 640

Cys Thr Ala Ala Ala Thr Gly Thr Gly Gly Gly Thr Thr Thr Ala Cys
                645                 650                 655

Gly Cys Thr Gly Cys Ala Gly Ala Thr Gly Gly Ala Cys Gly Ala Gly
            660                 665                 670

Thr Cys Ala Ala Cys Ala Gly Ala Thr Gly Thr Thr Gly Cys Cys Gly
        675                 680                 685

Gly Thr Cys Thr Thr Gly Cys Ala Ala Thr Cys Cys Thr Gly Cys Thr
    690                 695                 700

Thr Gly Thr Gly Thr Thr Thr Gly Thr Thr Ala Gly Gly Thr Ala Cys
705                 710                 715                 720

Ala Thr Ala Cys Ala Thr Gly Ala Ala Ala Gly Cys Thr Cys Thr Thr
                725                 730                 735

Thr Thr Gly Ala Gly Gly Ala Gly Gly Ala Thr Ala Thr Gly Thr Thr
            740                 745                 750

Gly Thr Thr Cys Thr Gly Cys Ala Ala Ala Gly Cys Ala Cys Thr Thr
        755                 760                 765

Cys Cys Cys Ala Cys Thr Cys Ala Gly Ala Cys Gly Ala Cys Ala Gly
    770                 775                 780

Gly Gly Gly Ala Gly Gly Ala Gly Ala Thr Thr Thr Thr Cys Ala Ala
785                 790                 795                 800

Thr Cys Thr Thr Cys Thr Cys Ala Ala Thr Gly Cys Cys Thr Ala Thr
                805                 810                 815

Thr Thr Cys Gly Ala Ala Ala Ala Gly Cys Ala Cys Thr Cys Cys Ala
            820                 825                 830

Thr Cys Cys Cys Ala Thr Gly Gly Ala Ala Thr Cys Thr Gly Thr Gly
        835                 840                 845

Thr Thr Ala Cys Cys Ala Cys Ala Thr Thr Thr Gly Cys Ala Cys Ala
    850                 855                 860

Gly Ala Cys Gly Gly Thr Gly Cys Cys Ala Ala Gly Gly Cys Ala Ala
865                 870                 875                 880

Thr Gly Gly Thr Ala Gly Gly Ala Gly Thr Thr Ala Thr Thr Ala Ala
```

```
            885                 890                 895

Ala Gly Gly Ala Gly Thr Cys Ala Thr Ala Gly Cys Gly Ala Gly Ala
        900                 905                 910

Ala Thr Ala Ala Ala Ala Ala Ala Ala Cys Thr Cys Gly Thr Cys Cys
    915                 920                 925

Cys Thr Gly Ala Thr Ala Thr Ala Ala Ala Ala Gly Cys Thr Ala Gly
    930                 935                 940

Cys Cys Ala Cys Thr Gly Thr Thr Gly Cys Cys Thr Gly Cys Ala Thr
945                 950                 955                 960

Cys Gly Cys Cys Ala Cys Gly Cys Thr Thr Thr Gly Gly Cys Thr Gly
                965                 970                 975

Thr Ala Ala Ala Gly Cys Gly Ala Ala Thr Ala Cys Cys Gly Ala Ala
            980                 985                 990

Thr Gly Cys Ala Thr Thr Gly Cys  Ala Cys Gly Ala Gly  Gly Thr Gly
        995                 1000                1005

Cys Thr  Cys Ala Ala Thr Gly  Ala Cys Gly Cys Thr  Gly Thr Thr
    1010                1015                1020

Ala Ala  Ala Ala Thr Gly Ala  Thr Cys Ala Ala Cys  Thr Thr Cys
    1025                1030                1035

Ala Thr  Cys Ala Ala Gly Thr  Cys Thr Cys Gly Gly  Cys Cys Gly
    1040                1045                1050

Thr Thr  Gly Ala Ala Thr Gly  Cys Gly Cys Gly Cys  Gly Thr Cys
    1055                1060                1065

Thr Thr  Cys Gly Cys Thr Thr  Thr Gly Cys Thr Gly  Thr Gly Thr
    1070                1075                1080

Gly Ala  Cys Gly Ala Thr Thr  Thr Gly Gly Gly Gly  Ala Gly Cys
    1085                1090                1095

Cys Thr  Gly Cys Ala Thr Ala  Ala Ala Ala Ala Thr  Cys Thr Thr
    1100                1105                1110

Cys Thr  Thr Cys Thr Thr Cys  Ala Thr Ala Cys Cys  Gly Ala Ala
    1115                1120                1125

Gly Thr  Gly Ala Gly Gly Thr  Gly Gly Cys Thr Gly  Thr Cys Thr
    1130                1135                1140

Ala Gly  Ala Gly Gly Ala Ala  Ala Gly Gly Thr Gly  Cys Thr Gly
    1145                1150                1155

Ala Cys  Cys Cys Gly Ala Thr  Thr Thr Thr Gly Gly  Gly Ala Ala
    1160                1165                1170

Cys Thr  Gly Ala Gly Ala Gly  Ala Thr Gly Ala Ala  Ala Thr Thr
    1175                1180                1185

Ala Gly  Ala Ala Thr Thr Thr  Thr Cys Thr Thr Cys  Ala Ala Cys
    1190                1195                1200

Gly Ala  Ala Ala Gly Gly Gly  Ala Ala Thr Thr Thr  Gly Cys Cys
    1205                1210                1215

Gly Gly  Gly Ala Ala Ala Thr  Thr Gly Ala Ala Cys  Gly Ala Cys
    1220                1225                1230

Ala Cys  Cys Ala Gly Thr Thr  Gly Gly Thr Thr Gly  Cys Ala Ala
    1235                1240                1245

Ala Ala  Thr Thr Thr Gly Gly  Cys Ala Thr Ala Thr  Ala Thr Ala
    1250                1255                1260

Gly Cys  Thr Gly Ala Cys Ala  Thr Ala Thr Thr Cys  Ala Gly Thr
    1265                1270                1275

Thr Ala  Thr Cys Thr Gly Ala  Ala Thr Gly Ala Ala  Gly Thr Thr
    1280                1285                1290
```

```
Ala Ala  Thr Cys Thr Thr Thr  Cys Cys Cys Thr Gly  Cys Ala Ala
    1295                 1300                 1305

Gly Gly  Gly Cys Cys Gly Ala  Ala Thr Ala Gly Cys  Ala Cys Ala
    1310                 1315                 1320

Ala Thr  Cys Thr Thr Cys Ala  Ala Gly Gly Thr Ala  Ala Ala Thr
    1325                 1330                 1335

Ala Gly  Cys Cys Gly Cys Ala  Thr Thr Ala Ala Cys  Ala Gly Thr
    1340                 1345                 1350

Ala Thr  Thr Ala Ala Ala Thr  Cys Ala Ala Ala Gly  Thr Thr Gly
    1355                 1360                 1365

Ala Ala  Gly Thr Thr Gly Thr  Gly Gly Gly Ala Ala  Gly Ala Gly
    1370                 1375                 1380

Thr Gly  Thr Ala Thr Ala Ala  Cys Gly Ala Ala Ala  Ala Ala Thr
    1385                 1390                 1395

Ala Ala  Cys Ala Cys Thr Gly  Ala Gly Thr Gly Thr  Thr Thr Thr
    1400                 1405                 1410

Gly Cys  Gly Ala Ala Cys Cys  Thr Cys Ala Ala Cys  Gly Ala Thr
    1415                 1420                 1425

Thr Thr  Thr Thr Thr Gly Gly  Ala Ala Ala Cys Thr  Thr Cys Ala
    1430                 1435                 1440

Ala Ala  Cys Ala Cys Thr Gly  Cys Gly Thr Thr Gly  Gly Ala Thr
    1445                 1450                 1455

Cys Cys  Ala Ala Ala Cys Cys  Thr Gly Ala Ala Gly  Thr Cys Thr
    1460                 1465                 1470

Ala Ala  Thr Ala Thr Thr Thr  Thr Gly Gly Ala Ala  Cys Ala Thr
    1475                 1480                 1485

Cys Thr  Cys Ala Ala Cys Gly  Gly Thr Cys Thr Thr  Ala Ala Gly
    1490                 1495                 1500

Ala Ala  Cys Ala Cys Cys Thr  Thr Thr Cys Thr Gly  Gly Ala Gly
    1505                 1510                 1515

Thr Ala  Thr Thr Thr Thr Cys  Cys Ala Cys Cys Thr  Ala Cys Gly
    1520                 1525                 1530

Thr Gly  Thr Ala Ala Thr Ala  Ala Thr Ala Thr Cys  Thr Cys Cys
    1535                 1540                 1545

Thr Gly  Gly Gly Thr Gly Gly  Ala Gly Ala Ala Thr  Cys Cys Thr
    1550                 1555                 1560

Thr Thr  Cys Ala Ala Thr Gly  Ala Ala Thr Gly Cys  Gly Gly Thr
    1565                 1570                 1575

Ala Ala  Cys Gly Thr Cys Gly  Ala Thr Ala Cys Ala  Cys Thr Cys
    1580                 1585                 1590

Cys Cys  Ala Ala Thr Ala Ala  Ala Ala Gly Ala Gly  Ala Gly Gly
    1595                 1600                 1605

Gly Ala  Ala Cys Ala Ala Thr  Thr Gly Ala Thr Thr  Gly Ala Cys
    1610                 1615                 1620

Ala Thr  Ala Cys Gly Gly Ala  Cys Thr Gly Ala Thr  Ala Cys Gly
    1625                 1630                 1635

Ala Cys  Ala Thr Thr Gly Ala  Ala Ala Thr Cys Thr  Thr Cys Ala
    1640                 1645                 1650

Thr Thr  Cys Gly Thr Gly Cys  Cys Thr Gly Ala Thr  Gly Gly Thr
    1655                 1660                 1665

Ala Thr  Ala Gly Gly Ala Cys  Cys Ala Thr Thr Cys  Thr Gly Gly
    1670                 1675                 1680
```

```
Ala Thr  Cys Ala Ala Ala Cys  Thr Gly Ala Thr Gly  Gly Ala Cys
    1685                1690                1695

Gly Ala  Ala Thr Thr Thr Cys  Cys Ala Gly Ala Ala  Ala Thr Thr
    1700                1705                1710

Ala Gly  Cys Ala Ala Ala Cys  Gly Ala Gly Cys Thr  Gly Thr Cys
    1715                1720                1725

Ala Ala  Ala Gly Ala Gly Cys  Thr Cys Ala Thr Gly  Cys Cys Ala
    1730                1735                1740

Thr Thr  Thr Gly Thr Ala Ala  Cys Cys Ala Cys Thr  Thr Ala Cys
    1745                1750                1755

Cys Thr  Cys Thr Gly Thr Gly  Ala Gly Ala Ala Ala  Thr Cys Ala
    1760                1765                1770

Thr Thr  Thr Thr Cys Cys Gly  Thr Cys Thr Ala Thr  Gly Thr Ala
    1775                1780                1785

Gly Cys  Cys Ala Cys Ala Ala  Ala Ala Ala Cys Ala  Ala Ala Ala
    1790                1795                1800

Thr Ala  Thr Cys Gly Ala Ala  Ala Thr Ala Gly Ala  Cys Thr Thr
    1805                1810                1815

Gly Ala  Thr Gly Cys Thr Gly  Ala Ala Gly Ala Cys  Gly Ala Thr
    1820                1825                1830

Ala Thr  Gly Cys Gly Ala Cys  Thr Cys Cys Ala Ala  Cys Thr Thr
    1835                1840                1845

Ala Cys  Thr Ala Cys Thr Ala  Thr Cys Cys Ala Thr  Cys Cys Ala
    1850                1855                1860

Gly Ala  Cys Ala Thr Thr Gly  Ala Cys Ala Ala Cys  Cys Thr Thr
    1865                1870                1875

Thr Gly  Thr Ala Ala Cys Ala  Ala Cys Ala Ala Gly  Cys Ala Gly
    1880                1885                1890

Gly Cys  Thr Cys Ala Gly Ala  Ala Ala Thr Cys Cys  Cys Ala Cys
    1895                1900                1905

Thr Gly  Ala
    1910
```

<210> SEQ ID NO 73
<211> LENGTH: 107
<212> TYPE: PRT
<213> ORGANISM: Artificial Sequence
<220> FEATURE:
<223> OTHER INFORMATION: FKBP12 -40-18091

<400> SEQUENCE: 73

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 74
<211> LENGTH: 321
<212> TYPE: DNA
<213> ORGANISM: Artificial Sequence
<220> FEATURE:
<223> OTHER INFORMATION: FKBP12 -40-18092

<400> SEQUENCE: 74
ggggtccagg tcgagactat ttcaccaggg gatgggcgaa catttccaaa aaggggccag 60
acttgcgtcg tgcattacac cgggatgctg gaggacggga agaaagtgga cagctccagg 120
gatcgcaaca agcccttcaa gttcatgctg ggaaagcagg aagtgatccg aggatgggag 180
gaaggcgtgg cacagatgtc agtcggccag cgggccaaac tgaccattag ccctgactac 240
gcttatggag caacaggcca cccagggatc attccccctc atgccaccct ggtcttcgat 300
gtggaactgc tgaagctgga g 321

<210> SEQ ID NO 75
<211> LENGTH: 5
<212> TYPE: PRT
<213> ORGANISM: Artificial Sequence
<220> FEATURE:
<223> OTHER INFORMATION: linker-40-18093

<400> SEQUENCE: 75

Gly Gly Gly Gly Ser
1 5

<210> SEQ ID NO 76
<211> LENGTH: 15
<212> TYPE: PRT
<213> ORGANISM: Artificial Sequence
<220> FEATURE:
<223> OTHER INFORMATION: linker-40-18094

<400> SEQUENCE: 76

Gly Gly Ala Gly Gly Ala Gly Gly Ala Gly Gly Ala Thr Cys Cys
1 5 10 15

<210> SEQ ID NO 77
<211> LENGTH: 282
<212> TYPE: PRT
<213> ORGANISM: Artificial Sequence
<220> FEATURE:
<223> OTHER INFORMATION: truncatedCas9-40-18095

<400> SEQUENCE: 77

Gly Phe Gly Asp Val Gly Ala Leu Glu Ser Leu Arg Gly Asn Ala Asp
1 5 10 15

Leu Ala Tyr Ile Leu Ser Met Glu Pro Cys Gly His Cys Leu Ile Ile
20 25 30

Asn Asn Val Asn Phe Cys Arg Glu Ser Gly Leu Arg Thr Arg Thr Gly
35 40 45

Ser Asn Ile Asp Cys Glu Lys Leu Arg Arg Arg Phe Ser Ser Leu His
50 55 60

Phe Met Val Glu Val Lys Gly Asp Leu Thr Ala Lys Lys Met Val Leu
65 70 75 80

Ala Leu Leu Glu Leu Ala Gln Gln Asp His Gly Ala Leu Asp Cys Cys
85 90 95

Val Val Val Ile Leu Ser His Gly Cys Gln Ala Ser His Leu Gln Phe
100 105 110

```
Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
        275                 280


<210> SEQ ID NO 78
<211> LENGTH: 843
<212> TYPE: DNA
<213> ORGANISM: Artificial Sequence
<220> FEATURE:
<223> OTHER INFORMATION: truncatedCas9-40-18096

<400> SEQUENCE: 78

tttggggacg tgggggccct ggagtctctg cgaggaaatg ccgatctggc ttacatcctg     60

agcatggaac cctgcggcca ctgtctgatc attaacaatg tgaacttctg cagagaaagc    120

ggactgcgaa cacggactgg ctccaatatt gactgtgaga agctgcggag aaggttctct    180

agtctgcact ttatggtcga agtgaaaggg gatctgaccg ccaagaaaat ggtgctggcc    240

ctgctggagc tggctcagca ggaccatgga gctctggatt gctgcgtggt cgtgatcctg    300

tcccacgggt gccaggcttc tcatctgcag ttccccggag cagtgtacgg aacagacggc    360

tgtcctgtca gcgtggagaa gatcgtcaac atcttcaacg gcacttcttg ccctagtctg    420

gggggaaagc caaaactgtt ctttatccag gcctgtggcg gggaacagaa agatcacggc    480

ttcgaggtgg ccagcaccag ccctgaggac gaatcaccag ggagcaaccc tgaaccagat    540

gcaactccat tccaggaggg actgaggacc tttgaccagc tggatgctat ctcaagcctg    600

cccactccta gtgacatttt cgtgtcttac agtaccttcc caggctttgt ctcatggcgc    660

gatcccaagt cagggagctg gtacgtggag acactggacg acatctttga acagtgggcc    720

cattcagagg acctgcagag cctgctgctg cgagtggcaa acgctgtctc tgtgaagggc    780

atctacaaac agatgcccgg gtgcttcaat ttctgagaa agaaactgtt ctttaagact    840

tcc                                                                  843


<210> SEQ ID NO 79
<211> LENGTH: 394
<212> TYPE: PRT
<213> ORGANISM: Artificial Sequence
<220> FEATURE:
```

<223> OTHER INFORMATION: Inducible proapoptotic polypeptides

<400> SEQUENCE: 79

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu Gly Gly Gly Gly Ser
            100                 105                 110

Gly Phe Gly Asp Val Gly Ala Leu Glu Ser Leu Arg Gly Asn Ala Asp
        115                 120                 125

Leu Ala Tyr Ile Leu Ser Met Glu Pro Cys Gly His Cys Leu Ile Ile
    130                 135                 140

Asn Asn Val Asn Phe Cys Arg Glu Ser Gly Leu Arg Thr Arg Thr Gly
145                 150                 155                 160

Ser Asn Ile Asp Cys Glu Lys Leu Arg Arg Arg Phe Ser Ser Leu His
                165                 170                 175

Phe Met Val Glu Val Lys Gly Asp Leu Thr Ala Lys Lys Met Val Leu
            180                 185                 190

Ala Leu Leu Glu Leu Ala Gln Gln Asp His Gly Ala Leu Asp Cys Cys
        195                 200                 205

Val Val Val Ile Leu Ser His Gly Cys Gln Ala Ser His Leu Gln Phe
    210                 215                 220

Pro Gly Ala Val Tyr Gly Thr Asp Gly Cys Pro Val Ser Val Glu Lys
225                 230                 235                 240

Ile Val Asn Ile Phe Asn Gly Thr Ser Cys Pro Ser Leu Gly Gly Lys
                245                 250                 255

Pro Lys Leu Phe Phe Ile Gln Ala Cys Gly Gly Glu Gln Lys Asp His
            260                 265                 270

Gly Phe Glu Val Ala Ser Thr Ser Pro Glu Asp Glu Ser Pro Gly Ser
        275                 280                 285

Asn Pro Glu Pro Asp Ala Thr Pro Phe Gln Glu Gly Leu Arg Thr Phe
    290                 295                 300

Asp Gln Leu Asp Ala Ile Ser Ser Leu Pro Thr Pro Ser Asp Ile Phe
305                 310                 315                 320

Val Ser Tyr Ser Thr Phe Pro Gly Phe Val Ser Trp Arg Asp Pro Lys
                325                 330                 335

Ser Gly Ser Trp Tyr Val Glu Thr Leu Asp Asp Ile Phe Glu Gln Trp
            340                 345                 350

Ala His Ser Glu Asp Leu Gln Ser Leu Leu Leu Arg Val Ala Asn Ala
        355                 360                 365

Val Ser Val Lys Gly Ile Tyr Lys Gln Met Pro Gly Cys Phe Asn Phe
    370                 375                 380

Leu Arg Lys Lys Leu Phe Phe Lys Thr Ser
385                 390
```

<210> SEQ ID NO 80
<211> LENGTH: 1182
<212> TYPE: DNA
<213> ORGANISM: Artificial Sequence
<220> FEATURE:
<223> OTHER INFORMATION: Inducible proapoptotic polypeptides

<400> SEQUENCE: 80

```
ggggtccagg tcgagactat ttcaccaggg gatgggcgaa catttccaaa aaggggccag     60
acttgcgtcg tgcattacac cgggatgctg gaggacggga agaaagtgga cagctccagg    120
gatcgcaaca agcccttcaa gttcatgctg ggaaagcagg aagtgatccg aggatgggag    180
gaaggcgtgg cacagatgtc agtcggccag cgggccaaac tgaccattag ccctgactac    240
gcttatggag caacaggcca cccagggatc attccccctc atgccaccct ggtcttcgat    300
gtggaactgc tgaagctgga gggaggagga ggatccggat ttggggacgt gggggccctg    360
gagtctctgc gaggaaatgc cgatctggct tacatcctga gcatggaacc ctgcggccac    420
tgtctgatca ttaacaatgt gaacttctgc agagaaagcg gactgcgaac acggactggc    480
tccaatattg actgtgagaa gctgcggaga aggttctcta gtctgcactt tatggtcgaa    540
gtgaaagggg atctgaccgc caagaaaatg gtgctggccc tgctggagct ggctcagcag    600
gaccatggag ctctggattg ctgcgtggtc gtgatcctgt cccacgggtg ccaggcttct    660
catctgcagt tccccggagc agtgtacgga acagacggct gtcctgtcag cgtggagaag    720
atcgtcaaca tcttcaacgg cacttcttgc cctagtctgg ggggaaagcc aaaactgttc    780
tttatccagg cctgtggcgg ggaacagaaa gatcacggct tcgaggtggc cagcaccagc    840
cctgaggacg aatcaccagg gagcaaccct gaaccagatg caactccatt ccaggaggga    900
ctgaggacct ttgaccagct ggatgctatc tcaagcctgc ccactcctag tgacattttc    960
gtgtcttaca gtaccttccc aggctttgtc tcatggcgcg atcccaagtc agggagctgg   1020
tacgtggaga cactggacga catctttgaa cagtgggccc attcagagga cctgcagagc   1080
ctgctgctgc gagtggcaaa cgctgtctct gtgaagggca tctacaaaca gatgcccggg   1140
tgcttcaatt ttctgagaaa gaaactgttc tttaagactt cc                      1182
```

<210> SEQ ID NO 81
<211> LENGTH: 463
<212> TYPE: PRT
<213> ORGANISM: Artificial Sequence
<220> FEATURE:
<223> OTHER INFORMATION: CSR-CD2z-46-17062

<400> SEQUENCE: 81

```
Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
```

```
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
        195                 200                 205

Asp Ile Tyr Leu Ile Ile Gly Ile Cys Gly Gly Gly Ser Leu Leu Met
    210                 215                 220

Val Phe Val Ala Leu Leu Val Phe Tyr Ile Thr Lys Arg Lys Lys Gln
225                 230                 235                 240

Arg Ser Arg Arg Asn Asp Glu Glu Leu Glu Thr Arg Ala His Arg Val
                245                 250                 255

Ala Thr Glu Glu Arg Gly Arg Lys Pro His Gln Ile Pro Ala Ser Thr
            260                 265                 270

Pro Gln Asn Pro Ala Thr Ser Gln His Pro Pro Pro Pro Pro Gly His
        275                 280                 285

Arg Ser Gln Ala Pro Ser His Arg Pro Pro Pro Pro Gly His Arg Val
    290                 295                 300

Gln His Gln Pro Gln Lys Arg Pro Pro Ala Pro Ser Gly Thr Gln Val
305                 310                 315                 320

His Gln Gln Lys Gly Pro Pro Leu Pro Arg Pro Arg Val Gln Pro Lys
                325                 330                 335

Pro Pro His Gly Ala Ala Glu Asn Ser Leu Ser Pro Ser Ser Asn Arg
            340                 345                 350

Val Lys Phe Ser Arg Ser Ala Asp Ala Pro Ala Tyr Lys Gln Gly Gln
        355                 360                 365

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
    450                 455                 460
```

<210> SEQ ID NO 82
<211> LENGTH: 184
<212> TYPE: PRT
<213> ORGANISM: Artificial Sequence
<220> FEATURE:
<223> OTHER INFORMATION: CD2 ECD with D11H-46-17119

<400> SEQUENCE: 82

```
Lys Glu Ile Thr Asn Ala Leu Glu Thr Trp Gly Ala Leu Gly Gln Asp
```

```
1               5                   10                  15

Ile Asn Leu Asp Ile Pro Ser Phe Gln Met Ser Asp Asp Ile Asp Asp
            20                  25                  30

Ile Lys Trp Glu Lys Thr Ser Asp Lys Lys Lys Ile Ala Gln Phe Arg
        35                  40                  45

Lys Glu Lys Glu Thr Phe Lys Glu Lys Asp Thr Tyr Lys Leu Phe Lys
    50                  55                  60

Asn Gly Thr Leu Lys Ile Lys His Leu Lys Thr Asp Asp Gln Asp Ile
65                  70                  75                  80

Tyr Lys Val Ser Ile Tyr His Thr Lys Gly Lys Asn Val Leu Glu Lys
                85                  90                  95

Ile Phe Asp Leu Lys Ile Gln Glu Arg Val Ser Lys Pro Lys Ile Ser
            100                 105                 110

Trp Thr Cys Ile Asn Thr Thr Leu Thr Cys Glu Val Met Asn Gly Thr
        115                 120                 125

Asp Pro Glu Leu Asn Leu Tyr Gln Asp Gly Lys His Leu Lys Leu Ser
    130                 135                 140

Gln Arg Val Ile Thr His Lys Trp Thr Thr Ser Leu Ser Ala Lys Phe
145                 150                 155                 160

Lys Cys Thr Ala Gly Asn Lys Val Ser Lys Glu Ser Ser Val Glu Pro
                165                 170                 175

Val Ser Cys Pro Glu Lys Gly Leu
            180


<210> SEQ ID NO 83
<211> LENGTH: 463
<212> TYPE: PRT
<213> ORGANISM: Artificial Sequence
<220> FEATURE:
<223> OTHER INFORMATION: CSR CD2z-D111H-46-17118

<400> SEQUENCE: 83

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr His Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
```

```
            180                 185                 190

Ser Lys Glu Ser Ser Val Glu Pro Val Ser Cys Pro Glu Lys Gly Leu
        195                 200                 205

Asp Ile Tyr Leu Ile Ile Gly Ile Cys Gly Gly Gly Ser Leu Leu Met
    210                 215                 220

Val Phe Val Ala Leu Leu Val Phe Tyr Ile Thr Lys Arg Lys Lys Gln
225                 230                 235                 240

Arg Ser Arg Arg Asn Asp Glu Glu Leu Glu Thr Arg Ala His Arg Val
                245                 250                 255

Ala Thr Glu Glu Arg Gly Arg Lys Pro His Gln Ile Pro Ala Ser Thr
            260                 265                 270

Pro Gln Asn Pro Ala Thr Ser Gln His Pro Pro Pro Pro Pro Gly His
        275                 280                 285

Arg Ser Gln Ala Pro Ser His Arg Pro Pro Pro Pro Gly His Arg Val
    290                 295                 300

Gln His Gln Pro Gln Lys Arg Pro Pro Ala Pro Ser Gly Thr Gln Val
305                 310                 315                 320

His Gln Gln Lys Gly Pro Pro Leu Pro Arg Pro Arg Val Gln Pro Lys
                325                 330                 335

Pro Pro His Gly Ala Ala Glu Asn Ser Leu Ser Pro Ser Ser Asn Arg
            340                 345                 350

Val Lys Phe Ser Arg Ser Ala Asp Ala Pro Ala Tyr Lys Gln Gly Gln
        355                 360                 365

Asn Gln Leu Tyr Asn Glu Leu Asn Leu Gly Arg Arg Glu Glu Tyr Asp
    370                 375                 380

Val Leu Asp Lys Arg Arg Gly Arg Asp Pro Glu Met Gly Gly Lys Pro
385                 390                 395                 400

Arg Arg Lys Asn Pro Gln Glu Gly Leu Tyr Asn Glu Leu Gln Lys Asp
                405                 410                 415

Lys Met Ala Glu Ala Tyr Ser Glu Ile Gly Met Lys Gly Glu Arg Arg
            420                 425                 430

Arg Gly Lys Gly His Asp Gly Leu Tyr Gln Gly Leu Ser Thr Ala Thr
        435                 440                 445

Lys Asp Thr Tyr Asp Ala Leu His Met Gln Ala Leu Pro Pro Arg
    450                 455                 460


<210> SEQ ID NO 84
<211> LENGTH: 89
<212> TYPE: PRT
<213> ORGANISM: Homo Sapiens

<400> SEQUENCE: 84

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85
```

<210> SEQ ID NO 85
<211> LENGTH: 90
<212> TYPE: PRT
<213> ORGANISM: Homo Sapiens

<400> SEQUENCE: 85

```
Met Leu Pro Ala Pro Lys Asn Leu Val Val Ser Glu Val Thr Glu Asp
1               5                   10                  15

Ser Leu Arg Leu Ser Trp Thr Ala Pro Asp Ala Ala Phe Asp Ser Phe
            20                  25                  30

Leu Ile Gln Tyr Gln Glu Ser Glu Lys Val Gly Glu Ala Ile Asn Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Lys Gly Gly His Arg
65                  70                  75                  80

Ser Asn Pro Leu Ser Ala Glu Phe Thr Thr
                85                  90
```

<210> SEQ ID NO 86
<211> LENGTH: 270
<212> TYPE: DNA
<213> ORGANISM: Homo Sapiens

<400> SEQUENCE: 86

```
atgctgcctg caccaaagaa cctggtggtg tctcatgtga cagaggatag tgccagactg     60

tcatggactg ctcccgacgc agccttcgat agttttatca tcgtgtaccg ggagaacatc    120

gaaaccggcg aggccattgt cctgacagtg ccagggtccg aacgctctta tgacctgaca    180

gatctgaagc ccggaactga gtactatgtg cagatcgccg gcgtcaaagg aggcaatatc    240

agcttccctc tgtccgcaat cttcaccaca                                     270
```

<210> SEQ ID NO 87
<211> LENGTH: 4
<212> TYPE: PRT
<213> ORGANISM: Artificial Sequence
<220> FEATURE:
<223> OTHER INFORMATION: A-B Loop

<400> SEQUENCE: 87

```
Thr Glu Asp Ser
1
```

<210> SEQ ID NO 88
<211> LENGTH: 7
<212> TYPE: PRT
<213> ORGANISM: Artificial Sequence
<220> FEATURE:
<223> OTHER INFORMATION: A-B Loop

<400> SEQUENCE: 88

```
Thr Ala Pro Asp Ala Ala Phe
1               5
```

<210> SEQ ID NO 89
<211> LENGTH: 6
<212> TYPE: PRT
<213> ORGANISM: Artificial Sequence
<220> FEATURE:
<223> OTHER INFORMATION: A-B Loop

<400> SEQUENCE: 89

Ser Glu Lys Val Gly Glu
1 5

<210> SEQ ID NO 90
<211> LENGTH: 4
<212> TYPE: PRT
<213> ORGANISM: Artificial Sequence
<220> FEATURE:
<223> OTHER INFORMATION: D-E Loop

<400> SEQUENCE: 90

Gly Ser Glu Arg
1

<210> SEQ ID NO 91
<211> LENGTH: 5
<212> TYPE: PRT
<213> ORGANISM: Artificial Sequence
<220> FEATURE:
<223> OTHER INFORMATION: E-F Loop

<400> SEQUENCE: 91

Gly Leu Lys Pro Gly
1 5

<210> SEQ ID NO 92
<211> LENGTH: 7
<212> TYPE: PRT
<213> ORGANISM: Artificial Sequence
<220> FEATURE:
<223> OTHER INFORMATION: F-G Loop

<400> SEQUENCE: 92

Lys Gly Gly His Arg Ser Asn
1 5

<210> SEQ ID NO 93
<211> LENGTH: 411
<212> TYPE: DNA
<213> ORGANISM: Artificial Sequence
<220> FEATURE:
<223> OTHER INFORMATION: PSMA centyrin

<400> SEQUENCE: 93
atgctgcctg caccaaagaa cctggtggtg tctcgggtga ccgaggactc tgccagactg 60
agctgggcca tcgacgagca gagggattgg ttcgagagct ttctgatcca gtatcaggag 120
tccgagaaag tgggcgaggc catcgtgctg acagtgcctg gcagcgagcg gtcctatgat 180
ctgaccggcc tgaagccagg cacagagtac accgtgtcca tctacggcgt gtatcacgtg 240
tacaggtcca atcctctgtc tgccatcttc accacaacca caacccctgc ccccagacct 300
cccacacccg cccctaccat cgcgagtcag cccctgagtc tgagacctga ggcctgcagg 360
ccagctgcag gaggagctgt gcacaccagg ggcctggact tcgcctgcga c 411

<210> SEQ ID NO 94
<211> LENGTH: 92
<212> TYPE: PRT
<213> ORGANISM: Artificial Sequence
<220> FEATURE:
<223> OTHER INFORMATION: PSMA centyrin

<400> SEQUENCE: 94

Met Leu Pro Ala Pro Lys Asn Leu Val Val Ser Arg Val Thr Glu Asp
1 5 10 15

```
Ser Ala Arg Leu Ser Trp Ala Ile Asp Glu Gln Arg Asp Trp Phe Glu
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Tyr His Val
65                  70                  75                  80

Tyr Arg Ser Asn Pro Leu Ser Ala Ile Phe Thr Thr
                85                  90


<210> SEQ ID NO 95
<211> LENGTH: 336
<212> TYPE: PRT
<213> ORGANISM: Artificial Sequence
<220> FEATURE:
<223> OTHER INFORMATION: PSMA CARTyrin

<400> SEQUENCE: 95

Met Ala Leu Pro Val Thr Ala Leu Leu Leu Pro Leu Ala Leu Leu Leu
1               5                   10                  15

His Ala Ala Arg Pro Met Leu Pro Ala Pro Lys Asn Leu Val Val Ser
            20                  25                  30

Arg Val Thr Glu Asp Ser Ala Arg Leu Ser Trp Ala Ile Asp Glu Gln
        35                  40                  45

Arg Asp Trp Phe Glu Ser Phe Leu Ile Gln Tyr Gln Glu Ser Glu Lys
    50                  55                  60

Val Gly Glu Ala Ile Val Leu Thr Val Pro Gly Ser Glu Arg Ser Tyr
65                  70                  75                  80

Asp Leu Thr Gly Leu Lys Pro Gly Thr Glu Tyr Thr Val Ser Ile Tyr
                85                  90                  95

Gly Val Tyr His Val Tyr Arg Ser Asn Pro Leu Ser Ala Ile Phe Thr
            100                 105                 110

Thr Thr Thr Thr Pro Ala Pro Arg Pro Pro Thr Pro Ala Pro Thr Ile
        115                 120                 125

Ala Ser Gln Pro Leu Ser Leu Arg Pro Glu Ala Cys Arg Pro Ala Ala
    130                 135                 140

Gly Gly Ala Val His Thr Arg Gly Leu Asp Phe Ala Cys Asp Ile Tyr
145                 150                 155                 160

Ile Trp Ala Pro Leu Ala Gly Thr Cys Gly Val Leu Leu Leu Ser Leu
                165                 170                 175

Val Ile Thr Leu Tyr Cys Lys Arg Gly Arg Lys Lys Leu Leu Tyr Ile
            180                 185                 190

Phe Lys Gln Pro Phe Met Arg Pro Val Gln Thr Thr Gln Glu Glu Asp
        195                 200                 205

Gly Cys Ser Cys Arg Phe Pro Glu Glu Glu Glu Gly Gly Cys Glu Leu
    210                 215                 220

Arg Val Lys Phe Ser Arg Ser Ala Asp Ala Pro Ala Tyr Lys Gln Gly
225                 230                 235                 240

Gln Asn Gln Leu Tyr Asn Glu Leu Asn Leu Gly Arg Arg Glu Glu Tyr
                245                 250                 255

Asp Val Leu Asp Lys Arg Arg Gly Arg Asp Pro Glu Met Gly Gly Lys
            260                 265                 270

Pro Arg Arg Lys Asn Pro Gln Glu Gly Leu Tyr Asn Glu Leu Gln Lys
        275                 280                 285
```

```
Asp Lys Met Ala Glu Ala Tyr Ser Glu Ile Gly Met Lys Gly Glu Arg
    290                 295                 300

Arg Arg Gly Lys Gly His Asp Gly Leu Tyr Gln Gly Leu Ser Thr Ala
305                 310                 315                 320

Thr Lys Asp Thr Tyr Asp Ala Leu His Met Gln Ala Leu Pro Pro Arg
                325                 330                 335
```

<210> SEQ ID NO 96
<211> LENGTH: 489
<212> TYPE: DNA
<213> ORGANISM: Artificial Sequence
<220> FEATURE:
<223> OTHER INFORMATION: BCMA VH

<400> SEQUENCE: 96

```
gaagttcagc tgcttgaatc tggcggaggc ctggttcaac ctggcggatc tctgagactg     60

agctgtgccg ccagcggctt caccttcagc aattacgcca tgacctggat cagacaggcc    120

cctggcaaag gcctggaatg ggtgtccgga attacaggcg acggcggcag caccttttac    180

gccgattctg tgaagggcag attcaccatc agccgggaca acagcaagaa caccctgtac    240

ctgcagatga acagcctgag agccgaggac accgccgtgt actactgcgt gaaggactgg    300

aacaccacca tgatcaccga gagaggccag ggcacactgg tcaccgtgtc ctctacaaca    360

acaccggcgc ctagacctcc aacaccagct cctacaatcg cgagtcagcc cctgtctctc    420

agacccgaag cctgcaggcc agctgcagga ggagctgtgc acaccagggg cctggacttc    480

gcctgcgac                                                            489
```

<210> SEQ ID NO 97
<211> LENGTH: 118
<212> TYPE: PRT
<213> ORGANISM: Artificial Sequence
<220> FEATURE:
<223> OTHER INFORMATION: BCMA VH

<400> SEQUENCE: 97

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Ile Arg Gln Ala Pro Gly Lys Gly Leu Glu Trp Val
        35                  40                  45

Ser Gly Ile Thr Gly Asp Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Asp Trp Asn Thr Thr Met Ile Thr Glu Arg Gly Gln Gly Thr
            100                 105                 110

Leu Val Thr Val Ser Ser
        115
```

<210> SEQ ID NO 98
<211> LENGTH: 362
<212> TYPE: PRT
<213> ORGANISM: Artificial Sequence
<220> FEATURE:
<223> OTHER INFORMATION: BCMA VCAR

<400> SEQUENCE: 98

```
Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Asn Tyr Ala Met Thr Trp Ile Arg Gln Ala Pro Gly Lys
    50                  55                  60

Gly Leu Glu Trp Val Ser Gly Ile Thr Gly Asp Gly Gly Ser Thr Phe
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Asp Trp Asn Thr Thr Met Ile Thr Glu
        115                 120                 125

Arg Gly Gln Gly Thr Leu Val Thr Val Ser Ser Thr Thr Thr Pro Ala
    130                 135                 140

Pro Arg Pro Pro Thr Pro Ala Pro Thr Ile Ala Ser Gln Pro Leu Ser
145                 150                 155                 160

Leu Arg Pro Glu Ala Cys Arg Pro Ala Ala Gly Gly Ala Val His Thr
                165                 170                 175

Arg Gly Leu Asp Phe Ala Cys Asp Ile Tyr Ile Trp Ala Pro Leu Ala
            180                 185                 190

Gly Thr Cys Gly Val Leu Leu Leu Ser Leu Val Ile Thr Leu Tyr Cys
        195                 200                 205

Lys Arg Gly Arg Lys Lys Leu Leu Tyr Ile Phe Lys Gln Pro Phe Met
    210                 215                 220

Arg Pro Val Gln Thr Thr Gln Glu Glu Asp Gly Cys Ser Cys Arg Phe
225                 230                 235                 240

Pro Glu Glu Glu Glu Gly Gly Cys Glu Leu Arg Val Lys Phe Ser Arg
                245                 250                 255

Ser Ala Asp Ala Pro Ala Tyr Lys Gln Gly Gln Asn Gln Leu Tyr Asn
            260                 265                 270

Glu Leu Asn Leu Gly Arg Arg Glu Glu Tyr Asp Val Leu Asp Lys Arg
        275                 280                 285

Arg Gly Arg Asp Pro Glu Met Gly Gly Lys Pro Arg Arg Lys Asn Pro
    290                 295                 300

Gln Glu Gly Leu Tyr Asn Glu Leu Gln Lys Asp Lys Met Ala Glu Ala
305                 310                 315                 320

Tyr Ser Glu Ile Gly Met Lys Gly Glu Arg Arg Arg Gly Lys Gly His
                325                 330                 335

Asp Gly Leu Tyr Gln Gly Leu Ser Thr Ala Thr Lys Asp Thr Tyr Asp
            340                 345                 350

Ala Leu His Met Gln Ala Leu Pro Pro Arg
        355                 360
```

NANOTRANSPOSON COMPOSITIONS AND METHODS OF USE

CROSS REFERENCE TO RELATED APPLICATIONS

This application is a U.S. National Phase Application, filed under 35 U.S.C. § 371 of International Patent Application No. PCT/2019/067758, filed Dec. 20, 2019, which claims priority to, and the benefit of, U.S. Ser. No. 62/783,133, filed Dec. 20, 2018; U.S. Ser. No. 62/815,335, filed Mar. 7, 2019 and U.S. Ser. No. 62/815,845, filed Mar. 8, 2019. The contents of each of these applications is herein incorporated by reference in their entirety.

INCORPORATION OF SEQUENCE LISTING

The contents of the file named "POTH-047_N01_US_Seg_Listing.ST25.txt" which was created on Jun. 14, 2021 and is 302,024 bytes in size, are hereby incorporated by reference it their entirety.

FIELD OF THE DISCLOSURE

The disclosure is directed to molecular biology, and more, specifically, to nanotransposons, cell compositions comprising nanotransposons, methods of making and methods of using the same.

BACKGROUND OF THE INVENTION

There has been a long-felt but unmet need in the art for compositions and methods of improved transposition for use in gene therapy. The disclosure provides nanotransposon compositions, methods of making and methods of using these compositions which comprise non-naturally occurring structural improvements to vectors carrying transposon sequences to improve the efficacy of transposition, particularly for use in human cells as a method of modifying cells for gene therapy.

SUMMARY OF THE INVENTION

The present disclosure provides a composition comprising: a first nucleic acid sequence comprising: (a) a first inverted terminal repeat (ITR), (b) a second ITR and (c) an intra-ITR sequence, wherein the intra-ITR sequence comprises a transposon sequence; and a second nucleic acid sequence comprising an inter-ITR sequence, wherein the length of the inter-ITR sequence is between 1 and 600 nucleotides, inclusive of the endpoints. In a preferred aspect, the length of the inter-ITR sequence is between 1 and 100 nucleotides, inclusive of the endpoints. The composition can be a transposon or can be a nanotransposon. In a preferred aspect, the transposon is a piggyBac transposon.

The first nucleic acid sequence and/or second nucleic acid sequence can further comprise an origin of replication sequence. The length of the origin of replication sequence can be between 1 and 450 nucleotides. The origin of replication sequence can comprise an R6K origin of replication.

The first nucleic acid sequence and/or second nucleic acid sequence can further comprise a sequence encoding a first selectable marker. The length of the first selectable marker can be between 1 and 200 nucleotides. The first selectable marker can be a sucrose selectable marker. In a preferred aspect, the sucrose selectable marker is an RNA-OUT selection marker.

The first nucleic acid sequence and/or second nucleic acid sequence may not comprise a recombination site, an excision site, a ligation site, or a combination thereof. The first nucleic acid sequence and/or second nucleic acid sequence may not comprise a sequence encoding foreign DNA.

The first nucleic acid sequence can further comprise at least one exogenous sequence and a sequence encoding a promoter capable of expressing an exogenous sequence in a mammalian cell. The first nucleic acid sequence can further comprise at least one sequence encoding an insulator. The first nucleic acid sequence can further comprise a polyadenosine (polyA) sequence. The sequence encoding a promoter capable of expressing an exogenous sequence in a mammalian cell is capable of expressing an exogenous sequence in a human cell. The promoter can be a constitutive promoter or an inducible promoter.

The at least one exogenous sequence can comprise a sequence encoding a non-naturally occurring antigen receptor, a sequence encoding a therapeutic polypeptide, or a combination thereof. In a preferred aspect, the non-naturally occurring antigen receptor comprises a chimeric antigen receptor (CAR). The CAR can comprise: (a) an ectodomain comprising an antigen recognition region, (b) a transmembrane domain, and (c) an endodomain comprising at least one costimulatory domain. The antigen recognition region can comprise at least one single chain variable fragment (scFv), single domain antibody, Centyrin, or a combination thereof. The single domain antibody can be a VHH or a VH.

The antigen recognition region can comprise at least one anti-BCMA Centyrin. Preferably, the anti-BCMA Centyrin comprises the amino acid sequence of SEQ ID NO: 29. The antigen recognition region can comprise at least one anti-BCMA VH. Preferably, the anti-BCMA VII comprises the amino acid sequence of SEQ ID NO: 97. The antigen recognition region can comprise at least one anti-PSMA Centyrin. Preferably, the anti-PSMA. Centyrin comprises the amino acid sequence of SEQ ID NO: 94.

The ectodomain can further comprise a signal peptide. The CAR further comprises a hinge region between the antigen recognition region and the transmembrane domain. The transmembrane domain can comprise a sequence encoding a CD8 transmembrane domain. The at least one costimulatory domain can comprise a CD3ζ, costimulatory domain, a 4-1BB costimulatory domain, or a combination thereof. The at least one costimulatory domain can comprise a CD3ζ, costimulatory domain and a 4-1BB costimulatory domain, and wherein the 4-1BB costimulatory domain is located between the transmembrane domain and the CD3ζ costimulatory domain. The at least one exogenous sequence can comprise a sequence encoding an inducible proapoptotic polypeptide, a sequence encoding a second selectable marker, a sequence encoding a chimeric stimulatory receptor (CSR), a sequence encoding a transposase enzyme, a sequence encoding a self-cleaving peptide, or a combination thereof. The second selectable marker can comprise a sequence encoding a dihydrofolate reductase (DHFR) mutein enzyme.

The present disclosure also provides a polynucleotide comprising a nucleic acid sequence encoding the composition (e.g., transposon or nanotransposon) as disclosed herein and/or a polynucleotide comprising a nucleic acid sequence encoding a CAR as disclosed herein.

The present disclosure also provides a cell comprising the composition (e.g., transposon or nanotransposon) as disclosed herein. The present disclosure also provides a population of cells, wherein a plurality of the population are modified to express the CAR or the composition (e.g., transposon or nanotransposon) as disclosed herein. In an aspect, the plurality of modified cells is a plurality of modified immune cells. In an aspect, the plurality of modified cells is a plurality of modified T-cells. In an aspect, at least 50% of plurality of modified T-cells express one or more cell-surface marker(s) comprising CD45RA and CD62L and do not express one or more cell-surface marker (s) comprising CD45RO.

The present disclosure also provides a pharmaceutical composition comprising the CAR or the composition (e.g., transposon or nanotransposon) as disclosed herein and further comprises a pharmaceutically acceptable carrier.

The present disclosure also provides a method of treating a proliferation disorder in a subject in need thereof by administering a therapeutically effective amount of any of a composition (e.g., transposon or nanotransposon), a CAR, a cell, a population of cells or a pharmaceutical composition as disclosed herein. In an aspect, the proliferation disorder is cancer. The cancer can be BCMA-positive cancer or a PSMA-positive cancer. The cancer can be a primary tumor, a metastatic cancer, a multiply resistant cancer, a progressive tumor or recurrent cancer. The cancer can be a solid tumor or a hematologic cancer. The cancer can be lung cancer, a brain cancer, a head and neck cancer, a breast cancer, a skin cancer, a liver cancer, a pancreatic cancer, a stomach cancer, a colon cancer, a rectal cancer, a uterine cancer, a cervical cancer, an ovarian cancer, a prostate cancer, a testicular cancer, a skin cancer, an esophageal cancer, a lymphoma, a leukemia, acute leukemia, acute lymphoblastic leukemia (ALL), acute lymphocytic leukemia, acute myeloid leukemia (AML), acute myelogenous leukemia, chronic myelocytic leukemia (CML), chronic lymphocytic leukemia (CLL), hairy cell leukemia, myelodysplastic syndrome (MDS), Hodgkin's disease, non-Hodgkin's lymphoma, or multiple myeloma.

Figure 1:
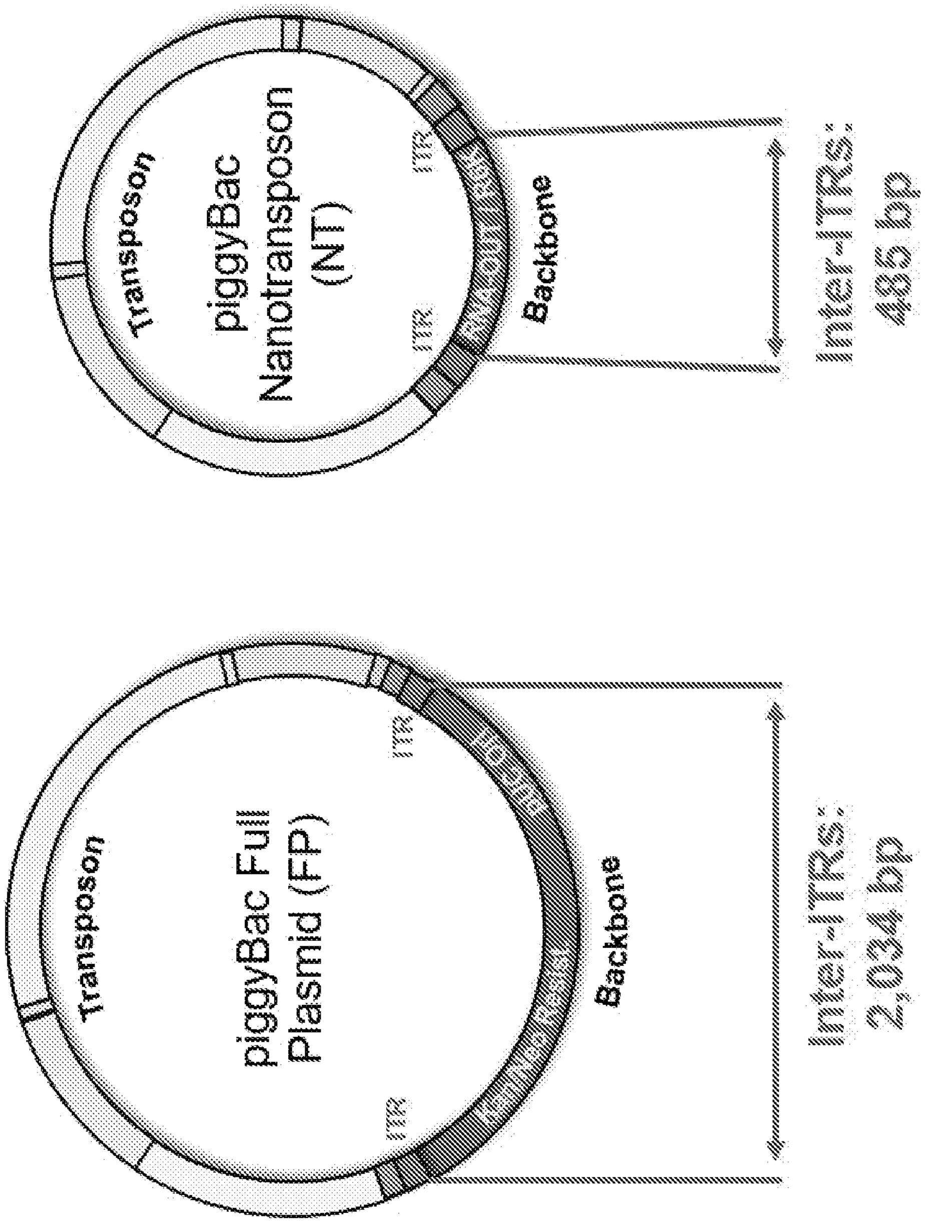
FIG. 1 is a pair of schematic diagrams comparing maps of a piggyBac full plasmid and a piggyBac nanotransposon (NT).

All documents cited herein, including any cross referenced or related patent or application is hereby incorporated herein by reference in its entirety for all purposes, unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

DETAILED DESCRIPTION OF THE INVENTION

The disclosure provides nanotransposons, compositions and cells comprising nanotransposons, methods of making nanotransposons and methods of using the nanotransposons, compositions and cells described herein.

The nanotransposons of the disclosure are designed to minimize the inter-ITR sequence of the nanotransposon to bring the first and second ITR sequences as close as possible, thereby increasing transposition efficacy and efficiency. The nanotransposons and compositions comprising nanotransposons of the disclosure are effective in every cell type; however, they are particularly effective for use in human cells. As described herein, nanotransposons of the disclosure may be used to increase transposition, and, consequently gene transfer to a human cell to a sufficiently high percentage of cells in a plurality of cells.

Without wishing to be bound by theory, by minimizing the inter-ITR sequence or distance, the corresponding transposase may be more able to bring both ITR sequences together, resulting in increased excision of the intra-ITR sequence from the nanotransposon and/or increased integration of the intra-ITR sequence into a target site. Furthermore, in preferred aspects of the disclosure, nanotransposons, backbones thereof and/or inter-ITR sequences comprise(s) no foreign DNA sequences. The lack of foreign DNA further improves transposition efficacy and efficiency, particularly when compared to a non-nanotransposon.

Compositions of the Disclosure

The present disclosure provides a composition comprising: a first nucleic acid sequence comprising: (a) a first inverted terminal repeat (ITR) or a sequence encoding a first ITR, (b) a second ITR or a sequence encoding a second ITR, and (c) an intra-ITR sequence or a sequence encoding an intra-ITR, wherein the intra-ITR sequence comprises a transposon sequence or a sequence encoding a transposon; and a second nucleic acid sequence comprising an inter-ITR sequence or a sequence encoding an inter-ITR, wherein the length of the inter-ITR sequence is equal to or less than 700 nucleotides. The second nucleic acid sequence is also referred to herein as the backbone region or non-integrating region. In an aspect, the composition is circular DNA or linear DNA. In an aspect, the composition is a plasmid or vector. In an aspect, the composition is a transposon. In a preferred aspect, the composition is a nanotransposon.

In some aspects, the length of the inter-ITR sequence is equal to or less than 650 nucleotides, equal to or less than 600 nucleotides, equal to or less than 550 nucleotides, equal to or less than 500 nucleotides, equal to or less than 450 nucleotides, equal to or less than 400 nucleotides, equal to or less than 350 nucleotides, equal to or less than 300 nucleotides, equal to or less than 250 nucleotides, equal to or less than 200 nucleotides, equal to or less than 150 nucleotides, equal to or less than 100 nucleotides, equal to or less than 50 nucleotides, equal to or less than 25 nucleotides, or equal to or less than 10 nucleotides. In some aspects, the length of the second nucleic acid sequence is equal to or less than 700 nucleotides, equal to or less than 650 nucleotides, equal to or less than 600 nucleotides, equal to or less than 550 nucleotides, equal to or less than 500 nucleotides, equal to or less than 450 nucleotides, equal to or less than 400 nucleotides, equal to or less than 350 nucleotides, equal to or less than 300 nucleotides, equal to or less than 250 nucleotides, equal to or less than 200 nucleotides, equal to or less than 150 nucleotides, equal to or less than 100 nucleotides, equal to or less than 50 nucleotides, equal to or less than 25 nucleotides, or equal to or less than 10 nucleotides.

The present disclosure provides a composition comprising: a first nucleic acid sequence comprising: (a) a first inverted terminal repeat (ITR) or a sequence encoding a first ITR, (h) a second Mk or a sequence encoding a second ITR, and (c) an intra-ITR sequence or a sequence encoding an intra-ITR, wherein the intra-ITR sequence comprises a transposon sequence or a sequence encoding a transposon; and a second nucleic acid sequence comprising an inter-ITR sequence or a sequence encoding an inter-ITR, wherein the length of the inter-ITR sequence is between 1 and 700 nucleotides, inclusive of the endpoints. The second nucleic acid sequence is also referred to herein as the backbone region or non-integrating region. In an aspect, the composition is circular DNA or linear DNA. In an aspect, the composition is a plasmid or vector. In an aspect, the composition is a transposon. In a preferred aspect, the composition is a nanotransposon.

In some aspects, the length of the inter-UR sequence is between 1 and 650 nucleotides, between 1 and 600 nucleotides, between 1 and 550 nucleotides, between 1 and 500 nucleotides, between 1 and 450 nucleotides, between 1 and 400 nucleotides, between 1 and 350 nucleotides, between 1 and 300 nucleotides, between 1 and 250 nucleotides, between 1 and 200 nucleotides, between 1 and 150 nucleotides, between 1 and 100 nucleotides, between 1 and 50 nucleotides, between 1 and 25 nucleotides or between 1 and 10 nucleotides, each range inclusive of the endpoints. In some aspects, the length of the second nucleic acid sequence is between 1 and 650 nucleotides, between 1 and 600 nucleotides, between 1 and 550 nucleotides, between 1 and 500 nucleotides, between 1 and 450 nucleotides, between 1 and 400 nucleotides, between 1 and 350 nucleotides, between 1 and 300 nucleotides, between 1 and 250 nucleotides, between 1 and 200 nucleotides, between 1 and 150 nucleotides, between 1 and 100 nucleotides, between 1 and 50 nucleotides, between 1 and 25 nucleotides or between 1 and 10 nucleotides, each range inclusive of the endpoints.

In some aspects, the length of the inter-ITR sequence is between 1 and 25 nucleotides, between 1 and 50 nucleotides, between 25 and 50 nucleotides, between 50 and 100 nucleotides, between 100 and 150 nucleotides, between 150 and 200 nucleotides, between 200 and 250 nucleotides, between 250 and 300 nucleotides, between 300 and 350 nucleotides, between 350 and 400 nucleotides, between 400 and 450 nucleotides, between 450 and 500 nucleotides, between 500 and 550 nucleotides, between 550 and 600 nucleotides, between 600 and 650 nucleotides, between 650 and 700 nucleotides, each range inclusive of the endpoints. In some aspects, the length of the second nucleic acid sequence is between 1 and 25 nucleotides, between 1 and 50 nucleotides, between 25 and 50 nucleotides, between 50 and 100 nucleotides, between 100 and 150 nucleotides, between 150 and 200 nucleotides, between 200 and 250 nucleotides, between 250 and 300 nucleotides, between 300 and 350 nucleotides, between 350 and 400 nucleotides, between 400 and 450 nucleotides, between 450 and 500 nucleotides, between 500 and 550 nucleotides, between 550 and 600 nucleotides, between 600 and 650 nucleotides, between 650 and 700 nucleotides, each range inclusive of the endpoints.

In some aspects, including the short nanotransposons (NTS) of the disclosure, the length of the inter-ITR sequence is between 1 and 10 nucleotides, between 10 and 20 nucleotides, between 20 and 30 nucleotides, between 30 and 40 nucleotides, between 40 and 50 nucleotides, between 50 and 60 nucleotides, between 60 and 70 nucleotides, between 70 and 80 nucleotides, between 80 and 90 nucleotides, or between 90 and 100 nucleotides, each range inclusive of the endpoints. In some aspects, including the short nanotransposons (NTS) of the disclosure, the length of the nucleic acid sequence is between 1 and 10 nucleotides, between 10 and 20 nucleotides, between 20 and 30 nucleotides, between 30 and 40 nucleotides, between 40 and 50 nucleotides, between 50 and 60 nucleotides, between 60 and 70 nucleotides, between 70 and 80 nucleotides, between 80 and 90 nucleotides, or between 90 and 100 nucleotides, each range inclusive of the endpoints.

In some aspects, the length of the intra-ITR sequence is greater than or equal to 100 nucleotides, greater than or equal to 500 nucleotides, greater than or equal to 1000 nucleotides, greater than or equal to 1500 nucleotides, greater than or equal to 2000 nucleotides, greater than or equal to 2500 nucleotides, greater than or equal to 3000 nucleotides, greater than or equal to 3500 nucleotides, greater than or equal to 4000 nucleotides, greater than or equal to 4500 nucleotides, greater than or equal to 5000 nucleotides, greater than or equal to 5500 nucleotides, greater than or equal to 6000 nucleotides, greater than or equal to 6500 nucleotides, greater than or equal to 7000 nucleotides, greater than or equal to 7500 nucleotides, greater than or equal to 8000 nucleotides, greater than or equal to 8500 nucleotides, greater than or equal to 9000 nucleotides, greater than or equal to 9500 nucleotides, greater than or equal to 10000 nucleotides (10 kilobases (kb)), greater than or equal to 50000 nucleotides (50 kb), greater than or equal to 100000 nucleotides (100 kb), greater than or equal to 150000 nucleotides (150 kb), greater than or equal to 200000 nucleotides (200 kb), greater than or equal to 250000 nucleotides (250 kb), greater than or equal to 300000 nucleotides (300 kb), greater than or equal to 350000 nucleotides (350 kb), greater than or equal to 400000 nucleotides (400 kb), greater than or equal to 450000 nucleotides (450 kb), greater than or equal to 500000 nucleotides (50 kb), or any number of nucleotides in between. In some aspects, the length of the second nucleic acid sequence is greater than or equal to 100 nucleotides, greater than or equal to 500 nucleotides, greater than or equal to 1000 nucleotides, greater than or equal to 1500 nucleotides, greater than or equal to 2000 nucleotides, greater than or equal to 2500 nucleotides, greater than or equal to 3000 nucleotides, greater than or equal to 3500 nucleotides, greater than or equal to 4000 nucleotides, greater than or equal to 4500 nucleotides, greater than or equal to 5000 nucleotides, greater than or equal to 5500 nucleotides, greater than or equal to 6000 nucleotides, greater than or equal to 6500 nucleotides, greater than or equal to 7000 nucleotides, greater than or equal to 7500 nucleotides, greater than or equal to 8000 nucleotides, greater than or equal to 8500 nucleotides, greater than or equal to 9000 nucleotides, greater than or equal to 9500 nucleotides, greater than or equal to 10000 nucleotides (10 kilobases (kb)), greater than or equal to 50000 nucleotides (50 kb), greater than or equal to 100000 nucleotides (100 kb), greater than or equal to 150000 nucleotides (150 kb), greater than or equal to 200000 nucleotides (200 kb), greater than or equal to 250000 nucleotides (250 kb), greater than or equal to 300000 nucleotides (300 kb), greater than or equal to 350000 nucleotides (350 kb), greater than or equal to 400000 nucleotides (400 kb), greater than or equal to 450000 nucleotides (450 kb), greater than or equal to 500000 nucleotides (50 kb), or any number of nucleotides in between.

The composition can further comprise an origin of replication sequence or a sequence encoding an replication sequence. The first nucleic acid sequence or the second nucleic acid sequence can further comprise an origin of replication sequence or a sequence encoding an replication sequence. Preferably, the first nucleic acid sequence comprises an origin of replication sequence or a sequence encoding an replication sequence.

In some aspects, the length of the origin of replication sequence is equal to or less than 450 nucleotides, equal to or less than 400 nucleotides, equal to or less than 350 nucleotides, equal to or less than 300 nucleotides, equal to or less than 250 nucleotides, equal to or less than 200 nucleotides, equal to or less than 150 nucleotides, equal to or less than 100 nucleotides, equal to or less than 50 nucleotides, equal to or less than 25 nucleotides, or equal to or less than 10 nucleotides. In some aspects, the length of the origin of replication sequence is between 1 and 450 nucleotides, between 1 and 400 nucleotides, between 1 and 350 nucleotides, between 1 and 300 nucleotides, between 1 and 250 nucleotides, between 1 and 200 nucleotides, between 1 and 150 nucleotides, between 1 and 100 nucleotides, between 1 and 50 nucleotides, between 1 and 25 nucleotides, or between 1 and 10 nucleotides, each range inclusive of the endpoints.

The origin of replication sequence can comprise an R6K origin of replication. The R6K origin of replication can comprise an R6K gamma origin of replication. The origin of replication sequence can comprise a mini origin of replication. The mini origin of replication can comprise an R6K mini origin of replication. The R6K mini origin of replication can comprise an R6K gamma mini origin of replication. The length of the R6K gamma mini origin of replication is 281 nucleotides (281 base pairs) and comprises, consists essentially of, or consists of the nucleic acid sequence of SEQ ID NO: 15.

The composition can further comprise first selectable marker or a sequence encoding a first selectable marker. The first nucleic acid sequence or the second nucleic acid sequence can further comprise a first selectable marker or a sequence encoding a first selectable marker. Preferably, the first nucleic acid sequence comprises a first selectable marker or a sequence encoding a first selectable marker.

In some aspects, the length of the first selectable marker is equal to or less than 450 nucleotides, equal to or less than 200 nucleotides, equal to or less than 150 nucleotides, equal to or less than 100 nucleotides, equal to or less than 50 nucleotides, equal to or less than 25 nucleotides, or equal to or less than 10 nucleotides. In some aspects, the length of the first selectable marker is between 1 and 200 nucleotides, between 1 and 150 nucleotides, between 1 and 100 nucleotides, between 1 and 50 nucleotides, between 1 and 25 nucleotides, or between 1 and 10 nucleotides, each range inclusive of the endpoints.

The first selectable marker can comprise a sucrose-selectable marker, a fluorescent marker, a cell surface marker, or a combination thereof. In a preferred aspect, the first selectable marker comprises, consists essentially of, or consists of a sucrose-selectable marker. In a preferred aspect, the sucrose-selectable marker comprises an RNA-OUT selection marker. The length of the RNA-OUT selection marker is 139 nucleotides (139 base pairs) and comprises, consists essentially of or consists of the nucleic acid sequence of SEQ ID NO: 16.

The sequence encoding a first ITR or the sequence encoding a second ITR can comprise a TFAA, a TTAT, or a TTAX recognition sequence. The sequence encoding a first ITR or the sequence encoding a second ITR can comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 nucleotides.

The sequence encoding a first ITR or the sequence encoding a second ITR can comprise, can consist essentially of, or can consist of a nucleic acid sequence at least 70%, 75%, 80%, 85%, 90%, 95%, 96%, 97%, 98%, 99% or 100% (or any percentage in between) identical to SEQ ID NO: 24, The sequence encoding a first or the sequence encoding a second ITR can comprise, can consist essentially of, or can consist of a nucleic acid sequence at least 70%, 75%, 80%, 85%, 90%, 95%, 96%, 97%, 98%, 99% or 100% (or any percentage in between) identical to SEQ ID NO: 25. The sequence encoding a first ITR or the sequence encoding a second ITR can comprise, can consist essentially of, or can consist of a nucleic acid sequence at least 70%, 75%, 80%, 85%, 90%, 95%, 96%, 97%, 98%, 99% or 100% (or any percentage in between) identical to SEQ ID NO: 26, The sequence encoding a first ITR or the sequence encoding a second Mk can comprise, can consist essentially of, or can consist of a nucleic acid sequence at least 70%, 75%, 80%, 85%, 90%, 95%, 96%, 97%, 98%, 99% or 100% (or any percentage in between) identical to SEQ ID NO: 27. The sequence encoding a first ITR or the sequence encoding a second ITR can comprise, can consist essentially of, or can consist of a nucleic acid sequence at least 70%, 75%, 80%, 85%, 90%, 95%, 96%, 97%, 98%, 99% or 100% (or any percentage in between) identical to SEQ ID NO: 2. The sequence encoding a first ITR or the sequence encoding a second ITR can comprise, can consist essentially of, or can consist of a nucleic acid sequence at least 70%, 75%, 80%, 85%, 90%, 95%, 96%, 97%, 98%, 99% or 100% (or any percentage in between) identical to SEQ ID NO: 14.

In an aspect, the sequence encoding a first ITR comprises the nucleic acid sequence of SEQ ID NO: 24 and the second sequence encoding a second ITR comprises the nucleic acid sequence of SEQ ID NO: 25. In an aspect, the sequence encoding a first ITR comprises the nucleic acid sequence of SEQ ID NO: 24 and the second sequence encoding a second ITR comprises the nucleic acid sequence of SEQ ID NO: 26. In an aspect, the sequence encoding a first ITR comprises the nucleic acid sequence of SEQ ID NO: 24 and the second sequence encoding a second ITR comprises the nucleic acid sequence of SEQ ID NO: 27.

The first nucleic acid sequence can further comprise at least one exogenous sequence and at least one promoter capable of expressing an exogenous sequence in a mammalian cell. In a preferred aspect, the promoter is capable of expressing an exogenous sequence in a human cell. In a preferred aspect, the transposon sequence of the composition comprises the at least one exogenous sequence and at least one promoter capable of expressing an exogenous sequence in a mammalian cell.

The promoter can be a constitutive promoter. The promoter can be an inducible promoter. The promoter can be a cell-type or tissue-type specific promoter. The promoter can be a EF1a promoter (SEQ ID NO: 4), a CMV promoter, an MND promoter, an SV40 promoter, a PGK1 promoter, a Ubc promoter, a CAG promoter, an H1 promoter, or a U6 promoter. In a preferred aspect, the promoter is a EF1a promoter. In an aspect, the first nucleic acid sequence comprises a first sequence encoding a first promoter capable of expressing a first exogenous sequence in a mammalian cell and a second sequence encoding a second promoter capable of expressing a second exogenous sequence in mammalian cell, wherein the first promoter is a constitutive promoter and wherein the second promoter is an inducible promoter. In an aspect, the first sequence encoding the first promoter and the second sequence encoding the second promoter are oriented in opposite directions.

The at least one exogenous sequence comprises, consists essentially of, or consists of a sequence encoding a non-naturally occurring antigen receptor, a sequence encoding a therapeutic polypeptide, or a combination thereof. The non-naturally occurring antigen receptor can comprise a chimeric antigen receptor (CAR), a T cell Receptor (TCR), a chimeric stimulatory receptor (CSR), an HLA class I histocompatibility antigen, alpha chain E recombinant polypeptide (HLA-E), Beta-2-Microglobulin (B2M) recombinant polypeptide, or a combination thereof. TCRs, CSRs, HLA-Es and B2Ms are described in detail herein. In a preferred aspect, the non-naturally occurring antigen receptor comprises a CAR.

The at least one exogenous sequence can further comprise, consist essential of, or consist of a sequence encoding an inducible proapoptotic polypeptide. Inducible proapoptotic polypeptides are described in detail herein.

The at least one exogenous sequence can further comprise, consist essential of, or consist of a sequence encoding a second selectable marker. The second selectable marker can encode a gene product essential for cell viability and survival. The second selectable marker can encode a gene product essential for cell viability and survival when challenged by selective cell culture conditions. Selective cell culture conditions may comprise a compound harmful to cell viability or survival and wherein the gene product confers resistance to the compound. Non-limiting examples of selection genes include neo (conferring resistance to neomycin), DHFR (encoding Dihydrofolate Reductase and conferring resistance to Methotrexate), TYMS (encoding Thymidylate Synthetase), MGMT (encoding O(6)-methylguanine-DNA methyltransferase), multidrug resistance gene (MDR1), ALDH1 (encoding Aldehyde dehydrogenase 1 family, member A1), FRANCF, RAD51C (encoding RAD51 Paralog C), GCS (encoding glucosylceramide synthase), NKX2.2 (encoding NK2 Homeobox 2), or any combination thereof.

The second selectable marker can be a detectable marker. The detectable marker can be a fluorescent marker, a cell-surface marker or a metabolic marker. In a preferred aspect, the second selectable marker comprises a sequence encoding a dihydrofolate reductase (DHFR) mutein enzyme. The DHFR mutein enzyme comprises, consists essentially of, or consists of the amino acid sequence of SEQ ID NO: 52. The DHFR mutein enzyme is encoded by a polynucleotide comprising, consisting essential of, or consisting of the nucleic acid sequence of SEQ ID NO: 53 or SEQ ID NO: 11. The amino acid sequence of the DHFR mutein enzyme can further comprise a mutation at one or more of positions 80, 113, or 153. The amino acid sequence of the DHFR mutein enzyme can comprise one or more of a substitution of a Phenylalanine (F) or a Leucine (L) at position 80, a substitution of a Leucine (L) or a Valine (V) at position 113, and a substitution of a Valine (V) or an Aspartic Acid (D) at position 153.

The at least one exogenous sequence can further comprise, consist essential of or consist of a sequence encoding at least one self-cleaving peptide. For example, a self-cleaving peptide can be located between a CAR and an inducible proapoptotic polypeptide; or, a self-cleaving peptide can be located between a CAR and second selectable marker.

The at least one exogenous sequence can further comprise, consist essential of, or consist of a sequence encoding at least two self-cleaving peptides. For example, a first self-cleaving peptide is located upstream or immediately upstream of a CAR and a second self-cleaving peptide is located downstream or immediately downstream of a CAR; or, the first self-cleaving peptide and the second self-cleaving peptide flank a CAR. For example, a first self-cleaving peptide is located upstream or immediately upstream of an inducible proapoptotic polypeptide and a second self-cleaving peptide is located downstream or immediately downstream of an inducible proapoptotic polypeptide; or, the first self-cleaving peptide and the second self-cleaving peptide flank an inducible proapoptotic polypeptide. For example, a first self-cleaving peptide is located upstream or immediately upstream of a second selectable marker and a second self-cleaving peptide is located downstream or immediately downstream of a second selectable marker; or, the first self-cleaving peptide and the second self-cleaving peptide flank a second selectable marker.

Non-limiting examples of self-cleaving peptides include a T2A peptide, GSG-T2A peptide, an E2A peptide, a GSG-E2A peptide, an F2A peptide, a GSG-F2A peptide, a P2A peptide, or a GSG-P2A peptide. A T2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 54. A GSG-T2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 55. A GSG-T2A polypeptide is encoded by a polynucleotide comprising or consisting of an nucleic acid sequence at least 75%, 80%, 85%, 90%, 95%, 96%, 97%, 98%, 99% or 100% (or any percentage in between) identical to SEQ ID NO: 7, SEQ ID NO: 8, SEC) ID NO: 10, SEQ ID NO: 56. A E2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 57. A GSG-E2A peptide comprises, consists essential of, or consists of; the amino acid sequence at least 75%, 80%, 85%, 90%, 95%, 96%, 97%, 98%, 99% or 100% (or any percentage in between) identical to SEQ ID NO: 58. A F2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 59. A GSG-F2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 60. A P2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 61. A GSG-P2A peptide comprises, consists essential of, or consists of, the amino acid sequence at least 75%, 80%, 85%, 90%, 95%, 96%, 97%, 98%, 99% or 100% (or any percentage in between) identical to SEQ ID NO: 62.

The first nucleic acid sequence comprising at least one exogenous sequence and at least one promoter capable of expressing an exogenous sequence in a mammalian cell can further comprise at least one sequence encoding an insulator. In an aspect, the first nucleic acid sequence can comprise a first sequence encoding a first insulator and a second sequence encoding a second insulator. In some embodiments the sequence encoding a first or second insulator comprises, consists essential of, or consists of, the nucleic acid sequence at least 75%, 80%, 85%, 90%, 95%, 96%, 97%, 98%, 99% or 100% (or any percentage in between) identical to SEQ ID NO: 3 or SEQ ID NO: 13.

The first nucleic acid sequence comprising at least one exogenous sequence and at least one promoter capable of expressing an exogenous sequence in a mammalian cell can further comprise a polyadenosine (polyA) sequence. The first nucleic acid sequence comprising at least one exogenous sequence, at least one promoter capable of expressing an exogenous sequence in a mammalian cell and at least one sequence encoding an insulator can further comprise a polyadenosine (polyA) sequence. The polyA sequence can be isolated or derived from a viral polyA sequence. The polyA sequence can be isolated or derived from an (SV40) polyA sequence. In some embodiments the sequence encoding a first or second insulator comprises, consists essential of, or consists of, the nucleic acid sequence at least 75%, 80%, 85%, 90%, 95%, 96%, 97%, 98%, 99% or 100% (or any percentage in between) identical to SEQ ID NO: 12.

In an aspect, the composition does not comprise a sequence encoding foreign DNA. In an aspect, the first nucleic acid sequence does not comprise a sequence encoding foreign DNA. In an aspect, the second nucleic acid sequence does not comprise a sequence encoding foreign DNA. In an aspect, the composition comprises a sequence encoding foreign DNA. In an aspect, the first nucleic acid sequence comprises a sequence encoding foreign DNA. In an aspect, the second nucleic acid sequence comprises a sequence encoding foreign DNA. Foreign DNA is an DNA sequence which is not derived or obtained from the same organism as the mammalian cell in which the exogenous sequence will be expressed. For example, foreign DNA could be DNA from a virus, rather than a mammal; or the foreign DNA could be DNA from a reptile, rather than a mammal. In another aspect, the foreign DNA could be from one mammal but that mammal is different from the mammal in which the exogenous sequence will be expressed. For example, the foreign DNA is from a rat rather than a human.

In an aspect, the composition does not comprise a recombination site, an excision site, a ligation site, or a combination thereof. In an aspect, the composition does not comprise a product of a recombination event, an excision event, a ligation event, or a combination thereof. In an aspect, the composition is not derived from a recombination event, an excision event, a ligation event, or a combination thereof.

In an aspect, the first nucleic acid sequence does not comprise a recombination site, an excision site, a ligation site, or a combination thereof. In an aspect, the first nucleic acid sequence does not comprise a product of a recombination event, an excision event, a ligation event, or a combination thereof. In an aspect, the first nucleic acid sequence is not derived from a recombination event, an excision event, a ligation event, or a combination thereof.

In an aspect, the second nucleic acid sequence does not comprise a recombination site, an excision site, a ligation site, or a combination thereof. In an aspect, the second nucleic acid sequence does not comprise a product of a recombination event, an excision event, a ligation event, or a combination thereof. In an aspect, the second nucleic acid sequence is not derived from a recombination event, an excision event, a ligation event, or a combination thereof.

A recombination site can comprise a sequence resulting from a recombination event, can comprise a sequence that is a product of a recombination event, or can comprise an activity of a recombinase (e.g., a recombinase site).

Chimeric Antigen Receptor (CAR)

The present disclosure also provides a composition (e.g., nanotransposon) comprising a CAR, wherein the CAR comprises an ectodomain comprising antigen recognition region; a transmembrane domain, and an endodomain comprising at least one costimulatory domain. The CAR can further comprise a hinge region between the antigen recognition domain and the transmembrane domain.

The antigen recognition region can comprise at least one single chain variable fragment (scFv), Centyrin, single domain antibody, or a combination thereof. In an aspect, the at least one single domain antibody is a VHH. In an aspect, the at least one single domain antibody is a VH.

scFv

The compositions of the disclosure (e.g., transposons or nanotransposons) can comprise a CAR; and in some aspects, the antigen recognition region of the CAR can comprise one or more scFv compositions to recognize and bind to a specific target protein/antigen. The antigen recognition region can comprise at least two scFvs. The antigen recognition region can comprise at least three says. In an aspect, a CAR of the disclosure is a bi-specific CAR comprising at least two scFvs that specifically bind two distinct antigens.

The scFv compositions comprise a heavy chain variable region and a light chain variable region of an antibody. An scFv is a fusion protein of the variable regions of the heavy (VH) and light (VL) chains of immunoglobulins, and the VH and VL domains are connected with a short peptide linker. An scFv can retain the specificity of the original immunoglobulin, despite removal of the constant regions and the introduction of the linker. In some aspects, the linker polypeptide comprises, consists essentially of, or consists of the amino acid sequence of SEQ ID NO: 33. The linker polypeptide can be encoded by a polynucleotide comprising, consisting essentially of, or consists of the nucleic acid sequence of SEQ ID NO: 34.

Centyrin

The compositions of the disclosure (e.g., transposons or nanotransposons) can comprise a CAR; and in some aspects, the antigen recognition region of the CAR can comprise one or more Centyrin compositions to recognize and bind to a specific target protein/antigen. Centyrins that specifically bind an antigen may be used to direct the specificity of a cell, (e.g., a cytotoxic immune cell) towards the specific antigen, A CAR comprising a Centyrin is referred to herein as a CARTyrin.

Centyrins of the disclosure may comprise a protein scaffold, wherein the scaffold is capable of specifically binding an antigen. Centyrins of the disclosure may comprise a protein scaffold comprising a consensus sequence of at least one fibronectin type III (FN3) domain, wherein the scaffold is capable of specifically binding an antigen. The at least one fibronectin type III (FN3) domain may be derived from a human protein. The human protein may be Tenascin-C. The consensus sequence comprises, consists essentially of, or consists of an amino acid sequence at least 74%, 75%, 80%, 85%, 90%, 95%, 96%, 97%, 98%, 99% or 100% (or any percentage in between) identical to SEQ ID NO: 84 or the consensus sequence comprises, consists essentially of, or consists of an amino acid sequence at least 74%, 75%, 80%, 85%, 90%, 95%, 96%, 97%, 98%, 99% or 100% (or any percentage in between) identical to SEQ ID NO: 85. The consensus sequence is encoded by a polynucleotide comprising, consisting essentially of, or consisting of a nucleic acid sequence at least 75%, 80%, 85%, 90%, 95%, 96%, 97%, 98%, 99% or 100% (or any percentage in between) identical to SEQ ID NO: 86.

The consensus sequence can be modified at one or more positions within (a) a A-B loop comprising or consisting of the amino acid residues TEDS (SEQ ID NO: 87) at positions 13-16 of the consensus sequence; (b) a B-C loop comprising or consisting of the amino acid residues TAPDAAF (SEQ ID NO: 88) at positions 22-28 of the consensus sequence; (c) a C-D loop comprising or consisting of the amino acid residues SEK VGE (SEQ ID NO: 89) at positions 38-43 of the consensus sequence; (d) a D-E loop comprising or consisting of the amino acid residues GSER (SEQ ID NO: 90) at positions 51-54 of the consensus sequence; (e) a E-F loop comprising or consisting of the amino acid residues GLKPG (SEQ ID NO: 91) at positions 60-64 of the consensus sequence; (f) a F-G-loop comprising or consisting of the amino acid residues KGGHRSN (SEQ ID NO: 92) at positions 75-81 of the consensus sequence; or (g) any combination of (a)-(f). Centyrins of the disclosure may comprise a consensus sequence of at least 5 fibronectin type III (ENS) domains, at least 10 fibronectin type III (FN3) domains or at least 15 fibronectin type III (FN3) domains.

The term "antibody mimetic" is intended to describe an organic compound that specifically binds a target sequence and has a structure distinct from a naturally-occurring antibody. Antibody mimetics may comprise a protein, a nucleic acid, or a small molecule. The target sequence to which an antibody mimetic of the disclosure specifically binds may be an antigen. Antibody mimetics may provide superior properties over antibodies including, but not limited to, superior solubility, tissue penetration, stability towards heat and enzymes (e.g., resistance to enzymatic degradation), and lower production costs. Exemplary antibody mimetics include, but are not limited to, an affibody, an affilin, an affimer, an affitin, an alphabody, an anticalin, and avimer (also known as avidity multimer), a DARPin (Designed Ankyrin Repeat Protein), a Fynomer, a Kunitz domain peptide, and a monobody.

Affibody molecules of the disclosure comprise a protein scaffold comprising or consisting of one or more alpha helix without any disulfide bridges. Preferably, affibody molecules of the disclosure comprise or consist of three alpha helices. For example, an affibody molecule of the disclosure may comprise an immunoglobulin binding domain. An affibody molecule of the disclosure may comprise the Z domain of protein A.

Affilin molecules of the disclosure comprise a protein scaffold produced by modification of exposed amino acids of, for example, either gamma-B crystallin or ubiquitin, molecules functionally mimic an antibody's affinity to antigen, but do not structurally mimic an antibody. In any protein scaffold used to make an affilin, those amino acids that are accessible to solvent or possible binding partners in a properly-folded protein molecule are considered exposed amino acids. Any one or more of these exposed amino acids may be modified to specifically bind to a target sequence or antigen.

Affimer molecules of the disclosure comprise a protein scaffold comprising a highly stable protein engineered to display peptide loops that provide a high affinity binding site for a specific target sequence. Exemplary affimer molecules of the disclosure comprise a protein scaffold based upon a cystatin protein or tertiary structure thereof. Exemplary affimer molecules of the disclosure may share a common tertiary structure of comprising an alpha-helix lying on top of an anti-parallel beta-sheet.

Affitin molecules of the disclosure comprise an artificial protein scaffold, the structure of which may be derived, for example, from a DNA binding protein (e.g., the DNA binding protein Sac7d). Affitins of the disclosure selectively bind a target sequence, which may be the entirety or part of an antigen. Exemplary affitins of the disclosure are manufactured by randomizing one or more amino acid sequences on the binding surface of a DNA binding protein and subjecting the resultant protein to ribosome display and selection. Target sequences of affitins of the disclosure may be found, for example, in the genome or on the surface of a peptide, protein, virus, or bacteria. In some aspects, an affitin molecule may be used as a specific inhibitor of an enzyme. Affitin molecules of the disclosure may include heat-resistant proteins or derivatives thereof.

Alphabody molecules of the disclosure may also be referred to as Cell-Penetrating Alphabodies (CPAB), Alphabody molecules of the disclosure comprise small proteins (typically of less than 10 kDa) that bind to a variety of target sequences (including antigens). Alphabody molecules are capable of reaching and binding to intracellular target sequences. Structurally, alphabody molecules of the disclosure comprise an artificial sequence forming single chain alpha helix (similar to naturally occurring coiled-coil structures). Alphabody molecules of the disclosure may comprise a protein scaffold comprising one or more amino acids that are modified to specifically bind target proteins. Regardless of the binding specificity of the molecule, alphabody molecules of the disclosure maintain correct folding and thermostability.

Anticalin molecules of the disclosure comprise artificial proteins that bind to target sequences or sites in either proteins or small molecules. Anticalin molecules of the disclosure may comprise an artificial protein derived from a human lipocalin. Anticalin molecules of the disclosure may be used in place of, for example, monoclonal antibodies or fragments thereof. Anticalin molecules may demonstrate superior tissue penetration and thermostability than monoclonal antibodies or fragments thereof. Exemplary anticalin molecules of the disclosure may comprise about 180 amino acids, having a mass of approximately 20 kDa. Structurally, anticalin molecules of the disclosure comprise a barrel structure comprising antiparallel beta-strands pairwise connected by loops and an attached alpha helix. In some aspects, anticalin molecules of the disclosure comprise a barrel structure comprising eight antiparallel beta-strands pairwise connected by loops and an attached alpha helix.

Avimer molecules of the disclosure comprise an artificial protein that specifically binds to a target sequence (which may also be an antigen). Avimers of the disclosure may recognize multiple binding sites within the same target or within distinct targets. When an avimer of the disclosure recognize more than one target, the avimer mimics function of a bi-specific antibody. The artificial protein avimer may comprise two or more peptide sequences of approximately 30-35 amino acids each. These peptides may be connected via one or more linker peptides. Amino acid sequences of one or more of the peptides of the avimer may be derived from an A domain of a membrane receptor. Avimers have a rigid structure that may optionally comprise disulfide bonds and/or calcium. Avimers of the disclosure may demonstrate greater heat stability compared to an antibody.

DARPins (Designed Ankyrin Repeat Proteins) of the disclosure comprise genetically-engineered, recombinant, or chimeric proteins having high specificity and high affinity for a target sequence. In some aspects, DARPins of the disclosure are derived from ankyrin proteins and, optionally, comprise at least three repeat motifs (also referred to as repetitive structural units) of the ankyrin protein. Ankyrin proteins mediate high-affinity protein-protein interactions. DARPins of the disclosure comprise a large target interaction surface.

Fynomers of the disclosure comprise small binding proteins (about 7 kDa) derived from the human Fyn SH3 domain and engineered to bind to target sequences and molecules with equal affinity and equal specificity as an antibody.

Kunitz domain peptides of the disclosure comprise a protein scaffold comprising a Kunitz domain. Kunitz domains comprise an active site for inhibiting protease activity. Structurally, Kunitz domains of the disclosure comprise a disulfide-rich alpha+beta fold. This structure is exemplified by the bovine pancreatic trypsin inhibitor. Kunitz domain peptides recognize specific protein structures and serve as competitive protease inhibitors. Kunitz domains of the disclosure may comprise Ecallantide (derived from a human lipoprotein-associated coagulation inhibitor (LACI)).

Monobodies of the disclosure are small proteins (comprising about 94 amino acids and having a mass of about 10 kDa) comparable in size to a single chain antibody. These genetically engineered proteins specifically bind target sequences including antigens. Monobodies of the disclosure may specifically target one or more distinct proteins or target sequences. In some aspects, monobodies of the disclosure comprise a protein scaffold mimicking the structure of human fibronectin, and more preferably, mimicking the structure of the tenth extracellular type III domain of fibronectin. The tenth extracellular type III domain of fibronectin, as well as a monobody mimetic thereof, contains seven beta sheets forming a barrel and three exposed loops on each side corresponding to the three complementarity determining regions (CDRs) of an antibody. In contrast to the structure of the variable domain of an antibody, a monobody lacks any binding site for metal ions as well as a central disulfide bond. Mufti specific monobodies may be optimized by modifying the loops BC and FG. Monobodies of the disclosure may comprise an adnectin.

VHH

The compositions of the disclosure (e.g., transposons or nanotransposons) can comprise a CAR; and in some aspects, the antigen recognition region of the CAR can comprise at least one single domain antibodies (SdAb) to recognize and bind to a specific target protein/antigen. In an aspect, the single domain antibody is a VHH. A VHH is a heavy chain antibody found in camelids. A VHH that specifically binds an antigen may be used to direct the specificity of a cell, (e.g., a cytotoxic immune cell) towards the specific antigen. The antigen recognition region can comprise at least two VHHs. The antigen recognition region can comprise at least three VHHs. In an aspect, a CAR of the disclosure is a bi-specific CAR comprising at least two that specifically bind two distinct antigens. A CAR comprising a is referred to herein as a VCAR.

At least one VHH protein or VCAR of the disclosure can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley &. Sons, Inc., NY (1994-2001); Colligan et al., Current Protocols in Protein Science, John Wiley & Sons, NY, N.Y., (1997-2001).

Amino acids from a VHH protein can be altered, added and/or deleted to reduce immunogenicity or reduce, enhance or modify binding, affinity, on-rate, off-rate, avidity, specificity, half-life, stability, solubility or any other suitable characteristic, as known in the art.

Optionally, VHH proteins can be engineered with retention of high affinity for the antigen and other favorable biological properties. To achieve this goal, the VHH proteins can be optionally prepared by a process of analysis of the parental sequences and various conceptual engineered products using three-dimensional models of the parental and engineered sequences. Three-dimensional models are commonly available and are familiar to those skilled in the art. Computer programs are available which illustrate and display probable three-dimensional conformational structures of selected candidate sequences and can measure possible immunogenicity (e.g., Immunofilter program of Xencor, Inc. of Monrovia, Calif.). Inspection of these displays permits analysis of the likely role of the residues in the functioning of the candidate sequence, i.e., the analysis of residues that influence the ability of the candidate VHH protein to bind its antigen. In this way, residues can be selected and combined from the parent and reference sequences so that the desired characteristic, such as affinity for the target antigen(s), is achieved. Alternatively, or in addition to, the above procedures, other suitable methods of engineering can be used. Screening VHH for specific binding to similar proteins or fragments can be conveniently achieved using nucleotide (DNA or RNA display) or peptide display libraries, for example, in vitro display. Competitive assays can be performed with the VHH or VCAR of the disclosure in order to determine what proteins, antibodies, and other antagonists compete for binding to a target protein with the VHH or VCAR of the present disclosure and/or share the epitope region. These assays as readily known to those of ordinary skill in the art evaluate competition between antagonists or ligands for a limited number of binding sites on a protein VH The compositions of the disclosure (e.g., transposons or nanotransposons) can comprise a CAR; and in some aspects, the antigen recognition region of the CAR can comprise at least one single domain antibodies (SdAb) to recognize and bind to a specific target protein/antigen. In an aspect, the single domain antibody is a VH. A VH is a single domain binder derived from common IgG. A VH that specifically binds an antigen may be used to direct the specificity of a cell, (e.g., a cytotoxic immune cell) towards the specific antigen. The antigen recognition region can comprise at least two VHs. The antigen recognition region can comprise at least three VHs. In an aspect, a CAR of the disclosure is a bi-specific CAR comprising at least two VHs that specifically bind two distinct antigens.

The VH can be isolated or derived from a human sequence. The VH can comprise a human CDR sequence and/or a human framework sequence and a non-human or humanized sequence (e.g., a rat Fc domain). In some aspects, the VH is a fully humanized VH. In some aspects, the VH is neither a naturally occurring antibody nor a fragment of a naturally occurring antibody. In some aspects, the VII is not a fragment of a monoclonal antibody. In some aspects, the VH is a UniDab antibody (TeneoBio). In some aspects, the VH is be modified to remove an domain or a portion thereof. In some aspects, a framework sequence of the VH is modified to, for example, improve expression, decrease immunogenicity or to improve function.

The VH can be fully engineered using the UniRat (TeneoBio) system and "NGS-based Discovery" to produce the VH. Using this method, the specific VH are not naturally-occurring and are generated using fully engineered systems. The VH are not derived from naturally-occurring monoclonal antibodies (mAbs) that were either isolated directly from the host (for example, a mouse, rat or human) or directly from a single clone of cells or cell line (hybridoma). These VHs were not subsequently cloned from said cell lines. Instead, VH sequences are fully-engineered using the UniRat system as transgenes that comprise human variable regions (VH domains) with a rat Fc domain, and are thus human/rat chimeras without a light chain and are unlike the standard mAb format. The native rat genes are knocked out and the only antibodies expressed in the rat are from transgenes with VH domains linked to a Rat Fc (UniAbs). These are the exclusive Abs expressed in the UniRat. Next generation sequencing (NGS) and bioinformatics are used to identify the full antigen-specific repertoire of the heavy-chain antibodies generated by UniRat after immunization. Then, a unique gene assembly method is used to convert the antibody repertoire sequence information into large collections of fully-human heavy-chain antibodies that can be screened in vitro for a variety of functions. In some aspects, fully humanized VH are generated by fusing the human VH domains with human Fcs in vitro (to generate a non-naturally occurring recombinant VH antibody), In some aspects, the VH are fully humanized, but they are expressed in vivo as human/rat chimera (human WI, rat Fe) without a light chain. Fully humanized VHs are expressed in vivo as human/rat chimera (human VH, rat Fe) without a light chain are about 80 kDa. (vs 150 kDa).

A CAR of the present disclosure may bind human antigen with at least one affinity selected from a $K_D$ of less than or equal to $10^{-9}$M, less than or equal to $10^{-10}$M, less than or equal to $10^{-11}$M, less than or equal to $10^{-12}$M, less than or equal to $10^{-13}$M, less than or equal to $10^{-14}$M, and less than or equal to $10^{-15}$M. The $K_D$ may be determined by any means, including, but not limited to, surface plasmon resonance.

In an aspect, the antigen recognition region of the disclosed CAR comprises at least one anti-BCMA Centyrin. The anti-BCMA Centyrin comprises, consists essentially of, or consists of the amino acid sequence at least 95%, 96%, 97%, 98%, 99% or 100% (or any percentage in between) identical to SEQ ID NO: 29. The anti-BCMA Centyrin is encoded by a polynucleotide comprising, consisting essentially of, or consisting of the nucleic acid sequence at least 95%, 96%, 97%, 98%, 99% or 100% (or any percentage in between) identical to SEQ ID NO: 28.

A CAR comprising the anti-BCMA Centyrin is referred to as a BCMA CARTyrin herein. In a preferred aspect, the BCMA CARTyrin comprises, consists essentially of, or consists of the amino acid sequence at least 95%, 96%, 97%, 98%, 99% or 100% (or any percentage in between) identical to SEQ ID NO:30. The BCMA CARTyrin is encoded by a polynucleotide comprising, consisting essentially of, or consisting of the nucleic acid sequence at least 95%, 96%, 97%, 98%, 99% or 100% (or any percentage in between) identical to SEQ ID NO: 9.

Figure 13:
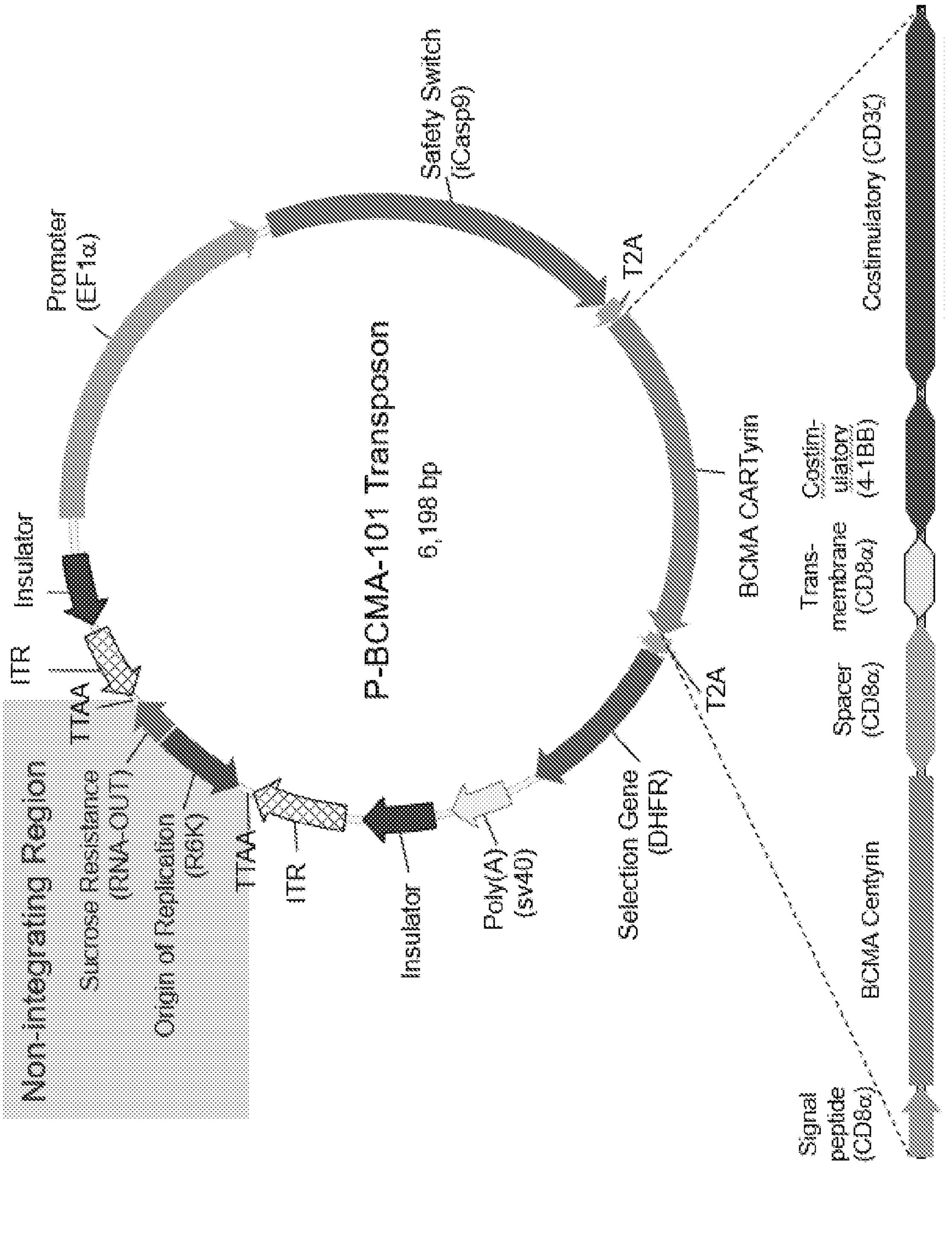
FIG. 13 is a schematic diagram depicting a P-BCMA-101 piggyBac NT encoding a BCMA Centyrin CAR (CARTyrin). The nanotransposon encodes ITR #1, Insulator #1, EF1alpha promoter, BMCA CARTyrin, SV40 PA, Insulator #2, and ITR #2. The sequence also encodes nanotransposon elements RNA-OUT and R6K origin.

A composition of the disclosure (e.g., nanotransposon) comprising a BCMA CARTyrin comprises, consists essentially of, or consists of the amino acid sequence at least 95%, 96%, 97%, 98%, 99% or 100% (or any percentage in between) identical to SEQ ID NO: 17. A composition of the disclosure (e.g., nanotransposon) comprising a BCMA CARTyrin is encoded by a polynucleotide comprising, consisting essentially of, or consisting of the nucleic acid sequence at least 95%, 96%, 97%, 98%, 99% or 100% (or any percentage in between) identical to SEQ ID NO: 1. A composition of the disclosure (e.g., nanotransposon) comprising the BCMA CARTyrin is also referred to herein as P-BCMA-101-Transposon (as illustrated in FIG. 13).

In an aspect, the antigen recognition region of the disclosed CAR comprises at least one anti-PSMA Centyrin. The anti-PSMA Centyrin comprises, consists essentially of, or consists of the amino acid sequence at least 95%, 96%, 97%, 98%, 99% or 100% (or any percentage in between) identical to SEQ ID NO: 94. The anti-PSMA Centyrin is encoded by a polynucleotide comprising, consisting essentially of, or consisting of the nucleic acid sequence at least 95%, 96%, 97%, 98%, 99% or 100% (or any percentage in between) identical to SEQ ID NO: 93.

A CAR comprising the anti-PSMA Centyrin is referred to as a PSMA CARTyrin herein. In a preferred aspect, the PSMA CARTyrin comprises, consists essentially of, or consists of the amino acid sequence at least 95%, 96%, 97%, 98%, 99% or 100% (or any percentage in between) identical to SEQ ID NO: 95. The PSMA CARTyrin is encoded by a polynucleotide comprising, consisting essentially of, or consisting of the nucleic acid sequence at least 95%, 96%, 97%, 98%, 99% or 100% (or any percentage in between) identical to SEQ ID NO: 19.

Figure 14:
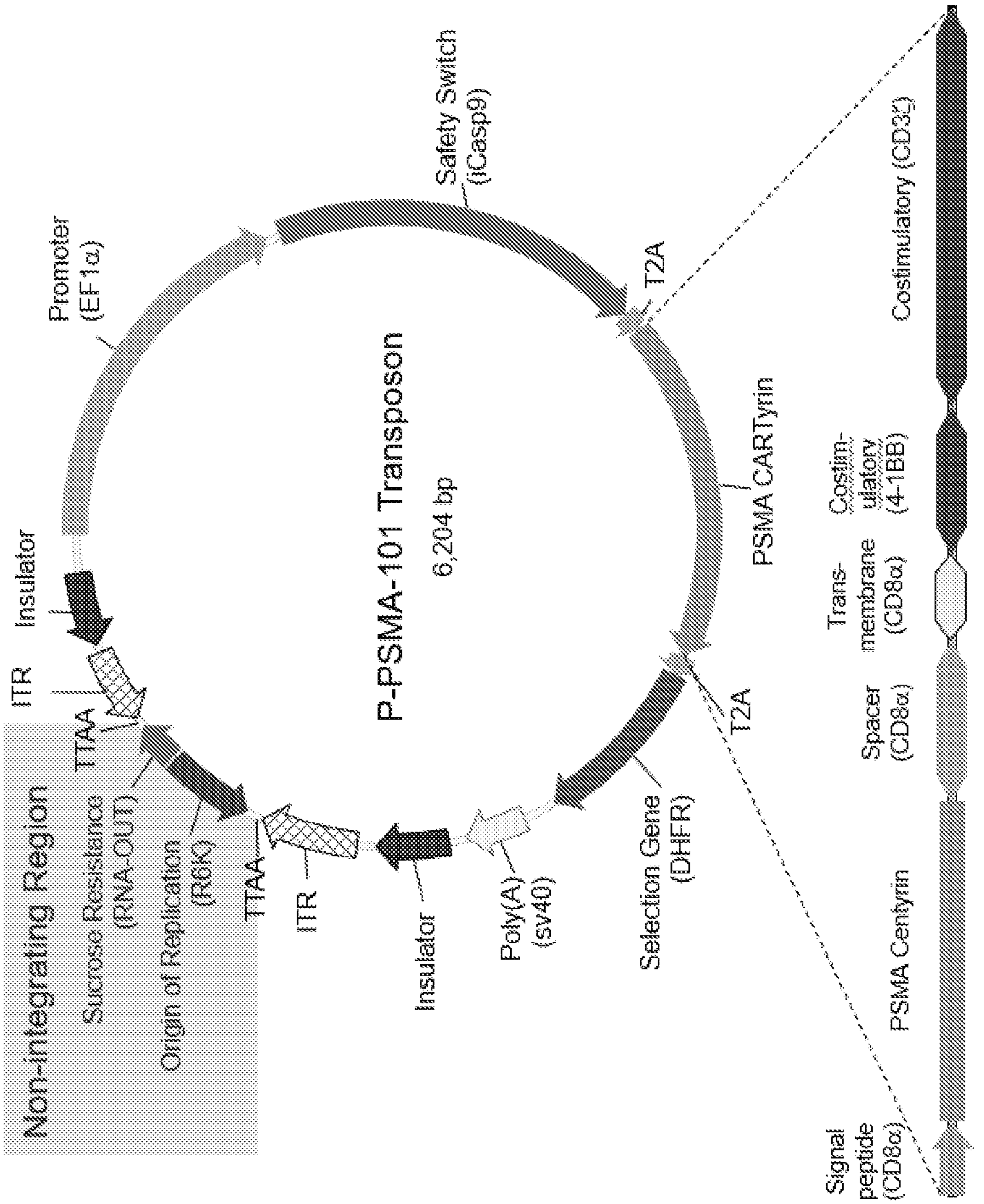
FIG. 14 is a schematic diagram depicting a P-PSMA-101 piggyBac NT encoding a PSMA CARTyrin. The nanotransposon encodes ITR #1, Insulator #1, EF1alpha promoter, PSMA CARTyrin, SV40 PA, Insulator #2, and ITR #2. The sequence also encodes nanotransposon elements RNA-OUT and R6K origin.

A composition of the disclosure (e.g., nanotransposon) comprising a PSMA CARTyrin comprises, consists essentially of, or consists of the amino acid sequence at least 95%, 96%, 97%, 98%, 99% or 100% (or any percentage in between) identical to SEQ ID NO: 20. A composition of the disclosure (e.g., nanotransposon) comprising a PSMA CAR-Tyrin is encoded by a polynucleotide comprising, consisting essentially of, or consisting of the nucleic acid sequence at least 95%, 96%, 97%, 98%, 99% or 100% (or any percentage in between) identical to SEQ ID NO: 18. A composition of the disclosure (e.g., nanotransposon) comprising the PSMA CARTyrin is also referred to herein as P-PSMA-101 Transposon (as illustrated in FIG. 14).

In an aspect, the antigen recognition region of the disclosed CAR comprises at least one anti-BCMA VH. The anti-BCMA VH comprises, consists essentially of, or consists of the amino acid sequence at least 95%, 96%, 97%, 98%, 99% or 100% (or any percentage in between) identical to SEQ ID NO: 97. The anti-BCMA VH is encoded by a polynucleotide comprising, consisting essentially of, or consisting of the nucleic acid sequence at least 95%, 96%, 97%, 98%, 99% or 100% (or any percentage in between) identical to SEQ ID NO: 96.

A CAR comprising the anti-BCMA VH is referred to as a BCMA VCAR herein. In a preferred aspect, the BCMA VCAR comprises, consists essentially of, or consists of the amino acid sequence at least 95%, 96%, 97%, 98%, 99% or 100% (or any percentage in between) identical to SEQ ID NO: 98. The BCMA VCAR is encoded by a polynucleotide comprising, consisting essentially of, or consisting of the nucleic acid sequence at least 95%, 96%, 97%, 98%, 99% or 100% (or any percentage in between) identical to SEQ ID NO: 22.

Figure 15:
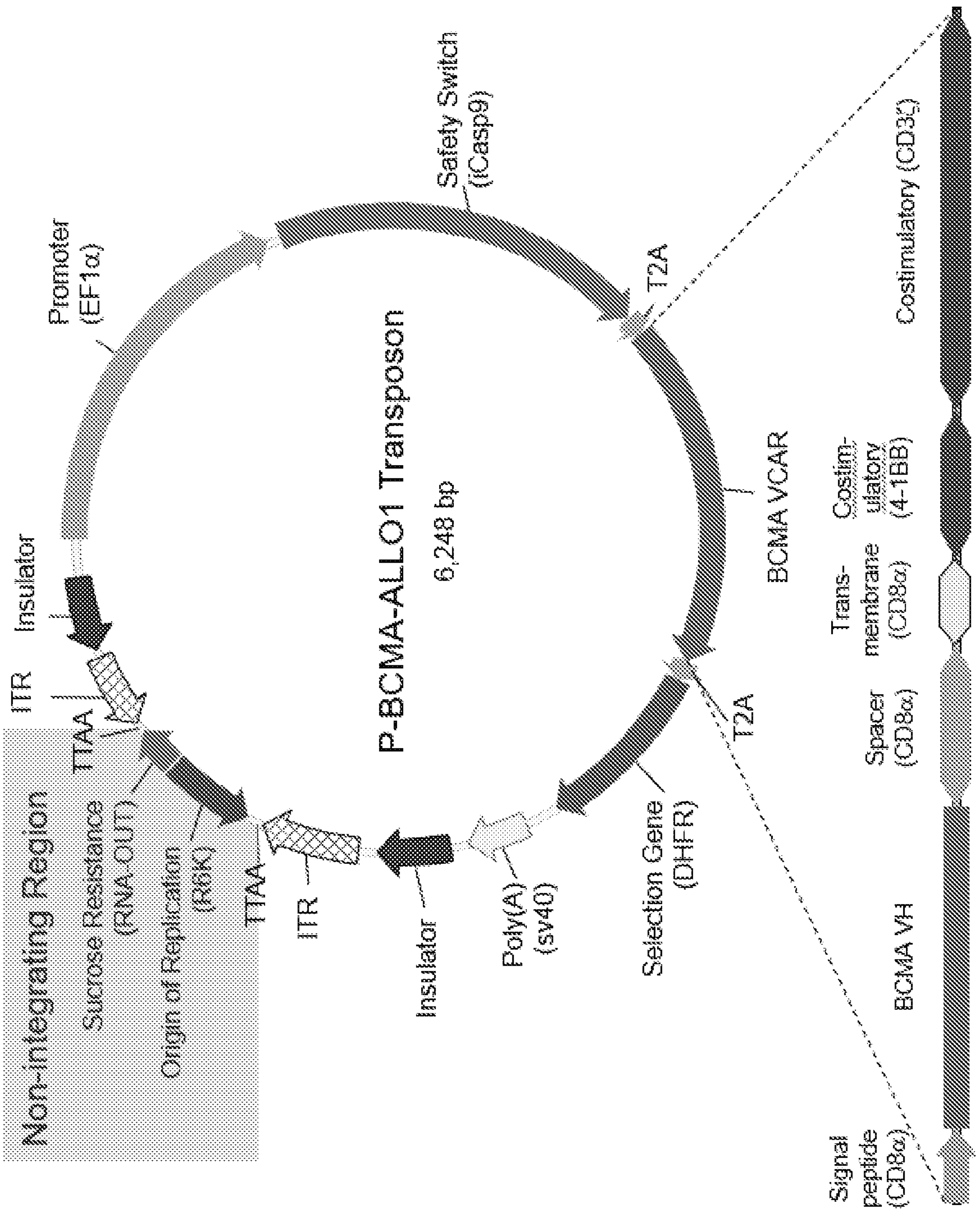
FIG. 15 is a schematic diagram depicting a P-BCMA-ALLO1 piggyBac nanotransposon encoding a BCMA VH CAR (VCAR). The nanotransposon encodes ITR #1, Insulator #1, EF1 alpha promoter, BMCA VCAR, SV40 PA, Insulator #2, and ITR #2. The sequence also encodes nanotransposon elements RNA-OUT and R6K origin.

A composition of the disclosure (e.g., nanotransposon) comprising a BCMA VCAR comprises, consists essentially of, or consists of the amino acid sequence at least 95%, 96%, 97%, 98%, 99% or 100% (or any percentage in between) identical to SEQ ID NO: 23. A composition of the disclosure (e.g., nanotransposon) comprising a BCMA VCAR is encoded by a polynucleotide comprising, consisting essentially of, or consisting of the nucleic acid sequence at least 95%, 96%, 97%, 98%, 99% or 100% (or any percentage in between) identical to SEQ ID NO: 21. A composition of the disclosure (e.g., nanotransposon) comprising the BCMA VCAR is also referred to herein as P-BCMA-ALLO1-Transposon (as illustrated in FIG. 15).

The ectodomain can comprise a signal peptide. The signal peptide can comprise a sequence encoding a human CD2, CD3δ, CD3ε, CD3γ, CD3ζ, CD4, CD8α, CD19, CD28, 4-1BB or GM-CSFR signal peptide. In a preferred aspect, the signal peptide comprises, consists essentially of, or consists of: a human CD8 alpha (CD8α) signal peptide (SP) or a portion thereof. The human CD8α SP comprises, consists essentially of, or consists of an amino acid sequence at least 75%, 80%, 85%, 90%, 95%, 96%, 97%, 98%, 99% or 100% (or any percentage in between) identical to SEQ ID NO: 31. Preferably, the human CD8α SP comprises, consists essentially of, or consists of the amino acid sequence of SEQ ID NO: 31.

The human CD8α. SP is encoded by a polynucleotide comprising, consisting essentially of or consisting of a nucleic acid sequence at least 75%, 80%, 85%, 90%, 95%, 96%, 97%, 98%, 99% or 100% (or any percentage in between) identical to SEQ ID NO: 32. Preferably, the human CD8α SP is encoded by a polynucleotide comprising, consisting essentially of, or consisting of the amino acid sequence of SEQ ID NO: 32.

The hinge domain or hinge region can comprise a human CD8α, IgG4, CD4 sequence, or a combination thereof. In a preferred aspect, the hinge can comprise, consist essentially of, or consist of a human CD8 alpha (CD8α) hinge or a portion thereof. The human CD8α, hinge comprises, consists essentially, of or consists of an amino acid sequence at least 75%, 80%, 85%, 90%, 95%, 96%, 97%, 98%, 99% or 100% (or any percentage in between) identical to SEQ ID NO: 35. Preferably, the human CD8α hinge domain comprises, consists essentially of, or consists of the amino acid sequence of SEQ ID NO: 35.

The human CD8α hinge is encoded by a polynucleotide comprising, consisting essentially of or consisting of a nucleic acid sequence at least 75%, 80%, 85%, 90%, 95%, 96%, 97%, 98%, 99% or 100% (or any percentage in between) identical to SEQ ID NO: 36, Preferably, the human CD8α hinge domain is encoded by a polynucleotide comprising, consisting essentially of or consisting of the nucleic acid sequence of SEQ ID NO: 36.

The transmembrane domain can comprise, consist essentially of, or consist of a sequence encoding a human CD2, CD3δ, CD3ε, CD3γ, CD3ζ, CD4, CD8α, CD19, CD28, 4-113B or GM-CSFR transmembrane domain. Preferably, the transmembrane domain can comprise, consist essentially of, or consist of a human CD8 alpha (CD8α) transmembrane domain, or a portion thereof. The CD8α transmembrane domain comprises, consists essentially of or consists of an amino acid sequence at least 75%, 80%, 85%, 90%, 95%, 96%, 97%, 98%, 99% or 100% (or any percentage in between) identical to SEQ ID NO: 37. Preferably, the human CD8α transmembrane domain comprises, consists essentially of, or consists of the amino acid sequence of SEQ ID NO: 37.

The CD8α transmembrane domain is encoded by a polynucleotide comprising, consisting essentially of, or consisting of a nucleic acid sequence at least 75%, 80%, 85%, 90%, 95%, 96%, 97%, 98%, 99% or 100% (or any percentage in between) identical to SEQ ID NO: 38. Preferably, the CD8α transmembrane domain is encoded by a polynucleotide comprising, consisting essentially of, or consisting of the nucleic acid sequence of SEQ ID NO: 38.

The at least one costimulatory domain can comprise, consist essentially of, or consist of a human 4-1 BB, CD28, CD3 zeta (CD3ζ), CD40, ICOS, MyD88, OX-40 intracellular domain, or any combination thereof. Preferably, the at least one costimulatory domain comprises a CD3ζ, a 4-1BB costimulatory domain, or a combination thereof.

The 4-1BB intracellular domain comprises, consists essentially of, or consists of an amino acid sequence at least 75%, 80%, 85%, 90%, 95%, 96%, 97%, 98%, 99% or 100% (or any percentage in between) identical to SEQ ID NO: 39. Preferably, the 4-1BB intracellular domain comprises, consists essentially of, or consists of the amino acid sequence of SEQ ID NO: 39.

The 4-1BB intracellular domain is encoded by a polynucleotide comprising, consisting essentially of or consisting of a nucleic acid sequence at least 75%, 80%, 85%, 90%, 95%, 96%, 97%, 98%, 99% or 100% (or any percentage in between) identical to SEQ ID NO: 40. Preferably, the 4-1BB intracellular domain is encoded by a polynucleotide comprising, consisting essentially of or consisting of the nucleic acid sequence of SEQ ID NO: 40.

The CD3c intracellular domain comprises, consists essentially of, or consists of an amino acid sequence at least 75%, 80%, 85%, 90%, 95%, 96%, 97%, 98%, 99% or 100% for any percentage in between) identical to SEQ ID NO: 41. Preferably, the CD37 intracellular domain comprises, consists essentially of, or consists of the amino acid sequence of SEQ ID NO: 41.

The CD3ζ intracellular domain is encoded by a polynucleotide comprising, consisting essentially of, or consisting of a nucleic acid sequence at least 75%, 80%, 85%, 90%, 95%, 96%, 97%, 98%, 99% or 100% (or any percentage in between) identical to SEQ ID NO: 42. Preferably, the CD3ζ, intracellular domain is encoded by a polynucleotide comprising, consisting essentially of, or consisting of the nucleic acid sequence of SEQ ID NO: 42.

Transposon and Vector Compositions

Transposition Systems

The present disclosure provides a transposon or a nanotransposon comprising: a first nucleic acid sequence comprising: (a) a first inverted terminal repeat (ITR) or a sequence encoding a first ITR, (h) a second ITR or a sequence encoding a second ITR, and (c) an intra-ITR sequence or a sequence encoding an intra-ITR, wherein the intra-ITR sequence comprises a transposon sequence or a sequence encoding a transposon; and a second nucleic acid sequence comprising an inter-ITR sequence or a sequence encoding an inter-ITR, wherein the length of the inter-ITR sequence is equal to or less than 700 nucleotides.

The transposon or nanotransposon of the disclosure comprises a protein scaffold (e.g., a CAR comprising at least one scFv, single domain antibody or Centyrin). The transposon or nanotransposon can be a plasmid DNA transposon comprising a sequence encoding a protein scaffold (e.g., a CAR comprising at least one scFv, single domain antibody or Centyrin) flanked by two cis-regulatory insulator elements. The transposon or nanotransposon can further comprises a plasmid comprising a sequence encoding a transposase. The sequence encoding the transposase may be a DNA sequence or an RNA sequence. Preferably, the sequence encoding the transposase is an mRNA sequence.

The transposon or nanotransposon of the present disclosure can be a piggyBac™ (PB) transposon. In some aspects when the transposon is a PB transposon, the transposase is a piggyBac™ (PB) transposase a piggyBac-like (PBL) transposase or a Super piggyBac™ (SPB) transposase. Preferably, the sequence encoding the SPB transposase is an mRNA sequence.

Non-limiting examples of PB transposons and PB, PBL and SPB transposases are described in detail in U.S. Pat. Nos. 6,218,182; 6,962,810; 8,399,643 and PCT Publication No. WO 2010/099296.

The PB, PBL and SPB transposases recognize transposon-specific inverted terminal repeat sequences (ITRs) on the ends of the transposon, and inserts the contents between the ITRs at the sequence 5'-TTAT-3' within a chromosomal site (a TTAT target sequence) or at the sequence 5'-TTAA-3' within a chromosomal site (a TTAA target sequence). The target sequence of the PB or PBL transposon can comprise or consist of 5'-CTAA-3', 5'-TTAG-3', 5'-ATAA-3', 5'-TCAA-3', 5' AGTT-3', 5-ATTA-3', 5'-GTTA-3', 5'-TTGA-3', 5'TTTA-3', 5'-TTAC-3', 5'-ACTA-3', 5'-AGGG-3', 5'-CTAG-3', 5'-TGAA-3', 5'-AGGT-3',5'-ATCA-3', 5'-CTCC-3', 5'-TAAA-3', 5'-TCTC-3', 5'TGAA-3', 5'-AAAT-3', 5'-AATC-3', 5'-ACAA-3', 5'-ACAT-3', 5'-ACTC-3', 5'-AGTG-3', 5'-ATAG-3', 5'-CAAA-3', 5'-CACA-3', 5'-CATA-3', 5'-CCAG-3', 5'-CCCA-3', 5'-CGTA-3', 5'-GTCC-3', 5'-TAAG-3', 5'-TCTA-3', 5'-TGAG-3', 5'-TGTT-3', 5'-TTCA-3'5'-TTCT-3' and 5'-TTTT-3'. The PB or PBL transposon system has no payload limit for the genes of interest that can be included between the ITRs.

Exemplary amino acid sequence for one or more PB, PBL and SPB transposases are disclosed in U.S. Pat. Nos. 6,218,185; 6,962,810 and 8,399,643 In a preferred aspect, the PB transposase comprises or consists of an amino acid sequence at least 75%, 80%, 85%, 90%, 95%, 96%, 97%, 98%, 99% or 100% (or any percentage in between) identical to SEQ ID NO: 63.

The PB or PBL transposase can comprise or consist of an amino acid sequence having an amino acid substitution at two or more, at three or more or at each of positions 30, 165, 282, or 538 of the sequence of SEQ ID NO: 63. The transposase can be a SPB transposase that comprises or consists of the amino acid sequence of the sequence of SEQ ID NO: 63 wherein the amino acid substitution at position 30 can be a substitution of a valine (V) for an isoleucine (I), the amino acid substitution at position 165 can be a substitution of a serine (S) for a glycine (G), the amino acid substitution at position 282 can be a substitution of a valine (V) for a methionine (M), and the amino acid substitution at position 538 can be a substitution of a lysine (K) for an asparagine (N). In a preferred aspect, the SPB transposase comprises or consists of an amino acid sequence at least 75%, 80%, 85%, 90%, 95%, 96%, 97%, 98%, 99% or 100% (or any percentage in between) identical to SEQ ID NO: 64.

In certain aspects wherein the transposase comprises the above-described mutations at positions 30, 165, 282 and/or 538, the PB, PBL and SPB transposases can further comprise an amino acid substitution at one or more of positions 3, 46, 82, 103, 119, 125, 177, 180, 185, 187, 200, 207, 209, 226, 235, 240, 241, 243, 258, 296, 298, 311, 315, 319, 327, 328, 340, 421, 436, 456, 470, 486, 503, 552, 570 and 591 of the sequence of SEQ ID NO: 63 or SEQ ID NO: 64 are described in more detail in PCT Publication No. WO 2019/173636 and PCT/US2019/049816.

The PB, PBL or SPB transposases can be isolated or derived from an insect, vertebrate, crustacean or urochordate as described in more detail in PCT Publication No. WO 2019/173636 and PCT/US2019/049816. In preferred aspects, the PB, PBL or SPB transposases is be isolated or derived from the insect *Trichoplusia ni* (GenBank Accession No. AAA87375) *Bombyx mori* (GenBank Accession No. BAD11135).

A hyperactive PB or PBL transposase is a transposase that is more active than the naturally occurring variant from which it is derived. In a preferred aspect, a hyperactive PB or PBL transposase is isolated or derived from *Bombyx mori* or *Xenopus tropicalis*. Examples of hyperactive PB or PBL transposases are disclosed in U.S. Pat. Nos. 6,218,185; 6,962,810, 8,399,643 and WO 2019/173636. A list of hyperactive amino acid substitutions is disclosed in U.S. Pat. No. 10,041,077.

In some aspects, the PB or PBL transposase is integration deficient. An integration deficient PB or PBL transposase is a transposase that can excise its corresponding transposon, but that integrates the excised transposon at a lower frequency than a corresponding wild type transposase. Examples of integration deficient PB or PBL transposases are disclosed in U.S. Pat. Nos. 6,218,185; 6,962,810, 8,399,643 and WO 2019/173636. A list of integration deficient amino acid substitutions is disclosed in U.S. Pat. No. 10,041,077.

In some aspects, the PB or PBL transposase is fused to a nuclear localization signal. Examples of PB or PBL transposases fused to a nuclear localization signal are disclosed in U.S. Pat. Nos. 6,218,185; 6,962,810, 8,399,643 and WO 2019/173636.

A transposon or nanotransposon of the present disclosure can be a Sleeping Beauty transposon. In some aspects, when the transposon is a Sleeping Beauty transposon, the transposase is a Sleeping Beauty transposase (for example as disclosed in U.S. Pat. No. 9,228,180) or a hyperactive Sleeping Beauty (SB100X) transposase. In a preferred aspect, the Sleeping Beauty transposase comprises or consists of an amino acid sequence at least 75%, 80%, 85%, 90%, 95%, 96%, 97%, 98%, 99% or 100% (or any percentage in between) identical to SEQ ID NO: 65. In a preferred aspect, hyperactive Sleeping Beauty (SB100X) transposase comprises or consists of an amino acid sequence at least 75%, 80%, 85%, 90%, 95%, 96%, 97%, 98%, 99% or 100% (or any percentage in between) identical to SEQ ID NO: 66.

A transposon or nanotransposon of the present disclosure can be a Helraiser transposon. An exemplary Helraiser transposon includes Helibat1, which comprises or consists of a nucleic acid sequence at least 75%, 80%, 85%, 90%, 95%, 96%, 97%, 98%, 99%, 100% (or any percentage in between) identical to SEQ ID NO: 67. In some aspects, when the transposon is a Helraiser transposon, the transposase is a Helitron transposase (for example, as disclosed in WO 2019/173636), In a preferred aspect, Helitron transposase comprises or consists of an amino acid sequence at least 75%, 80%, 85%, 90%, 95%, 96%, 97%, 98%, 99% or 100% (or any percentage in between) identical to SEQ ID NO: 68.

A transposon or nanotransposon of the present disclosure can be a Tol2 transposon. An exemplary Tol2 transposon, including inverted repeats, subterminal sequences and the Tol2 transposase, comprises or consists of a nucleic acid sequence at least 75%, 80%, 85%, 90%, 95%, 96%, 97%, 98%, 99% or 100% (or any percentage in between) identical to SEQ ID NO: 69. In some aspects, when the transposon is a Tol2 transposon, the transposase is a Tol2 transposase (for example, as disclosed in WO 2019/173636). In a preferred aspect, Tol2 transposase comprises or consists of an amino acid sequence at least 75%, 80%, 85%, 90%, 95%, 96%, 97%, 98%, 99% or 100% (or any percentage in between) identical to SEQ ID NO: 70.

A transposon or nanotransposon of the present disclosure can be a TcBuster transposon. In some aspects, when the transposon is a TcBuster transposon, the transposase is a TcBuster transposase or a hyperactive TcBuster transposase (for example, as disclosed in WO 2019/173636). The TcBuster transposase can comprise or consist of a naturally occurring amino acid sequence or a non-naturally occurring amino acid sequence. In a preferred aspect, a TcBuster transposase comprises or consists of an amino acid sequence at least 75%, 80%, 85%, 90%, 95%, 96%, 97%, 98%, 99% or 100% (or any percentage in between) identical to SEQ ID NO: 71. The polynucleotide encoding a TcBuster transposase can comprise or consist of a naturally occurring nucleic acid sequence or a non-naturally occurring nucleic acid sequence. In a preferred aspect, a TcBuster transposase is encoded by a polynucleotide comprising or consisting of an nucleic acid sequence at least 75%, 80%, 85%, 90%, 95%, 96?, 97%, 98%, 99% or 100% (or any percentage in between) identical to SEQ ID NO: 72.

In some aspects, a mutant TcBuster transposase comprises one or more sequence variations when compared to a wild type TcBuster transposase as described in more detail in PCT Publication No. WO 2019/173636 and PCT/US2019/049816.

The cell delivery compositions (e.g., transposons) disclosed herein can comprise a nucleic acid encoding a therapeutic protein or therapeutic agent. Examples of therapeutic proteins include those disclosed in PCT Publication No. WO 2019/173636 and PCT/US2019/049816.

Vector Systems

In some aspects, a composition of the present disclosure (e.g., nanotransposon) can be utilized with in combination with another transposon or nanotransposon or with vector. A vector of the present disclose can be a viral vector or a recombinant vector. Viral vectors can comprise a sequence isolated or derived from a retrovirus, a lentivirus, an adenovirus, an adeno-associated virus or any combination thereof. The viral vector may comprise a sequence isolated or derived from an adeno-associated virus (AAV). The viral vector may comprise a recombinant AAV (rAAV). Exemplary adeno-associated viruses and recombinant adeno-associated viruses comprise two or more inverted terminal repeat (ITR) sequences located in cis next to a sequence encoding an say or a CAR of the disclosure. Exemplary adeno-associated viruses and recombinant adeno-associated viruses include, but are not limited to all serotypes (e.g., AAV1, AAV2, AAV3, AAV4, AAV5, AAV6, AAV7, AAV8, and AAV9). Exemplary adeno-associated viruses and recombinant adeno-associated viruses include, but are not limited to, self-complementary AAV (scAAV) and AAV hybrids containing the genome of one serotype and the capsid of another serotype (e.g., AAV2/5, AAV-DJ and AAV-DJ8). Exemplary adeno-associated viruses and recombinant adeno-associated viruses include, but are not limited to, rAAV-LK03.

A vector of the present disclose can be a nanoparticle. Non-limiting examples of nanoparticle vectors include nucleic acids (e.g., RNA, DNA, synthetic nucleotides, modified nucleotides or any combination thereof), amino acids (L-amino acids, D-amino acids, synthetic amino acids, modified amino acids, or any combination thereof), polymers (e.g., polymersomes), micelles, lipids (e.g., liposomes), organic molecules (e.g., carbon atoms, sheets, fibers, tubes), inorganic molecules (e.g., calcium phosphate or gold) or any combination thereof. A nanoparticle vector can be passively or actively transported across a cell membrane.

The cell delivery compositions (e.g., transposons, vectors) disclosed herein can comprise a nucleic acid encoding a therapeutic protein or therapeutic agent. Examples of therapeutic proteins include those disclosed in PCT Publication No. WO 2019/173636 and PCT/US2019/049816.

Cells and Modified Cells of the Disclosure

Cells and modified cells of the disclosure can be mammalian cells. Preferably, the cells and modified cells are human cells. Cells and modified cells of the disclosure can be immune cells. The immune cells of the disclosure can comprise lymphoid progenitor cells, natural killer (NK) cells, T lymphocytes (T-cell), stem memory T cells ($T_{SCM}$ cells), central memory cells ($T_{CM}$), stem cell-like T cells, B lymphocytes (B-cells), antigen presenting cells (APCs), cytokine induced killer (OK) cells, myeloid progenitor cells, neutrophils, basophils, eosinophils, monocytes, macrophages, platelets, erythrocytes, red blood cells (RBCS), megakaryocytes or osteoclasts.

The immune precursor cells can comprise any cells which can differentiate into one or more types of immune cells. The immune precursor cells can comprise multipotent stem cells that can self-renew and develop into immune cells. The immune precursor cells can comprise hematopoietic stem cells (HSCs) or descendants thereof. The immune precursor cells can comprise precursor cells that can develop into immune cells. The immune precursor cells can comprise hematopoietic progenitor cells (HPCs).

Hematopoietic stem cells (HSCs) are multipotent, self-renewing cells. All differentiated blood cells from the lymphoid and myeloid lineages arise from HSCs. HSCs can be found in adult bone marrow, peripheral blood, mobilized peripheral blood, peritoneal dialysis effluent and umbilical cord blood.

HSCs can be isolated or derived from a primary or cultured stem cell. HSCs can be isolated or derived from an embryonic stem cell, a multipotent stem cell, a pluripotent stem cell, an adult stem cell, or an induced pluripotent stem cell (iPSC).

Immune precursor cells can comprise an HSC or an HSC descendent cell. Non-limiting examples of HSC descendent cells include multipotent stem cells, lymphoid progenitor cells, natural killer (NK) cells, lymphocyte cells (T-cells), B lymphocyte cells (B-cells), myeloid progenitor cells, neutrophils, basophils, eosinophils, monocytes and macrophages.

HSCs produced by the disclosed methods can retain features of "primitive" stem cells that, while isolated or derived from an adult stem cell and while committed to a single lineage, share characteristics of embryonic stem cells. For example, the "primitive" HSCs produced by the disclosed methods retain their "sternness" following division and do not differentiate. Consequently, as an adoptive cell therapy, the "primitive" HSCs produced by the disclosed methods not only replenish their numbers, but expand in vivo, "Primitive" HSCs produced by disclosed the methods can be therapeutically-effective when administered as a single dose.

Primitive HSCs can be CD34+. Primitive HSCs can be CD34+ and CD38−. Primitive HSCs can be CD34+, CD38− and CD90+. Primitive HSCs can be CD34+, CD38−, CD90+ and CD45RA−. Primitive HSCs can be CD34+, CD38−, CD90+, CD45RA−, and CD49f+. Primitive HSCs can be CD34+, CD38−, CD90+, CD45RA−, and CD49f+.

Primitive HSCs, HSCs, and/or HSC descendent cells can be modified according to the disclosed methods to express an exogenous sequence (e.g., a chimeric antigen receptor or therapeutic protein). Modified primitive HSCs, modified HSCs, and/or modified HSC descendent cells can be forward differentiated to produce a modified immune cell including, but not limited to, a modified T cell, a modified natural killer cell and/or a modified B-cell.

The modified immune or immune precursor cells can be NK cells. The NK cells can be cytotoxic lymphocytes that differentiate from lymphoid progenitor cells. Modified NK cells can be derived from modified hematopoietic stem and progenitor cells (HSPCs) or modified HSCs. In some aspects, non-activated NK cells are derived from CD3-depleted leukapheresis (containing CD14/CD19/CD56+ cells).

The modified immune or immune precursor cells can be B cells. B cells are a type of lymphocyte that express B cell receptors on the cell surface. B cell receptors bind to specific antigens. Modified B cells can be derived from modified hematopoietic stem and progenitor cells (HSPCs) or modified HSCs.

Modified T cells of the disclosure may be derived from modified hematopoietic stem and progenitor cells (HSPCs) or modified HSCs. Unlike traditional biologics and chemotherapeutics, the disclosed modified-T cells the capacity to rapidly reproduce upon antigen recognition, thereby potentially obviating the need for repeat treatments. To achieve this, in some aspects, modified-T cells not only drive an initial response, but also persist in the patient as a stable population of viable memory T cells to prevent potential relapses. Alternatively, in some aspects, when it is not desired, the modified-T cells do not persist in the patient.

Intensive efforts have been focused on the development of antigen receptor molecules that do not cause T cell exhaustion through antigen-independent (tonic) signaling, as well as of a modified-T cell product containing early memory T cells, especially stem cell memory ($T_{SCM}$) or stem cell-like T cells. Stem cell-like modified-T cells of the disclosure exhibit the greatest capacity for self-renewal and multipotent capacity to derive central memory ($T_{CM}$) T cells or $T_{CM}$ like cells, effector memory ($T_{EM}$) and effector T cells ($T_E$), thereby producing better tumor eradication and long-term modified-T cell engraftment. A linear pathway of differentiation may be responsible for generating these cells: Naïve T cells ($T_N$)>$T_{SCM}$>$T_{CM}$>$T_{EM}$>$T_E$>$T_{TE}$, whereby $T_N$ is the parent precursor cell that directly gives rise to $T_{SCM}$, which then, in turn, directly gives rise to $T_{CM}$, etc. Compositions of T cells of the disclosure can comprise one or more of each parental T cell subset with $T_{SCM}$ cells being the most abundant (e.g., $T_{SCM}$>$T_{CM}$>$T_{EM}$>$T_E$>$T_{TE}$).

The immune cell precursor can be differentiated into or is capable of differentiating into an early memory T cell, a stem cell like T-cell, a Naïve T cells ($T_N$), a $T_{SCM}$, a $T_{CM}$, a $T_{EM}$, a $T_E$, or a $T_{TE}$. The immune cell precursor can be a primitive HSC, an HSC, or a HSC descendent cell of the disclosure. The immune cell can be an early memory T cell, a stem cell like T-cell, a Naïve T cells ($T_N$), a $T_{SCM}$, a $T_{CM}$, a $T_{EM}$, a $T_E$, or a $T_{TE}$.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of a plurality of modified T cells in the population expresses one or more cell-surface marker(s) of an early memory T cell. The population of modified early memory T cells comprises a plurality of modified stem cell-like T cells. The population of modified early memory T cells comprises a plurality of modified $T_{SCM}$ cells. The population of modified early memory T cells comprises a plurality of modified $T_{CM}$ cells.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells in the population expresses one or more cell-surface marker(s) of a stem cell-like T cell. The population of modified stem cell-like T cells comprises a plurality of modified $T_{SCM}$ cells. The population of modified stem cell-like T cells comprises a plurality of modified $T_{CM}$ cells.

In some aspects, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% or any percentage in between of the plurality of modified T cells in the population expresses one or more cell-surface marker(s) of a stem memory T cell ($T_{SCM}$) or a $T_{SCM}$-like cell; and wherein the one or more cell-surface marker(s) comprise CD45RA and CD62L. The cell-surface markers can comprise one or more of CD62L, CD45RA, CD28, CCR7, CD127, CD45RO, CD95, CD95 and IL-2Rβ. The cell-surface markers can comprise one or more of CD45RA, CD95, IL-2Rβ, CCR7, and CD62L.

In some aspects, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% of the plurality of modified T cells in the population expresses one or more cell-surface marker(s) of a central memory T cell (km) or a $T_{CM}$-like cell; and wherein the one or more cell-surface marker(s) comprise CD45RO and CD62L. The cell-surface markers can comprise one or more of CD45RO, CD95, CCR7, and CD62L.

The methods of the disclosure can modify and/or produce a population of modified T cells, wherein at least 2%, 5%, 10%, 15%, 20%, 25%, 30%, 35%, 40%, 45%, 50%, 60%, 65%, 70%, 75%, 80%, 85%, 90%, 95%, 99% or any percentage in between of the plurality of modified T cells in the population expresses one or more cell-surface marker(s) of a naïve T cell ($T_N$). The cell-surface markers can comprise one or more of CD45RA, CCR7 and CD62L.

The methods of the disclosure can modify and/or produce a population of modified T cells, wherein at least 2%, 5%, 10%, 15%, 20%, 25%, 30%, 35%, 40%, 50%, 60%, 65%, 70%, 75%, 80%, 85%, 90%, 95%, 99% or any percentage in between of the plurality of modified T cells in the population expresses one or more cell-surface marker(s) of an effector T-cell (modified TEFF). The cell-surface markers can comprise one or more of CD45RA, CD95, and IL-2Rβ.

The methods of the disclosure can modify and/or produce a population of modified T cells, wherein at least 2%, 5%, 10%, 15%, 20%. 25%, 30%, 35%, 40%, 45%, 50%, 60%, 65%, 70%, 75%, 80%, 85%, 90%, 95%, 99% or any percentage in between of the plurality of modified T cells of the population expresses one or more cell-surface marker(s) of a stem cell-like T cell, a stem memory T cell ($T_{SCM}$) or a central memory T cell ($T_{CM}$).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 or wherein at least about 70% to about 99%, about 75% to about 95% or about 85% to about 95% of the population of modified cells express one or more cell-surface marker(s) comprising CD34 (e.g., comprise the cell-surface marker phenotype CD34+).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and do not express one or more cell-surface marker(s) comprising CD38, or wherein at least about 45% to about 90%, about 50% to about 80% or about 65% to about 75% of the population of modified cells express one or more cell-surface marker(s) comprising CD34 and do not express one or more cell-surface marker(s) comprising CD38 (e.g., comprise the cell-surface marker phenotype CD34+ and CD38−).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 0.1%, at least 0.2%, at least 0.3%, at leak 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and CD90 and do not express one or more cell-surface marker(s) comprising CD38, or wherein at least about 0.2% to about 40%, about 0.2% to about 30%, about 0.2% to about 2% or 0.5% to about 1.5% of the population of modified cells express one or more cell-surface marker(s) comprising CD34 and CD90 and do not express one or more cell-surface marker(s) comprising CD38 (e.g., comprise the cell-surface marker phenotype CD34+, CD38− and CD90+).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 999% or 100% of the plurality of cells of the population comprise the transgene or the sequence encoding the transgene, wherein at least 0.1%, at least 0.2%, at least 0.3%, at leak 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and CD90 and do not express one or more cell-surface marker(s) comprising CD38 and CD45RA, or wherein at least about 0.2% to about 40%, about 0.2% to about 30%, about 0.2% to about 2% or 0.5% to about 1.5% of the population of modified cells express one or more cell-surface marker(s) comprising CD34 and CD90 and do not express one or more cell-surface marker(s) comprising CD38 and CD45RA (e.g., comprise the cell-surface marker phenotype CD34+, CD38−, CD90+, CD45RA−).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34, CD90 and CD49f and do not express one or more cell-surface marker(s) comprising CD38 and CD45RA, or wherein at least about 0.02% to about 30%, about 0.02% to about 2%, about 0.04% to about 2% or about 0.04% to about 1% of the population of modified cells express one or more cell-surface marker(s) comprising CD34, CD90 and CD49f and do not express one or more cell-surface marker(s) comprising CD38 and CD45RA (e.g., comprise the cell-surface marker phenotype CD34+, CD38−, CD90+, CD45RA− and CD49f+).

A plurality of modified cells of the population comprise a transgene or a sequence encoding the transgene (e.g., a CAR), wherein at least 75%, at least 85%, at least 90%, at least 91%, at least 92%, at least 93%, at least 94%, at least 95%, at least 96%, at least 97%, at least 98%, at least 99%, at least 99.5%, at least 99.9% or 100% of the plurality of cells of the population comprise the transgene or the sequence encoding the transgene, wherein at least 0.01%, at least 0.02%, at least 0.03%, at least 0.04%, at least 0.05%, at least 0.06%, at least 0.07%, at least 0.08%, at least 0.09%, at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 3%, at least 4%, at least 5%, at least 10%, at least 15%, at least 20%, at least 25%, at least 30%, at least 35%, at least 40%, at leak 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, at least 99.9% or 100% of the population of modified cells express one or more cell-surface marker(s) comprising CD34 and CD90 and do not express one or more cell-surface marker(s) comprising CD45RA, or wherein at least about 0.2% to about 5%, about 0.2% to about 3% or about 0.4% to about 3% of the population of modified cells express one or more cell-surface marker(s) comprising CD34 and CD90 and do not express one or more cell-surface marker(s) comprising CD45RA (e.g., comprise the cell-surface marker phenotype CD34+, CD90+ and CD45RA−).

Compositions and methods of producing and/or expanding the immune cells or immune precursor cells (e.g., the disclosed modified T-cells) and buffers for maintaining or enhancing a level of cell viability and/or a stem-like phenotype of the immune cells or immune precursor cells (e.g., the disclosed modified T-cells) are disclosed elsewhere herein and are disclosed in more detail in U.S. Pat. No. 10,329,543 and PCT Publication No. WO2019/173636.

Cells and modified cells of the disclosure can be somatic cells. Cells and modified cells of the disclosure can be differentiated cells. Cells and modified cells of the disclosure can be autologous cells or allogenic cells. Allogeneic cells are engineered to prevent adverse reactions to engraftment following administration to a subject. Allogeneic cells may be any type of cell. Allogenic cells can be stem cells or can be derived from stem cells. Allogeneic cells can be differentiated somatic cells.

Methods of Expressing a Chimeric Antigen Receptor

The disclosure provides methods of expressing a CAR on the surface of a cell. The method comprises (a) obtaining a cell population; (b) contacting the cell population to a composition comprising a CAR or a sequence encoding the CAR, under conditions sufficient to transfer the CAR across a cell membrane of at least one cell in the cell population, thereby generating a modified cell population; (c) culturing the modified cell population under conditions suitable for integration of the sequence encoding the CAR; and (d) expanding and/or selecting at least one cell from the modified cell population that express the CAR on the cell surface.

In some aspects, the cell population can comprise leukocytes and/or CD4+ and CD8+ leukocytes. The cell population can comprise CD4+ and CD8+ leukocytes in an optimized ratio. The optimized ratio of CD4+ to CD8+ leukocytes does not naturally occur in vivo. The cell population can comprise a tumor cell.

In some aspects, the conditions sufficient to transfer the CAR or the sequence encoding the CAR, transposon, or vector across a cell membrane of at least one cell in the cell population comprises at least one of an application of one or more pulses of electricity at a specified voltage, a buffer, and one or more supplemental factor(s). In some aspects, the conditions suitable for integration of the sequence encoding the CAR comprise at least one of a buffer and one or more supplemental factor(s).

The buffer can comprise PBS, HBSS, OptiMEM, BTXpress, Amaxa Nucleofector, Human T cell nucleofection buffer or any combination thereof. The one or more supplemental factor(s) can comprise (a) a recombinant human cytokine, a chemokine, an interleukin or any combination thereof; (b) a salt, a mineral, a metabolite or any combination thereof; (c) a cell medium; (d) an inhibitor of cellular DNA sensing, metabolism, differentiation, signal transduction, one or more apoptotic pathway(s) or combinations thereof; and (e) a reagent that modifies or stabilizes one or more nucleic acids. The recombinant human cytokine, the chemokine, the interleukin or any combination thereof can comprise IL2, IL7, IL12, IL15, IL21, IL1, IL3, IL4, IL5, IL6, IL8, CXCL8, IL9, IL10, IL11, IL13, IL14, IL16, IL18, IL19, IL22, IL23, IL25, IL26, IL27, IL28, IL29, IL30, IL31 IL32, IL33, IL35, IL36, GM-CSF, IFN-gamma, alpha/IL-1F1, IL-1 beta/IL-1F2, IL-12 p70, IL-12/IL-35 p35, IL-13, IL-17/IL-17A, IL-17A/F Heterodimer, IL-17F, IL-18/IL-1F4, IL-23, IL-24, IL-32, IL-32 beta, IL-32 gamma, IL-33, LAP (TGF-beta 1), Lymphotoxin-alpha/TNF-beta, TGF-beta, TNF-alpha, TRANCE/TNFSF11/RANK L or any combination thereof. The salt, the mineral, the metabolite or any combination thereof can comprise HEPES, Nicotinamide, Heparin, Sodium Pyruvate, L-Glutamine, MEM Non-Essential Amino Acid Solution, Ascorbic Acid, Nucleosides, FBS/FCS, Human serum, serum-substitute, antibiotics, pH adjusters, Earle's Salts, 2-Mercaptoethanol, Human transferrin, Recombinant human insulin, Human serum albumin, Nucleofector PLUS Supplement, KCL, $MgCl_2$, $Na_2HPO_4$, $NAH_2PO_4$, Sodium lactobionate, Mannitol, Sodium succinate, Sodium Chloride, CINa, Glucose, $Ca(NO_3)_2$, Tris/HCl, $K_2HPO_4$, $KH_2PO_4$, Polyethylenimine, Poly-ethylene-glycol, Poloxamer 188, Poloxamer 181, Poloxamer 407, Polyvinylpyrrolidone, Pop313, Crown-5, or any combination thereof. The cell medium can comprise PBS, HBSS, OptiMEM, DMEM, RPMI 1640, AIM-V, X-VIVO 15, Cell- Gro DC Medium, CTS OpTimizer T Cell Expansion SFM, TexMACS Medium, PRIME-XV T Cell Expansion Medium, ImmunoCult-XF T Cell Expansion Medium or any combination thereof. The inhibitor of cellular DNA sensing, metabolism, differentiation, signal transduction, one or more apoptotic pathway(s) or combinations thereof comprise inhibitors of TLR9, MyD88, IRAK, TRAF6, TRAF3, IRF-7, NT-KB, Type 1 Interferons, pro-inflammatory cytokines, cGAS, STING, Sec5, TBK1, RNA pol III, RIG-1, IPS-1, FADD, RIP1, TRAF3, AIM2, ASC, Caspase1, Pro-IL1B, PI3K, Akt, Wnt3A, inhibitors of glycogen synthase kinase-3β (GSK-3 β) (e.g. TWS119), or any combination thereof. Examples of such inhibitors can include Bafilomycin, Chloroquine, Quinacrine, AC-YVAD-CMK, Z-VAD-FMK, Z-IETD-FMK or any combination thereof. The reagent that modifies or stabilizes one or more nucleic acids comprises a pH modifier, a DNA-binding protein, a lipid, a phospholipid, CaPO4, a net neutral charge DNA binding peptide with or without a NLS sequence, a TREX1 enzyme or any combination thereof.

The expansion and selection steps can occur concurrently or sequentially. The expansion can occur prior to selection. The expansion can occur following selection, and, optionally, a further (i.e. second) selection can occur following expansion. Concurrent expansion and selection can be simultaneous. The expansion and/or selection steps can proceed for a period of 10 to 14 days, inclusive of the endpoints.

The expansion can comprise contacting at least one cell of the modified cell population with an antigen to stimulate the at least one cell through the CAR, thereby generating an expanded cell population. The antigen can be presented on the surface of a substrate. The substrate can have any form, including, but not limited to a surface, a well, a bead or a plurality thereof, and a matrix. The substrate can further comprise a paramagnetic or magnetic component. The antigen can be presented on the surface of a substrate, wherein the substrate is a magnetic bead, and wherein a magnet can be used to remove or separate the magnetic beads from the modified and expanded cell population. The antigen can be presented on the surface of a cell or an artificial antigen presenting cell. Artificial antigen presenting cells can include, but are not limited to, tumor cells and stem cells.

In some aspects wherein the transposon or vector comprises a selection gene, the selection step comprises contacting at least one cell of the modified cell population with a compound to which the selection gene confers resistance, thereby identifying a cell expressing the selection gene as surviving the selection and identifying a cell failing to express the selection gene as failing to survive the selection step.

The disclosure provides a composition comprising the modified, expanded and selected cell population of the methods described herein.

A more detailed description of methods for expressing a CAR on the surface of a cell is disclosed in PCT Publication No. WO 2019/049816 and PCT/US2019/049816.

The present disclosure provides a cell or a population of cells wherein the cell comprises a composition comprising (a) an inducible transgene construct, comprising a sequence encoding an inducible promoter and a sequence encoding a transgene, and (b) a receptor construct, comprising a sequence encoding a constitutive promoter and a sequence encoding an exogenous receptor, such as a CAR, wherein, upon integration of the construct of (a) and the construct of (b) into a genomic sequence of a cell, the exogenous receptor is expressed, and wherein the exogenous receptor, upon binding a ligand or antigen, transduces an intracellular signal that targets directly or indirectly the inducible promoter regulating expression of the inducible transgene (a) to modify gene expression.

The composition can modify gene expression by decreasing gene expression. The composition can modify gene expression by transiently modifying gene expression (e.g., for the duration of binding of the ligand to the exogenous receptor). The composition can modify gene expression acutely (e.g., the ligand reversibly binds to the exogenous receptor). The composition can modify gene expression chronically (e.g., the ligand irreversibly binds to the exogenous receptor).

The exogenous receptor can comprise an endogenous receptor with respect to the genomic sequence of the cell. Exemplary receptors include, but are not limited to, intracellular receptors, cell-surface receptors, transmembrane receptors, ligand-gated ion channels, and G-protein coupled receptors.

The exogenous receptor can comprise a non-naturally occurring receptor. The non-naturally occurring receptor can be a synthetic, modified, recombinant, mutant or chimeric receptor. The non-naturally occurring receptor can comprise one or more sequences isolated or derived from a I-cell receptor (TCR). The non-naturally occurring receptor can comprise one or more sequences isolated or derived from a scaffold protein. In some aspects, including those wherein the non-naturally occurring receptor does not comprise a transmembrane domain, the non-naturally occurring receptor interacts with a second transmembrane, membrane-bound and/or an intracellular receptor that, following contact with the non-naturally occurring receptor, transduces an intracellular signal. The non-naturally occurring receptor can comprise a transmembrane domain. The non-naturally occurring receptor can interact with an intracellular receptor that transduces an intracellular signal. The non-naturally occurring receptor can comprise an intracellular signaling domain. The non-naturally occurring receptor can be a chimeric ligand receptor (CLR). The CLR can be a chimeric antigen receptor (CAR).

The sequence encoding the inducible promoter of comprises a sequence encoding an NFκB promoter, a sequence encoding an interferon (IFN) promoter or a sequence encoding an interleukin-2 promoter. In some aspects, the promoter is an IFNγ promoter. The inducible promoter can be isolated or derived from the promoter of a cytokine or a chemokine. The cytokine or chemokine can comprise IL2, IL3, IL4, IL5, IL6, IL10, IL12, IL13, IL17A/F, IL21, IL22, IL23, transforming growth factor beta (TGFβ), colony stimulating factor 2 (GM-CSF), interferon gamma (IFNγ), Tumor necrosis factor alpha (TNFα), LTα, perforin, Granzyme C (Gzmc), Granzyme B (Gzmb), C-C motif chemokine ligand 5 (CCL5), C-C motif chemokine ligand 4 (Ccl4), C-C motif chemokine ligand 3 (Ccl3), X-C motif chemokine ligand 1 (Xcl1) or LIF interleukin 6 family cytokine (Lif).

The inducible promoter can be isolated or derived from the promoter of a gene comprising a surface protein involved in cell differentiation, activation, exhaustion and function. In some aspects, the gene comprises CD69, CD71, CTLA4, PD-1, TIGIT, LAG3, TIM-3, GITR, MHCII, COX-2, FASL or 4-1BB.

The inducible promoter can be isolated or derived from the promoter of a gene involved in CD metabolism and differentiation. The inducible promoter can be isolated or derived from the promoter of Nr4a1, Nr4a3, Tnfrsf9 (4-1BB), Sema7a, Zfp3612, Gadd45b, Dusp5, Dusp6 and Neto2.

In some aspects, the inducible transgene construct comprises or drives expression of a signaling component downstream of an inhibitory checkpoint signal, a transcription factor, a cytokine or a cytokine receptor, a chemokine or a chemokine receptor, a cell death or apoptosis receptor/ligand, a metabolic sensing molecule, a protein conferring sensitivity to a cancer therapy, and an oncogene or a tumor suppressor gene. Non-limiting examples of which are disclosed in PCT Publication No. WO 2019/173636 and PCT Application No. PCT/US2019/049816.

Armored Cells

The modified cells of disclosure (e.g., CAR T-cells) can be further modified to enhance their therapeutic potential. Alternatively, or in addition, the modified cells may be further modified to render them less sensitive to immunologic and/or metabolic checkpoints. Modifications of this type "armor" the cells, which, following the modification, may be referred to here as "armored" cells (e.g., armored T-cells). Armored cells may be produced by, for example, blocking and/or diluting specific checkpoint signals delivered to the cells (e.g., checkpoint inhibition) naturally, within the tumor immunosuppressive microenvironment.

An armored cell of the disclosure can be derived from any cell, for example, a T cell, a. NK cell, a hematopoietic progenitor cell, a peripheral blood (PB) derived T cell (including a T cell isolated or derived from G-CSF-mobilized peripheral blood), or an umbilical cord blood (UCB) derived T cell. An armored cell (e.g., armored T-cell) can comprise one or more of a chimeric ligand receptor (CLR comprising a protein scaffold, an antibody, an ScFv, or an antibody mimetic)/chimeric antigen receptor (CAR comprising a protein scaffold, an antibody, an ScFv, or an antibody mimetic), a CARTyrin (a CAR comprising a Centyrin), and/or a VC AR (a CAR comprising a camelid VHH or a single domain VH). An armored cell (e.g., armored T-cell) can comprise an inducible proapoptotic polypeptide as disclosed herein. An armored cell (e.g., armored T-cell) can comprise an exogenous sequence. The exogenous sequence can comprise a sequence encoding a therapeutic protein. Exemplary therapeutic proteins may be nuclear, cytoplasmic, intracellular, transmembrane, cell-surface bound, or secreted proteins. Exemplary therapeutic proteins expressed by the armored cell (e.g., armored T-cell) may modify an activity of the armored cell or may modify an activity of a second cell. An armored cell (e.g., armored T-cell) can comprise a selection gene or a selection marker. An armored cell (e.g., armored I-cell) can comprise a synthetic gene expression cassette (also referred to herein as an inducible transgene construct).

The modified cells of disclosure (e.g., CAR T-cells) can be further modified to silence or reduce expression one or more gene(s) encoding receptor(s) of inhibitory checkpoint signals to produce an armored cell (e.g., armored CAR T-cell). Receptors of inhibitory checkpoint signals are expressed on the cell surface or within the cytoplasm of a cell. Silencing or reducing expressing of the gene encoding the receptor of the inhibitory checkpoint signal results a loss of protein expression of the inhibitory checkpoint receptors on the surface or within the cytoplasm of an armored cell. Thus, armored cells having silenced or reduced expression of one or more genes encoding an inhibitory checkpoint receptor is resistant, non-receptive or insensitive to checkpoint signals. The resistance or decreased sensitivity of the armored cell to inhibitory checkpoint signals enhances the therapeutic potential of the armored cell in the presence of these inhibitory checkpoint signals. Non-limiting examples of inhibitory checkpoint signals (and proteins that induce immunosuppression) are disclosed in PCT Publication No. WO 2019/173636. Preferred examples of inhibitory checkpoint signals that may be silenced include, but are not limited to, PD-1 and TGFβRII.

The modified cells of disclosure (e.g., CAR T-cells) can be further modified to silence or reduce expression of one or more gene(s) encoding intracellular proteins involved in checkpoint signaling to produce an armored cell (e.g., armored CAR T-cell), The activity of the modified cells may be enhanced by targeting any intracellular signaling protein involved in a checkpoint signaling pathway, thereby achieving checkpoint inhibition or interference to one or more checkpoint pathways. Non-limiting examples of intracellular signaling proteins involved in checkpoint signaling are disclosed in PCT Publication No. WO 2019/173636.

The modified cells of disclosure (e.g., CAR T-cells) can be further modified to silence or reduce expression of one or more gene(s) encoding a transcription factor that hinders the efficacy of a therapy to produce an armored cell (e.g., armored CAR T-cell). The activity of modified cells may be enhanced or modulated by silencing or reducing expression (or repressing a function) of a transcription factor that hinders the efficacy of a therapy. Non-limiting examples of transcription factors that may be modified to silence or reduce expression or to repress a function thereof include, but are not limited to, the exemplary transcription factors are disclosed in PCT Publication No. WO 2019/173636.

The modified cells of disclosure (e.g., CAR T-cells) can be further modified to silence or reduce expression of one or more gene(s) encoding a cell death or cell apoptosis receptor to produce an armored cell (e.g., armored CAR T-cell). Interaction of a death receptor and its endogenous ligand results in the initiation of apoptosis. Disruption of an expression, an activity, or an interaction of a cell death and/or cell apoptosis receptor and/or ligand render a modified cell less receptive to death signals, consequently, making the armored cell more efficacious in a tumor environment. Non-limiting examples of cell death and/or cell apoptosis receptors and ligands are disclosed in PCT Publication No. WO 2019/173636. A preferred example of cell death receptor which may be modified is Fas (CD95).

The modified cells of disclosure (e.g., CAR T-cells) can be further modified to silence or reduce expression of one or more gene(s) encoding a metabolic sensing protein to produce an armored cell (e.g., armored CAR T-cell). Disruption to the metabolic sensing of the immunosuppressive tumor microenvironment (characterized by low levels of oxygen, pH, glucose and other molecules) by a modified cell leads to extended retention of T-cell function and, consequently, more tumor cells killed per cell. Non-limiting examples of metabolic sensing genes and proteins are disclosed in PCT Publication No. WO 2019/173636. A preferred example, HIP1a and VHL play a role in T-cell function while in a hypoxic environment. An armored T-cell may have silenced or reduced expression of one or more genes encoding HIF1a or VHL.

The modified cells of disclosure (e.g., CAR T-cells) can be further modified to silence or reduce expression of one or more gene(s) encoding proteins that that confer sensitivity to a cancer therapy, including a monoclonal antibody, to produce an armored cell (e.g., armored CAR T-cell). Thus, an armored cell can function and may demonstrate superior function or efficacy whilst in the presence of a cancer therapy (e.g., a chemotherapy, a monoclonal antibody therapy, or another anti-tumor treatment). Non-limiting examples of proteins involved in conferring sensitivity to a cancer therapy are disclosed in PCT Publication No. WO 2019/173636.

The modified cells of disclosure (e.g., CAR T-cells) can be further modified to silence or reduce expression of one or more gene(s) encoding a growth advantage factor to produce an armored cell (e.g., armored CAR T-cell). Silencing or reducing expression of an oncogene can confer a growth advantage for the cell. For example, silencing or reducing expression (e.g., disrupting expression) of a TET2 gene during a CAR T-cell manufacturing process results in the generation of an armored CAR T-cell with a significant capacity for expansion and subsequent eradication of a tumor when compared to a non-armored CAR. T-cell lacking this capacity for expansion. This strategy may be coupled to a safety switch (e.g., an iC9 safety switch described herein), which permits the targeted disruption of an armored CAR. T-cell in the event of an adverse reaction from a subject or uncontrolled growth of the armored CAR T-cell. Non-limiting examples of growth advantage factors are disclosed in PCT Publication No. WO 2019/173636.

The modified cells of disclosure (e.g., CAR T-cells) can be further modified to express a modified/chimeric checkpoint receptor to produce an armored T-cell of the disclosure.

The modified/chimeric checkpoint receptor can comprise a null receptor, decoy receptor or dominant negative receptor. A null receptor, decoy receptor or dominant negative receptor can be modified/chimeric receptor/protein. A null receptor, decoy receptor or dominant negative receptor can be truncated for expression of the intracellular signaling domain. Alternatively, or in addition, a null receptor, decoy receptor or dominant negative receptor can be mutated within an intracellular signaling domain at one or more amino acid positions that are determinative or required for effective signaling, Truncation or mutation of null receptor, decoy receptor or dominant negative receptor can result in loss of the receptor's capacity to convey or transduce a checkpoint signal to the cell or within the cell.

For example, a dilution or a blockage of an immunosuppressive checkpoint signal from a PD-L1 receptor expressed on the surface of a tumor cell may be achieved by expressing a modified/chimeric PD-1 null receptor on the surface of an armored cell (e.g., armored CAR T-cell), which effectively competes with the endogenous (non-modified) PD-1 receptors also expressed on the surface of the armored cell to reduce or inhibit the transduction of the immunosuppressive checkpoint signal through endogenous PD-1 receptors of the armored cell. In this non-limiting example, competition between the two different receptors for binding to PD-L1 expressed on the tumor cell reduces or diminishes a level of effective checkpoint signaling, thereby enhancing a therapeutic potential of the armored cell expressing the PD-1 null receptor.

The modified/chimeric checkpoint receptor can comprise a null receptor, decoy receptor or dominant negative receptor that is a transmembrane receptor, a membrane-associated or membrane-linked receptor/protein or an intracellular receptor/protein. Exemplary null, decoy, or dominant negative intracellular receptors/proteins include, but are not limited to, signaling components downstream of an inhibitory checkpoint signal, a transcription factor, a cytokine or a cytokine receptor, a chemokine or a chemokine receptor, a cell death or apoptosis receptor/ligand, a metabolic sensing molecule, a protein conferring sensitivity to a cancer therapy, and an oncogene or a tumor suppressor gene. Non-limiting examples of cytokines, cytokine receptors, chemokines and chemokine receptors are disclosed in PCT Publication No. WO 2019/173636.

The modified/chimeric checkpoint receptor can comprise a switch receptor. Exemplary switch receptors comprise a modified/chimeric receptor/protein wherein a native or wild type intracellular signaling domain is switched or replaced with a different intracellular signaling domain that is either non-native to the protein and/or not a wild-type domain. For example, replacement of an inhibitory signaling domain with a stimulatory signaling domain would switch an immunosuppressive signal into an immunostimulatory signal. Alternatively, replacement of an inhibitory signaling domain with a different inhibitory domain can reduce or enhance the level of inhibitory signaling. Expression or overexpression, of a switch receptor can result in the dilution and/or blockage of a cognate checkpoint signal via competition with an endogenous wild-type checkpoint receptor (not a switch receptor) for binding to the cognate checkpoint receptor expressed within the immunosuppressive tumor microenvironment. Armored cells (e.g., armored CAR T-cells) can comprise a sequence encoding a switch receptor, leading to the expression of one or more switch receptors, and consequently, altering an activity of an armored cell. Armored cells (e.g., armored CAR T-cells) can express a switch receptor that targets an intracellularly expressed protein downstream of a checkpoint receptor, a transcription factor, a cytokine receptor, a death receptor, a metabolic sensing molecule, a cancer therapy, an oncogene, and/or a tumor suppressor protein or gene.

Exemplary switch receptors can comprise or can be derived from a protein including, but are not limited to, the signaling components downstream of an inhibitory checkpoint signal, a transcription factor, a cytokine or a cytokine receptor, a chemokine or a chemokine receptor, a cell death or apoptosis receptor/ligand, a metabolic sensing molecule, a protein conferring sensitivity to a cancer therapy, and an oncogene or a tumor suppressor gene.

The modified cells of disclosure (e.g., CAR T-cells) can be further modified to express a CLR/CAR that mediates conditional gene expression to produce an armored T-cell. The combination of the CLR/CAR and the condition gene expression system in the nucleus of the armored T-cell constitutes a synthetic gene expression system that is conditionally activated upon binding of cognate ligand(s) with CLR or cognate antigen(s) with CAR. This system may help to 'armor' or enhance therapeutic potential of modified T-cells by reducing or limiting synthetic gene expression at the site of ligand or antigen binding, at or within the tumor environment for example.

Gene Editing Compositions and Methods

A modified cell be produced by introducing a transgene into the cell. The introducing step may comprise delivery of a nucleic acid sequence, a transgene, and/or a genomic editing construct via a non-transposition delivery system.

Introducing a nucleic acid sequence, transgene and/or a genomic editing construct into a cell ex vivo, in vivo, in vitro or in situ can comprise one or more of topical delivery, adsorption, absorption, electroporation, spin-fection, co-culture, transfection, mechanical delivery, sonic delivery, vibrational delivery, magnetofection or by nanoparticle-mediated delivery. Introducing a nucleic acid sequence, a transgene and/or a genomic editing construct into a cell ex vivo, in vivo, in vitro or in situ can comprise liposomal transfection, calcium phosphate transfection, fugene transfection, and dendrimer-mediated transfection. Introducing a nucleic acid sequence, a transgene, and/or a genomic editing construct into a cell ex vivo, in vivo, in vitro or in situ by mechanical transfection can comprise cell squeezing, cell bombardment, or gene gun techniques. Introducing a nucleic acid sequence, transgene and/or a genomic editing construct into a cell ex vivo, in vivo, in vitro or in situ by nanoparticle-mediated transfection can comprise liposomal delivery, delivery by micelles, and delivery by polymerosomes.

Introducing a nucleic acid sequence, transgene and/or a genomic editing construct into a cell ex vivo, in vivo, in vitro or in situ can comprise a non-viral vector. The non-viral vector can comprise a nucleic acid. The non-viral vector can comprise plasmid DNA, linear double-stranded DNA (dsDNA), linear single-stranded DNA (ssDNA), DoggyBone™ DNA, nanoplasmids, minicircle DNA, single-stranded oligodeoxynucleotides (ssODN), DDNA, oligonucleotides, single-stranded mRNA (ssRNA), and double-stranded mRNA (dsRNA), The non-viral vector can comprise a transposon as described herein.

Introducing a nucleic acid sequence, transgene and/or a genomic editing construct into a cell ex vivo, in vivo, in vitro or in situ can comprise a viral vector. The viral vector can be a non-integrating non-chromosomal vector. Non-limiting examples of non-integrating non-chromosomal vectors include adeno-associated virus (AAV), adenovirus, and herpes viruses. The viral vector can be an integrating chromosomal vector. Non-limiting examples of integrating chromosomal vectors include adeno-associated vectors (AAV), Lentiviruses, and gamma-retroviruses.

Introducing a nucleic acid sequence, transgene and/or a genomic editing construct into a cell ex vivo, in vivo, in vitro or in situ can comprise a combination of vectors. Non-limiting examples of vector combinations include viral and non-viral vectors, a plurality of non-viral vectors, or a plurality of viral vectors. Non-limiting examples of vector combinations include a combination of a DNA-derived and an RNA-derived vector, a combination of an RNA and a reverse transcriptase, a combination of a transposon and a transposase, a combination of a non-viral vector and an endonuclease, and a combination of a viral vector and an endonuclease.

Genome modification can comprise introducing a nucleic acid sequence, transgene and/or a genomic editing construct into a cell ex vivo, in vivo, in vitro or in situ to stably integrate a nucleic acid sequence, transiently integrate a nucleic acid sequence, produce site-specific integration of a nucleic acid sequence, or produce a biased integration of a nucleic acid sequence. The nucleic acid sequence can be a transgene.

Genome modification can comprise introducing a nucleic acid sequence, transgene and/or a genomic editing construct into a cell ex vivo, in vivo, in vitro or in situ to stably integrate a nucleic acid sequence. The stable chromosomal integration can be a random integration, a site-specific integration, or a biased integration. The site-specific integration can be non-assisted or assisted. The assisted site-specific integration is co-delivered with a site-directed nuclease. The site-directed nuclease comprises a transgene with 5' and 3' nucleotide sequence extensions that contain a percentage homology to upstream and downstream regions of the site of genomic integration. The transgene with homologous nucleotide extensions enable genomic integration by homologous recombination, microhomology-mediated end joining, or nonhomologous end-joining. The site-specific integration can occur at a safe harbor site. Genomic safe harbor sites are able to accommodate the integration of new genetic material in a manner that ensures that the newly inserted genetic elements function reliably (for example, are expressed at a therapeutically effective level of expression) and do not cause deleterious alterations to the host genome that cause a risk to the host organism. Non-limiting examples of potential genomic safe harbors include intronic sequences of the human albumin gene, the adeno-associated virus site 1 (AAVS1), a naturally occurring site of integration of AAV virus on chromosome 19, the site of the chemokine (C-C motif) receptor 5 (CCR5) gene and the site of the human ortholog of the mouse Rosa26 locus.

The site-specific transgene integration can occur at a site that disrupts expression of a target gene. Disruption of target gene expression can occur by site-specific integration at introns, exons, promoters, genetic elements, enhancers, suppressors, start codons, stop codons, and response elements. Non-limiting examples of target genes targeted by site-specific integration include TRAC, TRAB, PDI, any immunosuppressive gene, and genes involved in allo-rejection.

The site-specific transgene integration can occur at a site that results in enhanced expression of a target gene. Enhancement of target gene expression can occur by site-specific integration at introns, exons, promoters, genetic elements, enhancers, suppressors, start codons, stop codons, and response elements.

Enzymes can be used to create strand breaks in the host genome to facilitate delivery or integration of the transgene. Enzymes can create single-strand breaks or double-strand breaks. Non-limiting examples of break-inducing enzymes include transposases, integrases, endonucleases, CRISPR-Cas9, transcription activator-like effector nucleases (TALEN), zinc finger nucleases (LPN), Cas-CLOVER™, and CPF1. Break-inducing enzymes can be delivered to the cell encoded in DNA, encoded in mRNA, as a protein, or as a nucleoprotein complex with a guide RNA (gRNA).

The site-specific transgene integration can be controlled by a vector-mediated integration site bias. Vector-mediated integration site bias can controlled by the chosen lentiviral vector or by the chosen gamma-retroviral vector.

The site-specific transgene integration site can be a non-stable chromosomal insertion. The integrated transgene can be become silenced, removed, excised, or further modified. The genome modification can be a non-stable integration of a transgene. The non-stable integration can be a transient non-chromosomal integration, a semi-stable non chromosomal integration, a semi-persistent non-chromosomal insertion, or a non-stable chromosomal insertion. The transient non-chromosomal insertion can be epi-chromosomal or cytoplasmic. In an aspect, the transient non-chromosomal insertion of a transgene does not integrate into a chromosome and the modified genetic material is not replicated during cell division.

The genome modification can be a semi-stable or persistent non-chromosomal integration of a transgene. A DNA vector encodes a Scaffold/matrix attachment region (S-MAR) module that binds to nuclear matrix proteins for episomal retention of a non-viral vector allowing for autonomous replication in the nucleus of dividing cells.

The genome modification can be a non-stable chromosomal integration of a transgene. The integrated transgene can become silenced, removed, excised, or further modified.

The modification to the genome by transgene insertion can occur via host cell-directed double-strand breakage repair (homology-directed repair) by homologous recombination (HR), microhomology-mediated end joining (MMEJ), nonhomologous end joining (NHEJ), transposase enzyme-mediated modification, integrase enzyme-mediated modification, endonuclease enzyme-mediated modification, or recombinant enzyme-mediated modification. The modification to the genome by transgene insertion can occur via CRISPR-Cas9, TALEN, ZFNs, Cas-CLOVER™, and cpf1.

In gene editing systems that involve inserting new or existing nucleotides/nucleic acids, insertion tools (e.g., DNA template vectors, transposable elements (transposons or retrotransposons) must be delivered to the cell in addition to the cutting enzyme (e.g., a nuclease, recombinase, integrase or transposase). Examples of such insertion tools for a recombinase may include a DNA vector. Other gene editing systems require the delivery of an integrase along with an insertion vector, a transposase along with a transposon/retrotransposon, etc. An example recombinase that may be used as a cutting enzyme is the CRE recombinase. Non-limiting examples of integrases that may be used in insertion tools include viral based enzymes taken from any of a number of viruses including AAV, gamma retrovirus, and lentivirus. Examples transposons/retrotransposons that may be used in insertion tools are described in more detail herein.

A cell with an ex vivo, in vivo, in vitro or in situ genomic modification can be a germline cell or a somatic cell. The modified cell can be a human, non-human, mammalian, rat, mouse, or dog cell. The modified cell can be differentiated, undifferentiated, or immortalized. The modified undifferentiated cell can be a stem cell. The modified undifferentiated cell can be an induced pluripotent stem cell. The modified cell can be an immune cell. The modified cell can be a T cell, a hematopoietic stem cell, a natural killer cell, a macrophage, a dendritic cell, a monocyte, a megakaryocyte, or an osteoclast. The modified cell can be modified while the cell is quiescent, in an activated state, resting, in interphase, in prophase, in metaphase, in anaphase, or in telophase. The modified cell can be fresh, cryopreserved, bulk, sorted into sub-populations, from whole blood, from leukapheresis, or from an immortalized cell line. A detailed description for isolating cells from a leukapheresis product or blood is disclosed in in PCT Publication No. WO 2019/173636 and PCT/US2019/049816.

The present disclosure provides a gene editing composition and/or a cell comprising the gene editing composition. The gene editing composition can comprise a sequence encoding a DNA binding domain and a sequence encoding a nuclease protein or a nuclease domain thereof. The sequence encoding a nuclease protein or the sequence encoding a nuclease domain thereof can comprise a DNA sequence, an RNA sequence, or a combination thereof. The nuclease or the nuclease domain thereof can comprise one or more of a CRISPR/Cas protein, a Transcription Activator-Like Effector Nuclease (TALEN), a Zinc Finger Nuclease (ZFN), and an endonuclease.

The nuclease or the nuclease domain thereof can comprise a nuclease-inactivated. Cas (dCas) protein and an endonuclease. The endonuclease can comprise a Clo051 nuclease or a nuclease domain thereof. The gene editing composition can comprise a fusion protein. The fusion protein can comprise a nuclease-inactivated Cas9 (dCas9) protein and a Clo051 nuclease or a Clo051 nuclease domain. The gene editing composition can further comprise a guide sequence. The guide sequence comprises an RNA sequence.

The disclosure provides compositions comprising a small, Cas9 (Cas9) operatively-linked to an effector. The disclosure provides a fusion protein comprising, consisting essentially of or consisting of a DNA localization component and an effector molecule, wherein the effector comprises a small, Cas9 (Cas9). A small Cas9 construct of the disclosure can comprise an effector comprising a type IIS endonuclease. A Staphylococcus aureus Cas9 with an active catalytic site comprises the amino acid sequence of SEQ ID NO: 43.

The disclosure provides compositions comprising an inactivated, small, Cas9 (dSaCas9) operatively-linked to an effector. The disclosure provides a fusion protein comprising, consisting essentially of or consisting of a DNA localization component and an effector molecule, wherein the effector comprises a small, inactivated Cas9 (dSaCas9). A small, inactivated Cas9 (dSaCas9) construct of the disclosure can comprise an effector comprising a type IIS endonuclease. A dSaCas9 comprises the amino acid sequence of SEQ ID NO: 44, which includes a D10A and a N580A mutation to inactivate the catalytic site.

The disclosure provides compositions comprising an inactivated Cas9 (dCas9) operatively-linked to an effector. The disclosure provides a fusion protein comprising, consisting essentially of or consisting of a DNA localization component and an effector molecule, wherein the effector comprises an inactivated Cas9 (dCas9). An inactivated Cas9 (dCas9) construct of the disclosure can comprise an effector comprising a type IIS endonuclease.

The dCas9 can be isolated or derived from *Streptococcus pyogenes*. The dCas9 can comprise a dCas9 with substitutions at amino acid positions 10 and 840, which inactivate the catalytic site. In some aspects, these substitutions are D10A and H840A. The dCas9 can comprise the amino acid sequence of SEQ ID NO: 45 or SEQ ID NO: 46.

An exemplary Clo051 nuclease domain comprises, consists essentially of or consists of, the amino acid sequence of SEQ ID NO: 47.

An exemplary dCas9-Clo051 (Cas-CLOVER) fusion protein can comprise, consist essentially of, or consist of, the amino acid sequence of SEQ ID NO: 48. The exemplary dCas9-Clo051 fusion protein can be encoded by a polynucleotide which comprises, consists essentially of, or consists of, the nucleic acid sequence of SEQ ID NO: 49. The nucleic acid encoding the dCas9-Clo051 fusion protein can be DNA or RNA.

An exemplary dCas9-Clo051 (Cas-CLOVER) fusion protein can comprise, consist essentially of, or consist of, the amino acid sequence of SEQ ID NO: 50. The exemplary dCas9-Clo051 fusion protein can be encoded by a polynucleotide which comprises, consists essentially of, or consists of; the nucleic acid sequence of SEQ ID NO: 51. The nucleic acid encoding the dCas9-Clo051 fusion protein can be DNA or RNA.

A cell comprising the gene editing composition can express the gene editing composition stably or transiently. Preferably, the gene editing composition is expressed transiently. The guide RNA can comprise a sequence complementary to a target sequence within a genomic DNA sequence. The target sequence within a genomic DNA sequence can be a target sequence within a safe harbor site of a genomic DNA sequence.

Gene editing compositions, including Cas-CLOVER, and methods of using these compositions for gene editing are described in detail in U.S. Patent Publication Nos. 2017/0107541, 2017/0114149, 2018/0187185 and U.S. Pat. No. 10,415,024.

Gene editing tools can also be delivered to cells using one or more poly(histidine)-based micelles. Poly(histidine) (e.g., poly(L-histidine)), is a pH-sensitive polymer due to the imidazole ring providing an electron lone pair on the unsaturated nitrogen. That is, poly(histidine) has amphoteric properties through protonation-deprotonation. In particular, at certain pHs, poly(histidine)-containing triblock copolymers may assemble into a micelle with positively charged poly (histidine) units on the surface, thereby enabling complexing with the negatively-charged gene editing molecule(s), Using these nanoparticles to bind and release proteins and/or nucleic acids in a pH-dependent manner may provide an efficient and selective mechanism to perform a desired gene modification. In particular, this micelle-based delivery system provides substantial flexibility with respect to the charged materials, as well as a large payload capacity, and targeted release of the nanoparticle payload. In one example, site-specific cleavage of the double stranded DNA is enabled by delivery of a nuclease using the poly(histidine)-based micelles. Without wishing to be bound by a particular theory, it is believed that believed that in the micelles that are formed by the various triblock copolymers, the hydrophobic blocks aggregate to form a core, leaving the hydrophilic blocks and poly(histidine) blocks on the ends to form one or more surrounding layer.

In an aspect, the disclosure provides triblock copolymers made of a hydrophilic block, a hydrophobic block, and a charged block. In some aspects, the hydrophilic block may be poly(ethylene oxide) (PEO), and the charged block may be poly(L-histidine). An example triblock copolymer that can be used is a PEO-b-PLA-b-PHIS, with variable numbers of repeating units in each block varying by design.

Diblock copolymers that can be used as intermediates for making triblock copolymers can have hydrophilic biocompatible poly(ethylene oxide) (PEO), which is chemically synonymous with PEG, coupled to various hydrophobic aliphatic poly(anhydrides), poly(nucleic acids), poly(esters), poly(ortho esters), poly(peptides), poly(phosphazenes) and poly(saccharides), including but not limited by poly(lactide) (PLA), poly(glycolide) (PLGA), poly(lactic-co-glycolic acid) (PLGA), poly(ε-caprolactone) (PCL), and poly (trimethylene carbonate) (PTMC). Polymeric micelles comprised of 100% PEGylated surfaces possess improved in vitro chemical stability, augmented in vivo bioavailability, and prolonged blood circulatory half-lives.

Polymeric vesicles, polymersomes and poly(Histidine)-based micelles, including those that comprise triblock copolymers, and methods of making the same, are described in further detail in U.S. Pat. Nos. 7,217,427; 7,868,512; 6,835,394; 8,808,748; 10,456,452; U.S. Publication Nos. 2014/0363496; 2017/0000743; and 2019/0255191; and PCT Publication No. WO 2019/126589.

Inducible Proapoptotic Polypeptides

The inducible proapoptotic polypeptides disclosed herein are superior to existing inducible polypeptides because the inducible proapoptotic polypeptides of the disclosure are far less immunogenic. The inducible proapoptotic polypeptides are recombinant polypeptides, and, therefore, non-naturally occurring. Further, the sequences that are recombined to produce inducible proapoptotic polypeptides that do not comprise non-human sequences that the host human immune system could recognize as "non-self" and, consequently, induce an immune response in the subject receiving the inducible proapoptotic polypeptide, a cell comprising the inducible proapoptotic polypeptide or a composition comprising the inducible proapoptotic polypeptide or the cell comprising the inducible proapoptotic polypeptide.

The disclosure provides inducible proapoptotic polypeptides comprising a ligand binding region, a linker, and a proapoptotic peptide, wherein the inducible proapoptotic polypeptide does not comprise a non-human sequence. In certain aspects, the non-human sequence comprises a restriction site. In certain aspects, the ligand binding region can be a multimeric ligand binding region. In certain aspects, the proapoptotic peptide is a caspase polypeptide. Non-limiting examples of caspase polypeptides include caspase 1, caspase 2, caspase 3, caspase 4, caspase 5, caspase 6, caspase 7, caspase 8, caspase 9, caspase 10, caspase 11, caspase 12, and caspase 14. Preferably, the caspase polypeptide is a caspase 9 polypeptide. The caspase 9 polypeptide can be a truncated caspase 9 polypeptide. Inducible proapoptotic polypeptides can be non-naturally occurring. When the caspase is caspase 9 or a truncated caspase 9, the inducible proapoptotic polypeptides can also be referred to as an "iC9 safety switch".

An inducible caspase polypeptide can comprise (a) a ligand binding region, (b) a linker, and (c) a caspase polypeptide, wherein the inducible proapoptotic polypeptide does not comprise a non-human sequence. In certain aspects, an inducible caspase polypeptide comprises (a) a ligand binding region, (b) a linker, and (c) a truncated caspase 9 polypeptide, wherein the inducible proapoptotic polypeptide does not comprise a non-human sequence.

The ligand binding region can comprise a FK506 binding protein 12 (FKBP12) polypeptide. The amino acid sequence of the ligand binding region that comprises a FK506 binding protein 12 (FKBP12) polypeptide can comprise a modification at position 36 of the sequence. The modification can be a substitution of valine (V) for phenylalanine (F) at position 36 (F36V). The FKBP12 polypeptide can comprise, consist essential of, or consist of, the amino acid sequence at least 75%, 80%, 85%, 90%, 95%, 96%, 97%, 98%, 99% or 100% (or any percentage in between) identical to SEQ ID NO: 73. The FKBP12 polypeptide can be encoded by a polynucleotide comprising or consisting of an nucleic acid sequence at least 75%, 80%, 85%, 90%, 95%, 96%, 97%, 98%, 99% or 100% (or any percentage in between) identical to SEQ ID NO: 74.

The linker region can comprise, consist essential of, or consist of, the amino acid sequence at least 75%, 80%, 85%, 90%, 95%, 96%, 97%, 98%, 99% or 100% (or any percentage in between) identical to SEQ ID NO: 75 or the linker region can be encoded by a polynucleotide comprising or consisting of an nucleic acid sequence at least 75%, 80%, 85%, 90%, 95%, 96%, 97%, 98%, 99% or 100% (or any percentage in between) identical to SEQ ID NO: 76. In some aspects, the nucleic acid sequence encoding the linker does not comprise a restriction site.

The truncated caspase 9 polypeptide can comprise an amino acid sequence that does not comprise an arginine (R) at position 87 of the sequence. Alternatively, or in addition, the truncated caspase 9 polypeptide can comprise an amino acid sequence that does not comprise an alanine (A) at position 282 the sequence. The truncated caspase 9 polypeptide can comprise, consist essential of, or consist of, the amino acid sequence at least 75%, 80%, 85%, 90%, 95%, 96%, 97%, 98%, 99% or 100% (or any percentage in between) identical to SEQ ID NO: 77 or the truncated caspase 9 polypeptide can be encoded by a polynucleotide comprising or consisting of an nucleic acid sequence at least 75%, 80%, 85%, 90%, 95%, 96%, 97%, 98%, 99% or 100% (or any percentage in between) identical to SEQ ID NO: 78.

In certain aspects when the polypeptide comprises a truncated caspase 9 polypeptide, the inducible proapoptotic polypeptide comprises, consists essential of, or consists of, the amino acid sequence at least 75%, 80%, 85%, 90%, 95%, 96%, 97%, 98%, 99% or 100% (or any percentage in between) identical to SEQ ID NO: 79 or the inducible proapoptotic polypeptide is encoded by a polynucleotide comprising or consisting of an nucleic acid sequence at least 75%, 80%, 85%, 90%, 95%, 96%, 97%, 98%, 99% or 100%

(or any percentage in between) identical to SEQ ID NO: 5, SEQ ID NO: 6, or SEQ ID NO: 80.

Inducible proapoptotic polypeptides can be expressed in a cell under the transcriptional regulation of any promoter known in the art that is capable of initiating and/or regulating the expression of an inducible proapoptotic polypeptide in that cell.

Activation of inducible proapoptotic polypeptides can be accomplished through, for example, chemically induced dimerization (CID) mediated by an induction agent to produce a conditionally controlled protein or polypeptide. Proapoptotic polypeptides not only inducible, but the induction of these polypeptides is also reversible, due to the degradation of the labile dimerizing agent or administration of a monomeric competitive inhibitor.

In certain aspects when the ligand binding region comprises a FKBP12 polypeptide having a substitution of valine (V) for phenylalanine (F) at position 36 (F36V), the induction agent can comprise AP1903, a synthetic drug (CAS Index Name: 2-Piperidinecarboxylic acid, 1-[(2S)-1-oxo-2-(3,4,5-trimethoxyphenyl)butyl]-, 1,2-ethanediylbis[imino(2-oxo-2,1-ethanediyl)oxy-3,1-phenylene[(1R)-3-(3,4-dimethoxyphenyl)propylidene]]ester, [2 S-[1(R*),2R*[S*[S*[1(R*),2R*]]]]]-(9Cl) CAS Registry Number: 195514-63-7; Molecular Formula: C78H98N4O20; Molecular Weight: 1411.65)); AP20187 (CAS Registry Number: 195514-80-8 and Molecular Formula: C82H107N5O20) or an AP20187 analog, such as, for example, AP1510. As used herein, the induction agents AP20187, AP1903 and AP1510 can be used interchangeably.

Inducible proapoptotic peptides and methods of inducing these peptides are described in detail in U.S. Patent Publication No. WO 2019/0225667 and PCT Publication No. WO 2018/068022.

Chimeric Stimulator Receptors and Recombinant HLA-E Polypeptides

Adoptive cell compositions that are "universally" safe for administration to any patient requires a significant reduction or elimination of alloreactivity. Towards this end, cells of the disclosure (e.g., allogenic cells) can be modified to interrupt expression or function of a T-cell Receptor (TCR) and/or a class of Major Histocompatibility Complex (MHC). The TCR mediates graft vs host (GvH) reactions whereas the MHC mediates host vs graft (HvG) reactions. In preferred aspects, any expression and/or function of the TCR is eliminated to prevent T-cell mediated GvH that could cause death to the subject. Thus, in a preferred aspect, the disclosure provides a pure TCR-negative allogeneic T-cell composition (e.g., each cell of the composition expresses at a level so low as to either be undetectable or non-existent).

Expression and/or function of MHC class I (MHC-I, specifically, HLA-A, HLA-B, and HLA-C) is reduced or eliminated to prevent HvG and, consequently, to improve engraftment of cells in a subject. Improved engraftment results in longer persistence of the cells, and, therefore, a larger therapeutic window for the subject. Specifically, expression and/or function of a structural element of MHC-I, Beta-2-Microglobulin (B2M), is reduced or eliminated.

The above strategies induce further challenges. T Cell Receptor (TCR) knockout (KO) in T cells results in loss of expression of CD3-zeta (CD3z or CD3ζ), which is part of the TCR complex. The loss of CD3ζ in TCR-KO T-cells dramatically reduces the ability of optimally activating and expanding these cells using standard stimulation/activation reagents, including, but not limited to, agonist anti-CD3 mAb. When the expression or function of any one component of the TCR complex is interrupted, all components of the complex are lost, including TCR-alpha (TCRα), TCR-beta (TCRβ), CD3-gamma (CD3γ), CD3-epsilon (CD3ε), CD3-delta (CD3δ), and CD3-zeta (CD3ζ). Both CD3ε and CD3ζ are required for T cell activation and expansion. Agonist anti-CD3 mAbs typically recognize CD3ζ and possibly another protein within the complex which, in turn, signals to CD3ζ CD3ζ provides the primary stimulus for T cell activation (along with a secondary co-stimulatory signal) for optimal activation and expansion. Under normal conditions, full T-cell activation depends on the engagement of the TCR in conjunction with a second signal mediated by one or more co-stimulatory receptors (e.g., CD28, CD2, 4-1BBL) that boost the immune response. However, when the TCR is not present, T cell expansion is severely reduced when stimulated using standard activation/stimulation reagents, including agonist anti-CD3 mAb. In fact, T cell expansion is reduced to only 20-40% of the normal level of expansion when stimulated using standard activation/stimulation reagents, including agonist anti-CD3 mAb.

Thus, the present disclosure provides a non-naturally occurring chimeric stimulatory receptor (CSR) comprising: (a) an ectodomain comprising a activation component, wherein the activation component is isolated or derived from a first protein; (b) a transmembrane domain; and (c) an endodomain comprising at least one signal transduction domain, wherein the at least one signal transduction domain is isolated or derived from a second protein; wherein the first protein and the second protein are not identical.

The activation component can comprise a portion of one or more of a component of a T-cell Receptor (TCR), a component of a TCR complex, a component of a TCR co-receptor, a component of a TCR co-stimulatory protein, a component of a TCR inhibitory protein, a cytokine receptor, and a chemokine receptor to which an agonist of the activation component binds. The activation component can comprise a CD2 extracellular domain or a portion thereof to which an agonist binds.

The signal transduction domain can comprise one or more of a component of a human signal transduction domain, T-cell Receptor (TCR), a component of a TCR complex, a component of a TCR co-receptor, a component of a TCR co-stimulatory protein, a component of a TCR inhibitory protein, a cytokine receptor, and a chemokine receptor. The signal transduction domain can comprise a CD3 protein or a portion thereof. The CD3 protein can comprise a CD3ζ protein or a portion thereof.

The endodomain can further comprise a cytoplasmic domain. The cytoplasmic domain can be isolated or derived from a third protein. The first protein and the third protein can be identical. The ectodomain can further comprise a signal peptide. The signal peptide can be derived from a fourth protein. The first protein and the fourth protein can be identical. The transmembrane domain can be isolated or derived from a fifth protein. The first protein and the fifth protein can be identical.

In some aspects, the activation component does not bind a naturally-occurring molecule. In some aspects, the activation component binds a naturally-occurring molecule but the CSR does not transduce a signal upon binding of the activation component to a naturally-occurring molecule. In some aspects, the activation component binds to a non-naturally occurring molecule. In some aspects, the activation component does not bind a naturally-occurring molecule but binds a non-naturally occurring molecule. The CSR can selectively transduces a signal upon binding of the activation component to a non-naturally occurring molecule.

In a preferred aspect, the present disclosure provides a non-naturally occurring chimeric stimulatory receptor (CSR) comprising: (a) an ectodomain comprising a signal peptide and an activation component, wherein the signal peptide comprises a CD2 signal peptide or a portion thereof and wherein the activation component comprises a CD2 extracellular domain or a portion thereof to which an agonist binds; (b) a transmembrane domain, wherein the transmembrane domain comprises a CD2 transmembrane domain or a portion thereof; and (c) an endodomain comprising a cytoplasmic domain and at least one signal transduction domain, wherein the cytoplasmic domain comprises a CD2 cytoplasmic domain or a portion thereof and wherein the at least one signal transduction domain comprises a CD3ζ protein or a portion thereof. In some aspects, the non-naturally CSR comprises an amino acid sequence at least 75%, 80%, 85%, 90%, 95%, 96%, 97%, 98%, 99% or 100% (or any percentage in between) identical to SEQ ID NO: 81. In a preferred aspect, the non-naturally occurring CSR comprises an amino acid sequence of SEQ ID NO: 81.

The present disclosure also provides a non-naturally occurring chimeric stimulatory receptor (CSR) wherein the ectodomain comprises a modification. The modification can comprise a mutation or a truncation of the amino acid sequence of the activation component or the first protein when compared to a wild type sequence of the activation component or the first protein. The mutation or a truncation of the amino acid sequence of the activation component can comprise a mutation or truncation of a CD2 extracellular domain or a portion thereof to which an agonist binds. The mutation or truncation of the CD2 extracellular domain can reduce or eliminate binding with naturally occurring CD58. In some aspects, the CD2 extracellular domain comprising the mutation or truncation comprises an amino acid sequence at least 75%, 80%, 85%, 90%, 95%, 96%, 97%, 98%, 99% or 100% (or any percentage in between) identical to SEQ ID NO: 82. In a preferred aspect, the CD2 extracellular domain comprising the mutation or truncation comprises an amino acid sequence of SEQ ID NO: 82.

In a preferred aspect, the present disclosure provides non-naturally occurring chimeric stimulatory receptor (CSR) comprising: (a) an ectodomain comprising a signal peptide and an activation component, wherein the signal peptide comprises a CD2 signal peptide or a portion thereof and wherein the activation component comprises a CD2 extracellular domain or a portion thereof to which an agonist binds and wherein the CD2 extracellular domain or a portion thereof to which an agonist binds comprises a mutation or truncation; (b) a transmembrane domain, wherein the transmembrane domain comprises a CD2 transmembrane domain or a portion thereof; and (c) an endodomain comprising a cytoplasmic domain and at least one signal transduction domain, wherein the cytoplasmic domain comprises a CD2 cytoplasmic domain or a portion thereof and wherein the at least one signal transduction domain comprises a CD3ζ protein or a portion thereof. In some aspects, the non-naturally CSR comprises an amino acid sequence at least 75%, 80%, 85%, 90%, 95%, 96%, 97%, 98%, 99% or 100% for any percentage in between) identical to SEQ ID NO: 83. In a preferred aspect, the non-naturally occurring CSR comprises an amino acid sequence of SEQ ID NO: 83.

The present disclosure provides a nucleic acid sequence encoding any CSR disclosed herein. The present disclosure provides a transposon or a vector comprising a nucleic acid sequence encoding any CSR disclosed herein.

The present disclosure provides a cell comprising any CSR disclosed herein. The present disclosure provides a cell comprising a nucleic acid sequence encoding any CSR disclosed herein. The present disclosure provides a cell comprising a vector comprising a nucleic acid sequence encoding any CSR disclosed herein. The present disclosure provides a cell comprising a transposon comprising a nucleic acid sequence encoding any CSR disclosed herein.

A modified cell disclosed herein can be an allogeneic cell or an autologous cell. In some preferred aspects, the modified cell is an allogeneic cell. In some aspects, the modified cell is an autologous T-cell or a modified autologous CAR T-cell. In some preferred aspects, the modified cell is an allogeneic T-cell or a modified allogeneic CAR T-cell.

The present disclosure provides a composition comprising any CSR disclosed herein. The present disclosure provides a composition comprising a nucleic acid sequence encoding any CSR disclosed herein. The present disclosure provides a composition comprising a vector comprising a nucleic acid sequence encoding any CSR disclosed herein. The present disclosure provides a composition comprising a transposon comprising a nucleic acid sequence encoding any CSR disclosed herein. The present disclosure provides a composition comprising a modified cell disclosed herein or a composition comprising a plurality of modified cells disclosed herein.

The present disclosure provides a modified T lymphocyte (T-cell), comprising: (a) a modification of an endogenous sequence encoding a T-cell Receptor (TCR), wherein the modification reduces or eliminates a level of expression or activity of the TCR; and (b) a chimeric stimulatory receptor (CSR) comprising: (i) an ectodomain comprising an activation component, wherein the activation component is isolated or derived from a first protein; (ii) a transmembrane domain; and (iii) an endodomain comprising at least one signal transduction domain, wherein the at least one signal transduction domain is isolated or derived from a second protein; wherein the first protein and the second protein are not identical.

The modified T-cell can further comprise an inducible proapoptotic polypeptide. The modified T-cell can further comprise a modification of an endogenous sequence encoding Beta-2-Microglobulin (B2M), wherein the modification reduces or eliminates a level of expression or activity of a major histocompatibility complex (MHC) class I (MHC-I).

The modified T-cell can further comprise a non-naturally occurring polypeptide comprising an HLA class I histocompatibility antigen, alpha chain E polypeptide. The non-naturally occurring polypeptide comprising a HLA-E polypeptide can further comprise a B2M signal peptide. The non-naturally occurring polypeptide comprising a HLA-E polypeptide can further comprise a B2M polypeptide. The non-naturally occurring polypeptide comprising an HLA-E polypeptide can further comprise a linker, wherein the linker is positioned between the B2M polypeptide and the HLA-E polypeptide. The non-naturally occurring polypeptide comprising an HLA-E polypeptide can further comprise a peptide and a B2M polypeptide. The non-naturally occurring polypeptide comprising an HLA-E can further comprise a first linker positioned between the B2M signal peptide and the peptide, and a second linker positioned between the B2M polypeptide and the peptide encoding the HLA-E.

The modified T-cell can further comprise a non-naturally occurring antigen receptor, a sequence encoding a therapeutic polypeptide, or a combination thereof. The non-naturally occurring antigen receptor can comprise a chimeric antigen receptor (CAR).

The CSR can be transiently expressed in the modified T-cell. The CSR can be stably expressed in the modified T-cell. The polypeptide comprising the HLA-E polypeptide can be transiently expressed in the modified T-cell. The polypeptide comprising the HLA-E polypeptide can be stably expressed in the modified T-cell. The inducible proapoptotic polypeptide can be transiently expressed in the modified T-cell. The inducible proapoptotic polypeptide can be stably expressed in the modified T-cell. The non-naturally occurring antigen receptor or a sequence encoding a therapeutic protein can be transiently expressed in the modified T-cell. The non-naturally occurring antigen receptor or a sequence encoding a therapeutic protein can be stably expressed in the modified T-cell.

Gene editing compositions, including but not limited to, RNA-guided fusion proteins comprising dCas9-Clo051, as described in detail herein, can be used to target and decrease or eliminate expression of an endogenous T-cell receptor. In preferred aspects, the gene editing compositions target and delete a gene, a portion of a gene, or a regulatory element of a gene (such as a promoter) encoding an endogenous T-cell receptor. Non-limiting examples of primers (including a T7 promoter, genome target sequence, and gRNA scaffold) for the generation of guide RNA (gRNA) templates for targeting and deleting TCR-alpha (TCR-α), targeting and deleting TCR-beta (TCR-β), and targeting and deleting beta-2-microglobulin (β2M) are disclosed in PCT Application No. PCT/US2019/049816.

Gene editing compositions, including but not limited to, RNA-guided fusion proteins comprising dCas9-Clo051, can be used to target and decrease or eliminate expression of an endogenous MHCI, MHCII, or MHC activator. In preferred aspects, the gene editing compositions target and delete a gene, a portion of a gene, or a regulatory element of a gene (such as a promoter) encoding one or more components of an endogenous MHO, WWII, or MHC activator. Non-limiting examples of guide RNAs (gRNAs) for targeting and deleting MHC activators are disclosed in PCI Application No. PCT/US2019/049816.

A detailed description of non-naturally occurring chimeric stimulatory receptors, genetic modifications of endogenous sequences encoding TCR-alpha (TCR-α), TCR-beta (TCR-β), and/or Beta-2-Microglobulin (β2M), and non-naturally occurring polypeptides comprising an HLA class I histocompatibility antigen, alpha chain E (HLA-E) polypeptide is disclosed in PCT Application No. PCT/US2019/049816.

Formulations, Dosages and Modes of Administration

The present disclosure provides formulations, dosages and methods for administration of the compositions described herein.

The disclosed compositions and pharmaceutical compositions can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990 and in the "Physician's Desk Reference", 52nd ed., Medical Economics (Montvale, N.J.) 1998. Pharmaceutically acceptable carriers can be routinely selected that are suitable for the mode of administration, solubility and/or stability of the protein scaffold, fragment or variant composition as well known in the art or as described herein.

Non-limiting examples of pharmaceutical excipients and additives suitable for use include proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Non-limiting examples of protein excipients include serum albumin, such as human serum albumin (HSA), recombinant human albumin (rHA), gelatin, casein, and the like. Representative amino acid/protein components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Non-limiting examples of carbohydrate excipients suitable for use include monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferably, the carbohydrate excipients are mannitol, trehalose, and/or raffinose.

The compositions can also include a buffer or a pH-adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers are organic acid salts, such as citrate.

Additionally, the disclosed compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

Many known and developed modes can be used for administering therapeutically effective amounts of the compositions or pharmaceutical compositions disclosed herein. Non-limiting examples of modes of administration include bolus, buccal, infusion, intrarticular, intrabronchial, intraabdominal, intracapsular, intracartilaginous, intracavitary, intracelial, intracerebellar, intracerebroventricular, intracolic, intracervical, intragastric, intrahepatic, intralesional, intramuscular, intramyocardial, intranasal, intraocular, intraosseous, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intratumoral, intravenous, intravesical, oral, parenteral, rectal, sublingual, subcutaneous, transdermal or vaginal means.

A composition of the disclosure can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

For parenteral administration, any composition disclosed herein can be formulated as a solution, suspension, emulsion, particle, powder, or lyophilized powder in association, or separately provided, with a pharmaceutically acceptable parenteral vehicle. Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semi synthetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446.

Formulations for oral administration rely on the co-administration of adjuvants (e.g., resorcinols and nonionic surfactants, such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Formulations for delivery of hydrophilic agents including proteins and protein scaffolds and a combination of at least two surfactants intended for oral, buccal, mucosal, nasal, pulmonary, vaginal transmembrane, or rectal administration are described in U.S. Pat. No. 6,309,663. The active constituent compound of the solid-type dosage form for oral administration can be mixed with at least one additive, including sucrose, lactose, cellulose, mannitol, trehalose, raffinose, maltitol, dextran, starches, agar, arginases, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant, such as magnesium stearate, paraben, preserving agent, such as sorbic acid, ascorbic acid, alpha-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug delivery systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. Nos. 5,879,681 and 5,871,753 and used to deliver biologically active agents orally are known in the art.

For pulmonary administration, preferably, a composition or pharmaceutical composition described herein is delivered in a particle size effective for reaching the lower airways of the lung or sinuses. The composition or pharmaceutical composition can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers (e.g., jet nebulizer, ultrasonic nebulizer), dry powder generators, sprayers, and the like. All such devices can use formulations suitable for the administration for the dispensing of a composition or pharmaceutical composition described herein in an aerosol. Such aerosols can be comprised of either solutions (both aqueous and non-aqueous) or solid particles. Additionally, a spray including a composition or pharmaceutical composition described herein can be produced by forcing a suspension or solution of at least one protein scaffold through a nozzle under pressure. In a metered dose inhaler (MDI), a propellant, a composition or pharmaceutical composition described herein, and any excipients or other additives are contained in a canister as a mixture including a liquefied compressed gas. Actuation of the metering valve releases the mixture as an aerosol, preferably containing particles in the size range of less than about 10 μm, preferably, about 1 μm to about 5 μm, and, most preferably, about 2 μm to about 3 μm. A more detailed description of pulmonary administration, formulations and related devices is disclosed in PCT Publication No. WO 2019/049816.

For absorption through mucosal surfaces, compositions include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670) Mucous surfaces suitable for application of the emulsions of the disclosure can include conical, conjunctival, buccal, sublingual, nasal, vaginal, pulmonary, stomachic, intestinal, and rectal routes of administration, Formulations for vaginal or rectal administration, e.g., suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration, excipients include sugars, calcium stearate, magnesium stearate, pregelinatined starch, and the like (U.S. Pat. No. 5,849,695). A more detailed description of mucosal administration and formulations is disclosed in KT Publication No. WO 2019/049816.

For transdermal administration, a composition or pharmaceutical composition disclosed herein is encapsulated in a delivery device, such as a liposome or polymeric nanoparticles, microparticle, microcapsule, or microspheres (referred to collectively as microparticles unless otherwise stated). A number of suitable devices are known, including microparticles made of synthetic polymers, such as polyhydroxy acids, such as polylactic acid, polyglycolic acid and copolymers thereof, polyorthoesters, polyanhydrides, and polyphosphazenes, and natural polymers, such as collagen, polyamine acids, albumin and other proteins, alginate and other polysaccharides, and combinations thereof (U.S. Pat. No. 5,814,599). A more detailed description of transdermal administration, formulations and suitable devices is disclosed in PCT Publication No. WO 2019/049816.

It can be desirable to deliver the disclosed compounds to the subject over prolonged periods of time, for example, for periods of one week to one year from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid, such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation, such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b), e.g., a zinc tannate salt. Additionally, the disclosed compounds or, preferably, a relatively insoluble salt, such as those just described, can be formulated in a gel, for example, an aluminum monostearate gel with, e.g., sesame oil, suitable for injection. Particularly preferred salts are zinc salts, zinc tannate salts, pamoate salts, and the like. Another type of slow release depot formulation for injection would contain the compound or salt dispersed for encapsulation in a slow degrading, non-toxic, non-antigenic polymer, such as a polylactic acid/polyglycolic acid polymer for example as described in U.S. Pat. No. 3,773,919. The compounds or, preferably, relatively insoluble salts, such as those described above, can also be formulated in cholesterol matrix silastic pellets, particularly for use in animals. Additional slow release, depot or implant formulations, e.g., gas or liquid liposomes, are known in the literature (U.S. Pat. No. 5,770,222 and "Sustained and Controlled Release Drug Delivery Systems", J. R. Robinson ed., Marcel Dekker, Inc., N.Y., 1978).

Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, 21st edition, Springhouse Corp., Springhouse, Pa., 2001; Health Professional's Drug Guide 2001, ed., Shannon, Wilson, Stang, Prentice-Hall, Inc, Upper Saddle River, N.J. Preferred doses can optionally include about 0.1-99 and/or 100-500 mg/kg/administration, or any range, value or fraction thereof, or to achieve a serum concentration of about 0.1-5000 μg/ml serum concentration per single or multiple administration, or any range, value or fraction thereof. A preferred dosage range for the compositions or pharmaceutical compositions disclosed herein is from about 1 mg/kg, up to about 3, about 6 or about 12 mg/kg of body weight of the subject.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably, 0.1 to 10 milligrams per kilogram per administration or in sustained release form is effective to obtain desired results.

As a non-limiting example, treatment of humans or animals can be provided as a one-time or periodic dosage of the compositions or pharmaceutical compositions disclosed herein about 0.1 to 100 mg/kg or any range, value or fraction thereof per day, on at least one of day 1-40, or, alternatively or additionally, at least one of week 1-52, or, alternatively or additionally, at least one of 1-20 years, or any combination thereof, using single, infusion or repeated doses.

Dosage forms suitable for internal administration generally contain from about 0.001 milligram to about 500 milligrams of active ingredient per unit or container. In these pharmaceutical compositions the active ingredient will ordinarily be present in an amount of about 0.5-99.999% by weight based on the total weight of the composition.

An effective amount can comprise an amount of about 0.001 to about 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

In aspects where the compositions to be administered to a subject in need thereof are modified cells as disclosed herein, the cells can be administered between about $1\times10^3$ and $1\times10^{15}$ cells; about $1\times10^4$ and $1\times10^{32}$ cells; about $1\times10^5$ and $1\times10^{10}$ cells; about $1\times10^6$ and $1\times10^9$ cells; about $1\times10^6$ and $1\times10^8$ cells; about $1\times10^6$ and $1\times10^7$ cells; or about $1\times10^6$ and $25\times10^6$ cells. In an aspect the cells are administered between about $5\times10^6$ and $25\times10^6$ cells.

A more detailed description of pharmaceutically acceptable excipients, formulations, dosages and methods of administration of the disclosed compositions and pharmaceutical compositions is disclosed in PCT Publication No. WO 2019/049816.

Methods of Using the Compositions of the Disclosure

The disclosure provides a the use of a disclosed composition for improving transposition efficiency. Specifically, the method comprising contacting a cell or a plurality of cells with a composition comprising: a first nucleic acid sequence comprising: (a) a first inverted terminal repeat (ITR) or a sequence encoding a first ITR, (b) a second ITR or a sequence encoding a second ITR, and (c) an intra-ITR sequence or a sequence encoding an intra-ITR, wherein the intra-ITR sequence comprises a transposon sequence or a sequence encoding a transposon; and a second nucleic acid sequence comprising an inter-ITR sequence or a sequence encoding an inter-ITR, wherein the length of the inter-ITR sequence is equal to or less than 700 nucleotides, wherein transposition efficiency within the cell or plurality of cells is improved when compared to an identical composition comprising a second nucleic acid sequence or inter-ITR sequence greater than 700 nucleotides. In an aspect, the transposition efficiency is improved by at least 5%, at least 10%, at least 15%, at least 20%, at least 25%, at least 30%, at least 35$, at least 40%, at least 45%, at least 50%, at least 55%, at least 60%, at least 65%, at least 70%, at least 75%, at least 80%, at least 85%, at least 90%, at least 95%, at least 90%.

The disclosure provides the use of a disclosed composition or pharmaceutical composition for the treatment of a disease or disorder in a cell, tissue, organ, animal, or subject, as known in the art or as described herein, using the disclosed compositions and pharmaceutical compositions, e.g., administering or contacting the cell, tissue, organ, animal, or subject with a therapeutic effective amount of the composition or pharmaceutical composition. In an aspect, the subject is a mammal. Preferably, the subject is human. The terms "subject" and "patient" are used interchangeably herein.

The disclosure provides a method for modulating or treating at least one malignant disease or disorder in a cell, tissue, organ, animal or subject. Preferably, the malignant disease is cancer. Non-limiting examples of a malignant disease or disorder include leukemia, acute leukemia, acute lymphoblastic leukemia (ALL), acute lymphocytic leukemia, B-cell, T-cell or FAB ALL, acute myeloid leukemia (AML), acute myelogenous leukemia, chronic myelocytic leukemia (CML), chronic lymphocytic leukemia (CLL), hairy cell leukemia, myelodysplastic syndrome (MDS), a lymphoma, Hodgkin's disease, a malignant lymphoma, non-Hodgkin's lymphoma, Burkitt's lymphoma, multiple myeloma, Kaposi's sarcoma, colorectal carcinoma, pancreatic carcinoma, nasopharyngeal carcinoma, malignant histiocytosis, paraneoplastic syndrome/hypercalcemia of malignancy, solid tumors, bladder cancer, breast cancer, colorectal cancer, endometrial cancer, head cancer, neck cancer, hereditary nonpolyposis cancer, Hodgkin's lymphoma, liver cancer, lung cancer, non-small cell lung cancer, ovarian cancer, pancreatic cancer, prostate cancer, renal cell carcinoma, testicular cancer, adenocarcinomas, sarcomas, malignant melanoma, hemangioma, metastatic disease, cancer related bone resorption, cancer related bone pain, and the like.

In preferred aspects, the treatment of a malignant disease or disorder comprises adoptive cell therapy. For example, in an aspect, the disclosure provides modified cells that express at least one disclosed protein scaffold and/or CAR comprising a protein scaffold (e.g., scFv, single domain antibody, Centyrin, delivered to the cell with a composition of the disclosure) that have been selected and/or expanded for administration to a subject in need thereof. Modified cells can be formulated for storage at any temperature including room temperature and body temperature. Modified cells can be formulated for cryopreservation and subsequent thawing. Modified cells can be formulated in a pharmaceutically acceptable carrier for direct administration to a subject from sterile packaging. Modified cells can be formulated in a pharmaceutically acceptable carrier with an indicator of cell viability and/or CAR expression level to ensure a minimal level of cell function and CAR expression. Modified cells can be formulated in a pharmaceutically acceptable carrier at a prescribed density with one or more reagents to inhibit further expansion and/or prevent cell death.

Any can comprise administering an effective amount of any composition or pharmaceutical composition disclosed herein to a cell, tissue, organ, animal or subject in need of such modulation, treatment or therapy. Such a method can optionally further comprise co-administration or combination therapy for treating such diseases or disorders, wherein the administering of any composition or pharmaceutical composition disclosed herein, further comprises administering, before concurrently, and/or after, at least one chemotherapeutic agent (e.g., an alkylating agent, an a mitotic inhibitor, a radiopharmaceutical).

In some aspects, the subject does not develop graft vs. host (GvH) and/or host vs. graft (HvG) following administration. In an aspect, the administration is systemic. Systemic administration can be any means known in the art and described in detail herein. Preferably, systemic administration is by an intravenous injection or an intravenous infusion. In an aspect, the administration is local. Local administration can be any means known in the art and described in detail herein. Preferably, local administration is by intratumoral injection or infusion, intraspinal injection or infusion, intracerebroventricular injection or infusion, intraocular injection or infusion, or intraosseous injection or infusion.

In some aspects, the therapeutically effective dose is a single dose. In some aspects, the single dose is one of at least 2, 5, 10, 15, 20, 25, 30, 35, 40, 45, 50, 55, 60, 65, 70, 75, 80, 85, 90, 95, 100 or any number of doses in between that are manufactured simultaneously. In some aspects, where the composition is autologous cells or allogeneic cells, the dose is an amount sufficient for the cells to engraft and/or persist for a sufficient time to treat the disease or disorder.

In one example, the disclosure provides a method of treating cancer in a subject in need thereof, comprising administering to the subject a composition comprising a protein scaffold or a CAR comprising a protein scaffold (e.g., e.g., scFv, single domain antibody, Centyrin) the antibody or CAR specifically binds to an antigen on a tumor cell. In aspects where the composition comprises a modified cell or cell population, the cell or cell population may be autologous or allogeneic.

In some aspects of the methods of treatment described herein, the treatment can be modified or terminated. Specifically, in aspects where the composition used for treatment comprises an inducible proapoptotic polypeptide, apoptosis may be selectively induced in the cell by contacting the cell with an induction agent. A treatment may be modified or terminated in response to, for example, a sign of recovery or a sign of decreasing disease severity/progression, a sign of disease remission/cessation, and/or the occurrence of an adverse event. In some aspects, the method comprises the step of administering an inhibitor of the induction agent to inhibit modification of the cell therapy, thereby restoring the function and/or efficacy of the cell therapy (for example, when a sign or symptom of the disease reappear or increase in severity and/or an adverse event is resolved).

Protein Scaffold Production, Screening and Purification

At least one protein scaffold (e.g., monoclonal antibody, a chimeric antibody, a single domain antibody, a VHH, a VH, a single chain variable fragment (scFv), a Centyrin, an antigen-binding fragment (Fab) or a Fab fragment) of the disclosure can be optionally produced by a cell line, a mixed cell line, an immortalized cell or clonal population of immortalized cells, as well known in the art. See, e.g., Ausubel, et al., ed., Current Protocols in Molecular Biology, John Wiley &. Sons, Inc., New York, N.Y. (1987-2001); Sambrook, et al., Molecular Cloning: A Laboratory Manual, 2nd Edition, Cold Spring Harbor, N.Y. (1989); Harlow and Lane, Antibodies, a Laboratory Manual, Cold. Spring Harbor, N.Y. (1989); Colligan, et al., eds., Current Protocols in Immunology, John Wiley & Sons, Inc., N.Y. (1994-2001); Colligan et al., Current Protocols in Protein Science, John Wiley & Sons, New York, N.Y., (1997-2001).

Amino acids from a protein scaffold can be altered, added and/or deleted to reduce immunogenicity or reduce, enhance or modify binding, affinity, on-rate, off-rate, avidity, specificity, half-life, stability, solubility or any other suitable characteristic, as known in the art.

Optionally, a protein scaffold can be engineered with retention of high affinity for the antigen and other favorable biological properties. To achieve this goal, the scaffold proteins can be optionally prepared by a process of analysis of the parental sequences and various conceptual engineered products using three-dimensional models of the parental and engineered sequences. Three-dimensional models are commonly available and are familiar to those skilled in the art. Computer programs are available which illustrate and display probable three-dimensional conformational structures of selected candidate sequences and can measure possible immunogenicity (e.g., Immunofilter program of Xencor, Inc. of Monrovia, Calif.). Inspection of these displays permits analysis of the likely role of the residues in the functioning of the candidate sequence, i.e., the analysis of residues that influence the ability of the candidate protein scaffold to bind its antigen. In this way, residues can be selected and combined from the parent and reference sequences so that the desired characteristic, such as affinity for the target antigen (s), is achieved. Alternatively, or in addition to, the above procedures, other suitable methods of engineering can be used.

Screening of a protein scaffold for specific binding to similar proteins or fragments can be conveniently achieved using nucleotide (DNA or RNA display) or peptide display libraries, for example, in vitro display. This method involves the screening of large collections of peptides for individual members having the desired function or structure. The displayed nucleotide or peptide sequences can be from 3 to 5000 or more nucleotides or amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. WO 91/17271, WO 91/18980, WO 91/19818, and WO 93/08278.

Other systems for generating libraries of peptides have aspects of both in vitro chemical synthesis and recombinant methods. See, PCT Patent Publication Nos. WO 92/05258, WO 92/14843, and WO 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge Antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge Antibody Technologies; U.S. Pat. No. 5,750,373, assigned to Genentech, U.S. Pat. Nos. 5,618,920, 5,595,898, 5,576,195, 5,698,435, 5,693,493, 5,698,417, assigned to Xoma, Colligan, supra; Ausubel, supra; or Sambrook, supra.

A protein scaffold of the disclosure can bind human or other mammalian proteins with a wide range of affinities (KD). In a preferred aspect, at least one protein scaffold of the present disclosure can optionally bind to a target protein with high affinity, for example, with a KD equal to or less than about $10^{-7}$ M, such as but not limited to, 0.1-9.9 (or any range or value therein) X $10^{-8}$, $10^{-9}$, $10^{-10}$, $10^{-11}$, $10^{-12}$, $10^{-13}$, $10^{-14}$, $10^{-15}$ or any range or value therein, as determined by surface plasmon resonance or the Kinexa method, as practiced by those of skill in the art.

The affinity or avidity of a protein scaffold for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W.H. Freeman and Company: New York, N.Y. (1992); and methods described herein). The measured affinity of a particular protein scaffold-antigen interaction can vary if measured under different conditions salt concentration, pH). Thus, measurements of affinity and other antigen-binding parameters (e.g., KD, Kon, Koff) are preferably made with standardized solutions of protein scaffold and antigen, and a standardized buffer, such as the buffer described herein.

Competitive assays can be performed with a protein scaffold in order to determine what proteins, antibodies, and other antagonists compete for binding to a target protein with the protein scaffold and/or share the epitope region. These assays as readily known to those of ordinary skill in the art evaluate competition between antagonists or ligands for a limited number of binding sites on a protein. The protein and/or antibody is immobilized or insolubilized before or after the competition and the sample bound to the target protein is separated from the unbound sample, for example, by decanting (where the protein/antibody was pre-insolubilized) or by centrifuging (where the protein/antibody was precipitated after the competitive reaction). Also, the competitive binding may be determined by whether function is altered by the binding or lack of binding of the protein scaffold to the target protein, e.g., whether the protein scaffold inhibits or potentiates the enzymatic activity of, for example, a label. ELISA and other functional assays may be used, as well known in the art.

Nucleic Acid Molecules

Nucleic acid molecules of the disclosure encoding a protein scaffold can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the disclosure can include nucleic acid molecules comprising an open reading frame (ORF), optionally, with one or more introns, e.g., but not limited to, at least one specified portion of at least one protein scaffold; nucleic acid molecules comprising the coding sequence for a protein scaffold or loop region that binds to the target protein; and nucleic acid molecules which comprise a nucleotide sequence substantially different from those described above but which, due to the degeneracy of the genetic code, still encode the protein scaffold as described herein and/or as known in the art. Of course, the genetic code is well known in the art. Thus, it would be routine for one skilled in the art to generate such degenerate nucleic acid variants that code for a specific protein scaffold of the present disclosure. See, e.g., Ausubel, et al., supra, and such nucleic acid variants are included in the present disclosure.

As indicated herein, nucleic acid molecules of the disclosure which comprise a nucleic acid encoding a protein scaffold can include, but are not limited to, those encoding the amino acid sequence of a protein scaffold fragment, by itself; the coding sequence for the entire protein scaffold or a portion thereof; the coding sequence for a protein scaffold, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example, ribosome binding and stability of mRNA); an additional coding sequence that codes for additional amino acids, such as those that provide additional functionalities. Thus, the sequence encoding a protein scaffold can be fused to a marker sequence, such as a sequence encoding a peptide that facilitates purification of the fused protein scaffold comprising a protein scaffold fragment or portion.

Polynucleotides Selectively Hybridizing to a Polynucleotide as Described Herein

The disclosure provides isolated nucleic acids that hybridize under selective hybridization conditions to a polynucleotide disclosed herein. Thus, the polynucleotides can be used for isolating, detecting, and/or quantifying nucleic acids comprising such polynucleotides. For example, polynucleotides of the present disclosure can be used to identify, isolate, or amplify partial or full-length clones in a deposited library. The polynucleotides can be genomic or cDNA sequences isolated, or otherwise complementary to, a cDNA from a human or mammalian nucleic acid library.

Preferably, the cDNA library comprises at least 80% full-length sequences, preferably, at least 85% or 90% full-length sequences, and, more preferably, at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides will encode at least a portion of a protein scaffold encoded by the polynucleotides described herein. The polynucleotides embrace nucleic acid sequences that can be employed for selective hybridization to a polynucleotide encoding a protein scaffold of the present disclosure. See, e.g., Ausubel, supra; Colligan, supra, each entirely incorporated herein by reference.

Construction of Nucleic Acids

The isolated nucleic acids of the disclosure can be made using (a) recombinant methods, (b) synthetic techniques, (c) purification techniques, and/or (d) combinations thereof, as well-known in the art.

The nucleic acids can conveniently comprise sequences in addition to a polynucleotide of the present disclosure. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the disclosure. For example, a hexa-histidine marker sequence provides a convenient means to purify the proteins of the disclosure. The nucleic acid of the disclosure, excluding the coding sequence, is optionally a vector, adapter, or linker for cloning and/or expression of a polynucleotide of the disclosure.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

Recombinant Methods for Constructing Nucleic Acids

The isolated nucleic acid compositions of this disclosure, such as RNA, cDNA, genomic DNA, or any combination thereof, can be obtained from biological sources using any number of cloning methodologies known to those of skill in the art. In some aspects, oligonucleotide probes that selectively hybridize, under stringent conditions, to the polynucleotides of the present disclosure are used to identify the desired sequence in a cDNA or genomic DNA library. The isolation of RNA, and construction of cDNA and genomic libraries are well known to those of ordinary skill in the art. (See, e.g., Ausubel, supra; or Sambrook, supra).

Nucleic Acid Screening and Isolation Methods

A cDNA or genomic library can be screened using a probe based upon the sequence of a polynucleotide of the disclosure. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent, such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the disclosure without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses antisense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the disclosure and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

Synthetic Methods for Constructing Nucleic Acids

The isolated nucleic acids of the disclosure can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences.

Recombinant Expression Cassettes

The disclosure further provides recombinant expression cassettes comprising a nucleic acid of the disclosure. A nucleic acid sequence of the disclosure, for example, a cDNA or a genomic sequence encoding a protein scaffold of the disclosure, can be used to construct a recombinant expression cassette that can be introduced into at least one desired host cell, A recombinant expression cassette will typically comprise a polynucleotide of the disclosure operably linked to transcriptional initiation regulatory sequences that will direct the transcription of the polynucleotide in the intended host cell. Both heterologous and non-heterologous (i.e., endogenous) promoters can be employed to direct expression of the nucleic acids of the disclosure.

In some aspects, isolated nucleic acids that serve as promoter, enhancer, or other elements can be introduced in the appropriate position (upstream, downstream or in the intron) of a non-heterologous form of a polynucleotide of the disclosure so as to up or down regulate expression of a polynucleotide of the disclosure. For example, endogenous promoters can be altered in vivo or in vitro by mutation, deletion and/or substitution.

Expression Vectors and Host Cells

The disclosure also relates to vectors that include isolated nucleic acid molecules of the disclosure, host cells that are genetically engineered with the recombinant vectors, and the production of at least one protein scaffold by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, ampicillin, zeocin (Sh bla gene), puromycin (par gene), hygromycin B (hygB gene), G418/Geneticin (neo gene), DHFR. (encoding Dihydrofolate Reductase and conferring resistance to Methotrexate), mycophenolic acid, or glutamine synthetase (GS, U.S. Pat. Nos. 5,122,464; 5,770,359; 5,827,739), blasticidin (hsd gene), resistance genes for eukaryotic cell culture as well as ampicillin, zeocin (Sh h/a gene), puromycin (par gene), hygromycin B (hygB gene), G418/Geneticin (neo gene), kanamycin, spectinomycin, streptomycin, carbenicillin, bleomycin, erythromycin, polymyxin B, or tetracycline resistance genes for culturing in *E. coli* and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

Expression vectors will preferably but optionally include at least one selectable cell surface marker for isolation of cells modified by the compositions and methods of the disclosure. Selectable cell surface markers of the disclosure comprise surface proteins, glycoproteins, or group of proteins that distinguish a cell or subset of cells from another defined subset of cells. Preferably the selectable cell surface marker distinguishes those cells modified by a composition or method of the disclosure from those cells that are not modified by a composition or method of the disclosure. Such cell surface markers include, e.g., but are not limited to, “cluster of designation” or “classification determinant” proteins (often abbreviated as “CD”) such as a truncated or full length form of CD19, CD271, CD34, CD22, CD20, CD33, CD52, or any combination thereof. Cell surface markers further include the suicide gene marker RQR8 B et al. Blood. 2014 Aug. 21; 124(8):1277-87).

Expression vectors will preferably but optionally include at least one selectable drug resistance marker for isolation of cells modified by the compositions and methods of the disclosure. Selectable drug resistance markers of the disclosure may comprise wild-type or mutant Neo, DHFR, TYMS, FRANCF, RAD51C, GCS, MDR1, ALDH1, NKX2.2, or any combination thereof.

At least one protein scaffold of the disclosure can be expressed in a modified form, such as a fusion protein, and can include not only secretion signals, but also additional heterologous functional regions. For instance, a region of additional amino acids, particularly charged amino acids, can be added to the N-terminus of a protein scaffold to improve stability and persistence in the host cell, during purification, or during subsequent handling and storage. Also, peptide moieties can be added to a protein scaffold of the disclosure to facilitate purification. Such regions can be removed prior to final preparation of a protein scaffold or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the disclosure. Alternatively, nucleic acids of the disclosure can be expressed in a host cell by turning on (by manipulation) in a host cell that contains endogenous DNA encoding a protein scaffold of the disclosure. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the protein scaffolds, specified portions or variants thereof, are bacterial, yeast, and mammalian cells as known in the art. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8,653 cells (ATCC Accession Number CRL-1580) and SP2/0-Ag14 cells (ATCC Accession Number CRL-1851). In a preferred aspect, the recombinant cell is a P3X63Ag8,653 or an SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al, supra; Sambrook, et al., supra. Other cells useful for production of nucleic acids or proteins of the present disclosure are known and/or available, for instance, from the American Type Culture Collection Catalogue of Cell Lines and Hybridomas www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Protein Scaffold Purification

A protein scaffold can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, New York, N.Y., (1997-2001), e.g., Chapters 1, 4, 6, 8, 9, 10, each entirely incorporated herein by reference.

A protein scaffold of the disclosure include purified products, products of chemical synthetic procedures, and products produced by recombinant techniques from a prokaryotic or eukaryotic host, including, for example, *E. coli*, yeast, higher plant, insect and mammalian cells. Depending upon the host employed in a recombinant production procedure, the protein scaffold of the disclosure can be glycosylated or can be non-glycosylated. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Amino Acid Codes

The amino acids that make up protein scaffolds of the disclosure are often abbreviated. The amino acid designations can be indicated by designating the amino acid by its single letter code, its three letter code, name, or three nucleotide codon(s) as is well understood in the art (see Alberts, B., et al., Molecular Biology of The Cell, Third Ed., Garland Publishing, Inc., New York, 1994). A protein scaffold of the disclosure can include one or more amino acid substitutions, deletions or additions, from spontaneous or mutations and/or human manipulation, as specified herein. Amino acids in a protein scaffold of the disclosure that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)), The latter procedure introduces single alanine mutations at every residue in the molecule. The resulting mutant molecules are then tested for biological activity, such as, but not limited to, at least one neutralizing activity. Sites that are critical for protein scaffold binding can also be identified by structural analysis, such as crystallization, nuclear magnetic resonance or photoaffinity labeling (Smith, et al., J. Mol. Biol. 224:899-904 (1992) and de Vos, et al., Science 255: 306-312 (1992)).

As those of skill will appreciate, the disclosure includes at least one biologically active protein scaffold of the disclosure. Biologically active protein scaffolds have a specific activity at least 20%, 30%, or 40%, and, preferably, at least 50%, 60%, or 70%, and, most preferably, at least 80%, 90%, or 95%-99% or more of the specific activity of the native (non-synthetic), endogenous or related and known protein scaffold. Methods of assaying and quantifying measures of enzymatic activity and substrate specificity are well known to those of skill in the art.

In another aspect, the disclosure relates to protein scaffolds and fragments, as described herein, which are modified by the covalent attachment of an organic moiety. Such modification can produce a protein scaffold fragment with improved pharmacokinetic properties e.g., increased in vivo serum half-life). The organic moiety can be a linear or branched hydrophilic polymeric group, fatty acid group, or fatty acid ester group. In particular aspect, the hydrophilic polymeric group can have a molecular weight of about 800 to about 120,000 Daltons and can be a polyalkane glycol (e.g., polyethylene glycol (PEG), polypropylene glycol (PPG), carbohydrate polymer, amino acid polymer or polyvinyl pyrolidone, and the fatty acid or fatty acid ester group can comprise from about eight to about forty carbon atoms.

The modified protein scaffolds and fragments of the disclosure can comprise one or more organic moieties that are covalently bonded, directly or indirectly, to the antibody. Each organic moiety that is bonded to a protein scaffold or fragment of the disclosure can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, a protein scaffold modified by the covalent attachment of polylysine is encompassed by the disclosure. Hydrophilic polymers suitable for modifying protein scaffolds of the disclosure can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the protein scaffold of the disclosure has a molecular weight of about 800 to about 150,000 Daltons as a separate molecular entity. For example, PEG5000 and PEG20,000, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying protein scaffolds of the disclosure can be saturated or can contain one or more units of unsaturation. Fatty acids that are suitable for modifying protein scaffolds of the disclosure include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-Δ9-octadecanoate (C18, oleate), all cis-Δ5,8,11,14-eicosatetraenoate (C20, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified protein scaffolds and fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acryloyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphoramide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example, a divalent C1-C12 group wherein one or more carbon atoms can be replaced by a heteroatom, such as oxygen, nitrogen or sulfur. Suitable linker moieties include, for example, tetraethylene glycol, —(CH2)3-, —H—(CH2)6-NH—(CH2)2-NH— and —CH2-CH2-CH2-CH2-CH2-O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified protein scaffolds of the disclosure can be produced by reacting a protein scaffold or fragment with a modifying agent. For example, the organic moieties can be bonded to the protein scaffold in a non-site specific manner by employing an amine-reactive modifying agent, for example, an NHS ester of PEG. Modified protein scaffolds and fragments comprising an organic moiety that is bonded to specific sites of a protein scaffold of the disclosure can be prepared using suitable methods, such as reverse proteolysis (Fisch et al., Bioconjugate Chem., 3:147-153 (1992); Werlen et al., Bioconjugate Chem., 5:411-417 (1994); Kumaran et at, Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

Definitions

As used throughout the disclosure, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more standard deviations. Alternatively, "about" can mean a range of up to 20%, or up to 10%, or up to 5%, or up to 1% of a given value.

Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The disclosure provides isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized, Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various aspects, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the disclosure or biologically active portion thereof is recombinantly produced, optimally culture medium represents less than about 30%, 20%, 10%, 5%, or 1% (by dry weight) of chemical precursors or non-protein-of-interest chemicals.

The disclosure provides fragments and variants of the disclosed DNA sequences and proteins encoded by these DNA sequences. As used throughout the disclosure, the term "fragment" refers to a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the disclosure.

Nucleic acids or proteins of the disclosure can be constructed by a modular approach including preassembling monomer units and/or repeat units in target vectors that can subsequently be assembled into a final destination vector. Polypeptides of the disclosure may comprise repeat monomers of the disclosure and can be constructed by a modular approach by preassembling repeat units in target vectors that can subsequently be assembled into a final destination vector. The disclosure provides polypeptide produced by this method as well nucleic acid sequences encoding these polypeptides. The disclosure provides host organisms and cells comprising nucleic acid sequences encoding polypeptides produced this modular approach.

The term "antibody" is used in the broadest sense and specifically covers single monoclonal antibodies (including agonist and antagonist antibodies) and antibody compositions with polyepitopic specificity. It is also within the scope hereof to use natural or synthetic analogs, mutants, variants, alleles, homologs and orthologs (herein collectively referred to as "analogs") of the antibodies hereof as defined herein. Thus, according to an aspect hereof, the term "antibody hereof" in its broadest sense also covers such analogs. Generally, in such analogs, one or more amino acid residues may have been replaced, deleted and/or added, compared to the antibodies hereof as defined herein.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, $F(ab')_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g., CHI in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). The term further includes single domain antibodies ("sdAB") which generally refers to an antibody fragment having a single monomeric variable antibody domain, (for example, from camelids). Such antibody fragment types will be readily understood by a person having ordinary skill in the art.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific.

The term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Aspects defined by each of these transition terms are within the scope of this disclosure.

The term "epitope" refers to an antigenic determinant of a polypeptide. An epitope could comprise three amino acids in a spatial conformation, which is unique to the epitope. Generally, an epitope consists of at least 4, 5, 6, or 7 such amino acids, and more usually, consists of at least 8, 9, or 10 such amino acids. Methods of determining the spatial conformation of amino acids are known in the art, and include, for example, x-ray crystallography and two-dimensional nuclear magnetic resonance.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Gene expression" refers to the conversion of the information, contained in a gene, into a gene product. A gene product can be the direct transcriptional product of a gene (e.g., mRNA, tRNA, rRNA, antisense RNA, ribozyme, shRNA, micro RNA, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" or "regulation" of gene expression refers to a change in the activity of a gene. Modulation of expression can include, but is not limited to, gene activation and gene repression.

The term "operatively linked" or its equivalents (e.g., "linked operatively") means two or more molecules are positioned with respect to each other such that they are capable of interacting to affect a function attributable to one or both molecules or a combination thereof.

Non-covalently linked components and methods of making and using non-covalently linked components, are disclosed. The various components may take a variety of different forms as described herein. For example, non-covalently linked (i.e., operatively linked) proteins may be used to allow temporary interactions that avoid one or more problems in the art. The ability of non-covalently linked components, such as proteins, to associate and dissociate enables a functional association only or primarily under circumstances where such association is needed for the desired activity. The linkage may be of duration sufficient to allow the desired effect.

A method for directing proteins to a specific locus in a genome of an organism is disclosed. The method may comprise the steps of providing a DNA localization component and providing an effector molecule, wherein the DNA localization component and the effector molecule are capable of operatively linking via a non-covalent linkage.

The term "scFv" refers to a single-chain variable fragment. scFv is a fusion protein of the variable regions of the heavy (VH) and light chains (VL) of immunoglobulins, connected with a linker peptide. The linker peptide may be from about 5 to 40 amino acids or from about 10 to 30 amino acids or about 5, 10, 15, 20, 25, 30, 35, or 40 amino acids in length. Single-chain variable fragments lack the constant Fc region found in complete antibody molecules, and, thus, the common binding sites (e.g., Protein G) used to purify antibodies. The term further includes a scFv that is an intrabody, an antibody that is stable in the cytoplasm of the cell, and which may bind to an intracellular protein.

The term "single domain antibody" means an antibody fragment having a single monomeric variable antibody domain which is able to bind selectively to a specific antigen. A single-domain antibody generally is a peptide chain of about 110 amino acids long, comprising one variable domain (VH) of a heavy-chain antibody, or of a common IgG, which generally have similar affinity to antigens as whole antibodies, but are more heat-resistant and stable towards detergents and high concentrations of urea. Examples are those derived from camelid or fish antibodies. Alternatively, single-domain antibodies can be made from common murine or human IgG with four chains.

The terms "specifically bind" and "specific binding" as used herein refer to the ability of an antibody, an antibody fragment or a nanobody to preferentially bind to a particular antigen that is present in a homogeneous mixture of different antigens. In some aspects, a specific binding interaction will discriminate between desirable and undesirable antigens in a sample. In some aspects, more than about ten- to 100-fold or more (e.g., more than about 1000- or 10,000-fold). "Specificity" refers to the ability of an immunoglobulin or an immunoglobulin fragment, such as a nanobody, to bind preferentially to one antigenic target versus a different antigenic target and does not necessarily imply high affinity.

A "target site" or "target sequence" is a nucleic acid sequence that defines a portion of a nucleic acid to which a binding molecule will bind, provided sufficient conditions for binding exist.

The terms "nucleic acid" or "oligonucleotide" or "polynucleotide" refer to at least two nucleotides covalently linked together. The depiction of a single strand also defines the sequence of the complementary strand. Thus, a nucleic acid may also encompass the complementary strand of a depicted single strand. A nucleic acid of the disclosure also encompasses substantially identical nucleic acids and complements thereof that retain the same structure or encode for the same protein.

Probes of the disclosure may comprise a single stranded nucleic acid that can hybridize to a target sequence under stringent hybridization conditions. Thus, nucleic acids of the disclosure may refer to a probe that hybridizes under stringent hybridization conditions.

Nucleic acids of the disclosure may be single- or double-stranded. Nucleic acids of the disclosure may contain double-stranded sequences even when the majority of the molecule is single-stranded. Nucleic acids of the disclosure may contain single-stranded sequences even when the majority of the molecule is double-stranded. Nucleic acids of the disclosure may include genomic DNA, cDNA, RNA, or a hybrid thereof. Nucleic acids of the disclosure may contain combinations of deoxyribo- and ribo-nucleotides. Nucleic acids of the disclosure may contain combinations of bases including uracil, adenine, thymine, cytosine, guanine, inosine, xanthine hypoxanthine, isocytosine and isoguanine. Nucleic acids of the disclosure may be synthesized to comprise non-natural amino acid modifications. Nucleic acids of the disclosure may be obtained by chemical synthesis methods or by recombinant methods.

Nucleic acids of the disclosure, either their entire sequence, or any portion thereof, may be non-naturally occurring. Nucleic acids of the disclosure may contain one or more mutations, substitutions, deletions, or insertions that do not naturally-occur, rendering the entire nucleic acid sequence non-naturally occurring. Nucleic acids of the disclosure may contain one or more duplicated, inverted or repeated sequences, the resultant sequence of which does not naturally-occur, rendering the entire nucleic acid sequence non-naturally occurring. Nucleic acids of the disclosure may contain modified, artificial, or synthetic nucleotides that do not naturally-occur, rendering the entire nucleic acid sequence non-naturally occurring.

Given the redundancy in the genetic code, a plurality of nucleotide sequences may encode any particular protein. All such nucleotides sequences are contemplated herein.

As used throughout the disclosure, the term "operably linked" refers to the expression of a gene that is under the control of a promoter with which it is spatially connected. A promoter can be positioned 5' (upstream) or 3' (downstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

As used throughout the disclosure, the term "promoter" refers to a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, EF-1 Alpha promoter, CAG promoter, SV40 early promoter or SV40 late promoter and the CMV IE promoter.

As used throughout the disclosure, the term "substantially complementary" refers to a first sequence that is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used throughout the disclosure, the term "substantially identical" refers to a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used throughout the disclosure, the term "variant" when used to describe a nucleic acid, refers to (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof or a sequences substantially identical thereto.

As used throughout the disclosure, the term "vector" refers to a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid. A vector may comprise a combination of an amino acid with a DNA sequence, an RNA sequence, or both a DNA and an RNA sequence.

As used throughout the disclosure, the term "variant" when used to describe a peptide or polypeptide, refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157: 105-132 (1982). The hydropathic index of an amino acid is based on a consideration of its hydrophobicity and charge. Amino acids of similar hydropathic indexes can be substituted and still retain protein function. In an aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "conservative" amino acid substitutions may be defined as set out in Tables A, B, or C below. In some aspects, fusion polypeptides and/or nucleic acids encoding such fusion polypeptides include conservative substitutions have been introduced by modification of polynucleotides encoding polypeptides of the disclosure. Amino acids can be classified according to physical properties and contribution to secondary and tertiary protein structure. A conservative substitution is a substitution of one amino acid for another amino acid that has similar properties. Exemplary conservative substitutions are set out in Table A.

TABLE A

Conservative Substitutions I

| Side chain characteristics | | Amino Acid |
|---|---|---|
| Aliphatic | Non-polar | G A P I L V F |
| | Polar—uncharged | C S T M N Q |
| | Polar—charged | D E K R |
| Aromatic | | H F W Y |
| Other | | N Q D E |

Alternately, conservative amino acids can be grouped as described in Lehninger, (Biochemistry, Second Edition; Worth Publishers, Inc. New York, N.Y. (1975), pp. 71-77) as set forth in Table B.

TABLE B

| Conservative Substitutions II | | |
|---|---|---|
| Side Chain Characteristic | | Amino Acid |
| Non-polar (hydrophobic) | Aliphatic: | A L I V P |
| | Aromatic: | F W Y |
| | Sulfur-containing: | M |
| | Borderline: | G Y |
| Uncharged-polar | Hydroxyl: | S T Y |
| | Amides: | N Q |
| | Sulthydryl: | C |
| | Borderline: | G Y |
| Positively Charged (Basic): | | K R H |
| Negatively Charged (Acidic): | | D E |

Alternately, exemplary conservative substitutions are set out in Table C.

TABLE C

| Conservative Substitutions III | |
|---|---|
| Original Residue | Exemplaty Substitution |
| Ala (A) | Val Leu Ile Met |
| Arg (R) | Lys His |
| Asn (N) | Gln |
| Asp (I)) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu He |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides of the disclosure are intended to include polypeptides bearing one or more insertions, deletions, or substitutions, or any combination thereof, of amino acid residues as well as modifications other than insertions, deletions, or substitutions of amino acid residues. Polypeptides or nucleic acids of the disclosure may contain one or more conservative substitution.

As used throughout the disclosure, the term "more than one" of the aforementioned amino acid substitutions refers to 2, 3, 4, 5, 6, 7, 8, 9, 10, 11, 12, 13, 14, 15, 16, 17, 18, 19, or 20 or more of the recited amino acid substitutions. The term "more than one" may refer to 2, 3, 4, or 5 of the recited amino acid substitutions.

Polypeptides and proteins of the disclosure, either their entire sequence, or any portion thereof, may be non-naturally occurring. Polypeptides and proteins of the disclosure may contain one or more mutations, substitutions, deletions, or insertions that do not naturally-occur, rendering the entire amino acid sequence non-naturally occurring. Polypeptides and proteins of the disclosure may contain one or more duplicated, inverted or repeated sequences, the resultant sequence of which does not naturally-occur, rendering the entire amino acid sequence non-naturally occurring. Polypeptides and proteins of the disclosure may contain modified, artificial, or synthetic amino acids that do not naturally-occur, rendering the entire amino acid sequence non-naturally occurring.

As used throughout the disclosure, "sequence identity" may be determined by using the stand-alone executable BLAST engine program for blasting two sequences (b12seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The terms "identical" or "identity" when used in the context of two or more nucleic acids or polypeptide sequences, refer to a specified percentage of residues that are the same over a specified region of each of the sequences. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used throughout the disclosure, the term "endogenous" refers to nucleic acid or protein sequence naturally associated with a target gene or a host cell into which it is introduced.

As used throughout the disclosure, the term "exogenous" refers to nucleic acid or protein sequence not naturally associated with a target gene or a host cell into which it is introduced, including non-naturally occurring multiple copies of a naturally occurring nucleic acid, e.g., DNA sequence, or naturally occurring nucleic acid sequence located in a non-naturally occurring genome location.

The disclosure provides methods of introducing a polynucleotide construct comprising a DNA sequence into a host cell. By "introducing" is intended presenting to the cell the polynucleotide construct in such a manner that the construct gains access to the interior of the host cell. The methods of the disclosure do not depend on a particular method for introducing a polynucleotide construct into a host cell, only that the polynucleotide construct gains access to the interior of one cell of the host. Methods for introducing polynucleotide constructs into bacteria, plants, fungi and animals are known in the art including, but not limited to, stable transformation methods, transient transformation methods, and virus-mediated methods.

Example 1: Improved Transposition with PiggyBac Nanotransposons

Figure 3:
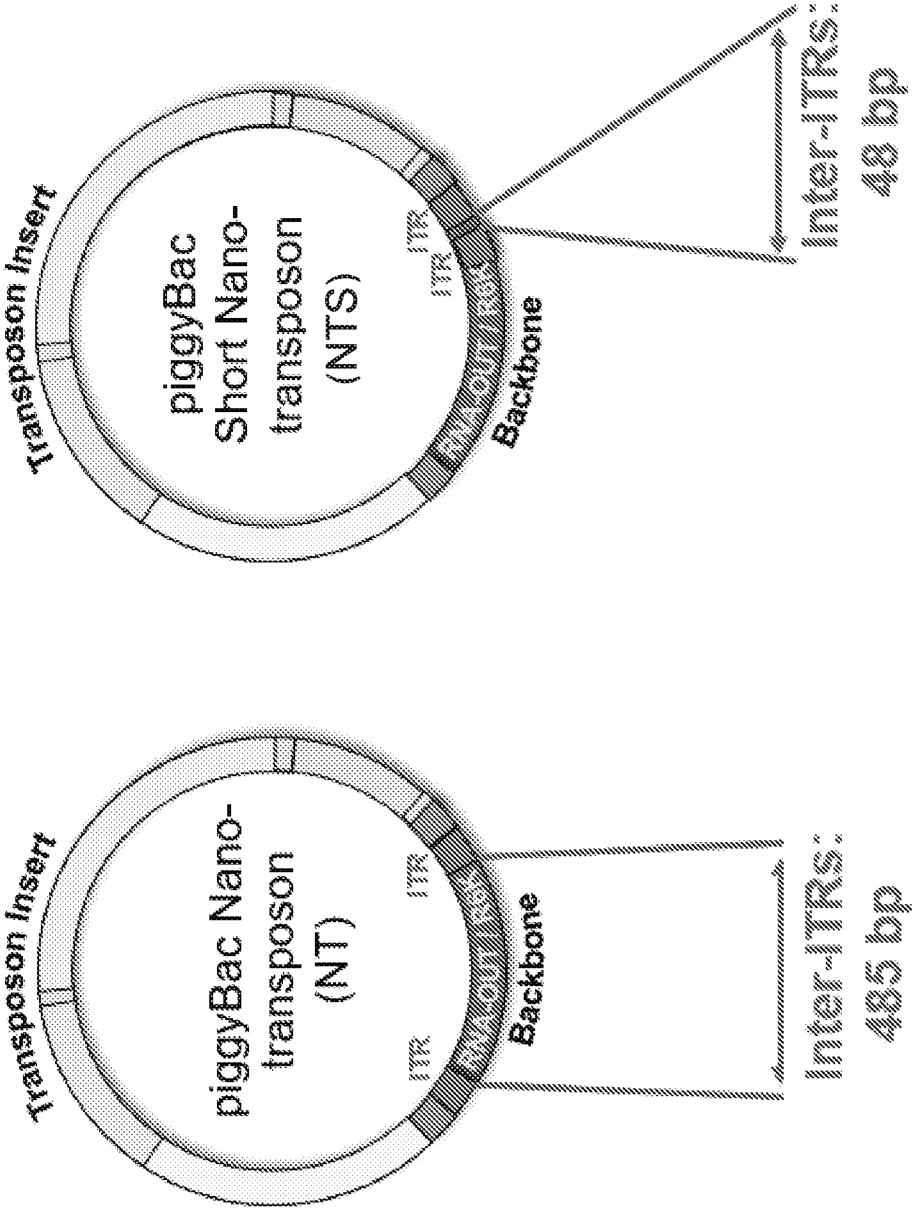
FIG. 3 is a pair of schematic diagrams comparing maps of a piggyBac NT and a piggyBac short NT.

The effect of shortening the piggyBac transposon plasmid backbone thereby decreasing the distance between Flits on transposition efficiency into the genome of human pan T cells was assessed. A full-sized piggyBac plasmid (FP) (FIG. 1), a piggyBac nanotransposon (NT) (FIG. 1) and a piggy- Bac Short Nanotransposon (NTS) (FIG. 3), each including a transposon encoding GFP, were constructed. The FP backbone encoded a bacterial pUC origin of replication as well as a Kan/Neo resistance gene. The NT backbone encoded an antibiotic-free, sucrose-selectable nanoplasmid backbone comprising an RNA-OUT element as well as a R6K mini origin of replication. The NTS differed from the NT in that the backbone RNA-OUT element and R6K mini origin of replication were placed inside the transposon element thereby further reducing the distance between ITRs. FIG. 1 illustrates the difference between the full plasmid and the NT nanotransposon. While size of the transposon remained constant (3,606 bp), the NT backbone was shorter, effectively reducing the distance flanking the ITRs over 4-fold from 2,034 bp to 493 bp as detailed in Table 1. FIG. 3 illustrates the difference between the piggyBac NT and a piggyBac NTS. While size of the transposon increased from 3,614 bp to 4,069 (to incorporate the RNA-OUT and R6K sequences), the NTS backbone was shorter, effectively reducing the distance flanking the ITRs over 10-fold from 485 bp to 48 bp as detailed in Table 2.

TABLE 1

| | Plasmid size | Transposon size | Distance flanking the ITRs |
|---|---|---|---|
| PB-FP | 5,640 | 3,606 | 2,034 |
| PB-NT | 4,099 | 3,606 | 493 |
| FOLD CHANGE | 1.38 | 1.00 | 4.13 |

TABLE 2

Figure 2:
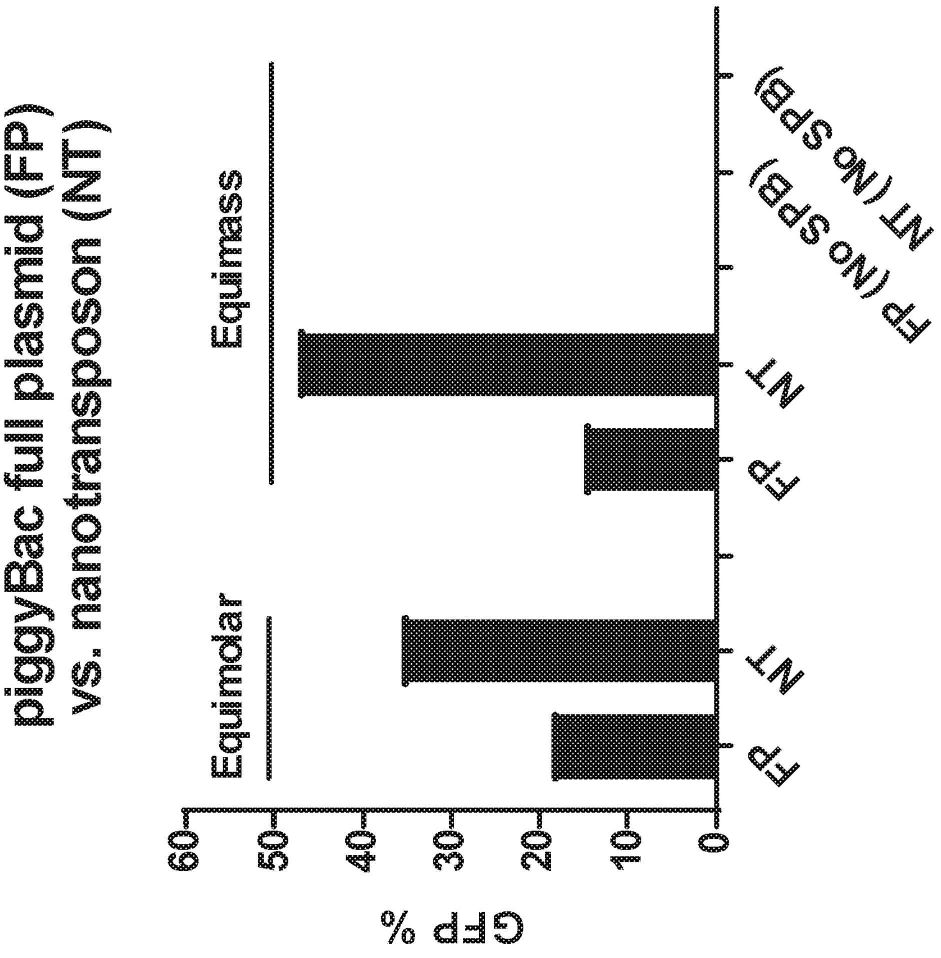
FIG. 2 is a graph depicting improved transposition with piggyBac NT in human pan T cells.

| | Plasmid size | Transposon size | Distance flanking the ITRs |
|---|---|---|---|
| PB-NT | 4,099 | 3,614 | 485 |
| PB-NTS | 4,117 | 4,069 | 48 |
| FOLD CHANGE | 1.00 | 0.89 | 10.10 |

piggyBac FP or piggyBac NT were delivered to human pan T cells via electroporation (EP) either with or without mRNA encoding the Super piggyBac transposase enzyme (SPB) (FIG. 2). Additionally, FP and NT were delivered to cells at either equimolar or equimass amounts. Following EP, cells were stimulated using standard TCR activation reagents and GFP expression was assessed by FACS 15 days later. These data show that reducing the distance flanking the ITRs over 4-fold (from 2,034 bp to 493 bp) resulted in a greater level of GFP transposition at both equimolar and equimass amounts when compared to the FP GFP transposon plasmid. In addition, GFP expression was the result of stable integration of the transposon since no GFP expression was detected in T cells electroporated in the absence of SPB.

Figure 4:
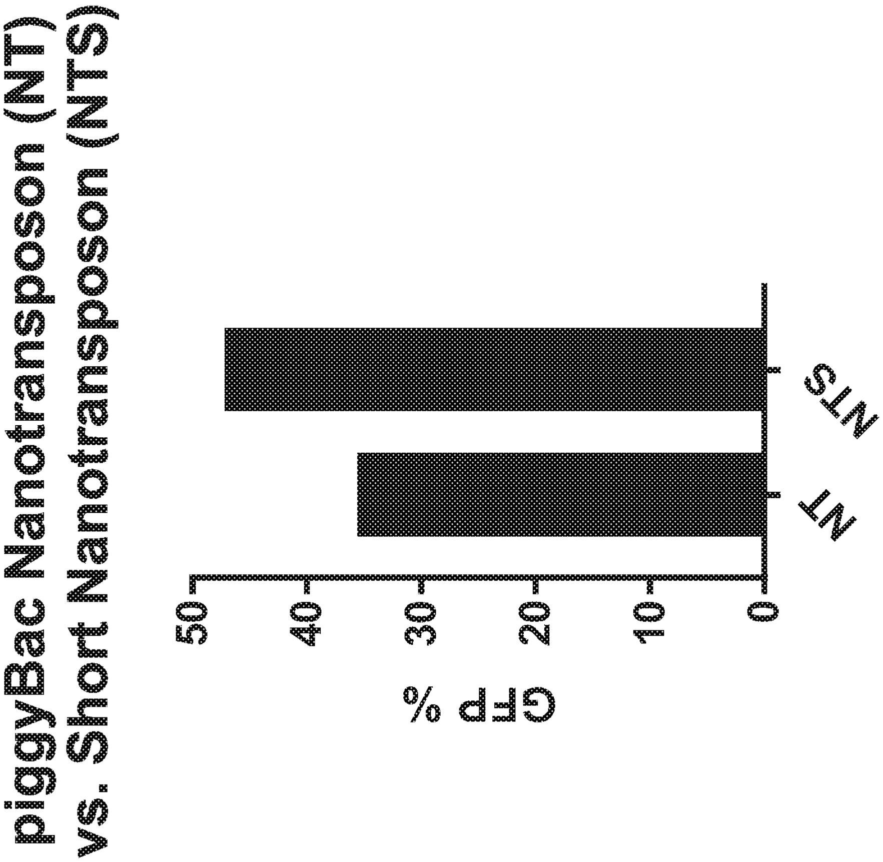
FIG. 4 is a graph showing that piggyBac transposition in human pan T cells is enhanced by reducing the inter-ITR sequence (e.g., decreasing the distance flanking the Has).

FIG. 1 and FIG. 2 demonstrate that shortening the piggyBac transposon plasmid backbone increased transposition efficiency of the transposon into human pan T cells. However, since total plasmid size was not the same between the FP and NT it remains unclear as to whether or not enhanced transposition efficiency by the NT was a result of either a smaller plasmid (equimolar; less DNA delivered to the cells), more total plasmids being delivered (equimass), or a shorter distance flanking the piggyBac ITRs. Since DNA delivered to human pan T cells can elicit immunomodulatory effects and can be toxic, enhanced transposition efficiency by the NT may be the result of either the delivery of less total DNA (equimolar) or delivery of more plasmids (equimass). To test this, a NTS was constructed where the nanoplasmid backbone was relocated to within the transposon, placed between the insulator and ITR (FIG. 3). While the size of the NT and the NTS remained constant (4,099 and 4,117 bp), the distance flanking the ITRs in the NTS was 10-fold shorter (from 485 bp to 48 bp) (Table 2). An equimolar/equimass amount of NT or NTS was delivered to human pan T cells via electroporation (EP) along with mRNA encoding SPB. Following EP, cells were stimulated using standard TCR activation reagents and GFP expression was assessed by FACS 15 days later. These data show that reducing the distance flanking the ITRs over 10-fold (from 485 bp to 48 bp), while keeping the total plasmid size constant, resulted in a greater level of GFP transposition by the NIS when compared to the NT GFP nanotransposon (FIG. 4).

Example 2: Transposition of BCMA CAR and PSMA CAR Nanotransposons

Figure 5:
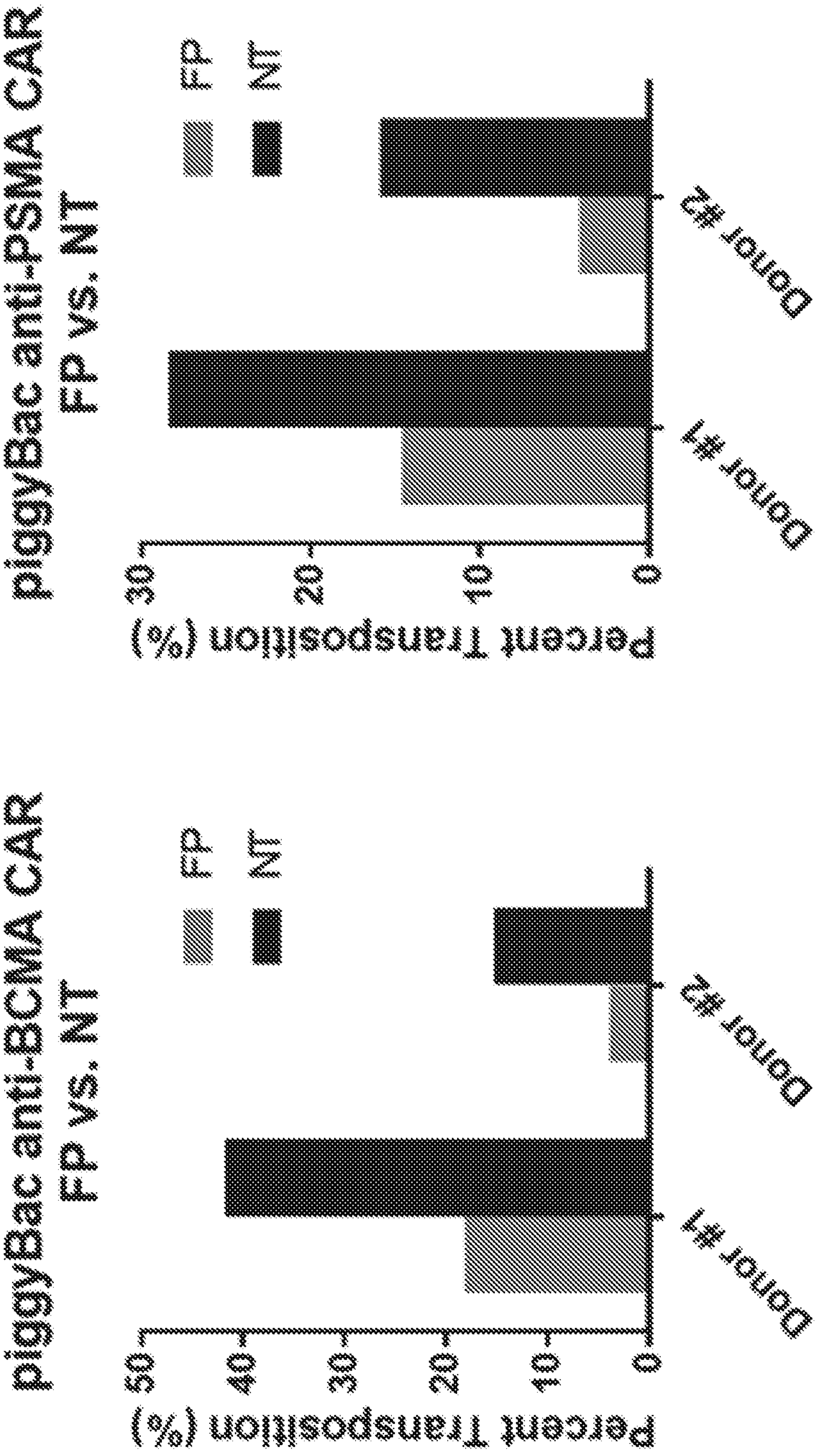
FIG. 5 is a pair of graphs showing increased transposition with an anti-BCMA chimeric antigen receptor (CAR) NT and an anti-PSMA CAR NT in human pan T cells.
Figure 6:
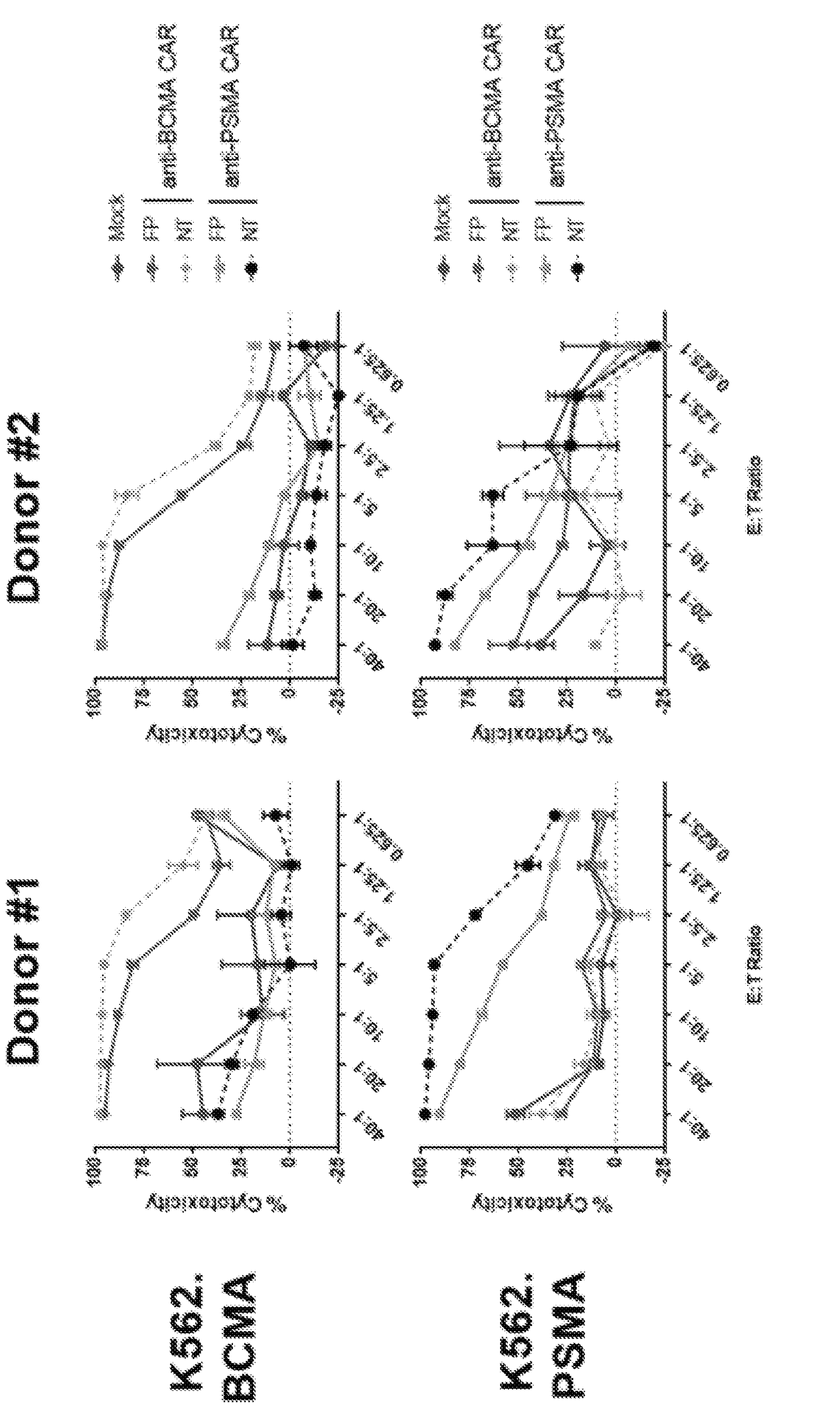
FIG. 6 is a series of graphs showing that human CAR-T cells produced using an anti-BCMA CAR NT or an anti-PSMA CAR NT were capable of killing target tumor cells.
Figure 7:
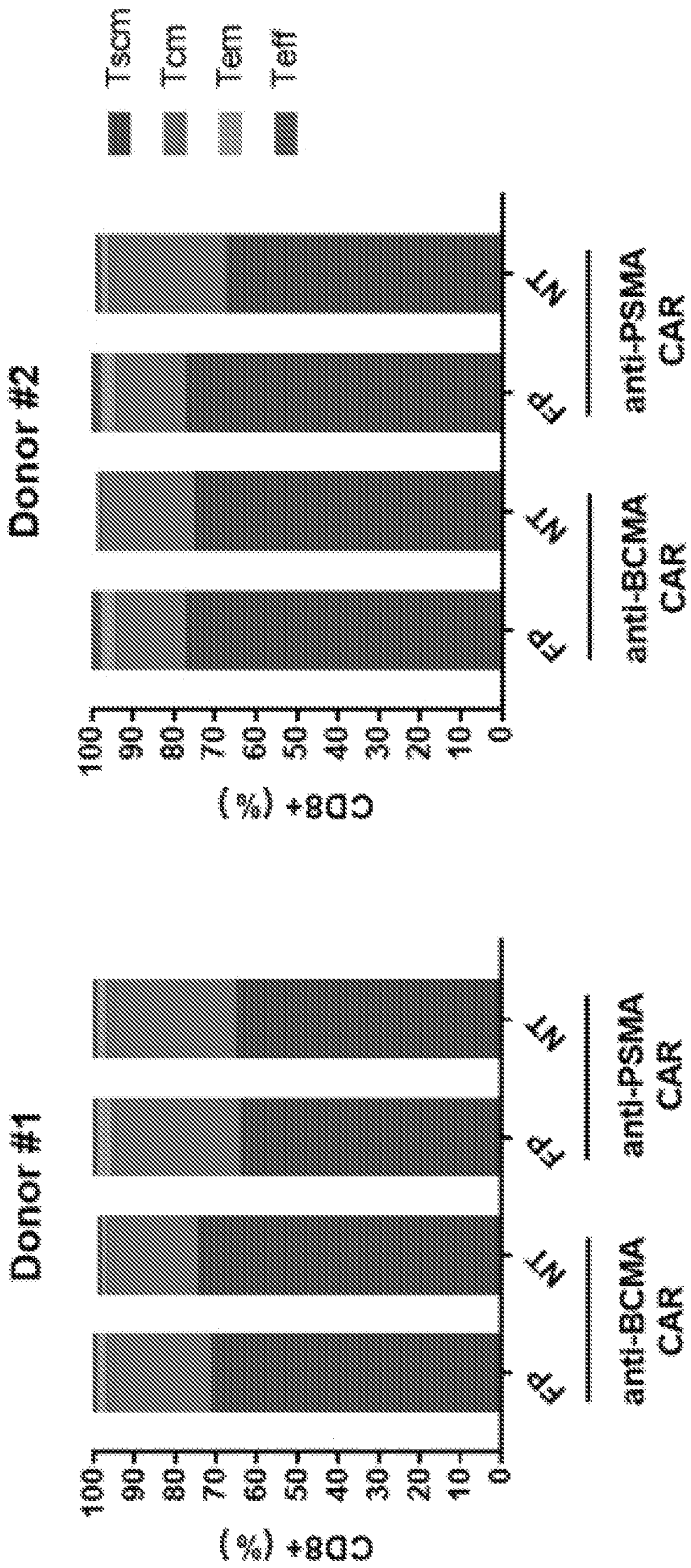
FIG. 7 is a series of graphs showing that human CAR-T cells produced using an anti-BCMA CAR NT or an anti-PSMA CAR NT were comparable in phenotypic composition.
Figure 8:
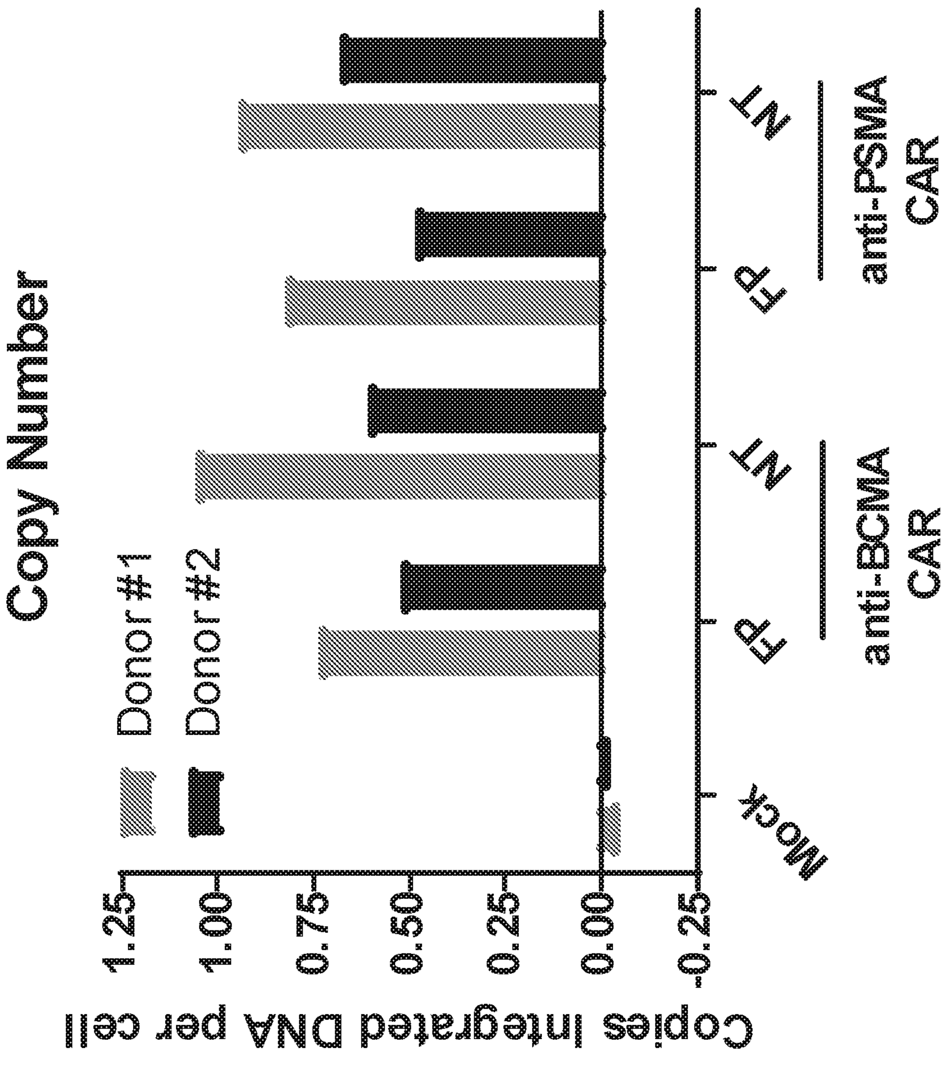
FIG. 8 is a series of graphs showing that human CAR-T cells produced using an anti-BCMA CAR NT or an anti-PSMA CAR NT have similar integrated copy number.

Anti-BCMA CAR and Anti-PSMA CAR encoding full-sized piggyBac plasmids (FP) or piggyBac nanotransposon (NT) were delivered in equimass amounts to human pan T cells via electroporation (EP) along with mRNA encoding the Super piggyBac transposase enzyme (FIG. 5). Following EP, cells were stimulated using standard TCR activation reagents in the absence of selection reagents and CAR expression was assessed by FACS 5 days later. These data show that both NTs resulted in a greater level of transposition at equimass amounts when compared to the FP transposon plasmid. This was true when CAR-T cells were produced from human pan T cells from two different normal donors. Anti-BCMA CAR and Anti-PSMA CAR T cells produced using either full-sized piggyBac plasmids (FP) or piggyBac nanotransposon (NT) were produced as described herein. Killing of K562 cells engineered to express either BCMA (K562.BCMA) or PSMA (K562.PSMA) by CAR-T cells at the indicated effector to target ratios (FIG. 6), These data show that all CAR-T cells, whether produced using FP or NT, were capable of killing target tumor cells in an antigen-dependent manner. This was true for CAR-T cells that were produced from human pan T cells from two different normal donors. FIG. 7 is a series of graphs showing that human CAR-T cells produced using anti-BCMA CAR or anti-PSMA CAR nanotransposons (NT) were comparable in phenotypic composition. Anti-BCMA CAR and Anti-PSMA CAR T cells produced using either full-sized piggyBac plasmids (FP) or piggyBac nanotransposon (NT) were manufactured as described herein. Phenotypic analysis of memory T cell markers and activation/exhaustion markers (data not shown) was performed. These data show that all CAR-T cells, whether produced using FP or NT, exhibited a similar phenotypic composition of CD45RA+CD62L+ (Tscm), CD45RA-CD62L+ (Tcm), CD45RA-CD62L− (Tem), and CD45RA+CD62L− (Teff) cells. In addition, comparable levels of expression of CCR7 (CD197), CD127, CD27, LAGS, TIM3, CXCR3, PD-1, and CD25 was observed (data not shown). This was true for CAR-T cells that were produced from human pan T cells from two different normal donors. Average copy number of integrated transposons was measured by quantitative PCR. These data show that in two different donors, all CAR-T cells, whether produced using FP or NT, exhibited a similar integrated copy number of transposons (FIG. 8).

Figure 9:
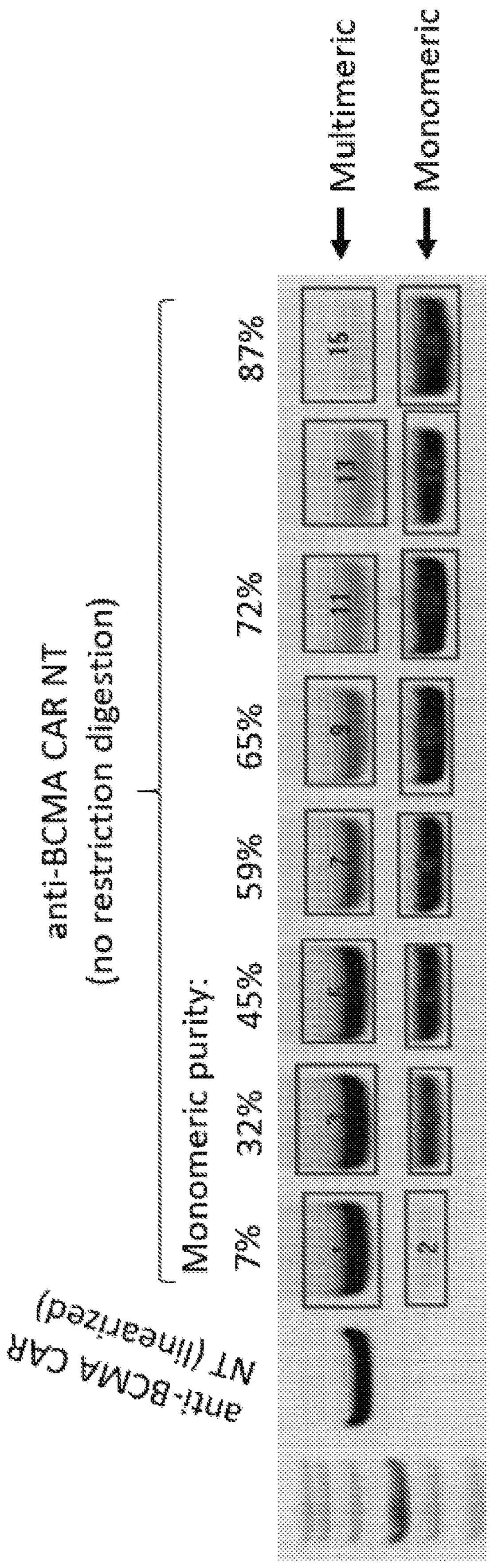
FIG. 9 is a photograph of a gel electrophoresis analysis demonstrating that monomeric NT purity is associated with transposition efficiency in human pan T cells.

Anti-BCMA CAR piggyBac nanotransposons at different monomeric purities was produced by mixing a highly multimeric lot (7% monomeric) with a highly monomeric lot (87% monomeric) at different ratios. Both lots were confirmed by genetic sequencing to be identical at the primary level and differed only at the tertiary level in monomeric or multimeric structure. Each new lot of mixed anti-BCMA CAR NT was run on an agarose gel in the absence of restriction digestion to reveal resultant ratios of monomeric to multimeric nanotransposon; lots of various monomeric purities were produced (7%, 32%, 45%, 59%, 65%, 72%, and 87%). On the gel, multimeric NT migrated slower than monomeric NT (FIG. 9). Bands of the gel depicted in FIG. 9 are boxed by rectangles to illustrate the multimeric (top) and monomeric (bottom) nanotransposon; numbering proceeds from top to bottom, left to right: 1 (multimeric) and 2 (monomeric) [7% monomeric purity], 3 and 4 [32% monomeric purity], 5 and 6 [45% monomeric purity], 7 and 8 [59% monomeric purity], 9 and 10 [65% monomeric purity], 11 and 12 [72% monomeric purity], 13 and 14 [blank], 15 and 16 [87% monomeric purity].

Figure 10:
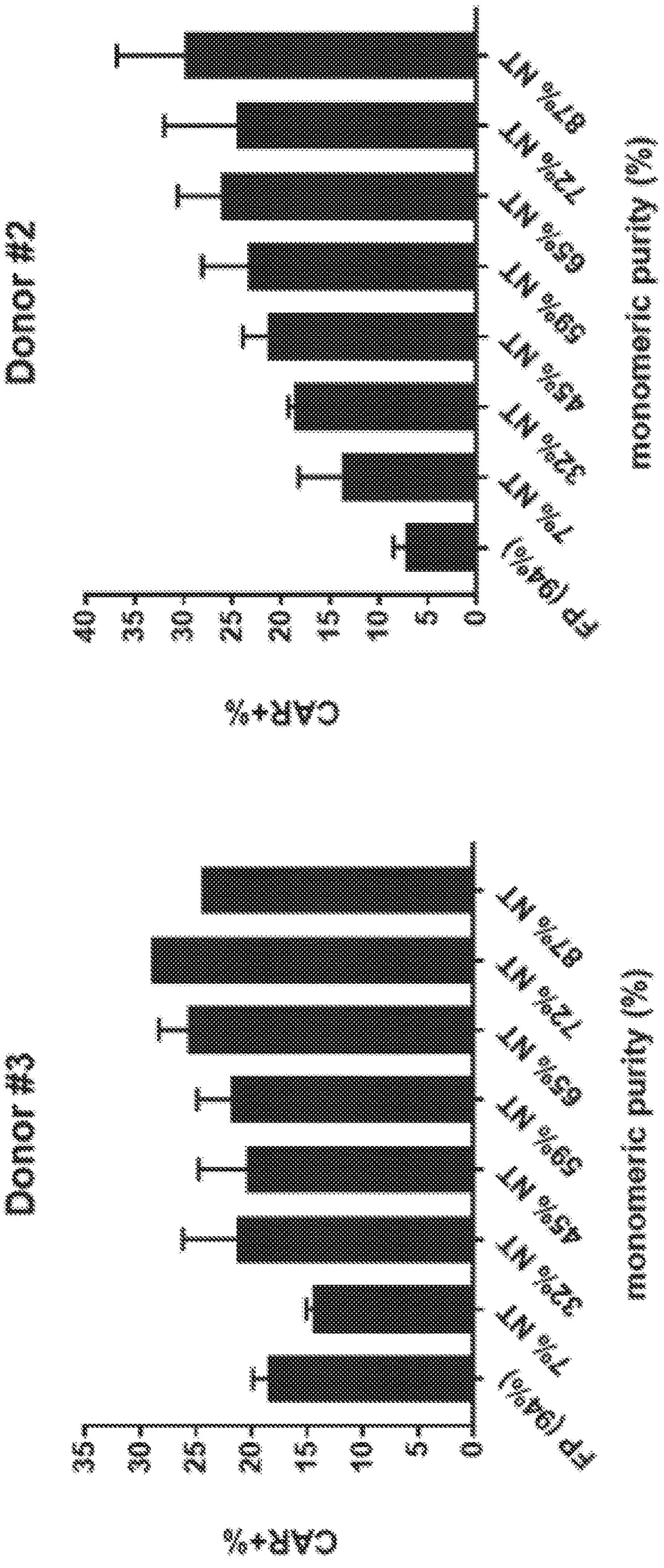
FIG. 10 is a pair of graphs showing that monomeric NT purity is associated with transposition efficiency in human pan T cells.

Anti-BCMA CAR piggyBac NT, at different monomeric purities, was delivered to human pan T cells via electroporation (EP) along with mRNA encoding the Super piggyBac transposase enzyme (FIG. 10). As a control, a full-sized anti-BCMA CAR plasmid (FP) at 94% monomeric purity was also delivered at an equimolar amount. Following EP, cells were stimulated using standard TCR activation reagents in the absence of selection reagents and CAR expression was assessed by FACS 5 days later. These data show in two separate donors (Donor #3 and Donor #2) that monomeric purity positively affects transposition efficiency. In addition, these data show that NT resulted in a greater level of transposition when compared to the FP transposon plasmid equimolar amounts.

Example 3: Preclinical Evaluation of the P-PSMA-101 Nanotransposon

Figure 11:
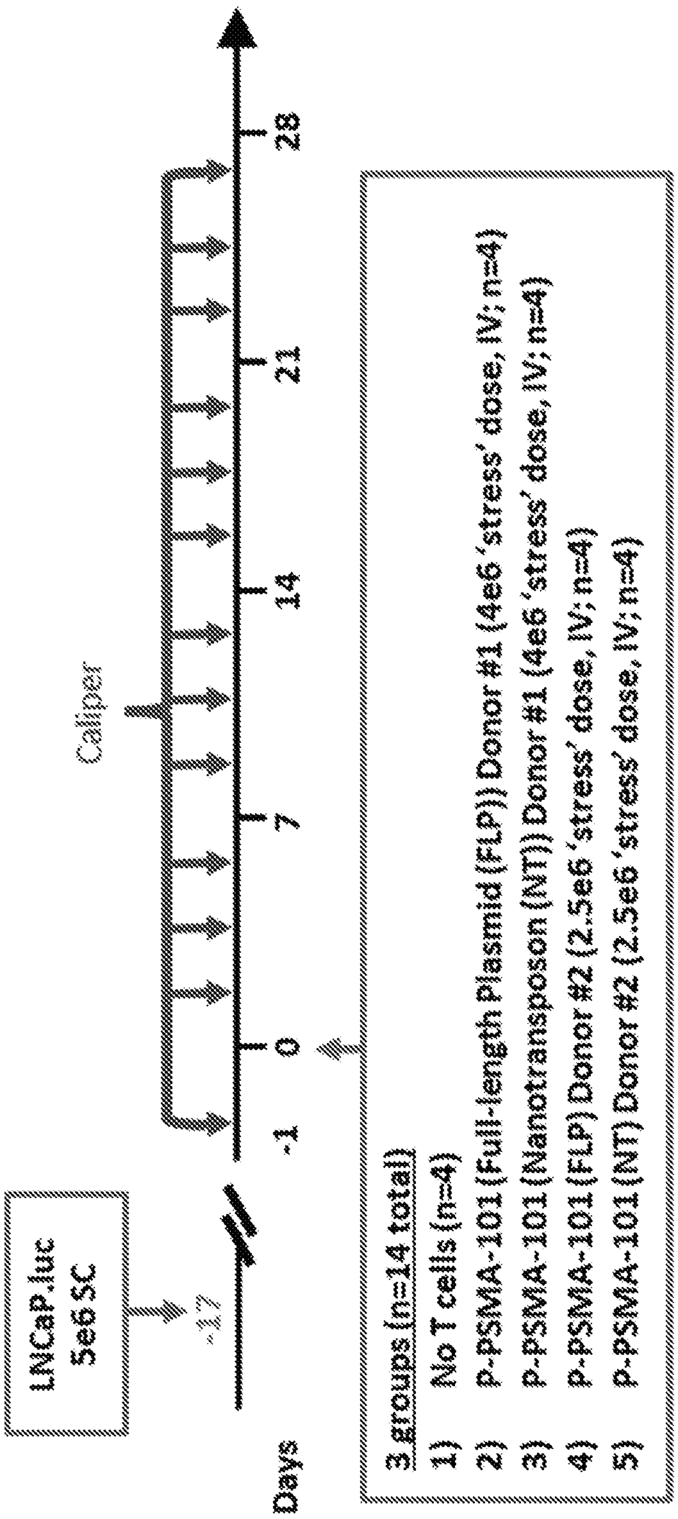
FIG. 11 is a schematic diagram showing preclinical evaluation of the P-PSMA-101 transposon when delivered by a full-length plasmid (FLP) versus a NT at stress doses using the Murine Xenograft Model.
Figure 12:
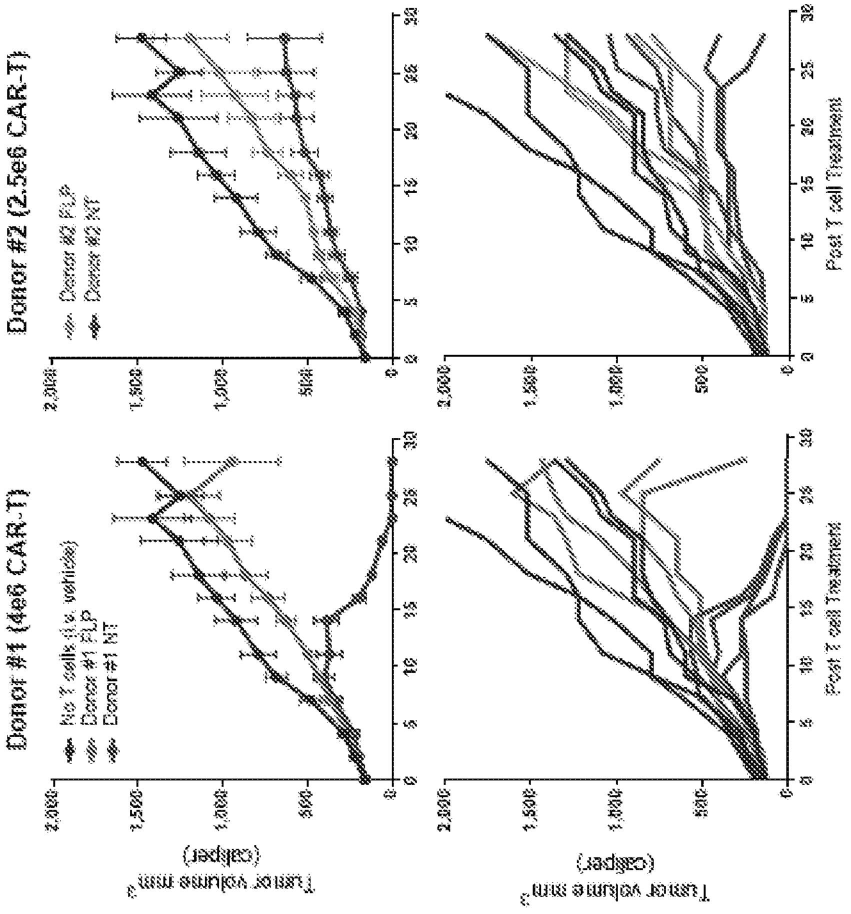
FIG. 12 is a series of graphs showing the tumor volume assessment of mice treated the P-PSMA-101 transposon when delivered by a FLP versus a NT.

The efficacy of the P-PSMA-101 transposon when delivered by a full-length plasmid (FLP) versus a nanotransposon (NT) at 'stress' doses using the Murine Xenograft Model was evaluated in a preclinical setting. The murine xenograft model using a luciferase-expressing LNCaP cell line (LNCaP.luc) injected subcutaneously (SC) into NSG mice was utilized to assess in vivo anti-tumor efficacy of the P-PSMA-101 transposon as delivered by a full-length plasmid (FLP) or a nanotransposon (NT) at two different 'stress' doses (2.5×10^6 or 4×10^6) of total CAR-T cells from two different normal donors (FIG. 11). All CAR-T cells were produced using piggyBac (PR) delivery of P-PSMA-101 transposon using either FLP or NT delivery. Mice were injected in the axilla with LNCaP and treated when tumors were established (100-200 $mm^3$ by caliper measurement). Mice were treated with two different 'stress' doses ($2.5\times10^6$ or $4\times10^6$) of P-PSMA-101 CAR-Ts by IV injection for greater resolution in detecting possible functional differences in efficacy between transposon delivery by the FLP and the NT. Tumor volume assessment by caliper measurement for control mice (black), Donor #1 FLP mice (red), Donor #1 NT mice (blue), Donor #2 FLP mice (orange), and Donor 42 NT mice (green) as displayed as group averages with error bars (top) and individual mice (bottom) (FIG. 12). The y-axis shows the tumor volume ($mm^3$) assessed by caliper measurement. The x-axis shows the number of days post T cell treatment. Delivered by NT, P-PSMA-101 transposon at a 'stress' dose demonstrated enhanced anti-tumor efficacy as measured by caliper in comparison to the FLP and control mice against established SC LNCaP.luc solid tumors.

What is claimed is:

1. A composition comprising:

a first nucleic acid sequence comprising: (a) a first inverted terminal repeat (ITR), (b) a second ITR and (c) an intra-ITR sequence, wherein the intra-ITR sequence comprises a transposon sequence; and a second nucleic acid sequence comprising an inter-ITR sequence, wherein the length of the inter-ITR sequence is between 1 and 450 nucleotides, inclusive of the endpoints.

2. The composition of claim 1, wherein the length of the inter-ITR sequence is between 1 and 100 nucleotides, inclusive of the endpoints.

3. The composition of claim 1, wherein the first nucleic acid sequence further comprises an origin of replication sequence.

4. The composition of claim 1, wherein the second nucleic acid sequence further comprises an origin of replication sequence.

5. The composition of claim 3 or 4, wherein the length of the origin of replication sequence is between 1 and 450 nucleotides.

6. The composition of claim 5, wherein the origin of replication sequence comprises an R6K origin of replication.

7. The composition of claim 1, wherein the first nucleic acid sequence or the second nucleic acid sequence further comprises a sequence encoding a first selectable marker.

8. The composition of claim 7, wherein the length of the first selectable marker is between 1 and 200 nucleotides.

9. The composition of claim 7, wherein the first selectable marker is a sucrose selectable marker.

10. The composition of claim 7, wherein the sucrose selectable marker is an RNA-OUT selection marker.

11. The composition of claim 1, wherein the first nucleic acid sequence does not comprise a recombination site, an excision site, a ligation site, or a combination thereof.

12. The composition of claim 1, wherein the second nucleic acid sequence does not comprise a recombination site, an excision site, a ligation site, or a combination thereof.

13. The composition of claim 1, wherein the first nucleic acid sequence does not comprise foreign DNA.

14. The composition of claim 1, wherein the second nucleic acid sequence does not comprise foreign DNA.

15. The composition of claim 1, wherein the first nucleic acid sequence further comprises at least one exogenous sequence and a promoter sequence capable of expressing an exogenous sequence in a mammalian cell.

16. The composition of claim 15, wherein the first nucleic acid sequence further comprises at least one insulator sequence.

17. The composition of claim 15, wherein the first nucleic acid sequence further comprises a polyadenosine (polyA) sequence.

18. The composition of claim 15, wherein the promoter sequence capable of expressing an exogenous sequence in a mammalian cell is capable of expressing an exogenous sequence in a human cell.

19. The composition of claim 18, wherein the promoter is a constitutive promoter.

20. The composition of claim 18, wherein the promoter is an inducible promoter.

21. The composition of claim 15, wherein the at least one exogenous sequence comprises a sequence encoding a non-naturally occurring antigen receptor, a sequence encoding a therapeutic polypeptide, or a combination thereof.

22. The composition of claim 21, wherein the non-naturally occurring antigen receptor comprises a chimeric antigen receptor (CAR).

23. The composition of claim 1, wherein the composition is a transposon.

24. The composition of claim 23, wherein the transposon is a piggyBac transposon.

25. A polynucleotide comprising a nucleic acid sequence encoding the composition of claim 1.

26. A cell comprising the composition of claim 1.

27. A population of cells, wherein a plurality of the population of cells are modified to express the CAR of claim 22.

28. The population of cells of claim 27, wherein at least 50% of plurality of modified T-cells express the CAR and express one or more cell-surface marker(s) comprising CD45RA and CD62L and do not express one or more cell-surface marker(s) comprising CD45RO.

29. A pharmaceutical composition comprising the composition of claim 1 and a pharmaceutically acceptable carrier.

30. A method of treating cancer in a subject in need thereof comprising administering a composition of claim 1.

31. The composition of claim 1, wherein the length of the inter-ITR sequence is between 1 and 400 nucleotides, inclusive of the endpoints.

32. The composition of claim 1, wherein the length of the inter-ITR sequence is between 1 and 300 nucleotides, inclusive of the endpoints.

33. The composition of claim 1, wherein the length of the inter-ITR sequence is between 1 and 200 nucleotides, inclusive of the endpoints.

* * * * *